(12) United States Patent
Labib et al.

(10) Patent No.: US 8,226,774 B2
(45) Date of Patent: Jul. 24, 2012

(54) METHOD FOR CLEANING PASSAGEWAYS SUCH AN ENDOSCOPE CHANNELS USING FLOW OF LIQUID AND GAS

(75) Inventors: Mohamed Emam Labib, Princeton, NJ (US); Ching-Yue Lai, Pennington, NJ (US); Yacoob Tabani, Basking Ridge, NJ (US); Ziye Qian, Monroe, NJ (US); Stanislav S. Dukhin, Goldens Bridge, NY (US); Joseph J. Murawski, Plainfield, NJ (US)

(73) Assignee: Princeton Trade & Technology, Inc., Princeton, NJ (US)

( * ) Notice: Subject to any disclaimer, the term of this patent is extended or adjusted under 35 U.S.C. 154(b) by 248 days.

(21) Appl. No.: 12/286,747

(22) Filed: Sep. 30, 2008

(65) Prior Publication Data

US 2010/0078046 A1    Apr. 1, 2010

(51) Int. Cl.
*B08B 9/027* (2006.01)
*B08B 9/032* (2006.01)
*B08B 3/08* (2006.01)
*B08B 5/02* (2006.01)

(52) U.S. Cl. ............... 134/22.12; 134/22.11; 134/22.18; 134/30; 134/34; 134/36

(58) Field of Classification Search ............... 134/22.12, 134/22.18, 22.14, 30, 36, 37
See application file for complete search history.

(56) References Cited

U.S. PATENT DOCUMENTS

| | | | |
|---|---|---|---|
| 2,151,671 A | 3/1939 | Wright | |
| 2,222,516 A | 11/1940 | Powell et al. | |
| 3,119,399 A | 1/1964 | Bender | |
| 3,162,427 A | 12/1964 | Knudson et al. | |
| 3,467,314 A | 9/1969 | Grubb | |
| 3,551,331 A | 12/1970 | Cescon | |
| 3,625,231 A | 12/1971 | Littrell, Jr. | |
| 3,811,408 A | 5/1974 | Thompson | |
| 4,166,031 A | 8/1979 | Hardy | |
| 4,169,123 A | 9/1979 | Moore et al. | |
| 4,209,402 A | 6/1980 | Gentles | |
| 4,219,333 A | 8/1980 | Harris | |
| 4,311,618 A | 1/1982 | Schafer-Burkhard | |
| 4,375,413 A | 3/1983 | Geel et al. | |
| 4,380,477 A | 4/1983 | Saunders | |
| 4,400,220 A | 8/1983 | Cole, Jr. | |
| 4,444,597 A | 4/1984 | Gortz et al. | |

(Continued)

FOREIGN PATENT DOCUMENTS

DE    893595    10/1953

(Continued)

OTHER PUBLICATIONS

Machine translation of EP0490117; Kuebler, Jun. 1992.*

(Continued)

*Primary Examiner* — Michael Kornakov
*Assistant Examiner* — Natasha Campbell
(74) *Attorney, Agent, or Firm* — Merchant & Gould, P.C.

(57) ABSTRACT

Apparatus and methods are disclosed for cleaning interiors of passageways in endoscopes or other luminal medical devices by flow of liquid and gas therethrough. The liquid flow may include rivulets, droplets or other liquid entities which move on the internal surfaces of the passageways, and may include a three-phase contact interface between liquid and dry solid and gas.

16 Claims, 47 Drawing Sheets

U.S. PATENT DOCUMENTS

| | | |
|---|---|---|
| 4,477,438 A | 10/1984 | Willcockson et al. |
| 4,517,081 A | 5/1985 | Amiot et al. |
| 4,525,220 A | 6/1985 | Sasa et al. |
| 4,622,140 A | 11/1986 | Lee et al. |
| 4,695,385 A | 9/1987 | Boag |
| 4,707,335 A | 11/1987 | Fentress et al. |
| 4,710,233 A | 12/1987 | Hohmann et al. |
| 4,744,951 A | 5/1988 | Cummings et al. |
| 4,767,539 A | 8/1988 | Ford |
| 4,781,764 A | 11/1988 | Leenaars |
| 4,787,404 A | 11/1988 | Klosterman et al. |
| 4,863,688 A | 9/1989 | Schmidt et al. |
| 4,881,563 A | 11/1989 | Christian |
| 4,902,352 A | 2/1990 | Christian |
| 5,007,461 A | 4/1991 | Naf |
| 5,045,352 A | 9/1991 | Mueller |
| 5,077,008 A | 12/1991 | Kralovic et al. |
| 5,127,961 A | 7/1992 | Aiton |
| 5,139,675 A | 8/1992 | Arnold et al. |
| 5,160,548 A | 11/1992 | Boisture |
| 5,178,830 A | 1/1993 | Riera Aixala |
| 5,244,468 A | 9/1993 | Harris |
| 5,279,799 A | 1/1994 | Moser |
| 5,286,301 A | 2/1994 | Albrecht |
| 5,322,571 A | 6/1994 | Plummer et al. |
| 5,344,652 A | 9/1994 | Hall, II et al. |
| 5,395,456 A | 3/1995 | Abrams et al. |
| 5,408,991 A | 4/1995 | Iida et al. |
| 5,415,191 A | 5/1995 | Mashino et al. |
| 5,425,815 A | 6/1995 | Parker et al. |
| 5,480,565 A | 1/1996 | Levin et al. |
| 5,494,530 A | 2/1996 | Graf |
| 5,529,701 A | 6/1996 | Grisham et al. |
| 5,589,507 A | 12/1996 | Hall, II et al. |
| 5,615,695 A | 4/1997 | Chambers |
| 5,616,616 A | 4/1997 | Hall, II et al. |
| 5,628,959 A | 5/1997 | Kross |
| 5,635,195 A | 6/1997 | Hall, II et al. |
| 5,651,893 A | 7/1997 | Kenley et al. |
| 5,656,302 A | 8/1997 | Cosentino et al. |
| 5,658,466 A | 8/1997 | Kawaguchi et al. |
| 5,662,811 A | 9/1997 | Grisham et al. |
| 5,698,100 A | 12/1997 | Levin et al. |
| 5,714,060 A | 2/1998 | Kenley et al. |
| 5,772,624 A | 6/1998 | Utterberg et al. |
| 5,795,404 A | 8/1998 | Murphy et al. |
| 5,840,343 A | 11/1998 | Hall, II et al. |
| 5,855,216 A | 1/1999 | Robinson |
| 5,896,828 A | 4/1999 | Kronschnabel et al. |
| 5,915,395 A | 6/1999 | Smith |
| 5,931,845 A | 8/1999 | Amyette |
| 5,934,566 A | 8/1999 | Kanno et al. |
| 5,941,257 A | 8/1999 | Gruszczynski |
| 5,944,997 A | 8/1999 | Pedersen et al. |
| 5,961,937 A | 10/1999 | Gobbato |
| 5,972,875 A | 10/1999 | Crutcher et al. |
| 6,027,572 A | 2/2000 | Labib et al. |
| 6,050,278 A | 4/2000 | Arnal et al. |
| 6,179,954 B1 | 1/2001 | Kawana et al. |
| 6,192,900 B1 | 2/2001 | Arnal et al. |
| 6,193,890 B1 | 2/2001 | Pedersen et al. |
| 6,207,201 B1 | 3/2001 | Piacenza |
| 6,261,457 B1 | 7/2001 | Wenthold et al. |
| 6,326,340 B1 | 12/2001 | Labib et al. |
| 6,423,152 B1 | 7/2002 | Landaas |
| 6,447,990 B1 | 9/2002 | Alfa |
| 6,454,871 B1 | 9/2002 | Labib et al. |
| 6,619,302 B2 | 9/2003 | Labib et al. |
| 6,717,019 B2 | 4/2004 | Lassila |
| 6,773,395 B2 | 8/2004 | Takase |
| 6,823,881 B1 | 11/2004 | Mishkin et al. |
| 6,857,436 B2 | 2/2005 | Labib et al. |
| 6,908,891 B2 | 6/2005 | Biering et al. |
| 6,945,257 B2 | 9/2005 | Tabani et al. |
| 7,762,949 B2 | 7/2010 | Nakao |
| 8,114,221 B2 | 2/2012 | Labib et al. |
| 2001/0047813 A1 | 12/2001 | Labib et al. |
| 2002/0112743 A1 | 8/2002 | Tabani et al. |
| 2002/0189647 A1 | 12/2002 | Labib et al. |
| 2003/0062066 A1 | 4/2003 | Gruszcaynski et al. |
| 2004/0007255 A1 | 1/2004 | Labib et al. |
| 2004/0118413 A1 | 6/2004 | Williams et al. |
| 2004/0118437 A1 | 6/2004 | Nguyen |
| 2005/0028845 A1 | 2/2005 | Labib et al. |
| 2005/0126599 A1 | 6/2005 | Labib et al. |
| 2005/0150831 A1 | 7/2005 | Tabani et al. |
| 2007/0027359 A1 | 2/2007 | Salman |
| 2008/0264454 A1 | 10/2008 | Tabani et al. |
| 2009/0229632 A1 | 9/2009 | Labib et al. |
| 2010/0078047 A1 | 4/2010 | Labib et al. |

FOREIGN PATENT DOCUMENTS

| | | |
|---|---|---|
| EP | 490117 A1 | 6/1992 |
| EP | 213157 B1 | 10/1992 |
| EP | 160014 B1 | 1/1993 |
| EP | 289523 B1 | 1/1995 |
| EP | 634229 B1 | 1/1995 |
| JP | 49-102159 A | 9/1974 |
| JP | 49-116868 | 11/1974 |
| JP | 59-69019 A | 4/1984 |
| JP | 60-67896 A | 4/1985 |
| JP | 8019556 | 5/1994 |
| JP | 6121769 | 1/1996 |
| JP | 8-289687 A | 11/1996 |
| JP | 11-104636 | 4/1999 |
| JP | 2002-011419 A | 1/2002 |
| JP | 2002-066486 | 3/2002 |
| SU | 1042826 A | 2/1981 |
| WO | WO 85/01449 | 4/1985 |
| WO | WO 86/05116 | 9/1986 |
| WO | WO 88/00494 | 1/1988 |
| WO | WO 95/10349 | 4/1995 |
| WO | WO 96/20737 | 7/1996 |
| WO | WO 98/58632 | 12/1998 |
| WO | WO 99/29401 | 6/1999 |
| WO | WO 00/00306 | 1/2000 |
| WO | WO 01/91931 | 12/2001 |

OTHER PUBLICATIONS

International Search Report for PCT/US2009/058861, dated Jan. 12, 2010.

Azzopardi, B., "Drops in annular two-phase flow," *Int. J. Multiphase Flow*, vol. 23, Suppl., pp. 1-53 (1997).

Barajas, A. et al., "The effects of contact angle on two-phase flow in capillary tubes," *Int. J. Multiphase Flow*, vol. 19, No. 2, pp. 337-346 (1993).

Henstock, W. et al., "The Interfactial Drag and the Height of the Wall Layer in Annular Flows," *AIChE Journal*, vol. 22, No. 6, pp. 990-999 (Nov. 1976).

Hobbe et al. "Use of Nuclepore Filters for Counting Bacteria by Fluorescence Microscopy," *Appl. and Environ. Microbiol.*, vol. 33, No. 5, pp. 1226-1228 (May 1977).

Klauer, J., "Piping: An examination of pipe self cleaning in high-purity water systems," *Ultrapure Water*, pp. 56-60 (Mar. 2001).

Kogure et al., "A tentative direct microscopic method for counting living marine bacteria," *Can. J. Microbiol.*, vol. 25, pp. 415-420 (1997).

Leypoldt, John K. & Cheung, Alfred K., "Characterization of Molecular Transport in Artificial Kidneys," Artifical Organs, International Socity for Artificial Organs, vol. 20, No. 5, pp. 381-389, Jan. 1996.

Reinemann, D., "Dairy operators guide to milking machine cleaning and sanitation," *Paper written for presnetation at the NRAES the Milking Systems and Parlors Conference*, 8 pages (Jan. 30, 2001).

Riedewald, F., "Biofilms in Pharmaceutical Waters," *Pharmaceutical Engineering*, 8 pages (Nov./Dec. 1997).

Triplett, K. et al., "Gas liquid two-phase flow in microchannels. Part 1: two-phase flow patterns," *International Journal of Multiphase Flow*, vol. 25, pp. 377-380, 387-393 (1999).

Woodmansee, D. et al., "Mechanism for the removal of droplets from a liquid surface by a parallel air flow," *Chemical Engineering Science*, vol. 24, pp. 299-307 (1969).

Web page print-out "510(k) Premarket Notification Database", 8 pages (Jan. 5, 2006).

Agreement between HDC Medical, Inc. and Guillermo J. Cohen Freue, 1 page, Dated Jun. 20, 2001.

Cameron, A., Basic Lubrication Theory, 3rd Edition, pp. 37-51, 93-125, John Wiley & Sons, New York, NY, (1981).

Fuller, D.D., Theory and Practice of Lubrication for Engineers, 2nd Edition, pp. 198-296, John Wiley & Sons, New York, NY, (1984).

Hays, "A Variational Approach to Lubrication Problems and the Solution of the Finite Journal Bearing," J. Basic Eng., 81:13-23 (1959.

Hubbe, "Detachment of Colloidal Hydrous Oxide Spheres From Flat Solids Exposed to Flow 1." Experimental System, Colloids and Surfaces, 16:227-248 (1985).

Hubbe, "Detachment of Colloidal Hydrous Oxide Spheres From Flat Solids Exposed to Flow 2." Mechanism of release, Colloids and Surfaces, 16:249-270 (1985).

Hubbe, "Detachment of Colloidal Hydrous Oxide Spheres From Flat Solids Exposed to Flow 3." Forces of adhesion, Colloids and Surfaces, 25:311-324 (1987).

Hubbe, "Theory of Detachment of Colloidal Particles From Flat Surfaces Exposed to Flow," Colloids and Surfaces, 12:151-178 (1984).

Kabin, et al., "Removal of Solid Organic Films From Rotating Disks Using Emulsion Cleaners," J. of Colloid and Interface Sci., 228:344-358 (2000).

Leal, L.G., Laminar Flow and Convective Transport Processes: Scaling Principles and Asymptotic Analysis, pp. 396-406, Butterworth-Heinemann, Newton, MA, (1992).

Lee, et al., "Motion of a Sphere in the Presence of a Plane Interface. Part 1. An Approximate Solution by Generalization of the Method of Lorentz," J. Fluid Mech., 93:705-726 (1979).

Lee, et al., "Motion of a Sphere in the Presence of a Plane Interface. Part 2. An Exact Solution in Bipolar Co-Ordinates," J. Fluid Mech., 98:193-224 (1980).

Reynolds, "On the Theory of Lubrication and Its Application to Mr. Beauchamp Tower's Experiments, Including Experimental Determination of the Viscosity of Olive Oil," Philosophical Transactions of the Royal Society of London, England, 177:157-234 (1887).

Ryan, et al., "Colloid Mobilization and Transporting Ground Water," Colloids and Surfaces, 107:1-56 (1996).

Truskey, et al., "The Effect of Fluid Shear Stress Upon Cell Adhesion to Fibronectin-Treated Surfaces," J. Biomed. Mater. Res., 24:1333-1353 (1990).

Truskey, et al., "Relationship Between 3T3 Cell Spreading and the Strength of Adhesion on Glass and Silane Surfaces," Biomater, 14(4):243-254 (1993).

Yiantsios, et al., "Detachment of Spherical Microparticles Adhering on Flat Surfaces by Hydrodynamic Forces," J. of Colloid and Interface Sci., 176:74-85 (1995).

Alfa et al., "Worst-case soiling levels for patient-used flexible endoscopes before and after cleaning," AJIC (1999): 392-401.

Schrimm et al., "A new method for validating and verifying the cleaning of tubular instruments," Zentr Steril (1994) 2: 313-324.

Alfa et al., "Automated washing with the reliance endoscope processing system and its equivalence to optimal manual cleaning," AJIC (2006) 34 (9): 561-570.

Ross et al., "Standard test method for foaming properties of surface-active agents: Method D1173-53," Am Soc for Testing Materials, Philadelphia PA 1953: 1-2.

Landau et al., "Fluid Mechanics," Course of Theoretical Physics (1958): Pergamon Press.

Nakagawa et al., "Rivulet meanders on a smooth hydrophobic surface," Int. J. Multiphase Flow (1992) 18 (3): 455-463.

Nakagawa et al., "Stream meanders on a smooth hydrophobic surface," J. Fluid. Mech. (1984) 149: 89-99.

Ghezzehei, T., "Constraints on flow regimes in wide-aperture fractures," Lawrence Berkeley National Laboratory Paper LBNL 54681, 2004.

Le Grand-Piteira et al., "Meandering rivulets on a plane: a simple balance between inertia and capillarity," Laboratoire de Physique et Mecaniqu des Milieux Heterrogenes (2008): 1-5.

Schmuki et al., "On the stability of rivulet flow," J. Fluid. Mech. (1990) 210: 125-143.

Taylor G.I., "Non-interacting colloidal particles in an external field," Colloidal Hydrodynamics (1934) 146: 189-186.

Gomez-Suarez et al., "Analysis of bacterial detachment from substratum surfaces by the passage of air-liquid interfaces," Applied and Enviro. Mircobiology (2001) 67 (6): 2531-2537.

Gilles de Gennes, P., Capillarity and wetting phenomena, Springer (2003).

European Office Action for EP Application No. 09 793 139.8 dated Feb. 17, 2012.

* cited by examiner

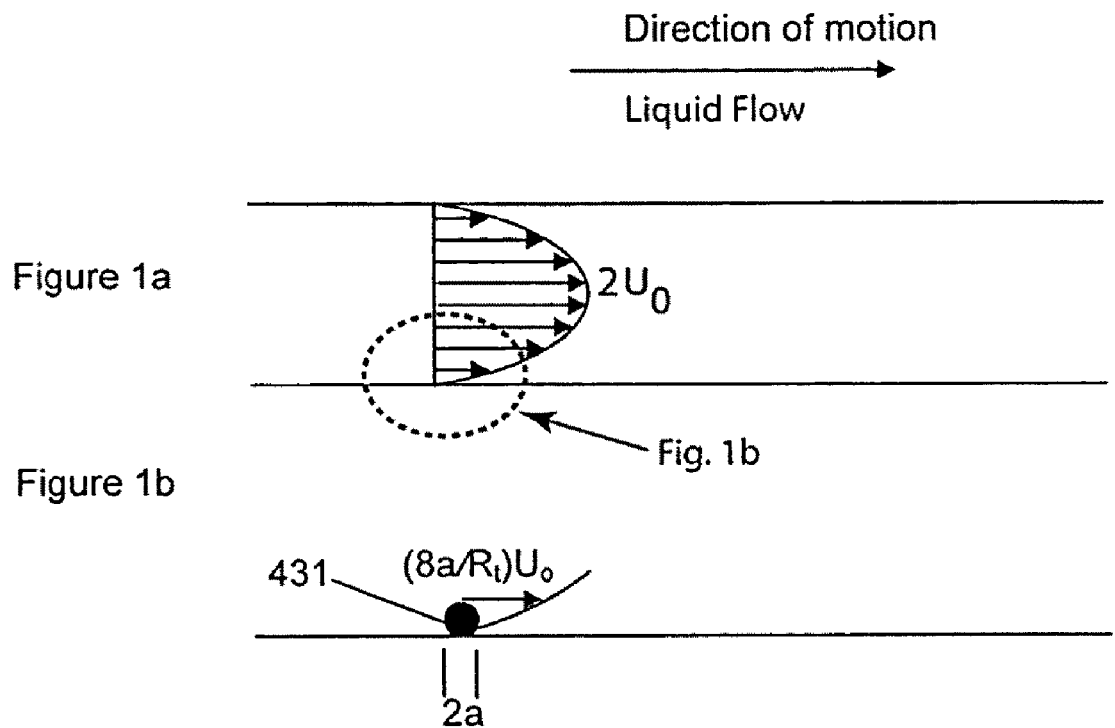
Figure 1a
Figure 1b
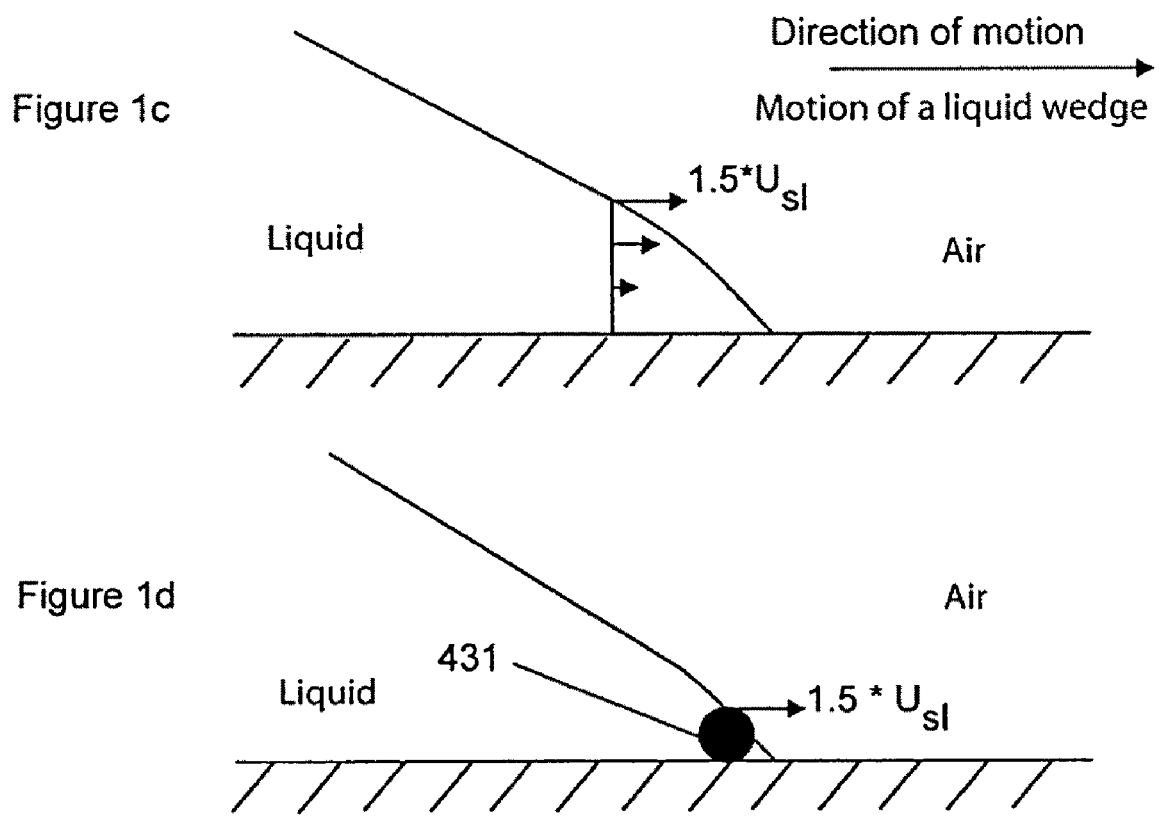
Figure 1c
Figure 1d t=0 t₁

Direction of flow

Prior Art

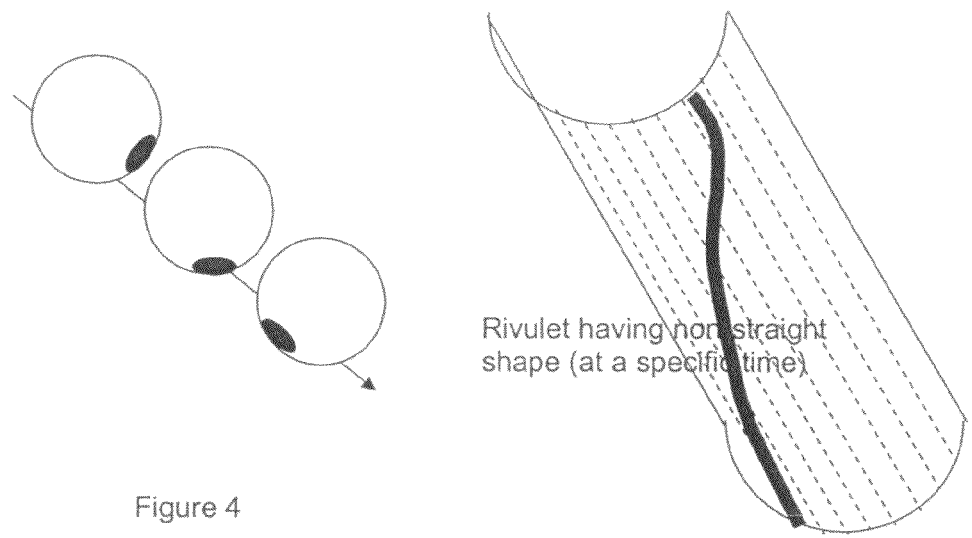
Figure 4
\*\*\*Similar updating of the following illustration at three different times\*\*\*
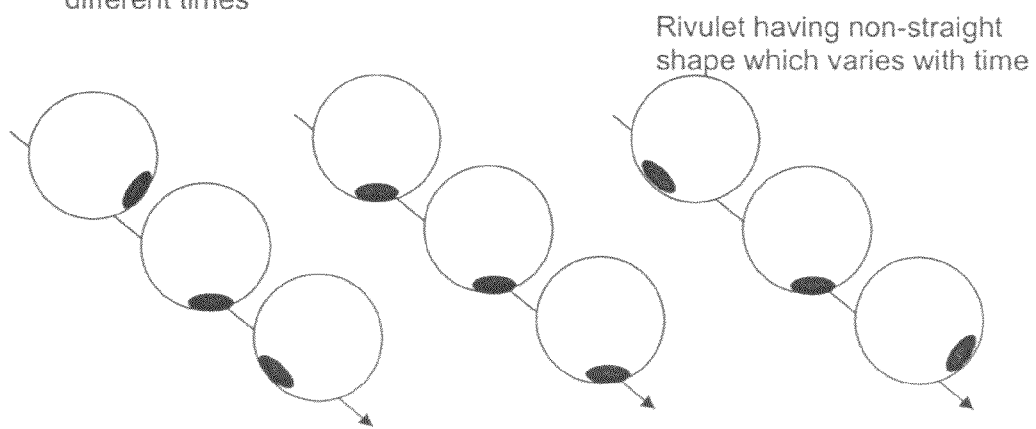

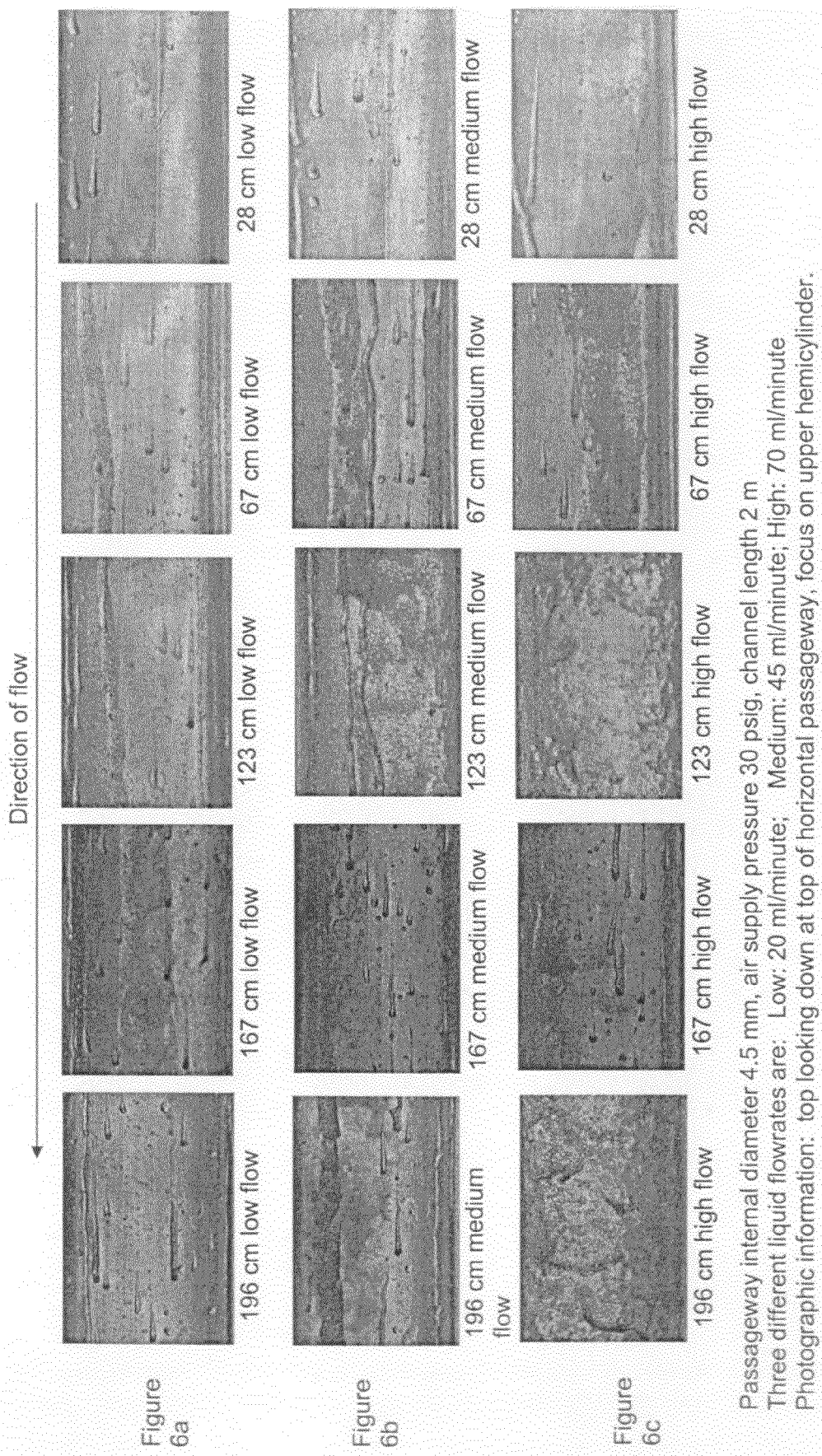

F = Foam
R = Rivulet Droplet Flow
S = Single Rivulet – No Meandering
Y = Single Rivulet with Meandering F = Foam
R = Rivulet Droplet Flow
S = Single Rivulet – No Meandering
Y = Single Rivulet with Meandering Small inside diameter passageway Inlet dynamic conditions Larger inside diameter passageway Static conditions Even larger inside diameter passageway Dynamic conditions Breaking up further along path

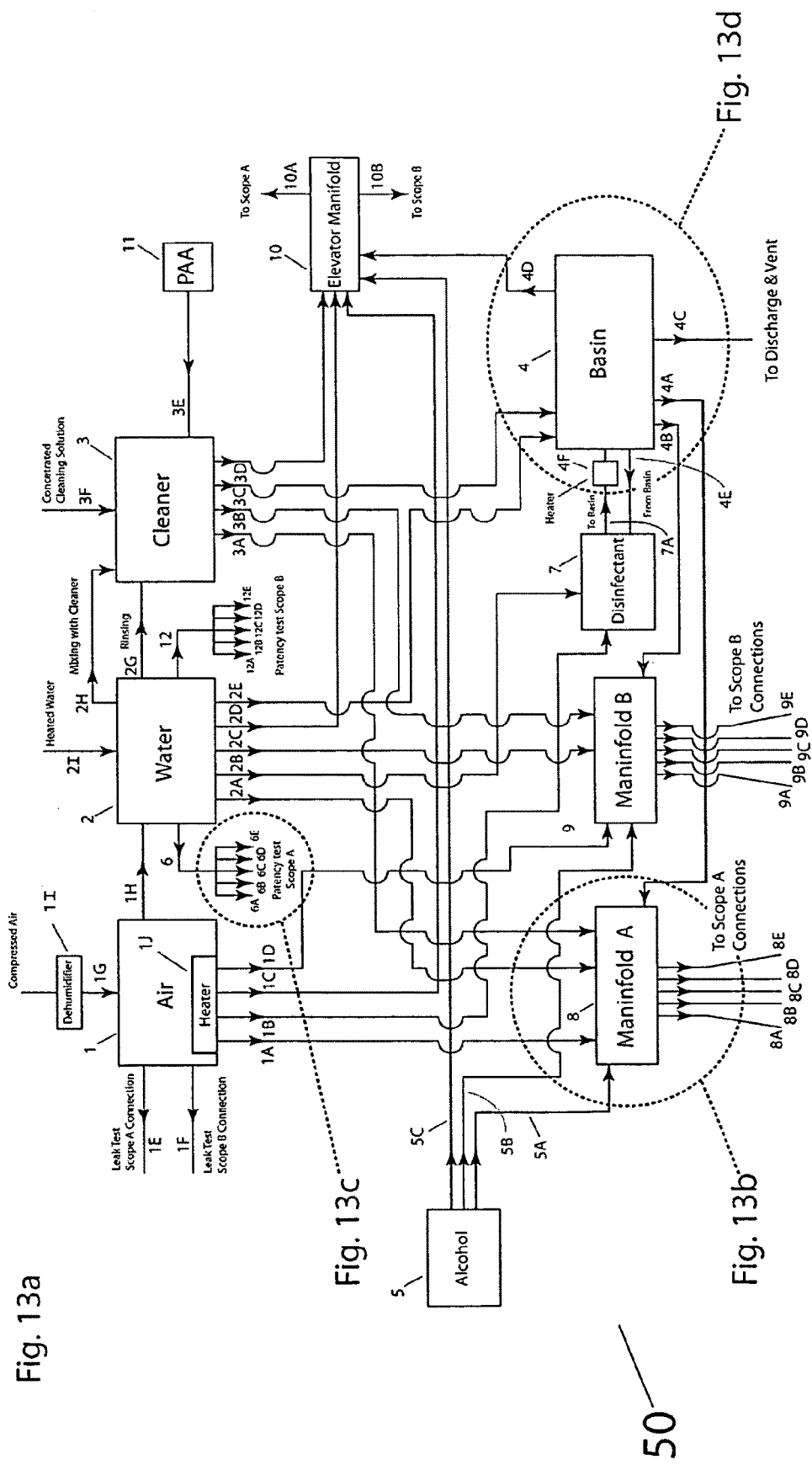

Patency Testing Scope A

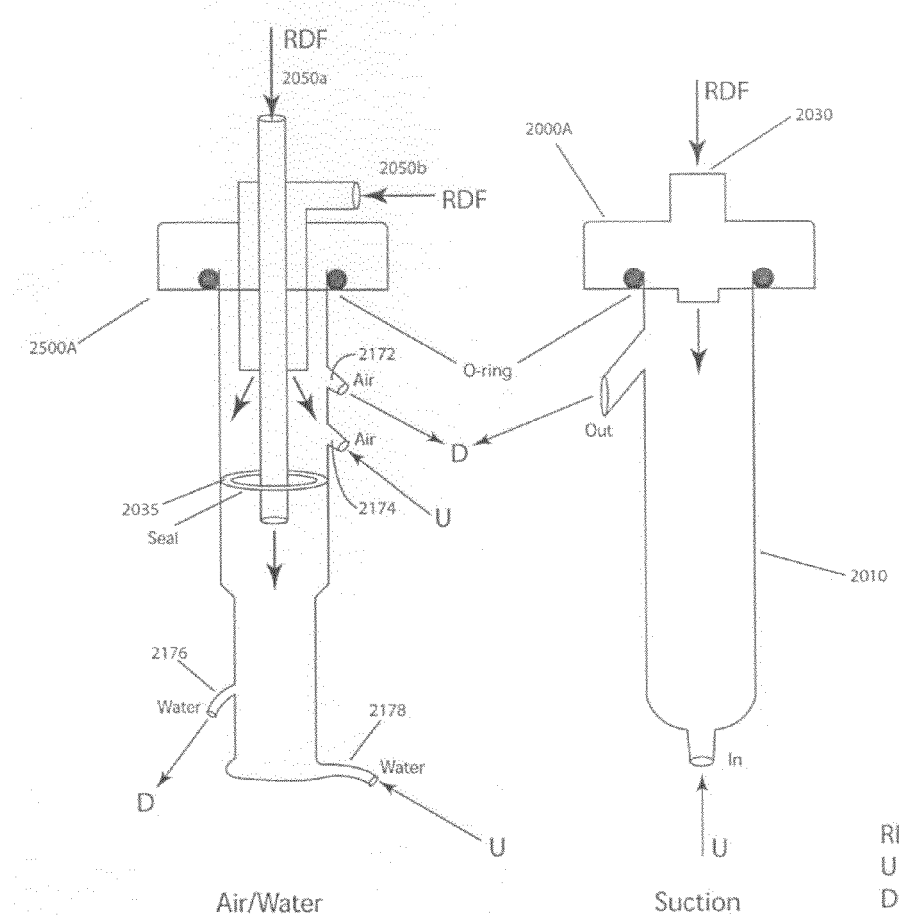

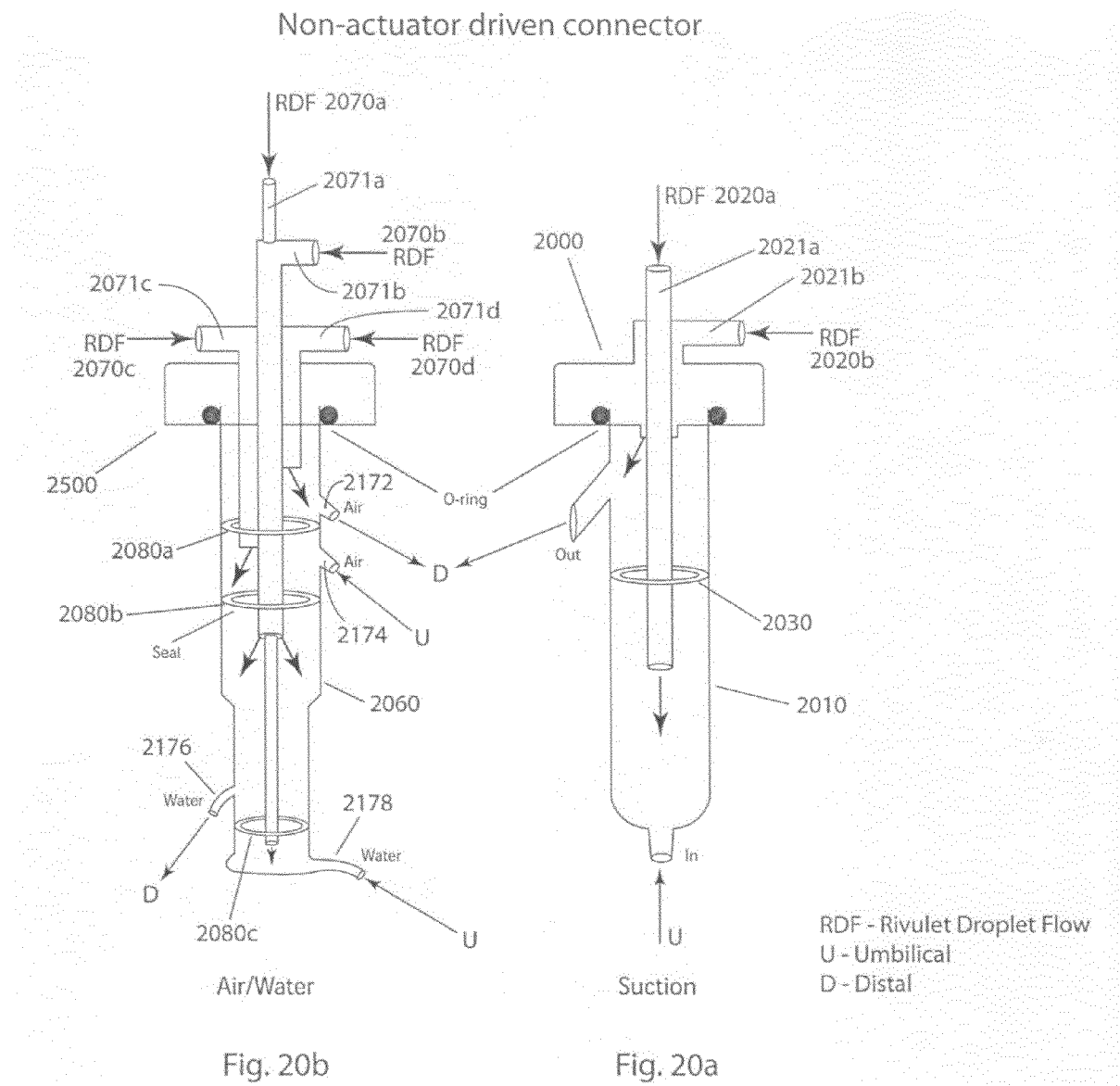

BEFORE  AFTER

BEFORE  AFTER

METHOD FOR CLEANING PASSAGEWAYS SUCH AN ENDOSCOPE CHANNELS USING FLOW OF LIQUID AND GAS

CROSS-REFERENCE TO RELATED APPLICATIONS

This application is related to U.S. patent application Ser. No. 12/286,749 that was filed with the United States Patent and Trademark Office on Sep. 30, 2008, the entire disclosure of which is incorporated herein by reference.

FIELD OF THE INVENTION

Embodiments of the invention pertain to the cleaning of passageways such as in medical instruments such as endoscopes.

BACKGROUND OF THE INVENTION

Medical instruments such as endoscopes and other luminal devices, having long narrow passageways, generally have to be cleaned between uses. Current cleaning methods for cleaning the interiors of long narrow passageways include single-phase liquid flow followed by single-phase gas flow, with the single-phase gas flow mostly used for drying. Use of mixed-phase flow has been disclosed in patent such as U.S. Pat. Nos. 6,027,572 and 6,857,436 and 6,454,871 all to Labib, in a flow regime such that gas-driven droplets of liquid strike contaminants and dislodge them. However, in some situations as in flexible endoscopes, there are pressure limitations which make it impossible or unlikely for gas-driven droplets to form or if formed, their concentration is very low and their velocity is too small to attain sufficient momentum to dislodge contaminants by impact of droplets. A different regime of cleaning has been disclosed in U.S. Pat. No. 4,781,764 to Leenaars, which has used surface tension forces at a moving interface between solid and liquid and gas to remove contaminants from an externally-facing surface of a flat plate. Leenaars' contaminants were inorganic, not biologically adhered, and the motion needed to effect cleaning was relatively slow. U.S. Pat. No. 5,279,799 to Moser discloses limited use of liquid and gas flow separately in cleaning endoscopes. There is industrial literature of two-phase liquid and gas flow but usually involving a wall which remains wet during the two-phase flow. In these respects and also in other respects, there remains room for improvement in both results and ease of performing cleaning.

SUMMARY OF THE INVENTION

In an embodiment of the invention, there is provided an apparatus capable of supplying to an internal passageway a flow of liquid and gas such that the liquid flowrate and the gas flowrate have a desired relationship with each other. The relationship may be appropriate to produce a desired flow regime such as rivulet droplet flow on the internal surface in at least some of the passageway. The relationship may be specific to a particular inside diameter and length of the passageway. Embodiments of the invention may be capable of providing liquid flow and gas flow at appropriate parameter values suitable to achieve meandering rivulet flow or fragmenting rivulet flow or both in at least some portions of a length of a passageway. In an embodiment of the invention, there may be provided apparatus appropriate to deliver a perimeter-normalized liquid flowrate of between 1 and 5 milliliters per minute per millimeter of perimeter of the passageway.

In an embodiment of the invention, there may be provided a cleaning liquid that creates high advancing contact angle of 50 degrees or higher and receding contact angle of more than 0 degree to allow the formation of the rivulets and of the rivulet droplet flow as described herein. In embodiments of the invention, there may be provided surfactants and other ingredients in the cleaning liquid such that three phase contact line can be formed during the liquid droplet flow to create detachment forces for the purpose of cleaning the surface of the passageway.

In an embodiment of the invention, there may be provided apparatus capable of causing motion of three phase contact interfaces along internal surfaces of a passageway suitably to clean the surfaces. In embodiments of the invention, there may be provided apparatus such that individual patches of surface of the internal surface of the passageway are sometimes wetted by moving liquid entities and in between such wettings, those same surfaces de-wet or become dry.

In an embodiment of the invention, there may be provided an apparatus capable of supplying to an internal passageway a flow of liquid and gas such that the liquid flowrate has a desired variation as a function of time. The variation as a function of time may be appropriate to produce a desired cleaning action.

In an embodiment of the invention, the apparatus may be capable of supplying liquid flow and gas flow to a passageway to be cleaned, such that the liquid flowrate and the gas flowrate are both substantially constant, and the apparatus may also be capable of supplying liquid flow and gas flow such that at least one of the liquid flowrate and the gas flowrate has a desired variation as a function of time.

Embodiments of the invention may be capable of providing liquid flowrates and gas flowrates to specific passageways or channels such that the magnitudes of the flowrates are unique to the specific passageway or channel or direction of flow. Embodiments of the invention may be capable of providing liquid flowrates and gas flowrates to specific passageways or channels such that the chronologies of the flowrates are unique to the specific passageway or channel or direction of flow.

Embodiments of the invention may be capable of providing a specific operating condition conducive to cleaning a first specific portion of a length of a passageway, and a second different operating condition conducive to cleaning a second specific portion of the length of the passageway.

Embodiments of the invention may be capable of providing liquid flow and gas flow at appropriate parameter values for an appropriate duration of time so as to achieve a desired Treatment Number.

Embodiments of the invention may be capable of providing time-varying gas flow such that periods of reduced gas flow in one channel occur during periods relatively large flow in another channel. In embodiments of the invention, pulsations of gas flowrate in respective channels may be coordinated such that periods of reduced gas flow in one channel occur during periods relatively large flow in another channel.

In an embodiment of the invention, the apparatus may be capable of performing rinsing using rivulet droplet flow.

In an embodiment of the invention, there may be provided an apparatus which measured flowrate of gas delivered, and sets the liquid flowrate responsive to the measured gas flowrate.

In embodiments of the invention, liquid and gas flow may be delivered to a cylinder well such that the liquid and gas distribute themselves among more than one channel or channel direction in proportions which closely resemble the proportion delivered to the cylinder well. In embodiments of the invention, there may be provided an introduction region in which gas flow and liquid flow have already come together upstream of the actual endoscope channel being cleaned.

In embodiments of the invention, liquid and gas flow for cleaning can be delivered to cylinder wells in the control handle of an endoscope. In embodiments of the invention, liquid and gas flow can be delivered either to the umbilical end of the endoscope or to cylinder wells in the control handle of the endoscope, and flow in the control handle section of the endoscope can be in either direction or any combination of directions for various channels. Embodiments of the invention can include appropriate valving to accomplish such flow directions. In an embodiment of the invention, there may be provided an apparatus which for certain time periods allows the flow of liquid and gas in both channel directions from a supply connection, and at other time periods allows the flow of liquid and gas only in one channel direction from a supply connection.

An embodiment of the invention may be capable of providing liquid and air to clean a passageway, wherein the air has been dehumidified, or heated, or both, with respect to ambient air that has been taken in.

Embodiments of the invention may include connectors for connecting to cylinder wells, such that the connector contains an actuator to direct which of various channels or channel directions receive flow. Embodiments of the invention include connectors for connecting to cylinder wells, such that dedicated flowpaths connect to specific channels or channel directions.

An embodiment of the invention comprises an external washing system including an eductor having an air intake so as to direct a flow of bubble-containing liquid at external surfaces of an endoscope.

Embodiments of the invention may use specific surfactants or types of surfactants or combinations of surfactants during cleaning with simultaneous liquid flow and gas flow such as rivulet droplet flow.

Embodiments of the invention comprise methods involving the use of any of the described apparatus.

BRIEF DESCRIPTION OF THE ILLUSTRATIONS

Embodiments of the invention are further described in the following illustrations.

FIG. 1a is an illustration of velocity profiles in a viscous liquid flow that fills an entire passageway. FIG. 1b illustrates local velocities of such a viscous flow in the vicinity of a contaminant particle attached to the wall. FIG. 1c illustrates, in connection with viscous forces from a sliding liquid entity, velocity components associated with the sliding liquid entity. FIG. 1d illustrates the sliding liquid entity encountering a contaminant particle.

FIG. 2a is an illustration of a sliding liquid entity on a solid surface, surrounded by gas and thereby creating three-phase contact interface. FIG. 2b is a cross-section of FIG. 2a illustrating definitions of contact angles. FIG. 2c illustrates, in connection with surface tension forces, a liquid entity approaching a contaminant particle. FIG. 2d illustrates, in connection with surface tension related forces, a liquid entity beginning to encounter a contaminant particle. FIGS. 2e and 2f illustrate force diagrams for surface tension related forces exerted by a liquid entity upon a contaminant particle.

FIG. 4 is an illustration of possible rivulet behavior on an internal surface of a cylindrical passageway.

Figure 5A:
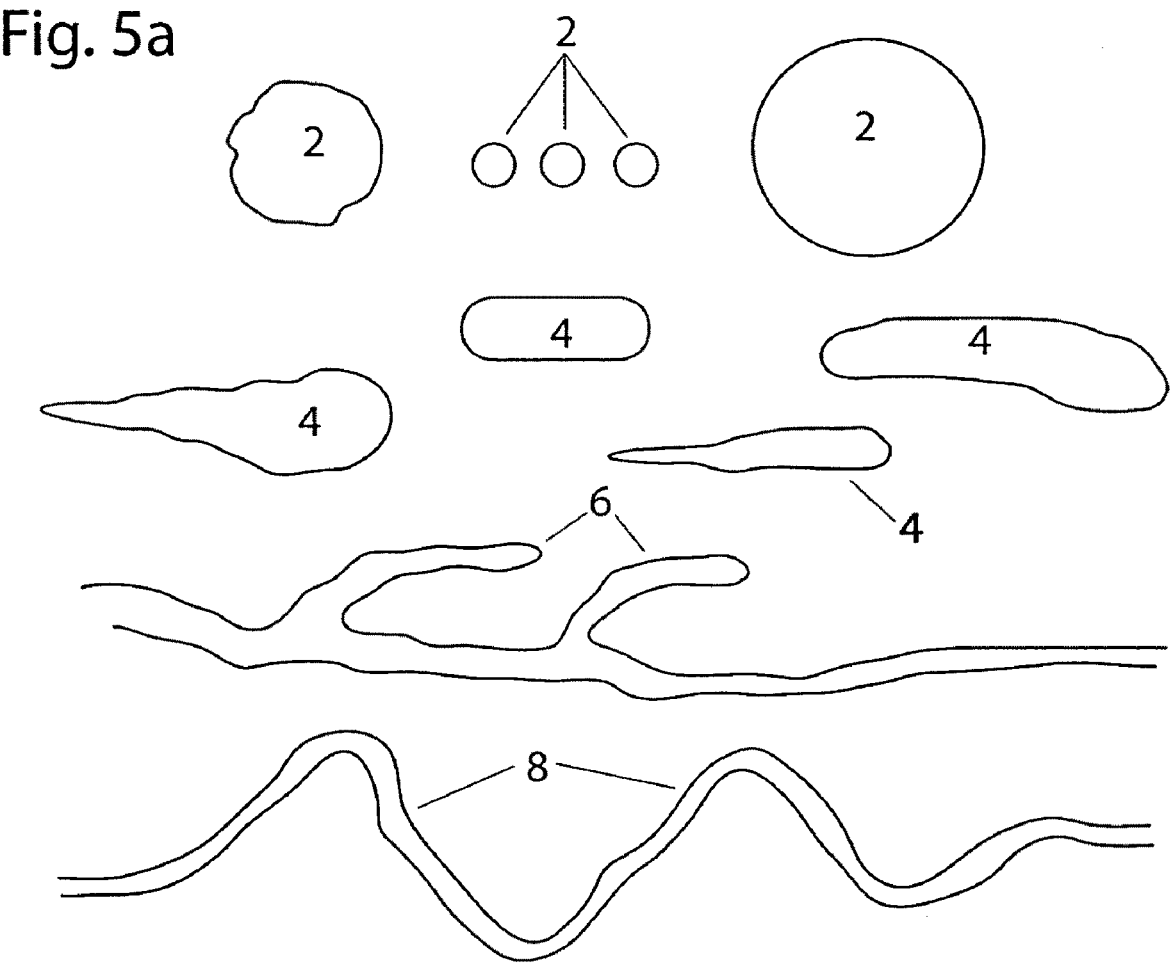
Figure 5B:
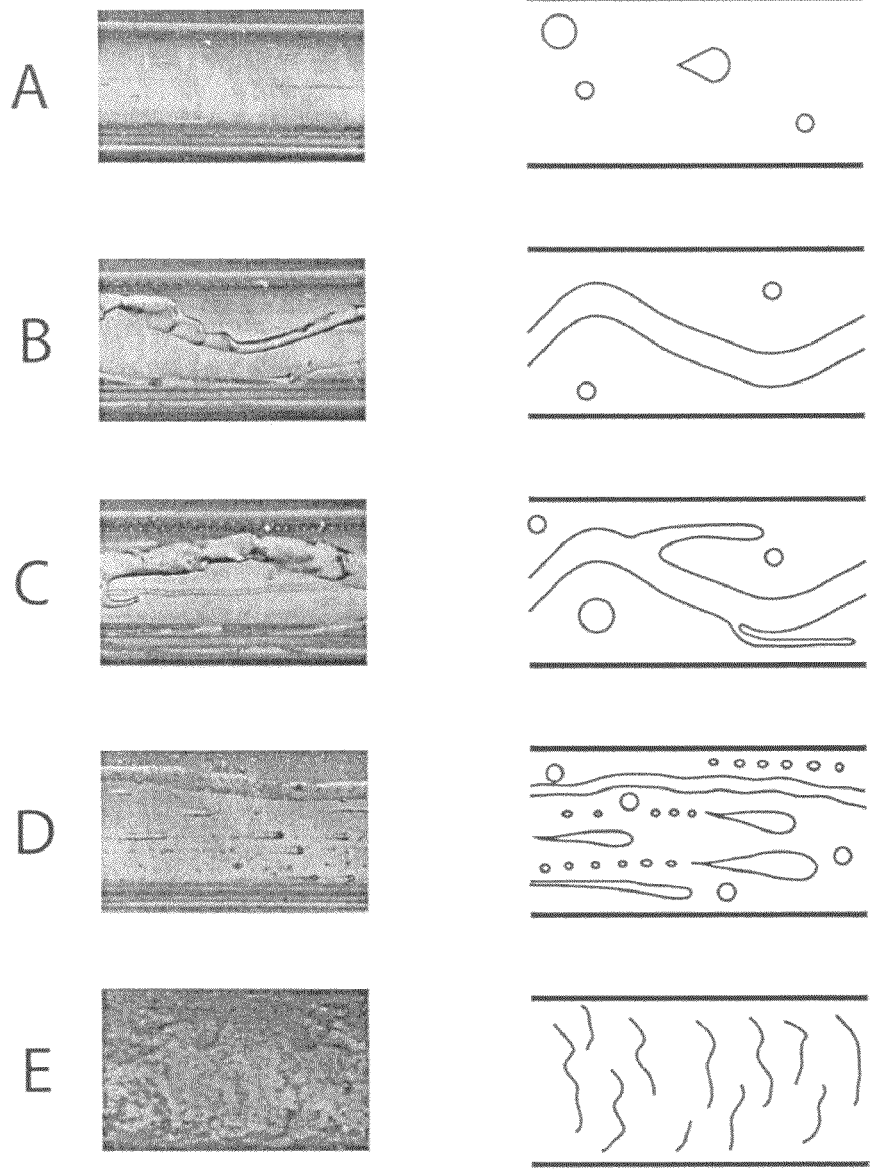
Figure 5C:
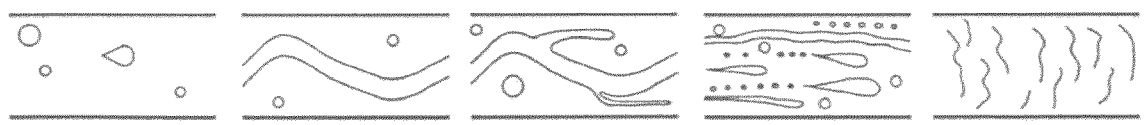

FIG. 5a is a schematic illustration of possible appearance of various forms of sliding liquid entities in a passageway. FIG. 5b schematically illustrates liquid entities as a function of amount of liquid flowrate. FIG. 5c schematically illustrates liquid entities as a function of position along a passageway.

FIG. 6a is a collection of actual photographs illustrating fluid conditions at five positions along the length of a passageway. These are for a liquid flowrate which is considered to be less than optimum to achieve cleaning using moving three-phase contact. FIG. 6b is a similar collection of five photographs. These are for a liquid flowrate which is considered to be appropriate for achieving cleaning by the described mechanism. FIG. 6c is a similar collection of five photographs. These are for a liquid flowrate which is considered to be larger than optimum for achieving cleaning by the described mechanism.

Figure 7A:
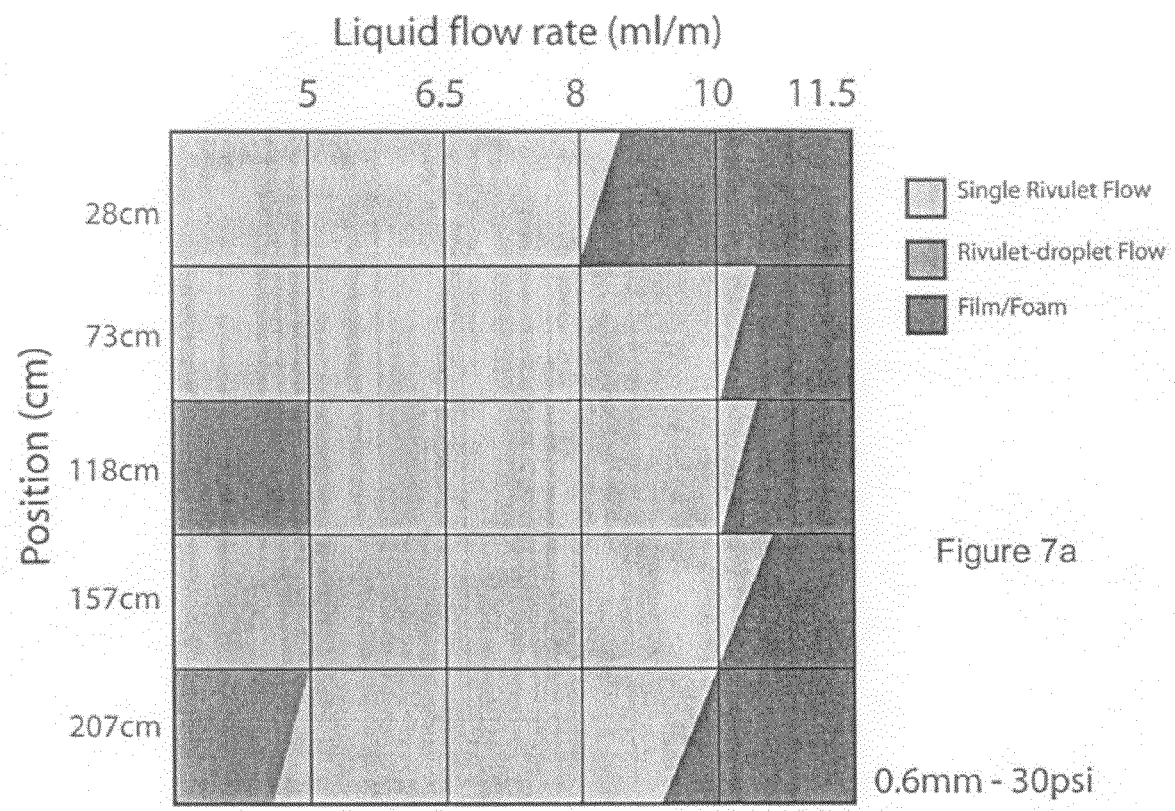
Figure 7B:
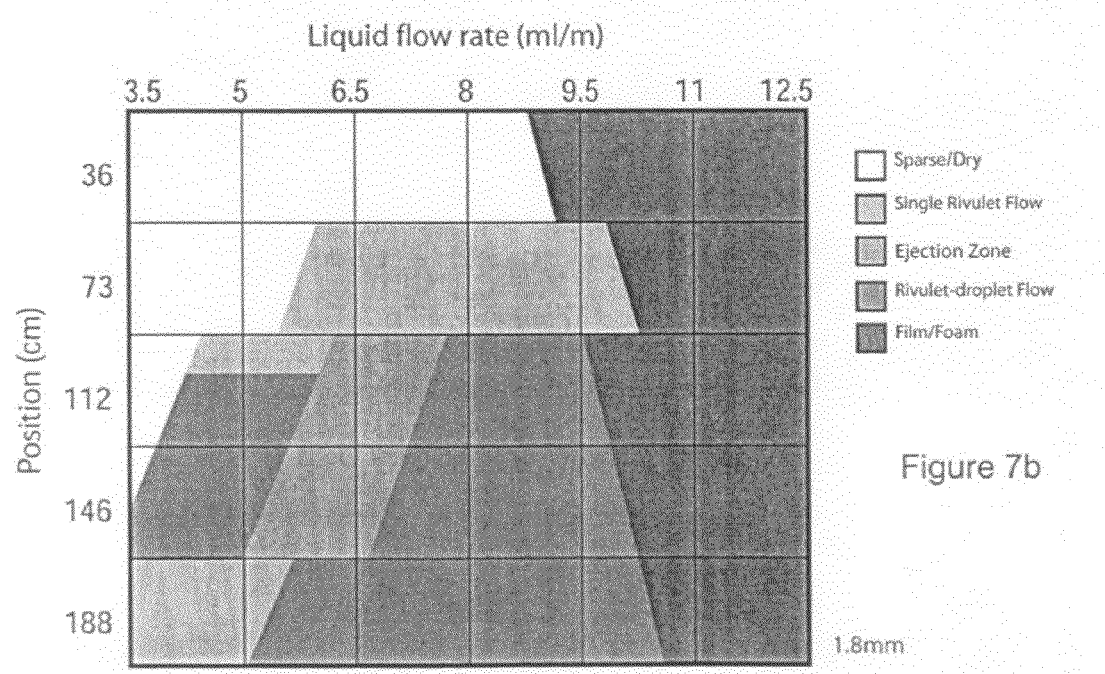
Figure 7C:
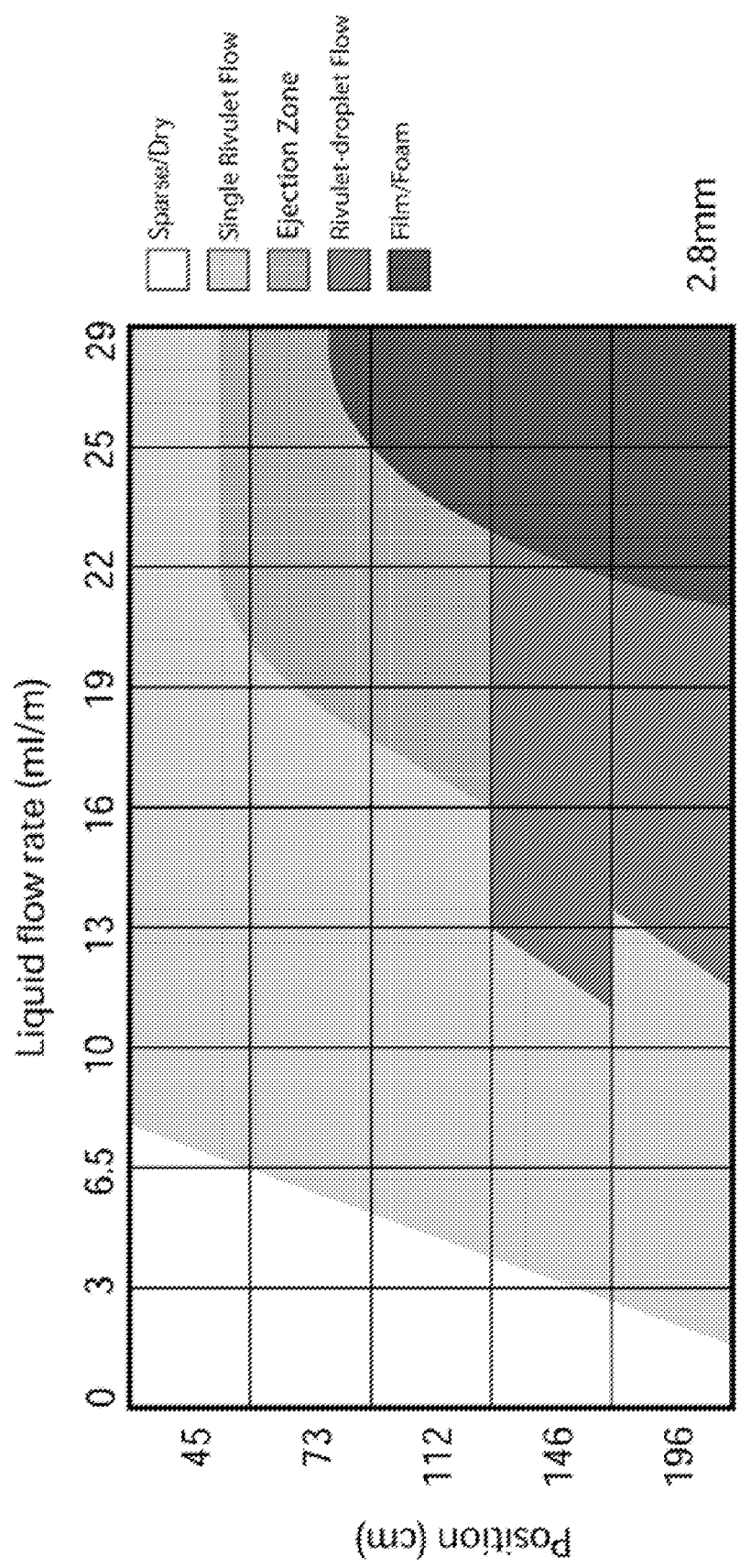
Figure 7D:
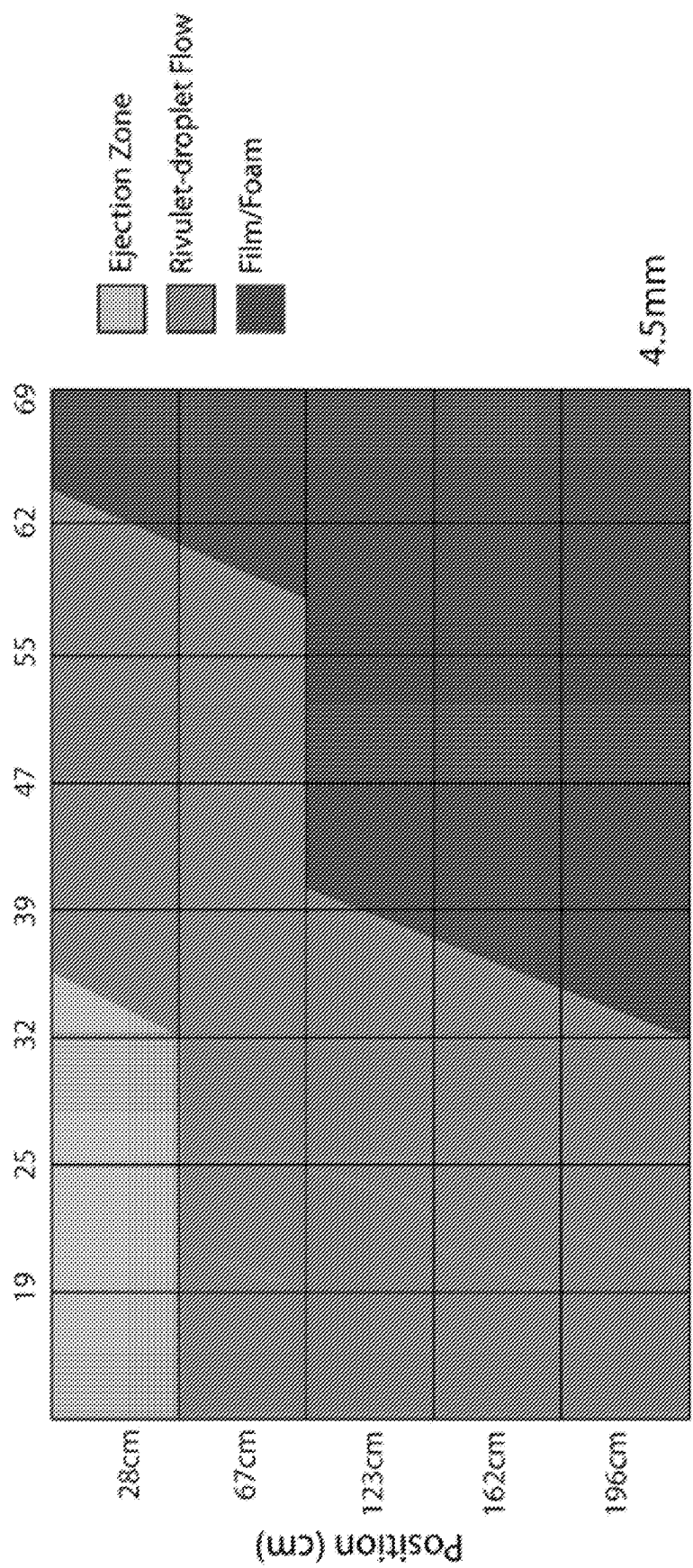
Figure 7E:
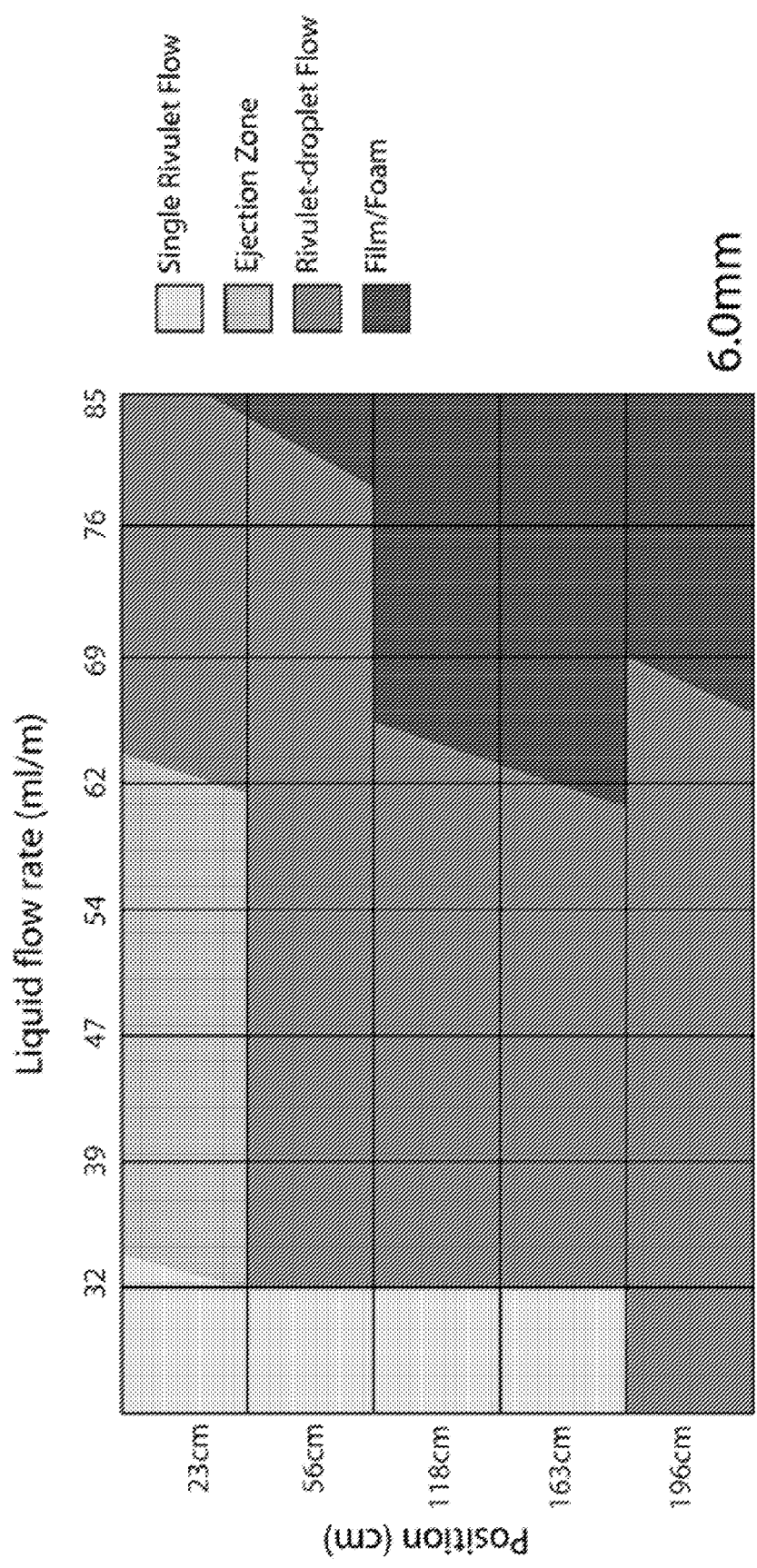

FIG. 7a is a map of fluid flow conditions as a function of position along the length of a passageway, and as a function of liquid flowrate. This is for a passageway having an inside diameter of 0.6 mm. FIG. 7b is a similar map for a passageway having an inside diameter of 1.8 mm. FIG. 7c is a similar map for a passageway having an inside diameter of 2.8 mm. FIG. 7d is a similar map for a passageway having an inside diameter of 4.5 mm. FIG. 7e is a similar map for a passageway having an inside diameter of 6.0 mm.

Figure 8:
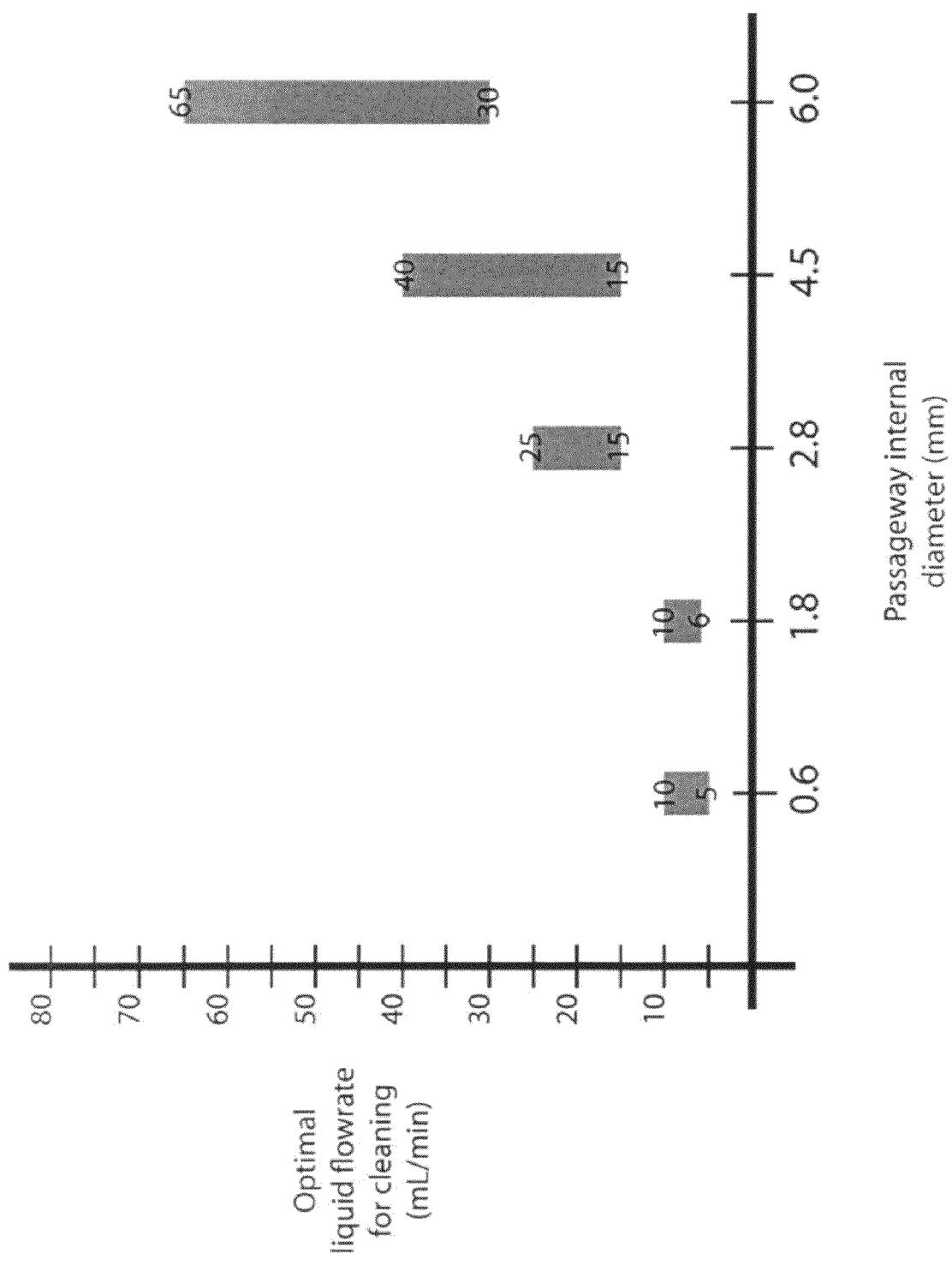

FIG. 8 is a compilation of information from FIGS. 7a-e, further illustrating optimum liquid flowrate for various passageway inside diameters.

Figure 9A:
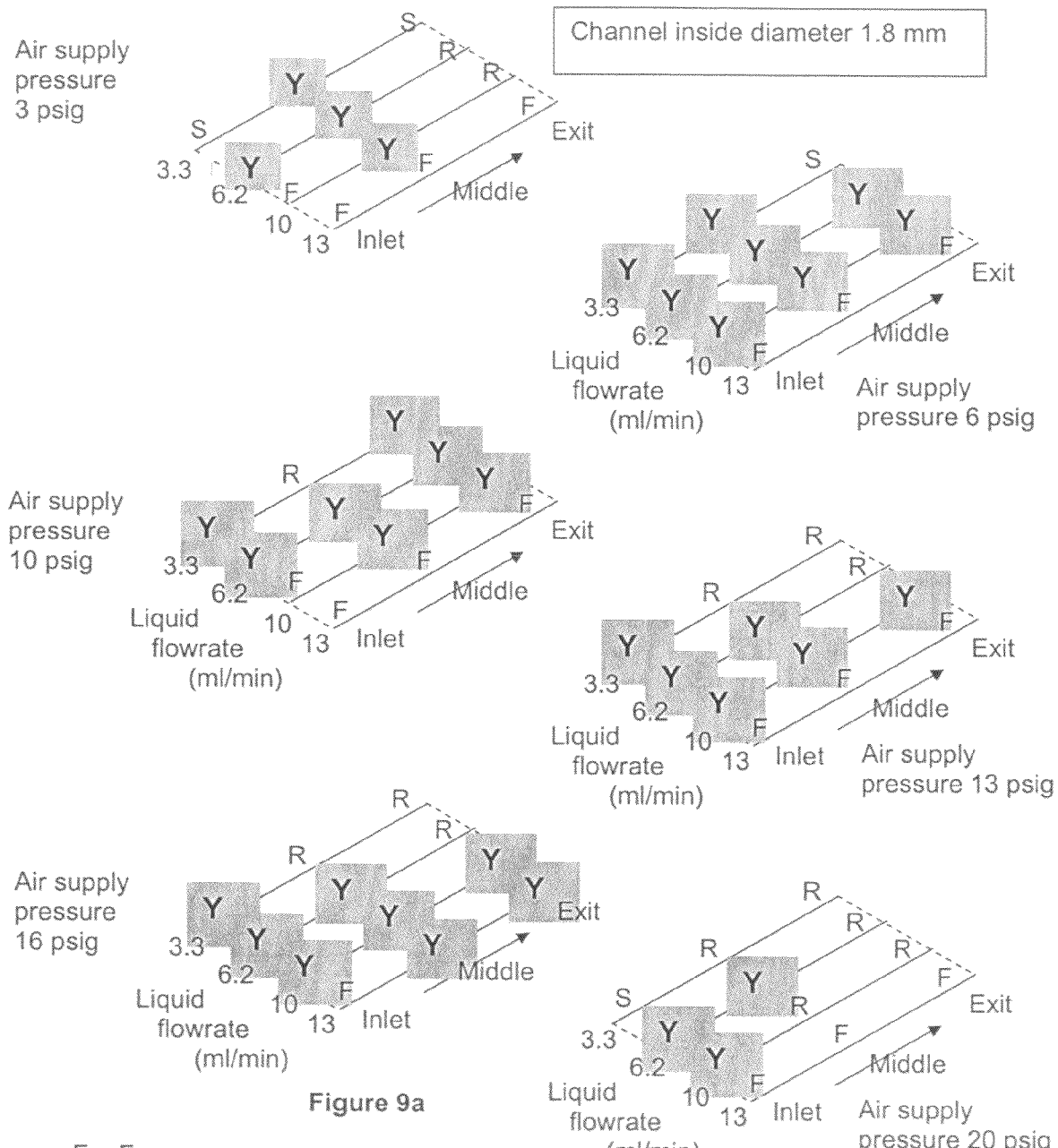
Figure 9B:
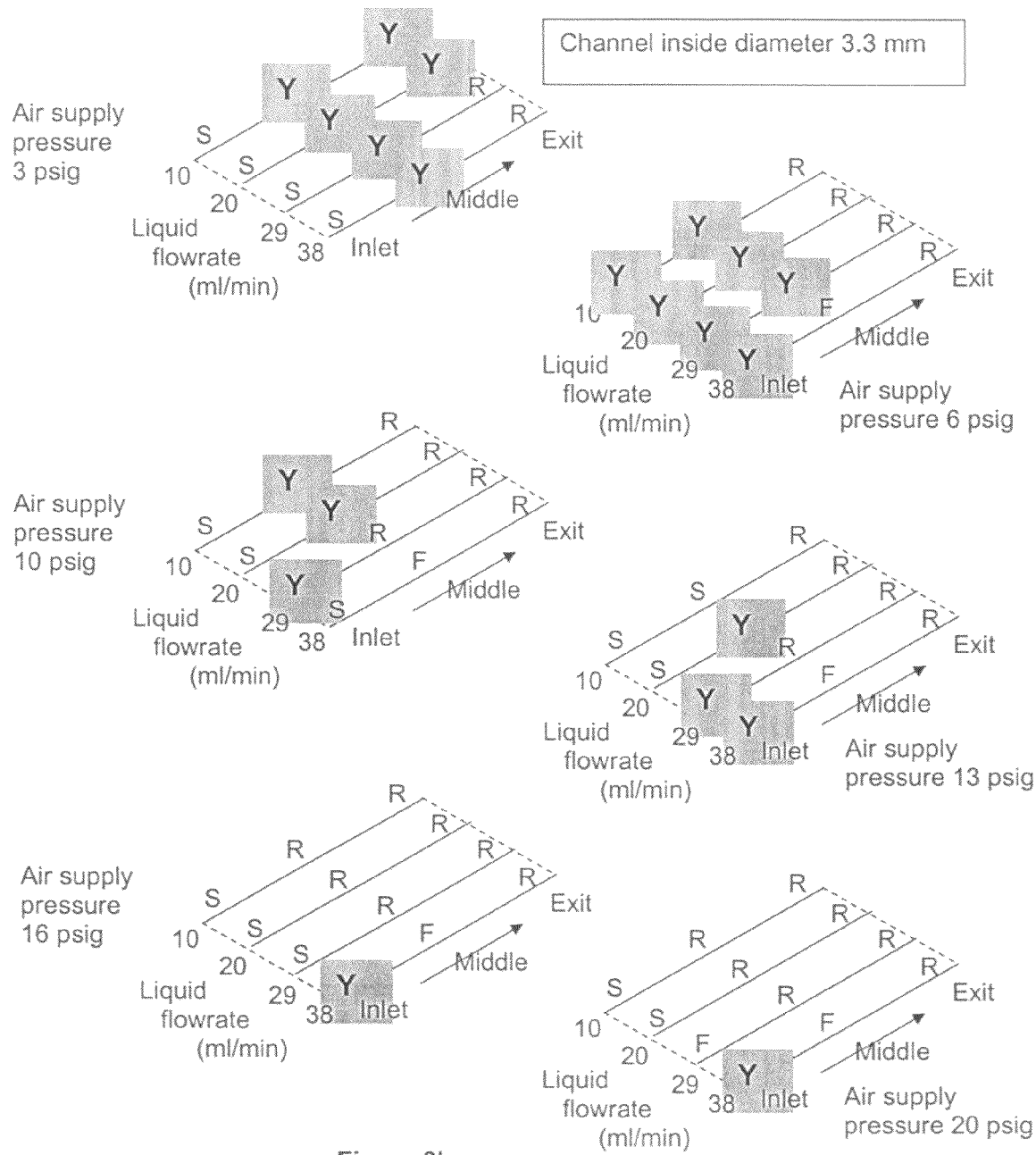

FIGS. 9a and 9b are illustrations of where conditions suitable for cleaning do or do not occur under various operating conditions.

Figure 10A:
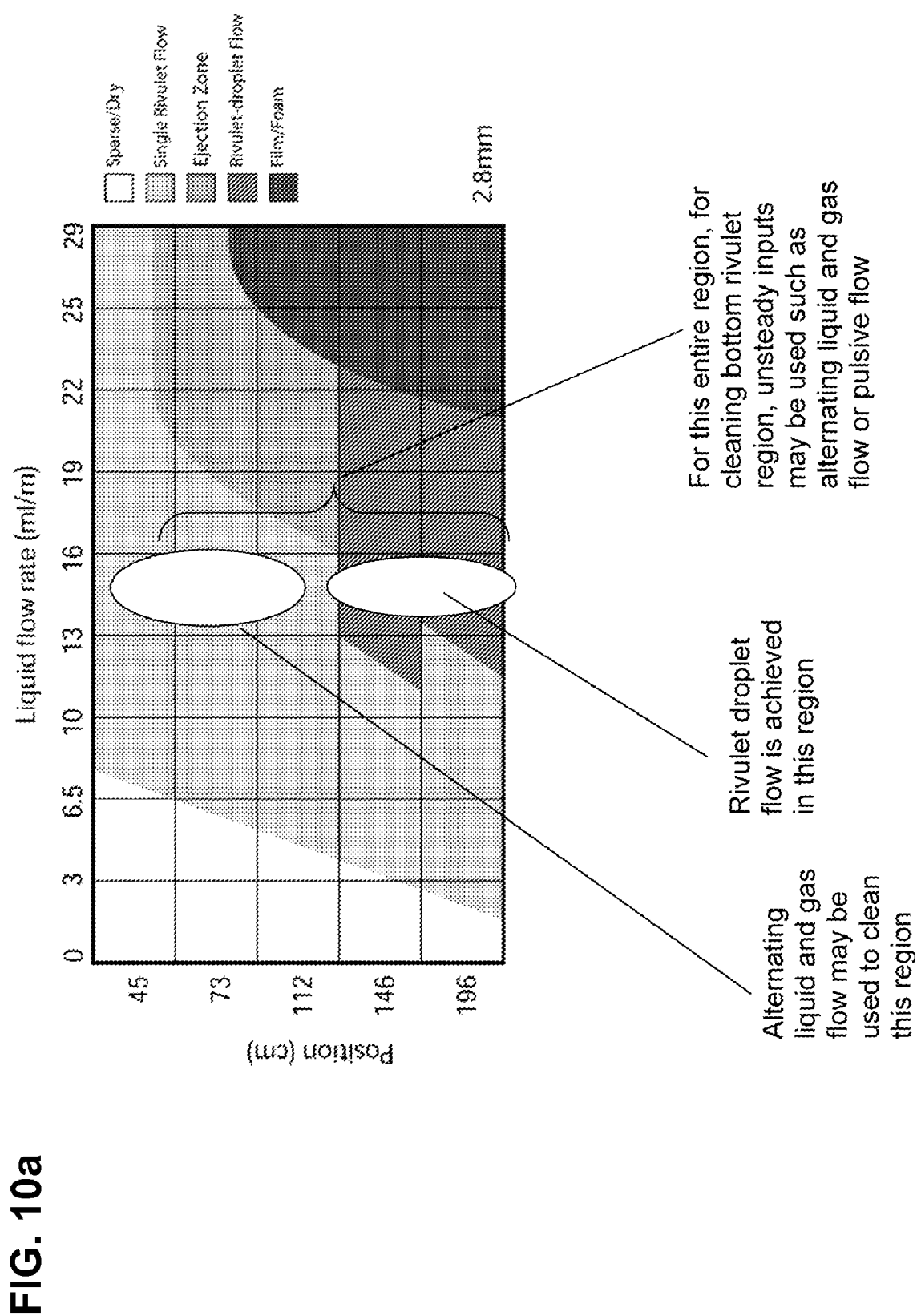
Figure 10B:
Figure 10C:
Figure 10D:
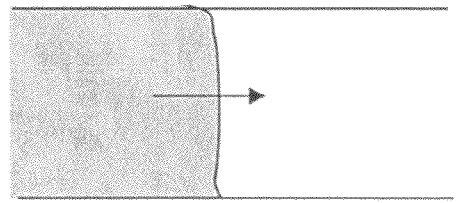
Figure 10E:
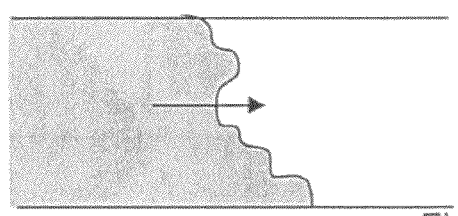

FIG. 10a illustrates on one of the flow maps where cleaning with steady-state inputs is possible and where cleaning with unsteady inputs may be desirable. FIG. 10b through FIG. 10e are schematic illustrations of various possible conditions regarding whether an entire cross-section of a passageway is or is not entirely wetted. FIG. 10b shows a relatively small inside diameter passageway which is naturally filled with a meniscus. FIG. 10c shows a somewhat larger inside diameter passageway which does not support a meniscus across its cross-section. FIG. 10d shows a relatively large inside diameter passageway whose cross-section can be filled with liquid on a dynamic basis. FIG. 10e shows the same passageway further along during passage of a plug, with the leading surface of the plug becoming irregular.

Figure 11:
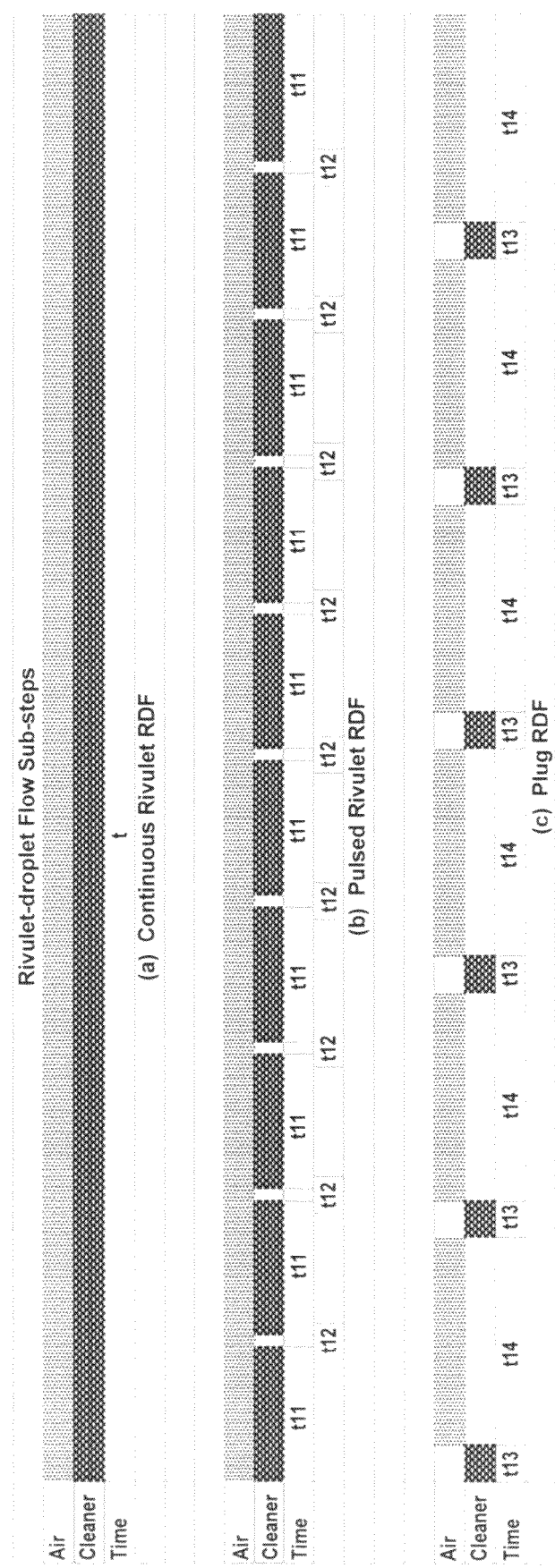

FIG. 11 is a timeline illustrating sequences of events related to creating passage of three-phase contact by a transient mechanism which is not exactly meandering rivulets.

Figure 12:
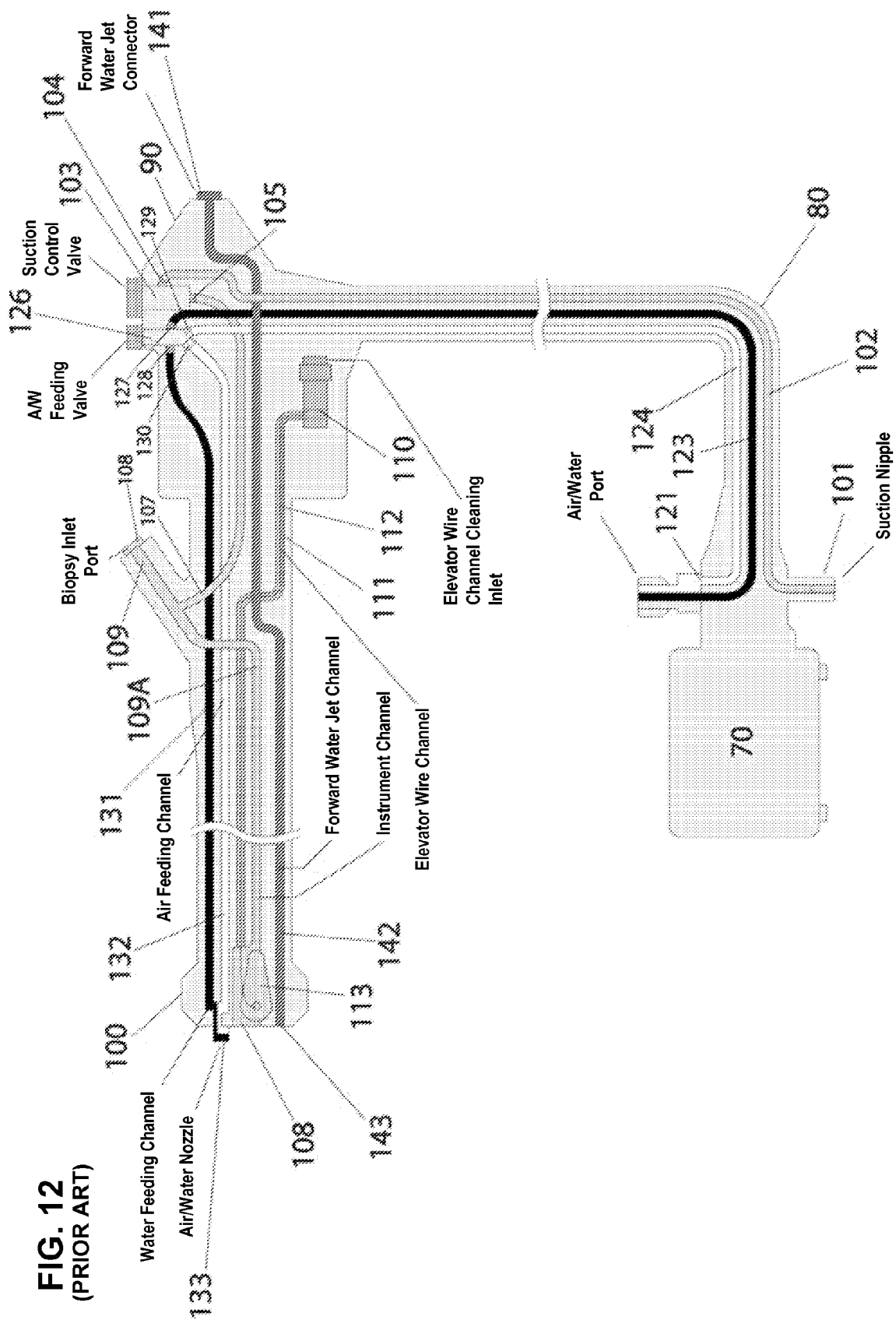

FIG. 12 is a schematic illustration of overall features of a typical endoscope.

Figure 13B:
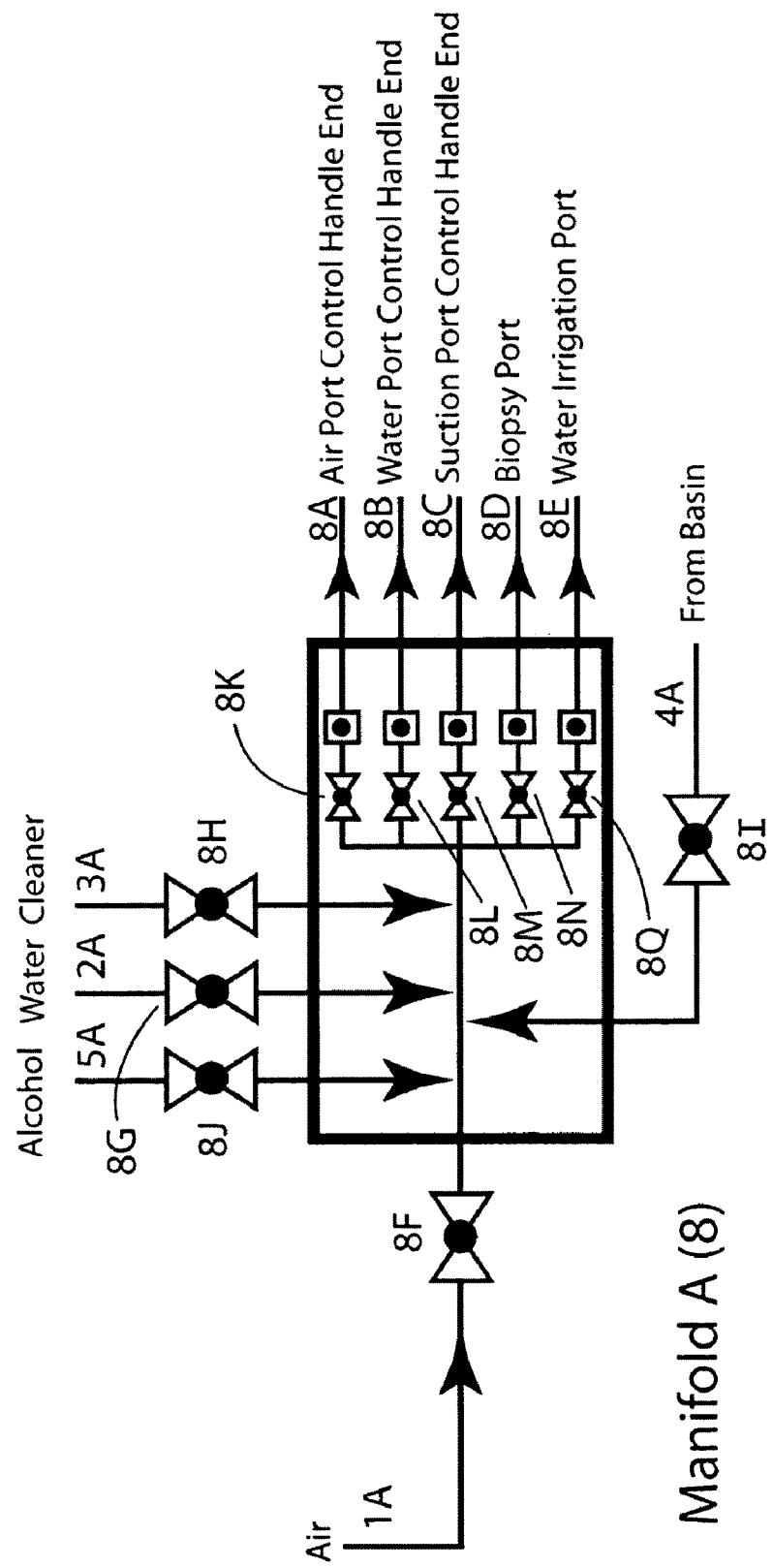
Figure 13C:
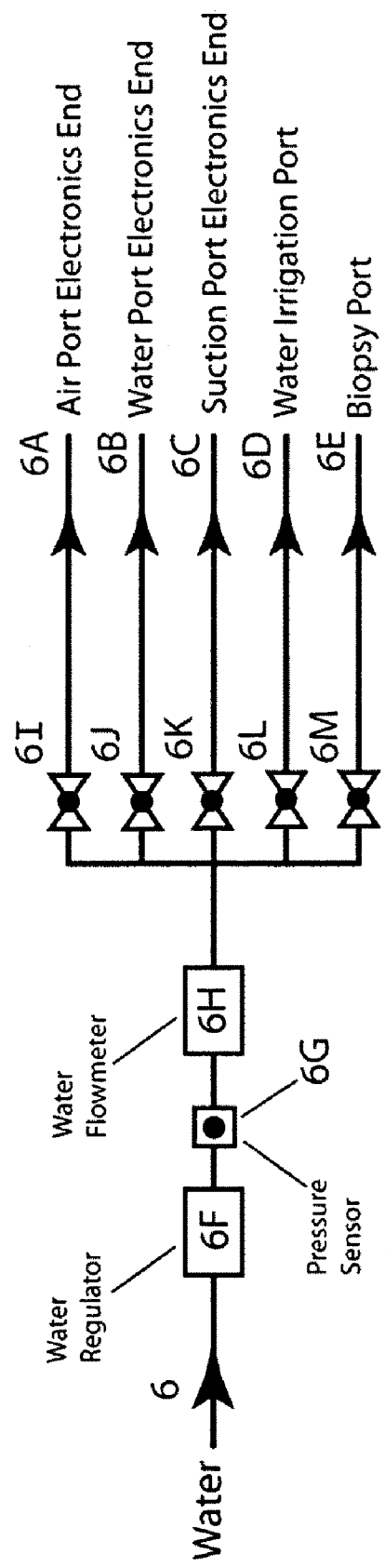
Figure 13D:
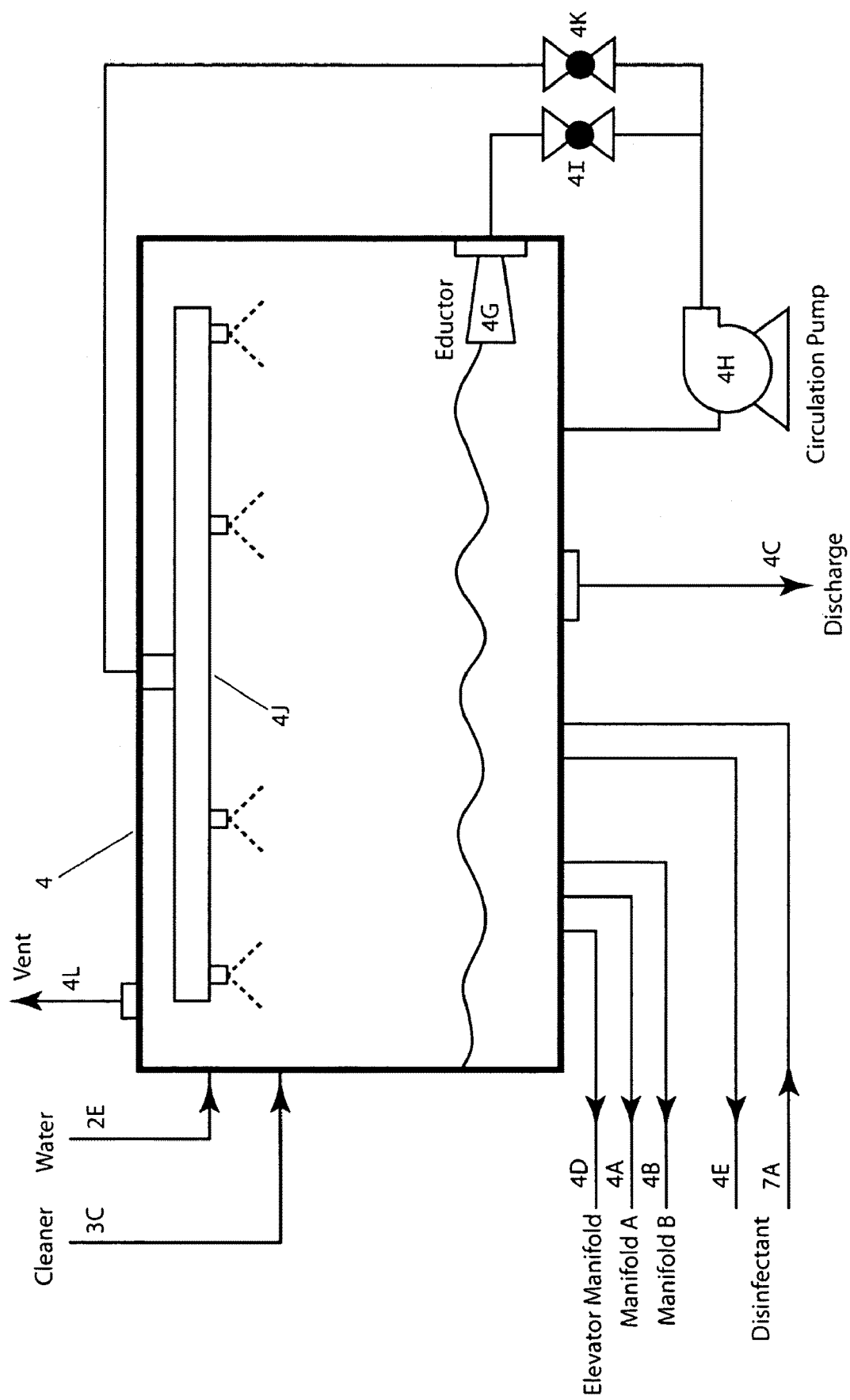

FIG. 13a is an overall schematic system diagram of an endoscope reprocessing apparatus. FIG. 13b shows detail around a manifold for performing cleaning. FIG. 13c shows detail related to a patency test. FIG. 13d shows detail related to the basin for cleaning or disinfecting external surfaces of an endoscope.

Figure 14:
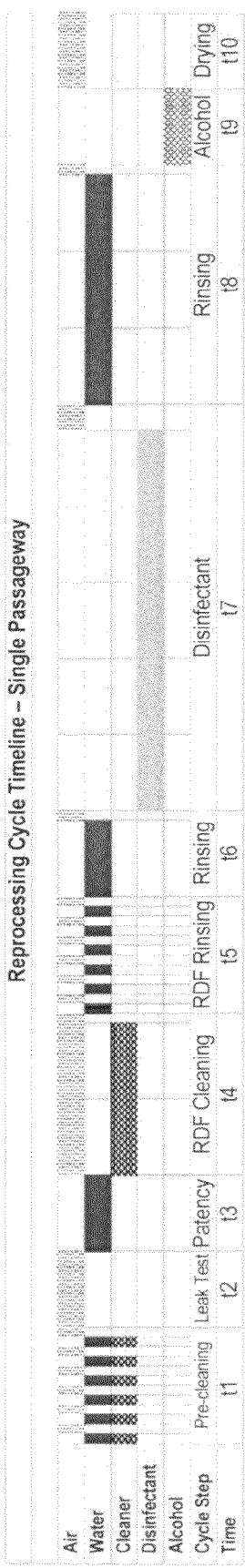

FIG. 14 is a time sequencing showing performance of various steps during the cleaning of an endoscope passageway.

FIG. 15 is a time sequencing showing performance of various steps during the simultaneous processing of two endoscopes by a single endoscope reprocessing apparatus.

Figure 16A:
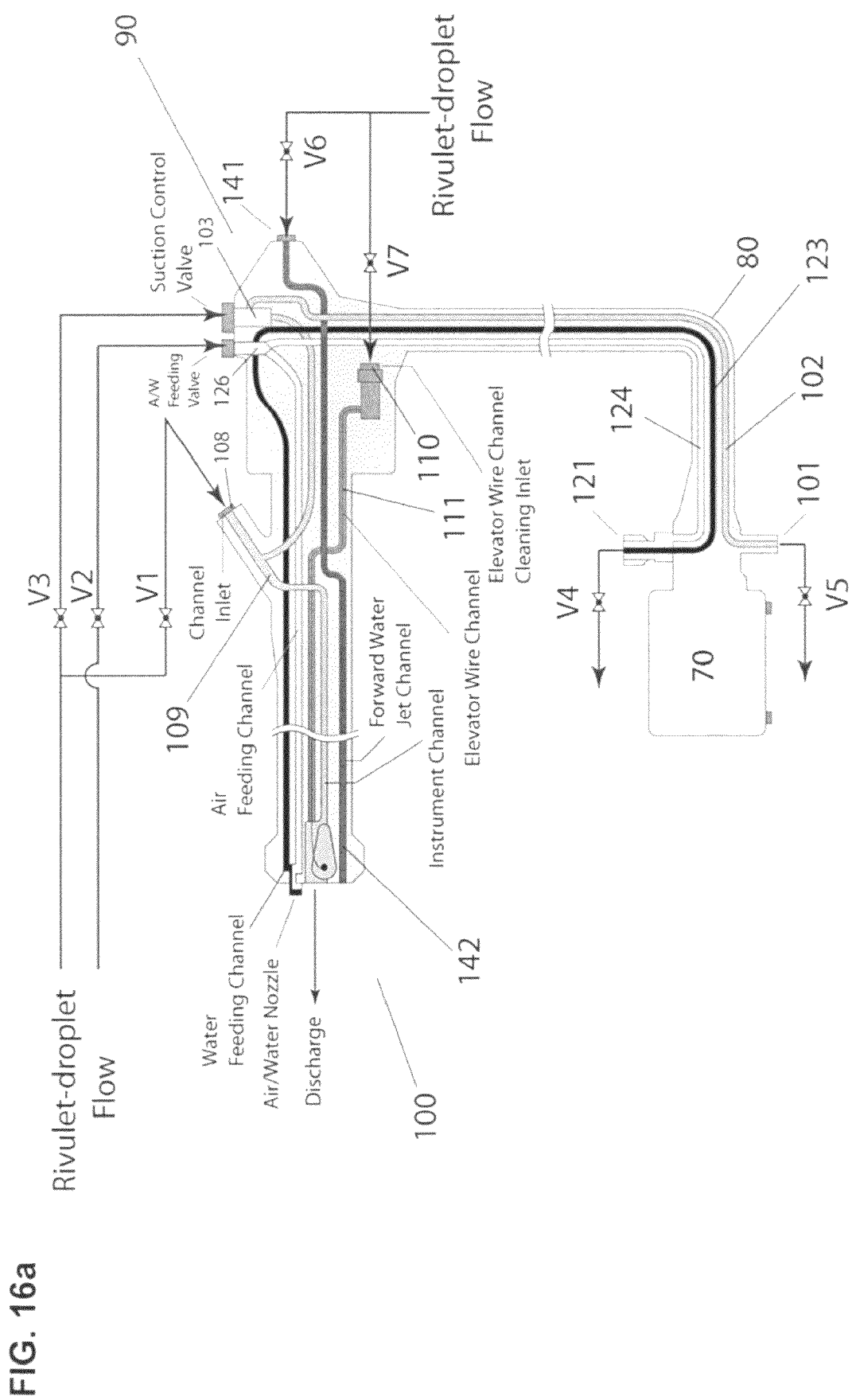
Figure 16B:
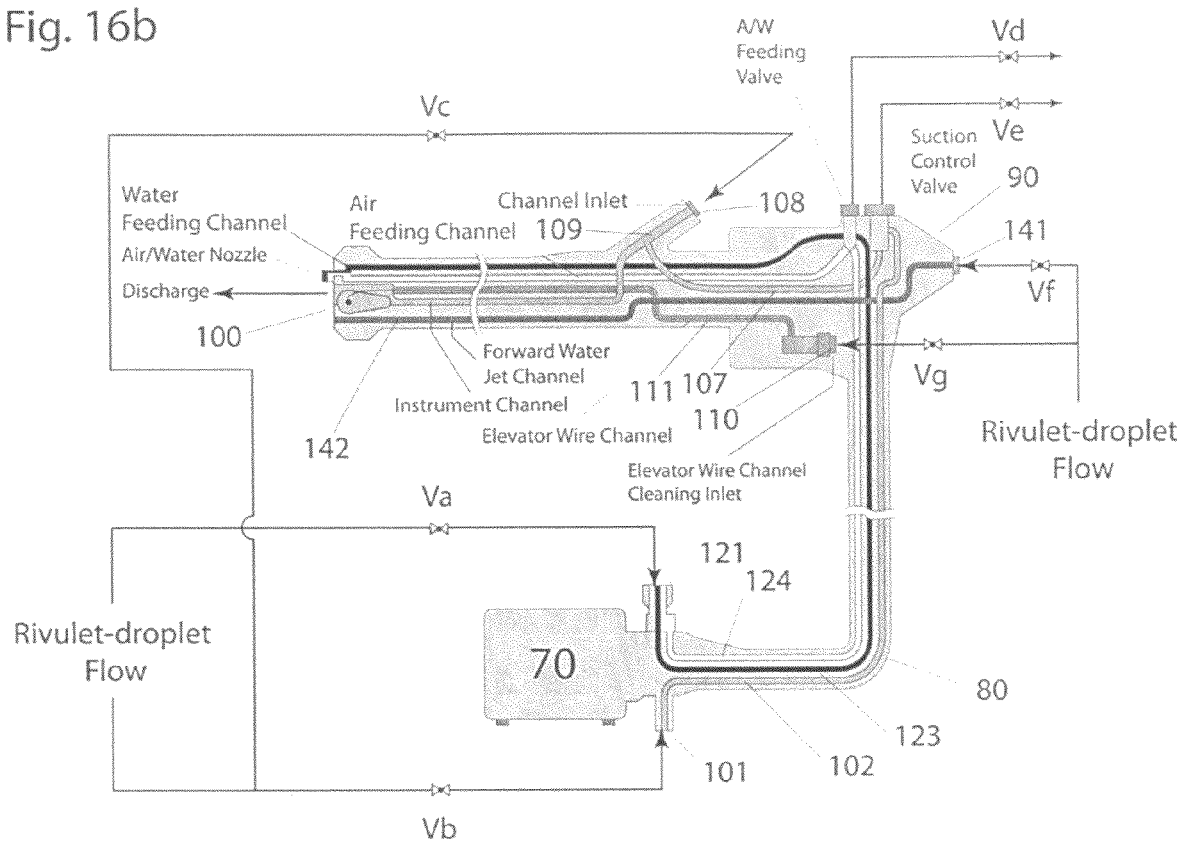

FIG. 16a illustrates one configuration of valving of the entrances and exits of certain channels in an endoscope. FIG. 16b illustrates another configuration of valving of the entrances and exits of certain channels in an endoscope.

Figure 17:
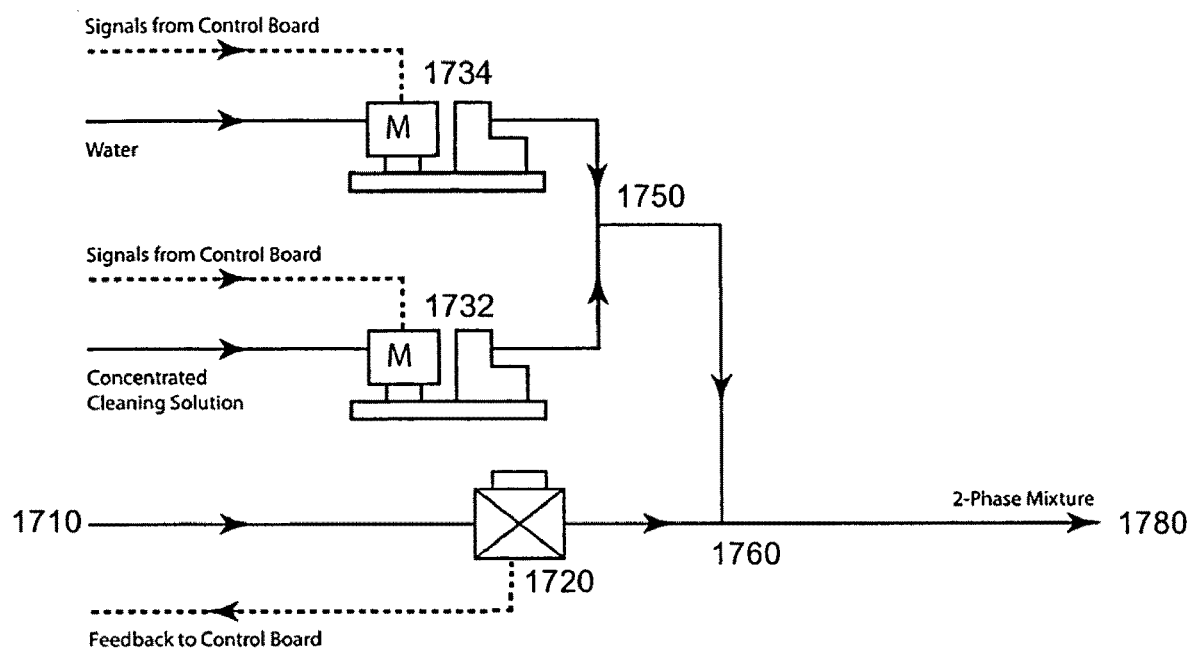

FIG. 17 is an illustration of a feedback control system for maintaining desired flow conditions.

Figure 18A:
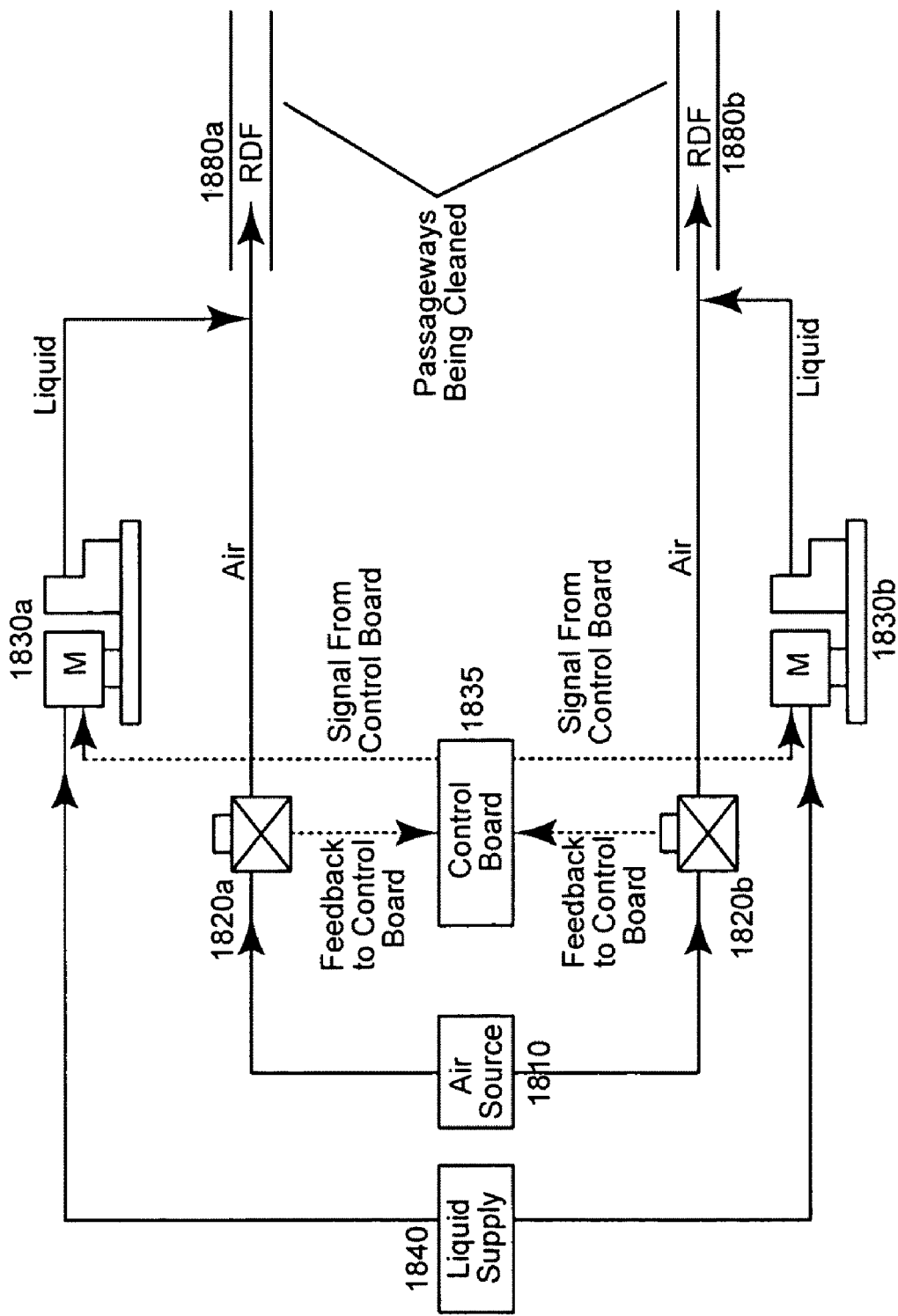
Figure 18B:
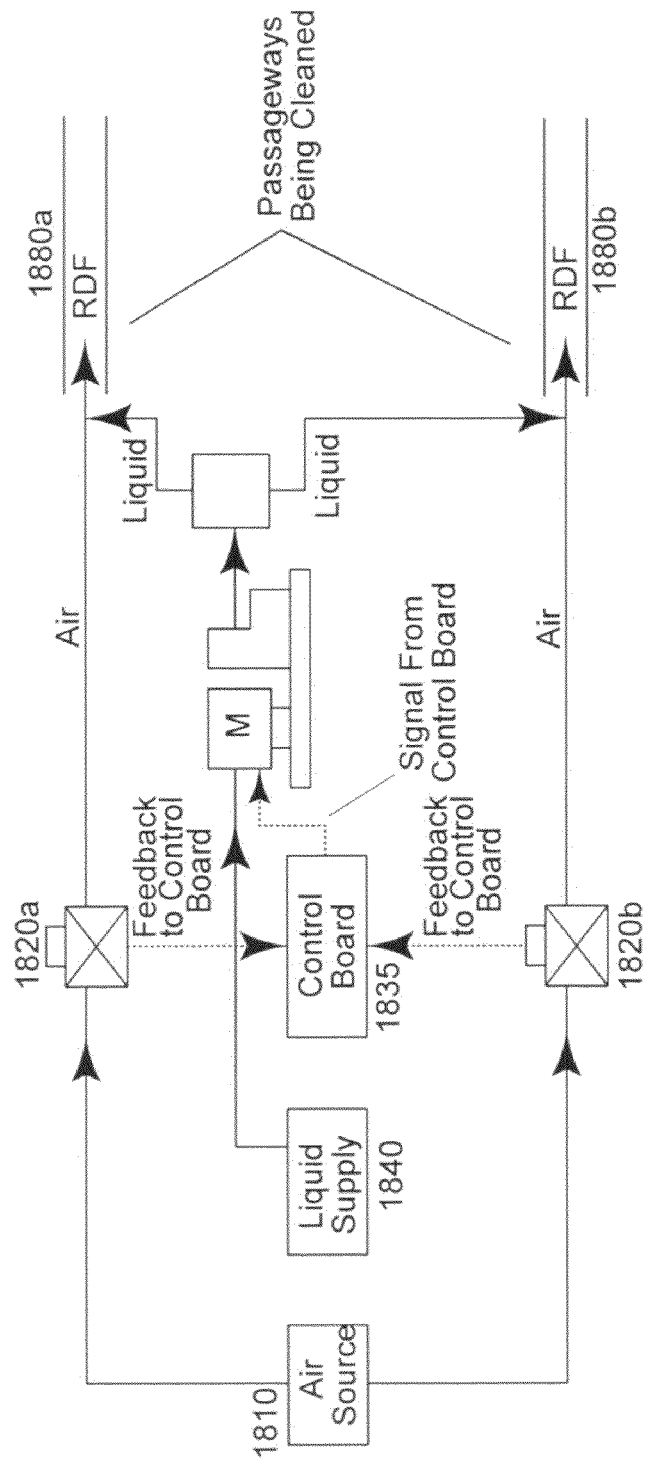

FIG. 18a is a block diagram showing a system for supplying two endoscope channels, with feedback, using two liquid metering pumps. FIG. 18b is a block diagram showing a system for supplying two endoscope channels, with feedback, using one liquid metering pump and a proportional valve.

Figure 19A:
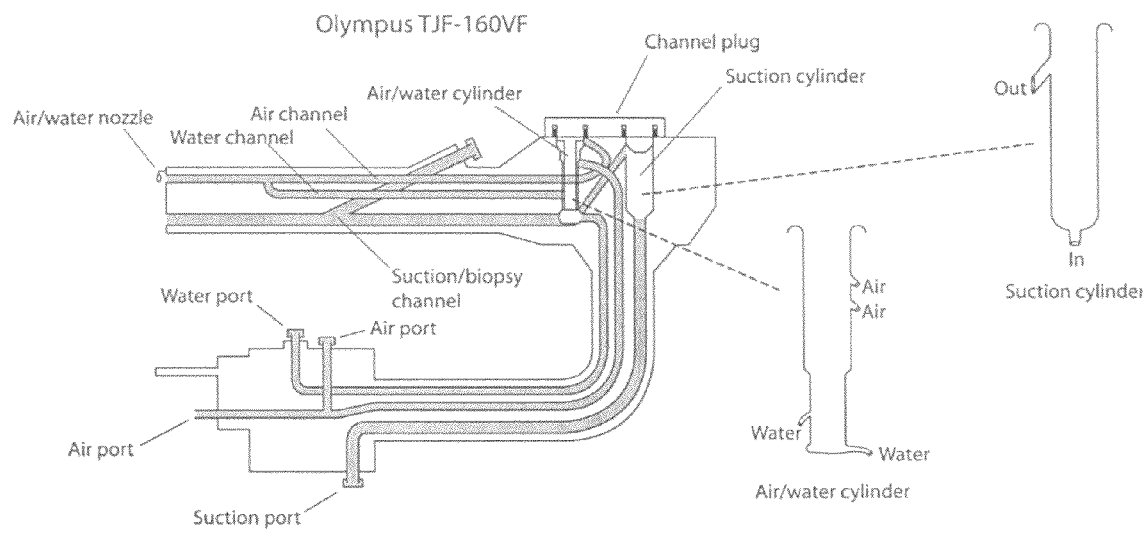

FIG. 19a is a cross-section of an endoscope showing detail about the cylinder wells in the control handle. FIG. 19b is a cross-sectional illustration of a fixed-position connector to cylinder well in the control handle of an endoscope, in which one incoming flowpath joins two directions of one channel in the cylinder well. FIG. 19c is a cross-sectional illustration of a fixed-position connector to a cylinder well in the control handle of an endoscope, in which two incoming flowpaths each join two directions of two channels in the cylinder well.

FIG. 20a is a cross-sectional illustration of a fixed-position connector joining a cylinder well such that the connector has two dedicated incoming flowpaths each supplying a particular direction of a channel. FIG. 20b is a cross-sectional illustration of a fixed-position connector and cylinder well such that the connector has four dedicated incoming flowpaths, with the four incoming flowpaths supplying two directions of two channels.

FIG. 21a, 21b, 21c, 21d are cross-sectional illustrations of a connector and cylinder well in which the connector is actuated so as to choose a particular passageway to supply flow to. FIG. 21a, 21b, 21c, 21d each illustrate different positions of the actuator-driven component.

Figure 22A:
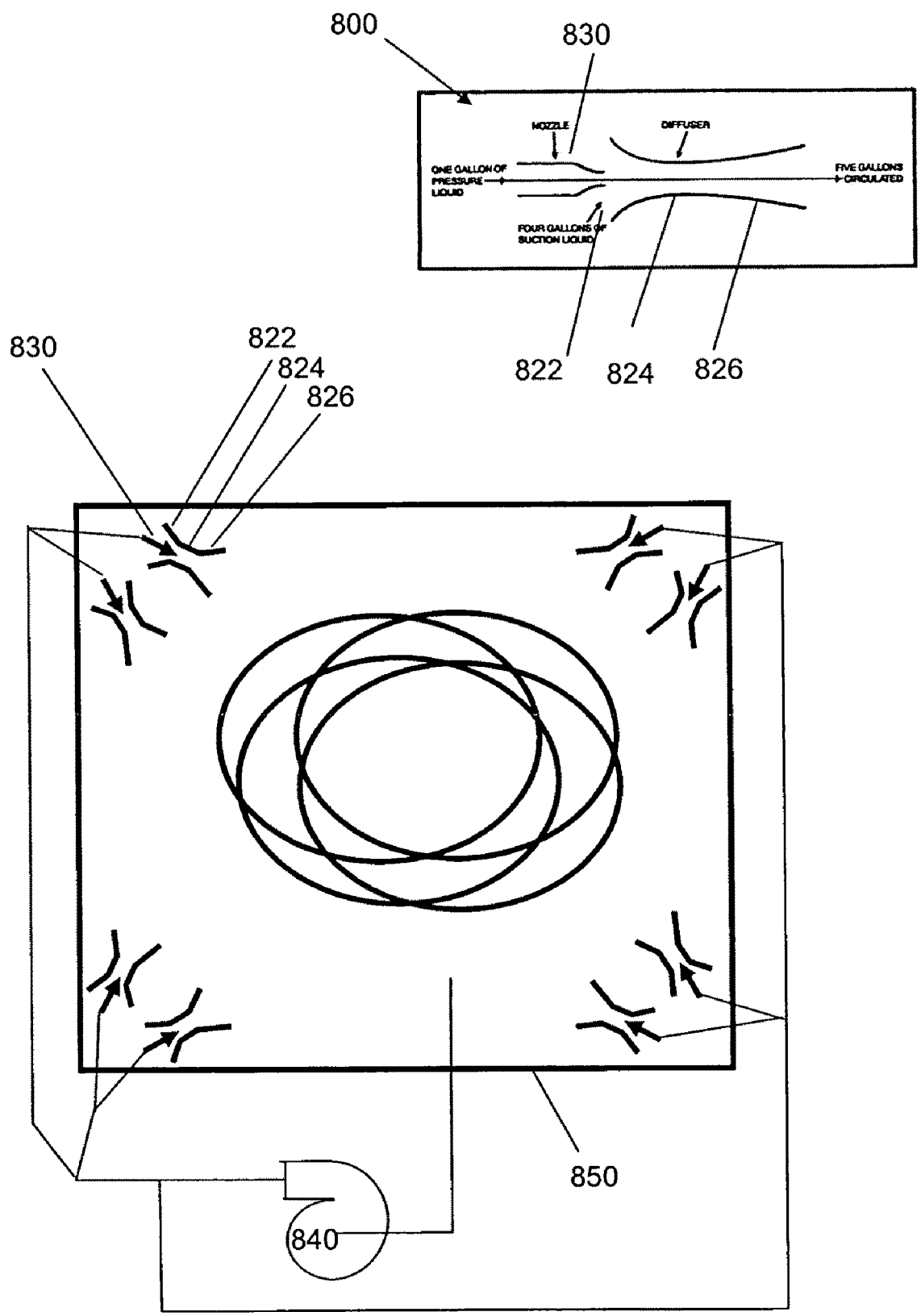
Figure 22B:
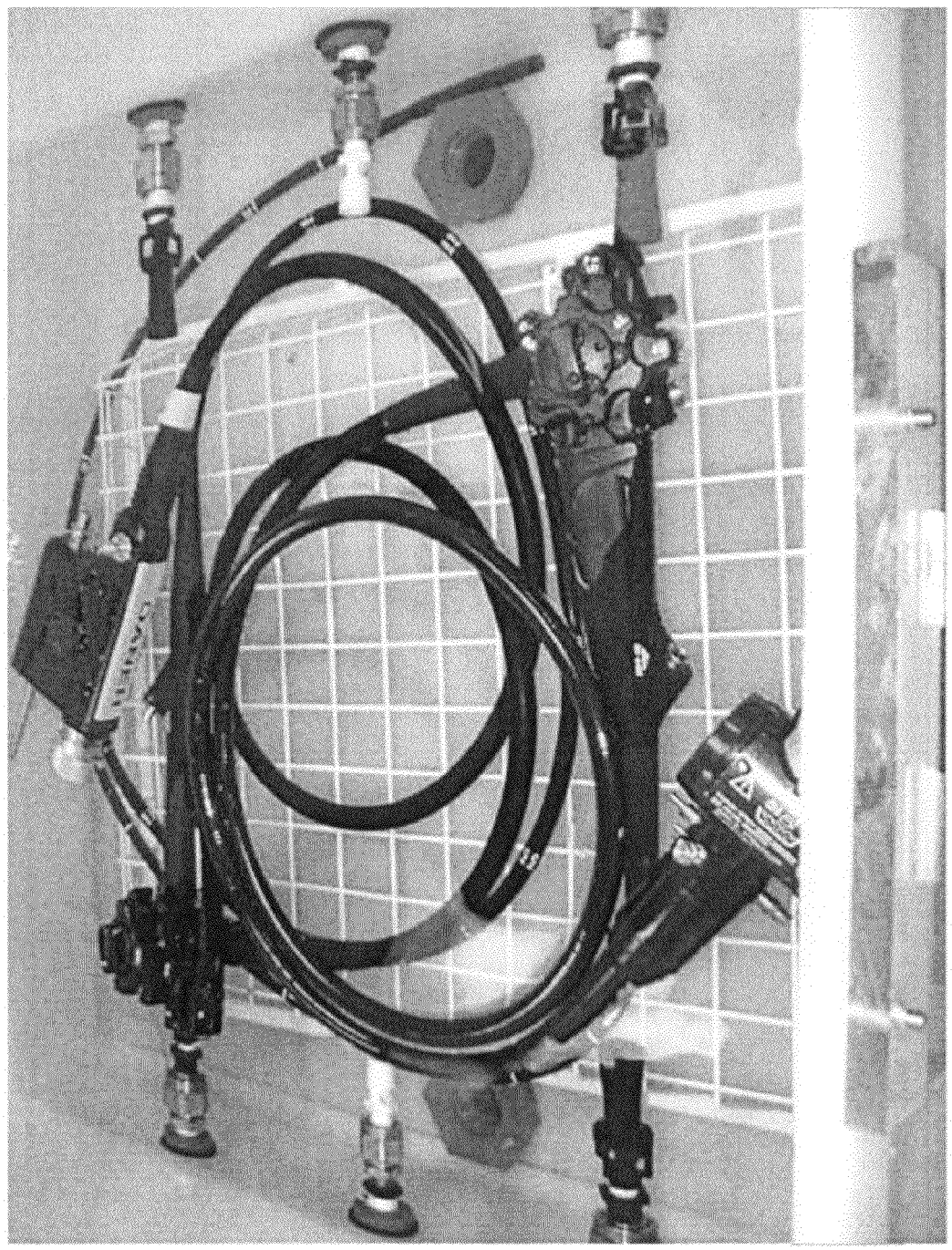
Figure 22C:
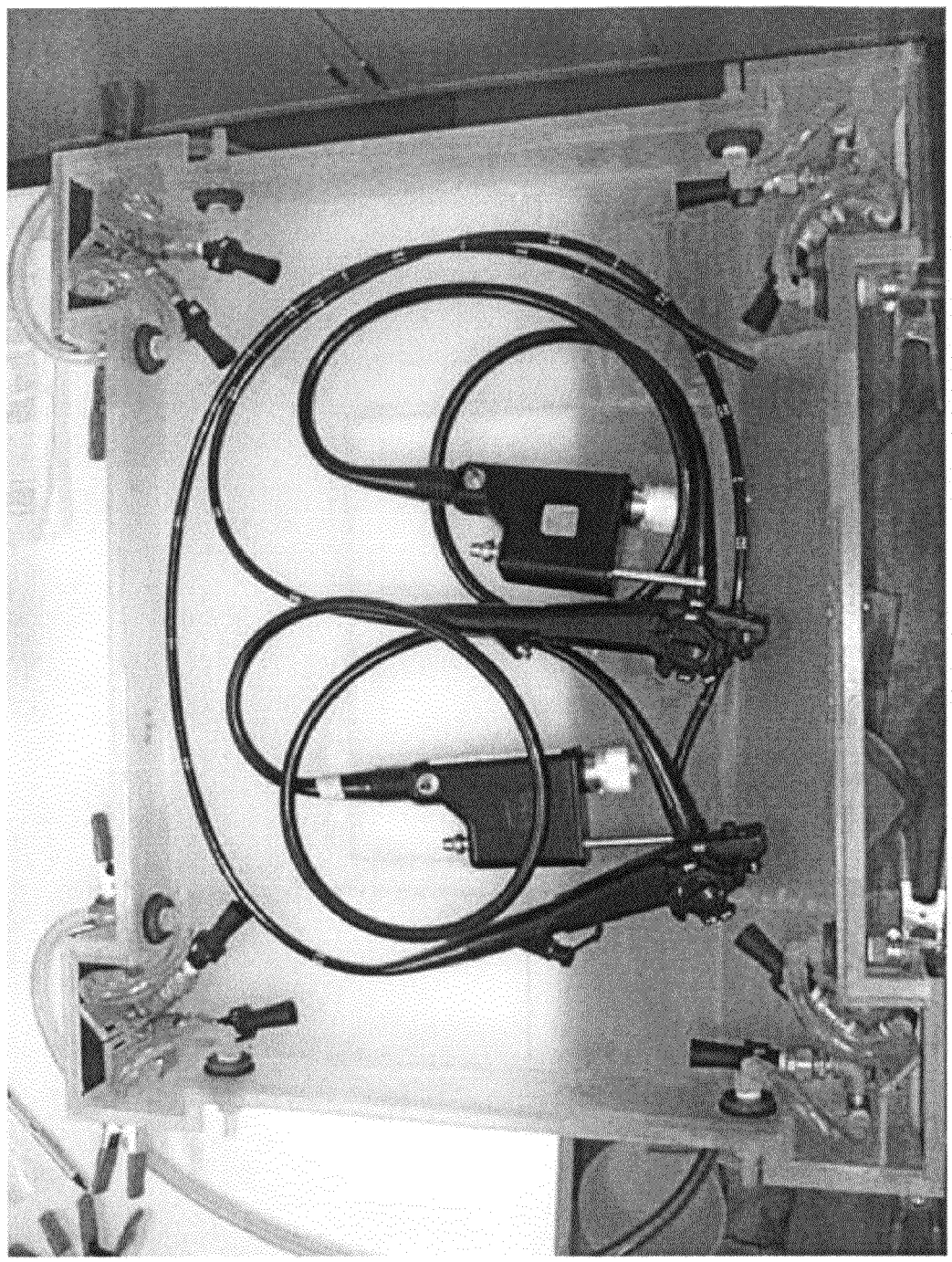
Figure 22D:
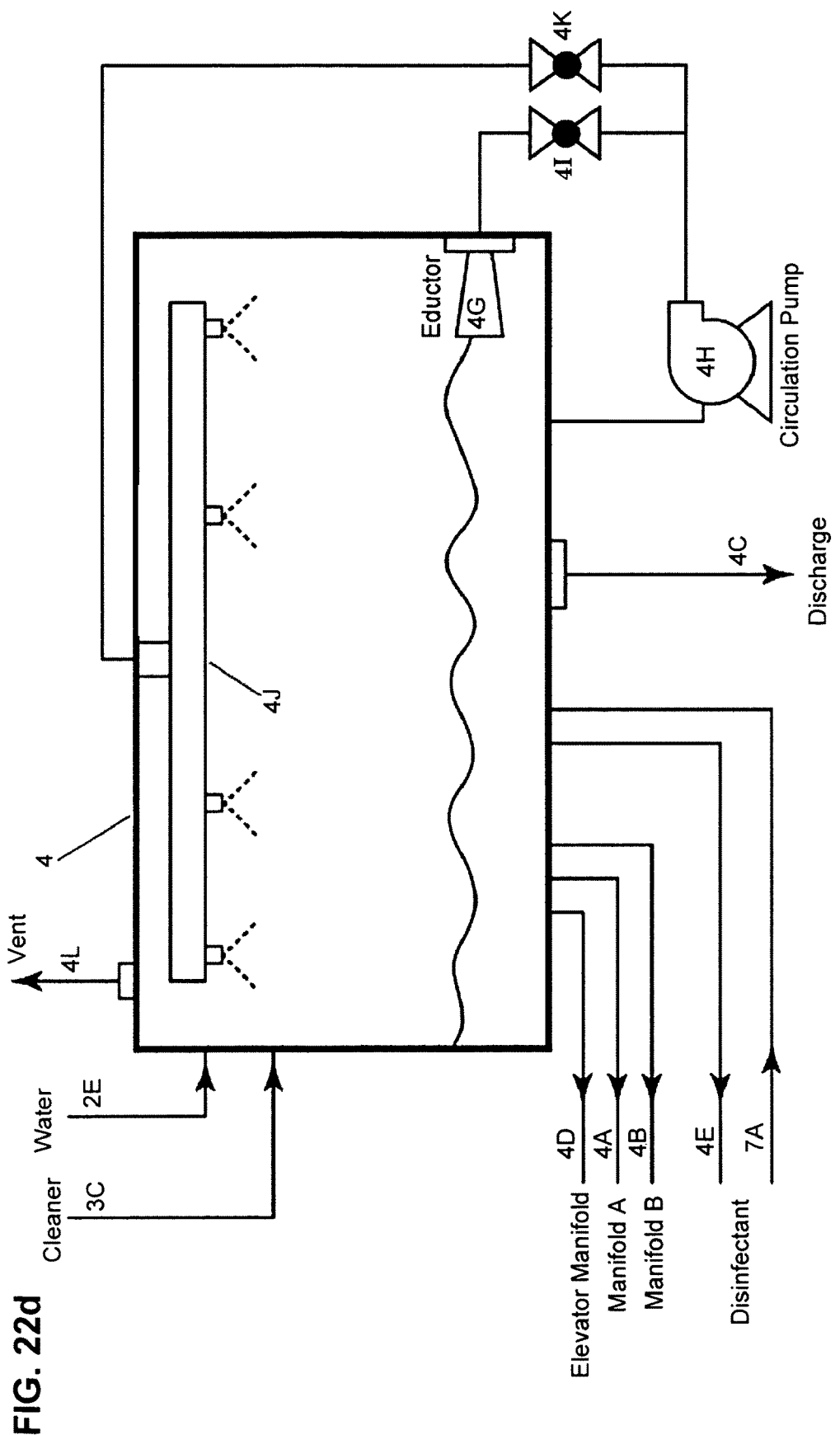
Figure 22E:
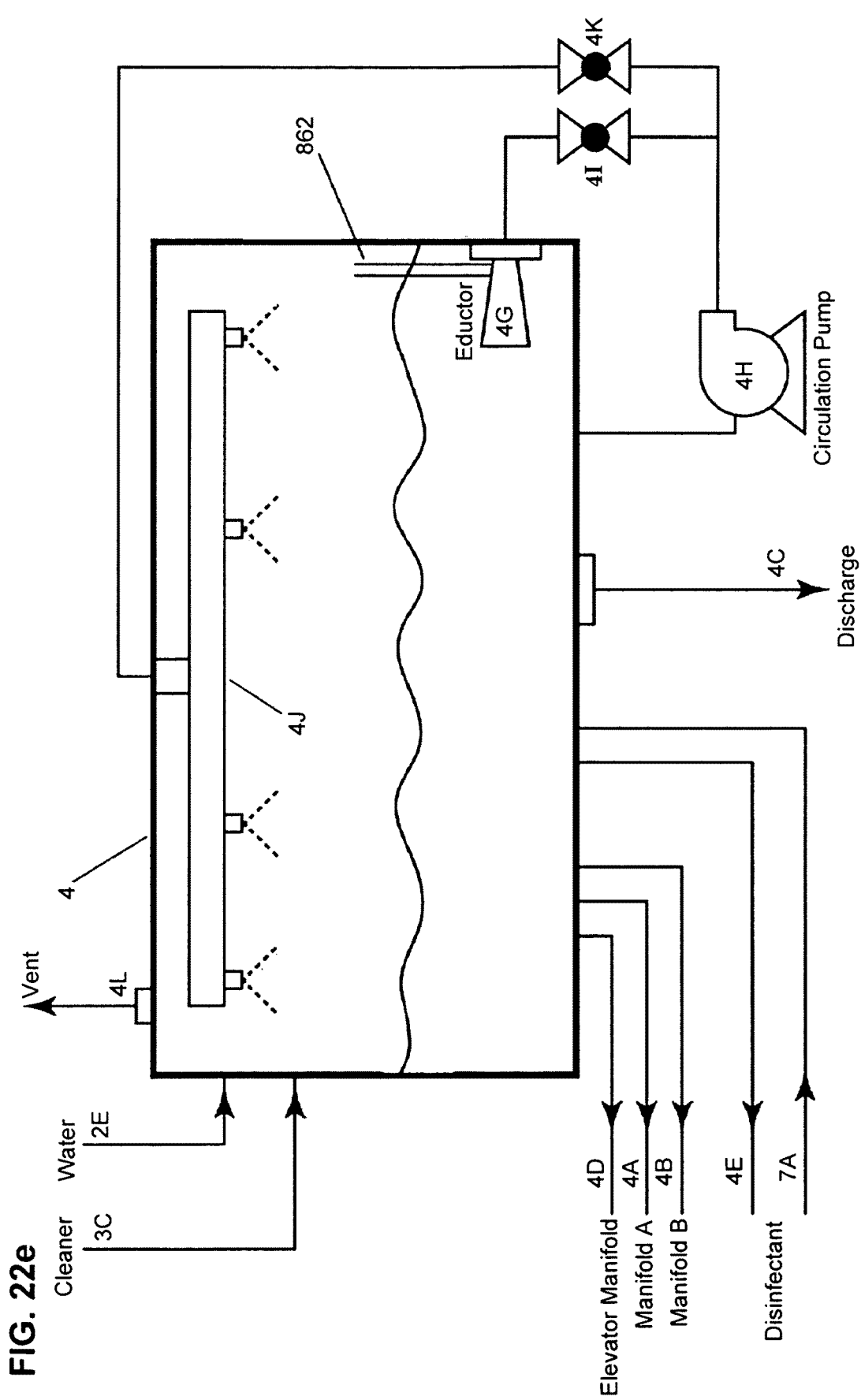

FIG. 22a is a top view of a basin with eductors and a flow circuit for directing flow at external surfaces of an endoscope. FIG. 22b illustrates an eductor which takes in air by virtue of being located near the liquid level of the basin. FIG. 22c illustrates an eductor having an air intake tube. FIGS. 22d, 22e are illustrations of designs of basins and eductors for cleaning the external surfaces of endoscopes.

Figure 23:
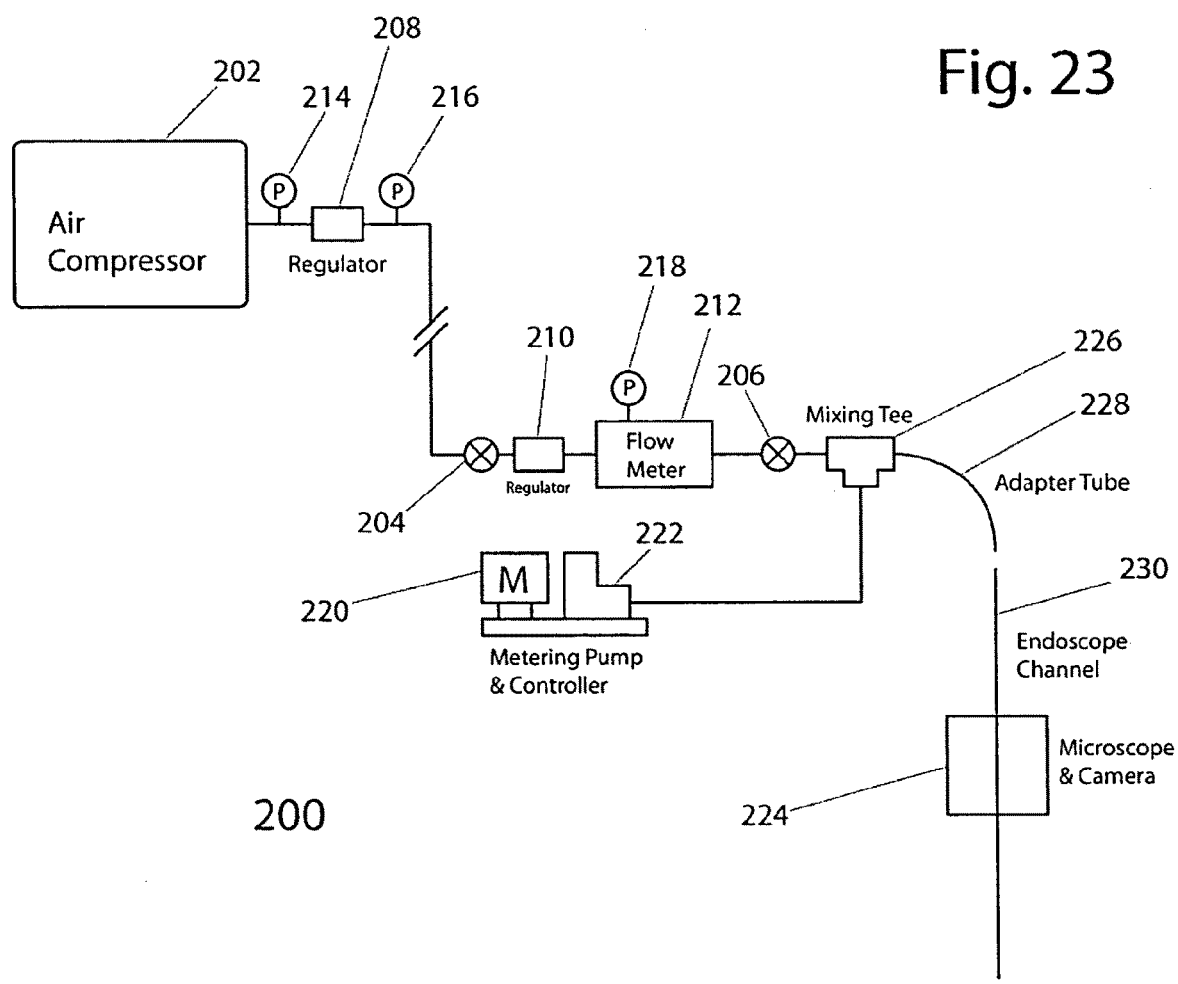
Figure 24:
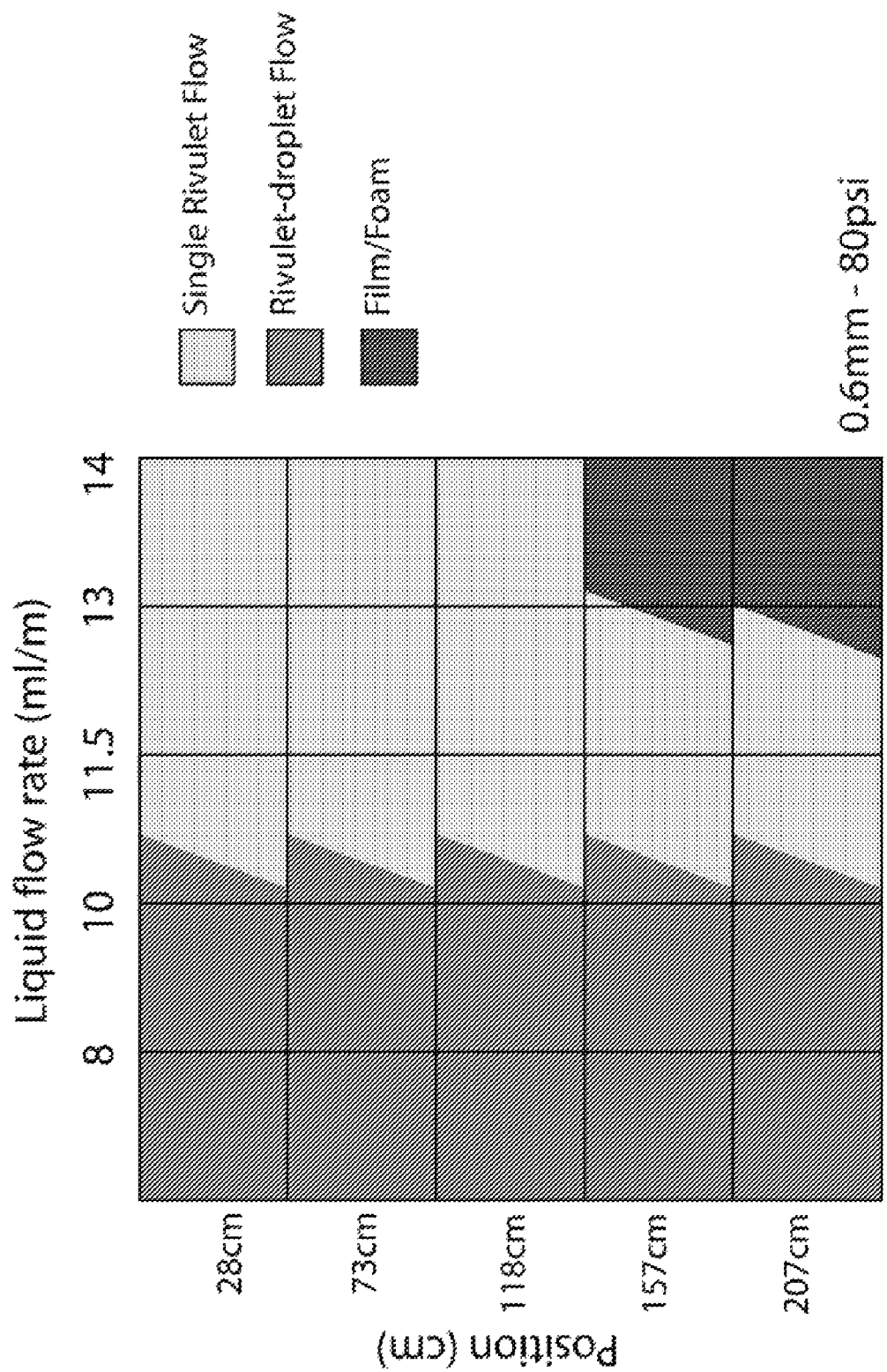
Figure 25A:
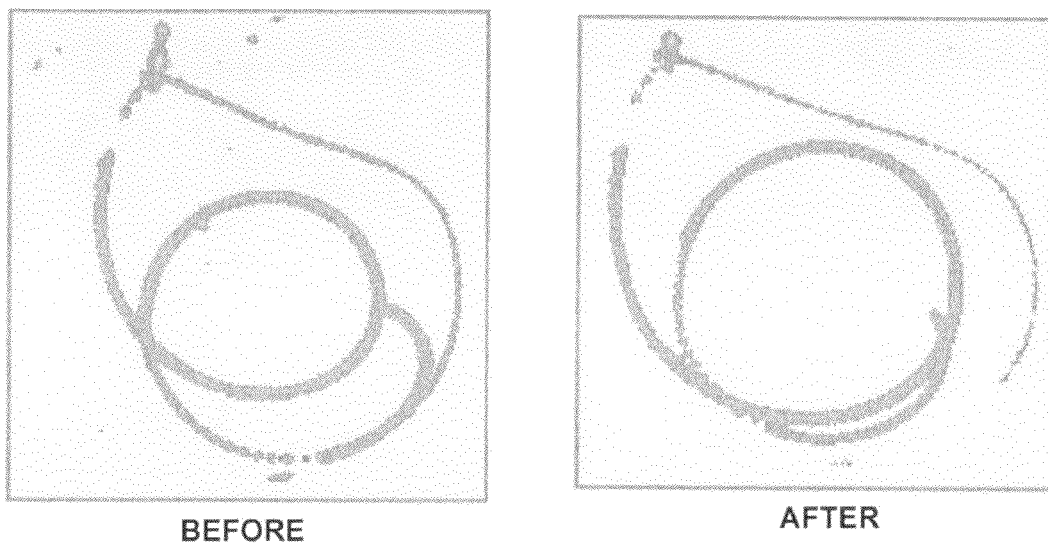
Figure 25B:
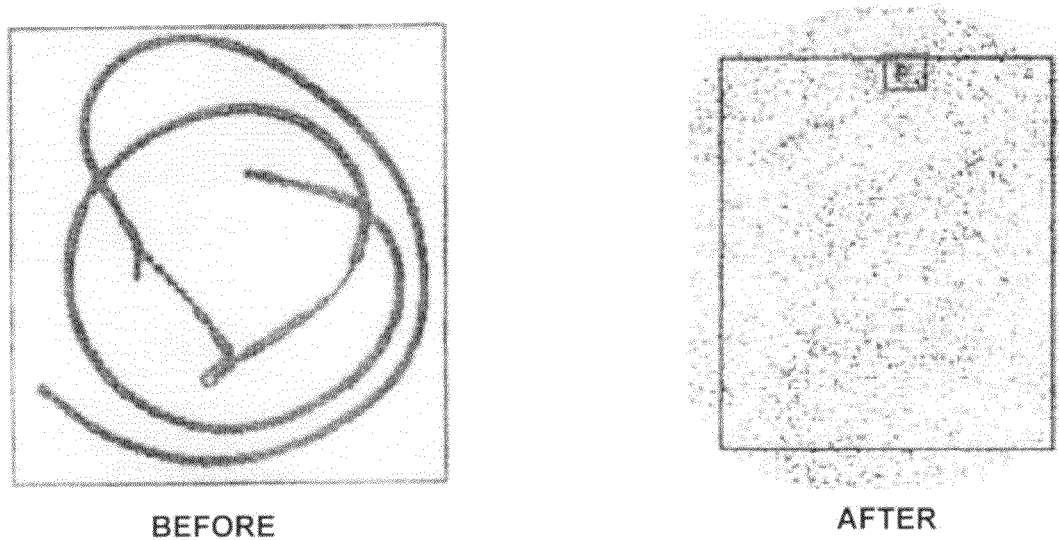
Figure 26A:
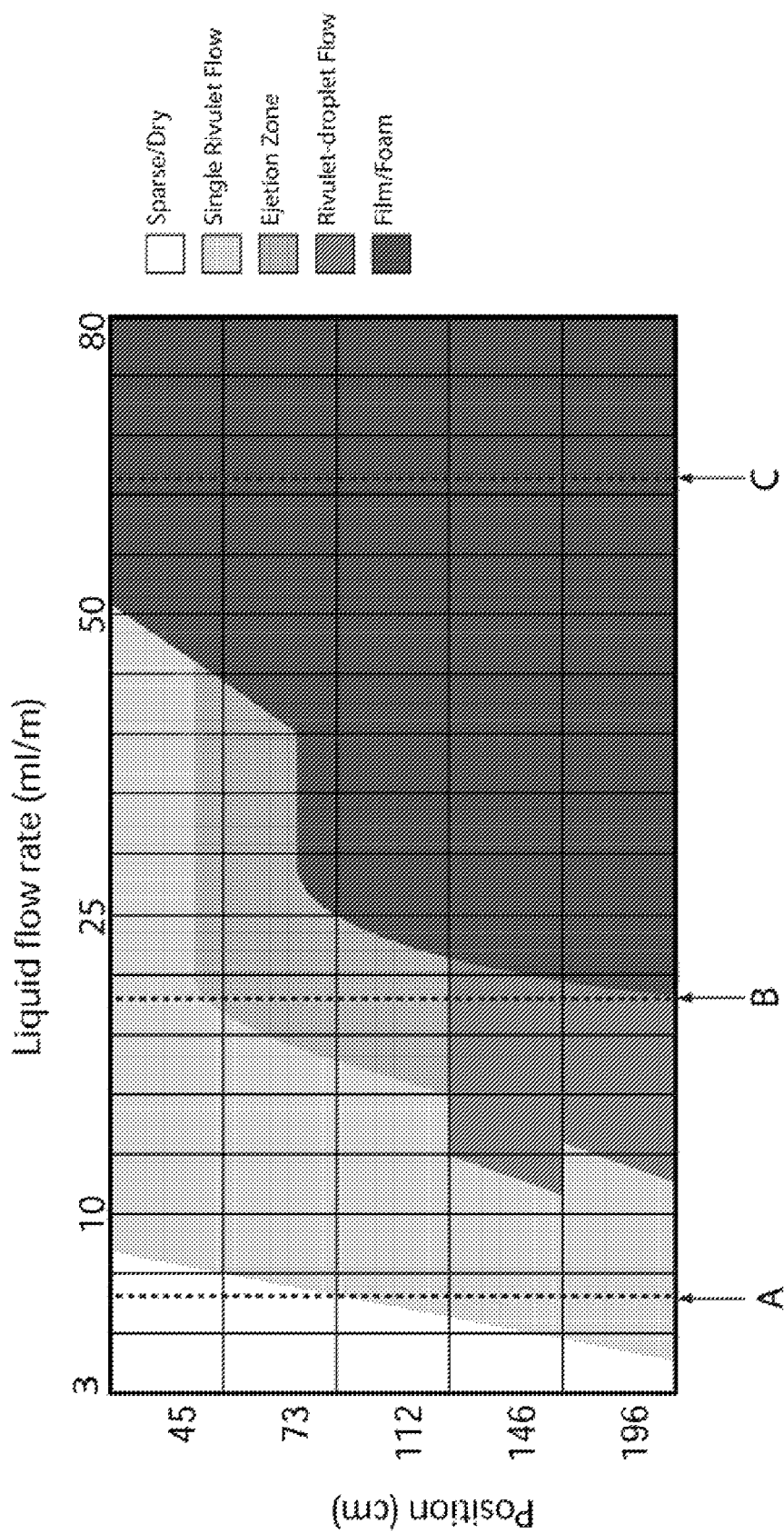
Figure 26B:
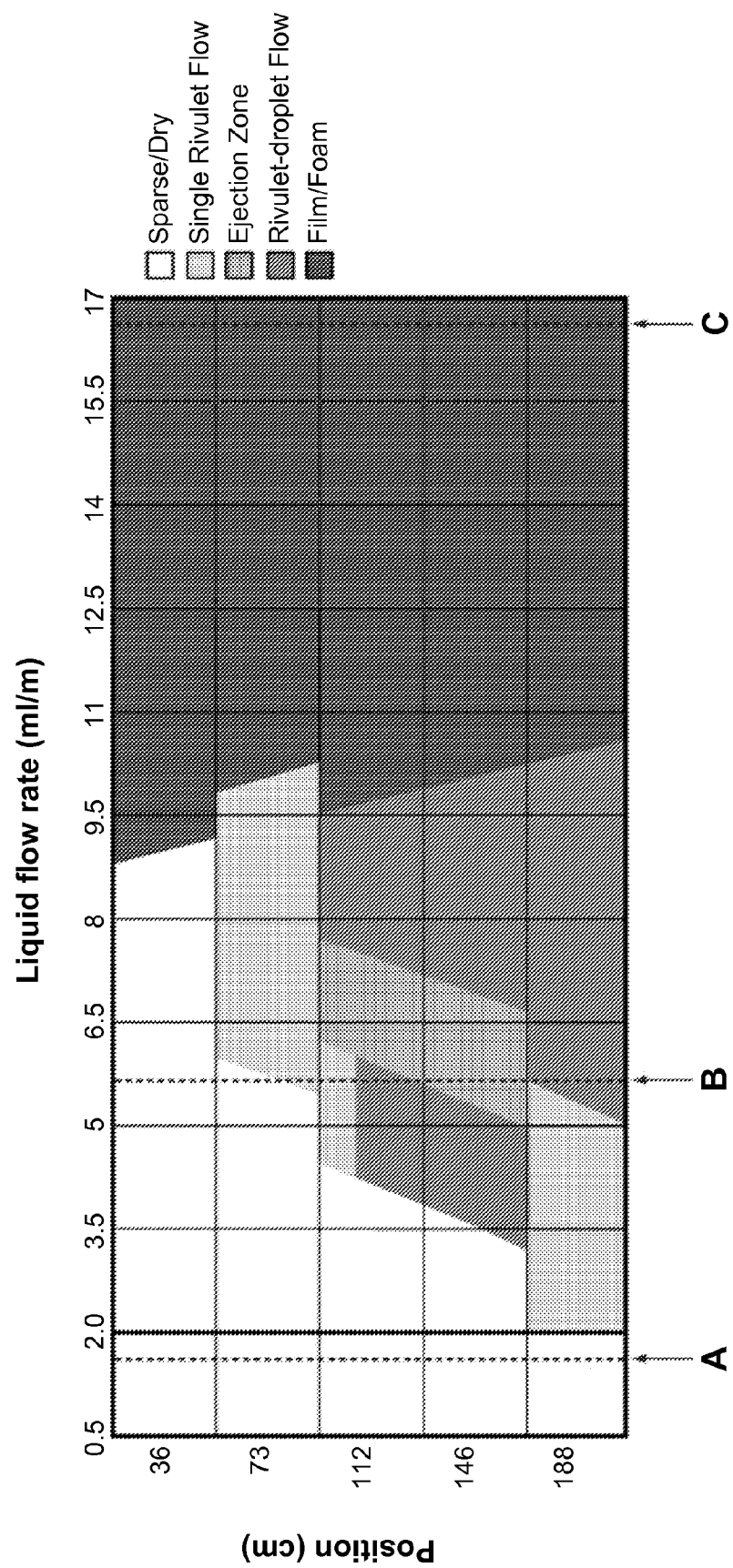

FIG. 23 illustrates an experimental set-up for photography.
FIG. 24 is another flow map taken at a different pressure.
FIGS. 25a and 25b illustrate data taken using radionuclides.
FIG. 26a and 26b are flow maps with an extra notation.

DETAILED DESCRIPTION OF THE INVENTION

Flow Regimes of Liquid and Gas Flow

Embodiments of the invention may be designed to create certain flow regimes within an internal passageway of an endoscope or other medical luminal instrument, for purposes of removing contaminants from the interior of the passageway. One previously-used way of dislodging a contaminant is by impact of a liquid droplet moving at a sufficiently large velocity in a stream of gas. However, in some situations it is not possible to provide sufficient gas velocity to create droplets or to create droplets having momentum sufficient to dislodge contaminants. This limitation may occur, for example, in situations where the device including the passageway is subject to a pressure limitation which is relatively low, and/or where the passageway is relatively long, such as in certain channels of endoscopes. For example, depending on the design of a particular endoscope and depending on the particular passageway within the endoscope, the maximum pressure which can be inputted into the passageway may be limited to 18 psig, or 24 psig, or 28 psig. (One particular channel of some endoscopes may have pressure limit of 70 psig.) The flow length of the passageway may be as long as several meters. These parameters in combination may limit the achievable gas velocities within the passageway. The presence of debris and contaminants can also reduce achievable gas velocity within a passageway.

Therefore, an embodiment of the present invention may use other physical mechanisms to accomplish cleaning. There are at least two possible physical mechanisms that can be active in detaching contaminants by the moving three phase contact line and menisci arising from the sliding motion of rivulets and surface flow entities formed during the rivulet droplet flow. One mechanism involves viscous shear, and the other mechanism involves surface tension. The three phase contact line may indicate the interface between solid (surface of passageway), liquid and air, or in other cases contaminant particle surface, liquid and air. The meniscus may be defined as a two-dimensional interface of a sliding entity moving on the wall of the passageway. In addition to these two mechanisms, it is further believed that still other physico-chemical effects may also be active helping to accomplish cleaning as well, especially in the presence of surfactants other components of the cleaning liquid. These mechanisms, for example, can include dissolution of contaminants or portions of contaminant particles, and desorption by action of the surfactant.

Viscous Forces on Contaminant Particles

In regard to viscous shear for removing a contaminant particle, it is instructive to compare viscous shear forces that might be generated by a conventional bulk flow of liquid filling an entire passageway, as compared to viscous shear that might be generated by a sliding liquid entity having three phase contact line and satisfying the criteria for high advancing contact angle and non-zero receding contact angle when encountering a particle. The comparison is illustrated in FIGS. 1a, 1b, 1c and 1d.

For a conventional bulk laminar flow of liquid flow through a passageway, the velocity profile is parabolic as illustrated in FIG. 1a. The velocity of the liquid is zero at the capillary wall and is maximum near the center of the capillary. The velocity as a function of radial position is given by the following equation.

$$V(z)=2U_o[1-(R_t-z)^2/R_t^2] \tag{1}$$

where V(z) is the velocity of the flow with a distance z from the capillary wall. $U_o$ is one half of the maximum velocity at the center of the flow, and $R_t$ is the radius of the capillary. In this equation, a represents distance measured away from the wall. In the immediate vicinity of the wall, where $z/(R_t \ll 1$, Equation 1 can further be simplified to give the velocity profile near the wall as $$V(z)=(4z/R_t)U_o \tag{2}$$

For determining hydrodynamic force that can be experienced by a contaminant particle attached to the wall, one may consider that a represents the radius of the contaminant particle. The most representative quantity to consider is the liquid velocity at the outermost point of the contaminant particle whose dimension is 2a. Thus, the liquid velocity at the outer edge of the contaminant particle is $(8a/R_t)U_o$. Thus, for a particle which is small compared to the radius of the capillary, the liquid velocity seen by the point on the particle farthest from the wall is only a small fraction of the maximum central velocity of the flow. This is illustrated in FIG. 1b.

A different situation presents itself for flow of a sliding liquid entity attached to the passageway wall and having a three phase contact line at its leading edge. It may be considered that the liquid entity advances with a sliding velocity of $U_{sl}$. It may further be considered that the leading edge of the sliding liquid entity appears as a wedge, and the wedge moves with a velocity profile V(z) which is zero at the capillary wall and approaching 1.5 $U_{sl}$ at the top of the wedge. This situation is described by Pierre-Gilles de Gennes, Francoise Brochard-Wyart, David Quere, "Capillarity and Wetting Phenomena", Springer, 2003. FIG. 1c (FIG. 6.6 in the de Gennes reference) illustrates the velocity profile within a sliding wedge. This situation occurs at any point on the sliding wedge, whether the point is near the tip of the wedge where the wedge is quite thin or further back from the tip of the wedge where the wedge is thicker. This is illustrated in FIG. 1c.

For purposes of removal of a contaminant particle, the situation of interest is when the contaminant particle attached to the wall is located within the approaching wedge at the distance x from contact line when it touches the water air interface. The smaller the particle is, the smaller the distance x. The mean velocity of liquid stream affecting particle is about 0.75 $U_{sl}$ because the velocity on the top of the wedge is 1.5 $U_{sl}$, and the velocity at the capillary wall is zero. FIG. 1d demonstrates that the liquid velocity which affects attached particles is at least 0.75 $U_{sl}$, no matter how small a particle is because for any small particle there is a distance x to contact line where it touches both surfaces.

For any given particle, it is possible to compare the cleaning effectiveness of a sliding liquid entity against the cleaning effectiveness of bulk liquid flow, by comparing the liquid velocity at the edge of the particle for a sliding liquid entity, against the liquid velocity at the edge of the particle for conventional bulk flow. This ratio is $$V \text{ edge (sliding liquid entity)}/V \text{ edge (bulk flow)} = (1.5)(U_{sl}/U_o)(R_t/a) \quad (3)$$

It can be seen that as the particle size represented by "a" becomes small, the advantage of a sliding liquid entity increases compared to bulk liquid flow. For example, when comparing with a bulk liquid flow with a maximum velocity of 200 cm/sec ($U_o$=100 cm/sec) in a tube which has a radius of 0.05 cm ($R_t$), the three phase contact line of a sliding liquid entity moving with $U_{sl}$=1 cm/sec can produce a 2 fold increase in detachment force compared to the detachment force of bulk liquid flow of 1 micron in radius, a 20 fold increase for the particles of 0.1 micron in radius, and a 200 fold increase for the particles of 0.01 micron in radius.

Thus, it is believed that for whatever are practical values of bulk flow maximum velocity and practical values of liquid entity sliding velocity, a sliding liquid entity can bring its velocity very close to the wall at the leading edge of an advancing wedge of the sliding liquid entity, whereas bulk flow cannot bring its maximum velocity near the wall. Thus, a sliding liquid entity has an advantage over bulk flow as far as exerting viscous force on small contaminant particles attached to the wall. However, it is not wished to be limited to this explanation.

Surface Tension Forces on Contaminant Particles

The second possible mechanism to achieve cleaning uses a mechanism that involves a moving three-phase interface on the interior surface of the passageway, i.e., an interface between liquid and gas at a solid surface. This cleaning mechanism may involve a portion of the surface being wetted by a liquid entity, and an adjacent portion of the surface being dry or nearly dry. As such an interface moves, it can generate forces that may act to dislodge contaminants. FIG. 2 schematically illustrates this situation.

It is believed that as a wet-dry interface moves along a solid surface, the wet-dry interface can exert a force on elements of the surfaces such as contaminants which may be adhered to the surface. This force may contribute to breaking the adhesion such contaminants have with the underlying solid surface such as by lifting such contaminants away from the underlying solid surface. This may be termed "capillary flotation." This can involve moving three-phase contact interfaces and menisci. (The term "three phase contact interface" may also be expressed in the literature as "three phase contact line.") However, it is not wished to be limited to this explanation or to situations where this is the only cleaning mechanism taking place. For purposes of this discussion, it is intended that the terms "wet" and "dry" are such as to allow formation of a three-phase contact interface at the interface between the "wet" region and the "dry" region. In addition to including a situation of a classical perfectly dry surface, the situation is also intended to include possible situations where there might be an extremely thin or intermittent liquid film present, but where the overall behavior displays characteristics similar to those of a liquid entity moving on a perfectly dry surface. The dry and wet conditions according to this description may also be expressed in terms of the advancing contact angle, receding contact angle and residual thin liquid film remaining after passage of three phase contact line. The term dry or nearly dry indicates that the thickness of the residual thin liquid film may be smaller than the dimension of the contaminant present on the surface.

Figure 2A:
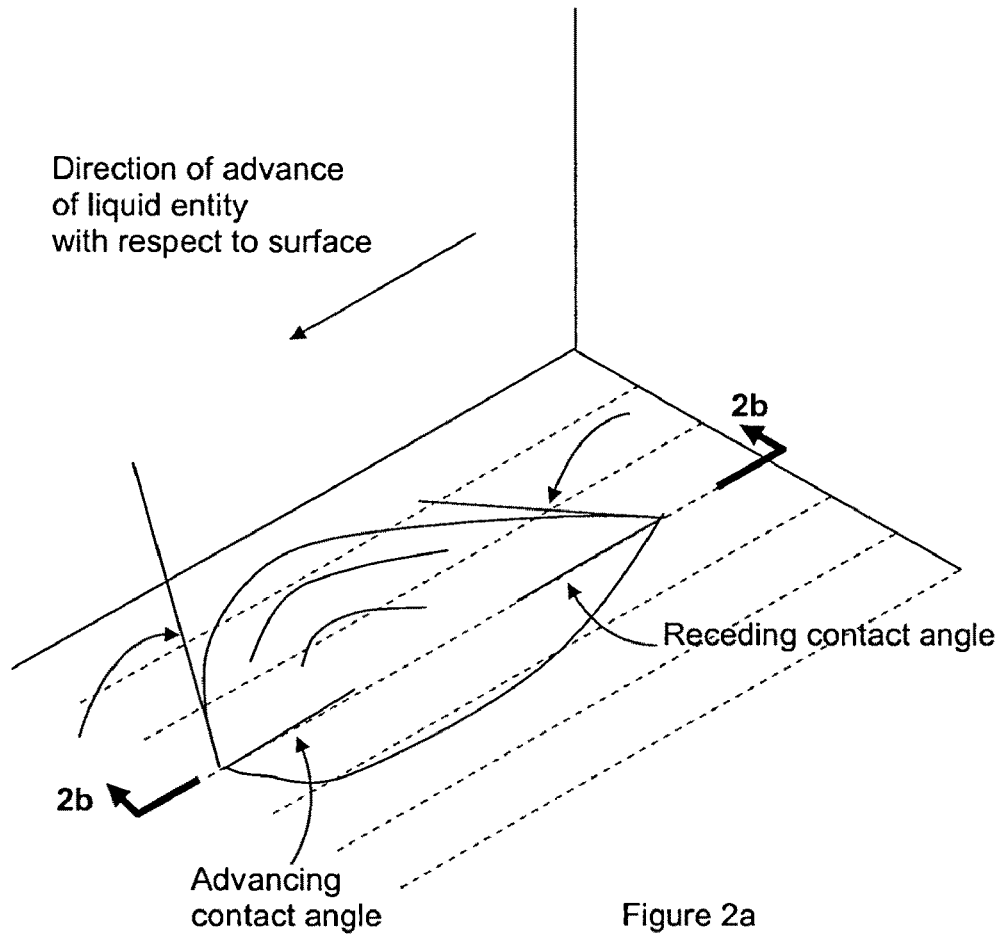
Figure 2B:
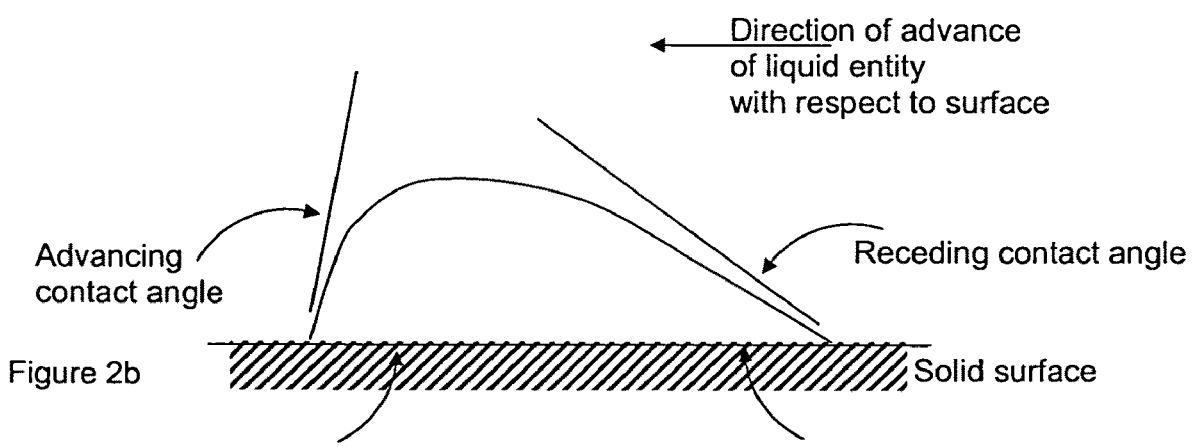

FIG. 2a illustrates a sliding liquid entity on a solid surface. FIG. 2b illustrates definition of advancing and receding contact angles associated with the sliding liquid entity.

Figure 2C:
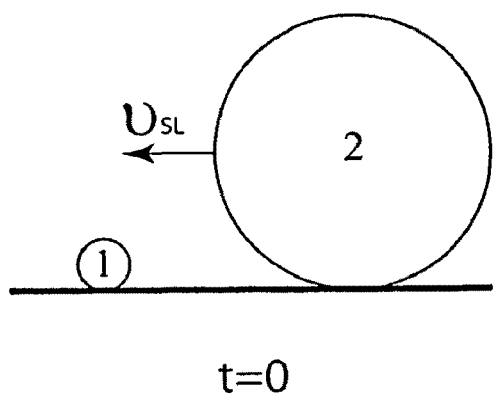
Figure 2D:
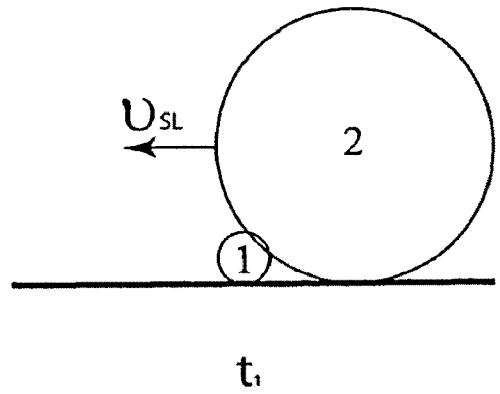
Figure 2E:
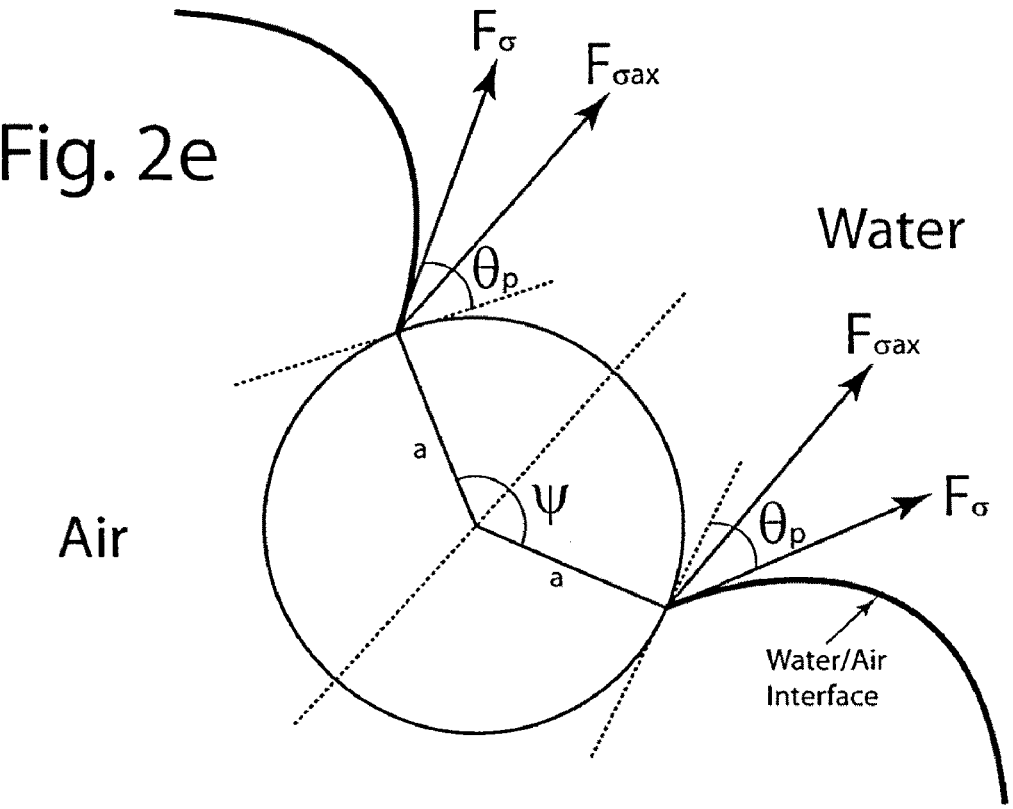
Figure 2F:
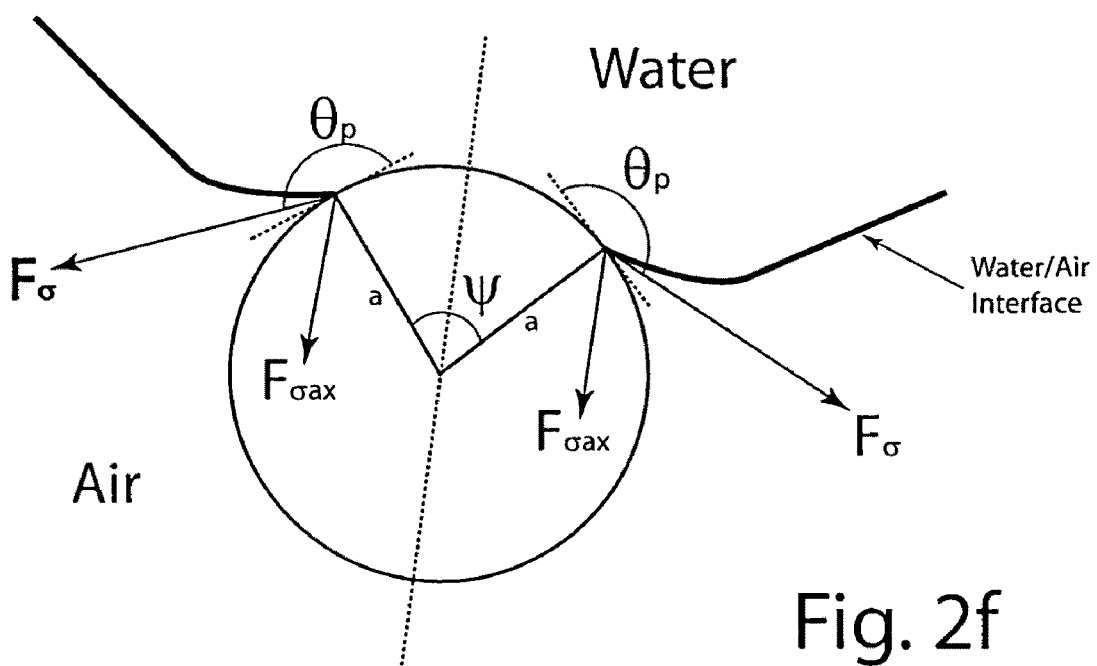

A mechanism of detachment can be caused by capillary tension forces at the liquid/air interface when a meniscus forms around a particle (FIGS. 2c, 2d, 2e and 2f). FIG. 2c depicts a contaminant particle attached to a wall being approached by the contact line of a sliding droplet. FIG. 2d shows the moment when the liquid/air interface touches the particle. FIGS. 2e and 2f only represent the vicinity of the particle during the process when capillary force is induced for two cases, a hydrophilic ($\theta_p$<90°) particle and hydrophobic particle ($\theta_p$>90°). According to this mechanism, touching the particle surface by a moving liquid initiates the onset of the capillary force, no matter whether a particle is hydrophilic or hydrophobic. However, the contact angle of the cleaning liquid with the particle plays a significant role in the detachment by this mechanism. Selection of surfactant mixture of the cleaning composition may be tailored to enhance detachment of contaminants by this mechanism.

Detachment of a hydrophilic particle: When the particle is hydrophilic, an aqueous liquid wets the particle surface leading to expanding the contact area at liquid/particle surface. This is characterized by expansion of the contact area perimeter Ψ which represents the contact line on the particle surface. The perimeter movement along the particle surface is accompanied by the deformation of the liquid surface at particle vicinity which is manifested by formation of a local meniscus (FIG. 2e). In this case, it is sufficient to take into account the surface tension of the liquid/air interface, i.e., the force which is directed along the interface). This force exists at any point of the contact line and has different directions. Assuming the particle wetting is axi-symmetrical and takes a shape similar to the contact line, we may introduce the local cylindrical system of coordinate with axial coordinate z and radial coordinate r. The radial components of local capillary forces cancel each other because of axial symmetry. The axial components are the same for any point of the contact line that yields the total axial capillary force. If the axial force is larger than the adhesion force, the capillary force will detach the particle. In this case, the contact angle for particle $\theta_p$ is less than 90°.

Interaction with a hydrophobic particle: When the particle is hydrophobic ($\theta_p$>90°) its wetting is suppressed and its penetration into the liquid is small due to a large value of contact angle as shown in FIG. 2f. As a result, the direction of capillary force is opposite to the one shown in FIG. 2e. In this case, the horizontal component (parallel to wall) of the arising capillary force will cause the particle to roll and consequently detach from the wall.

To describe nature of capillary force, the well-known equation for the attachment of a spherical particle to a rising bubble in flotation can be used. The capillary force equation for particle attachment to liquid/air interface is provided by Cristina Gomez-Suarez, et al., Applied and Environmental Microbiology, 67, 2531-2537 (2001), as follows:

$$F_{ca}=2\pi a\sigma \sin\Psi \sin(\theta-\Psi) \quad (4)$$

where a is the radius of the particle and $\sigma$ is the liquid surface tension. The capillary force is proportional to the length of contact line $2\pi a \sin\Psi$ and to the surface tension. $\sin(\theta-\Psi)$ arises at the transition from vector $F_\sigma$ to its projection $F_{\sigma ax}$ as shown in FIGS. 2e and 2f. Angle $\Psi$ varies during interaction and, in particular, takes value corresponding to the maximum of capillary force:

$$F_{ca}^{max}=2\pi a\sigma \sin^2(\theta/2)(\pi/2<\theta<\pi) \quad (5)$$

$$F_{ca}^{max}=2\pi a\sigma \sin^2[(\pi-\theta)/2](0<\theta<\pi/2) \quad (6)$$

Capillary detachment force compared with hydrodynamic detachment force induced by a three phase contact line: The hydrodynamic detachment force $F_h$ near sliding three-phase contact line is represented as:

$$F_h=4.5\pi\eta a U_{sl} \quad (7)$$

where $\eta$ is the liquid viscosity, a is the radius of the particle and $U_{sl}$ is the sliding velocity of the droplet or surface flow entity. The ratio of hydrodynamic force to the capillary force can be expressed as follows:

$$F_h/F_{ca}^{max}=(2.25/\sin^2\theta 2)Ca_{sl} \quad (8)$$

where $Ca_{sl}=\eta U_{sl}/\sigma$ is the capillary number which is very small. For example, assuming the sliding velocity $U_{sl}$ is 5 cm/sec, the liquid viscosity $\eta$ is $1\times10^{-2}$ g/cm·sec and the surface tension of the liquid $\sigma$ is 50 .g/s²(dynes/cm), the capillary number is about $10^{-3}$. Considering the contact angle, the ratio between hydrodynamic and capillary forces for different $\theta$ and $U_{sl}$ is included in the following Table.

| | $F_{ca}^{max}/F_h$ in Equation (8) | |
|---|---|---|
| | $U_{sl}$, cm/sec | |
| $\theta$ | 0.5 | 5 |
| $\pi$ | 4444 | 444 |
| $\pi/2$ | 2222 | 222 |
| 0 | 4444 | 444 |

Although in some cases capillary detachment force is clearly higher, there are situations when the hydrodynamic detachment force becomes important. If the particle contact with liquid/air interface cannot be provided, capillary detachment force will not be realized. In the meantime, hydrodynamic detachment force will still be present. Since the sliding velocities of surface flow entities span a wide range of values, it is believed that both mechanisms may operate together sometimes or one may dominate over the other depending on the channel diameters and operating conditions.

Capillary detachment force compared with bulk liquid flow: The hydrodynamic detachment force $F_{lf}$ created by a bulk liquid flow is expressed by the following equation:

$$F_{lf}=24\pi\eta U_o(a^2/R_t) \quad (9)$$

where $R_t$ is the radius of the capillary or small tubing and $U_o$ is one half of the maximum velocity of the liquid flow which occurs at the center of the flow. Comparison of the detachment forces caused by both bulk liquid flow and capillary interaction on a particle can be simplified as follows:

$$F_{lf}/F_{ca}\sim 12Ca_o(a/R_t) \quad (10)$$

where $$Ca_o=\eta(U_o/\sigma) \quad (11)$$

Applying the same parameters as used above, viscosity $\eta$ is $1\times10$-2 cm/s, the surface tension of water $\sigma$ is 50 g/sec² (dynes/cm), and assuming the maximum bulk liquid velocity is 200 cm/sec ($U_o$=100 cm/sec), $Ca_o$ is about 0.02. The hydrodynamic detachment force of liquid flow is order of magnitude weaker than the capillary detachment force.

Not wishing to be bound by this explanation, it is believed that both detachment mechanisms may operate depending on the nature of contaminants and the operating conditions, including the composition of the cleaning liquid used according to this invention.

In this mechanism of detachment, the meniscus formed at the leading edge of the fragment or drop makes contact with the contaminant and exerts a capillary force on the contaminant directed at least to some extent away from the surface of the channel (proportional to the normal component of surface tension force acting on the effective contact area). This detachment force may be expected to be a function of the surface tension of the liquid, the size of the contaminant (contact perimeter) and its wettability (contact angle). This force may be sufficient to detach the contaminant from the surface depending on the strength of the adhesive force holding the contaminant to the channel surface. It is believed that capillary flotation becomes increasingly effective when the advancing contact angle approaches 90 degrees or greater and the contaminant particles are below about 10 μm, especially below 5 μm. It is further possible that a receding contact angle of a sliding liquid entity or fragments can also generate such detachment forces.

The solid-liquid-gas interface may occur at either an advancing edge of a liquid entity, i.e., when a dry local region of the surface is becoming wet, or a retreating edge of a liquid entity i.e., when a wet local region of the surface is becoming dry. It is further noted that advancing and receding may generally coincide with the general direction of flow along a passageway or along the flow of a rivulet, but also the advancing and receding could also be associated with a component of motion transverse to an overall direction of flow along the length of a passageway. A representative form of transverse motion is meandering as described elsewhere herein. The motion of the liquid which causes the advancing or receding contact angle may be either along the general flow direction of the passageway, or may be perpendicular to the general flow direction of the passageway, or may be some combination of the two directions. All of these are illustrated in FIG. 2a-2d and also in FIG. 3a.

When the moving liquid entity provides, through either of these mechanisms or any combination thereof or any other mechanism, a sufficient force to detach a contaminant from the wall, the contaminant can then be swept along by the sliding liquid entity or drop or rivulet. The detached contaminant may be either moved along by the trailing edge of the liquid entity or may be captured at the liquid/gas interface of the liquid entity and thereby moved along. For either of these transport process it may be helpful that the receding contact angle is non-zero, i.e., the trailing edge of the surface flow entity can not be dragged out to form a trailing liquid film. The non-zero receding contact angle is believed to be more important in preventing film formation on the trailing surface than is the transport mechanism. The role of surfactants in the cleaning liquid is essential to controlling the advancing and receding contact angles of surface flow entities on the wall of the passageway. The surface hydrophobicity of the passageway also plays a role along with surfactant composition in determining the contact angle and on deciding the wet-dry condition during rivulet droplet flow.

Flow Regimes

One particular flow mode which can provide cleaning action is rivulet flow. In rivulet flow, a significant portion of the liquid can exist attached to the internal surface of the passageway and able to move in the general direction of the gas flow. At least some of the liquid can exist in the form of rivulets extending generally longitudinally along the direction of flow. Portions of the internal surface of the passageway which are not in actual contact with the rivulet may be substantially dry.

Rivulet flow has been studied in the case of liquid flowing down a smooth inclined plane under the action of gravity in an environment of stationary gas. (See for example by P. Schmuki and M. Laso, On the stability of rivulet flow, J Fluid. Mech. (1990) vol 215, pp 125-143). Rivulet pheonomena are also described in "Meandering rivulets on a plane: a simple balance between inertia and capillarity?" by Nolwenn Le GRrand-Pitiera, Adrian Daerr, Laurent LIMAT Feb. 2, 2008 arXiv:physics/0510089v2 [physics.flu-dyn] 7 Nov. 2006; and in Lawrence Berkeley National Laboratory Paper LBNL 54681, 2004, "Constraints on flow regimes in wide-aperture fractures" by Teamrat A. Ghezzehei (http://repositories.cdlib.org/lbnl/LBNL-54681); and in Stream meanders on a smooth hydrophobic surface, by Takeo Nakagawa and John C. Scott, J. Fluid Mech. (1984), vol. 149, pp. 89-99; and in Rivulet meanders on a smooth hydrophobic surface, by T. Nakagawa, Int. J. Multiphase Flow, Vol. 18, No. 3, pp. 455-463 (1992). Most of these references have studied rivulet flow down a flat inclined plane surrounded by stationary gas.

Several of these references categorize flow in these situations as having any of several regimes. Three of the several variables involved are inclination angle of the plate, and liquid flowrate, and contact angle of the liquid with the surface. In general, these variables have somewhat related effects which might be thought of as some indication of increasing energy or activity level. In the least active situation, which can occur for some combination of low inclination angle and low liquid flowrate, flow of liquid entities tends to be substantially straight. This is a stable situation.

Figure 3A:
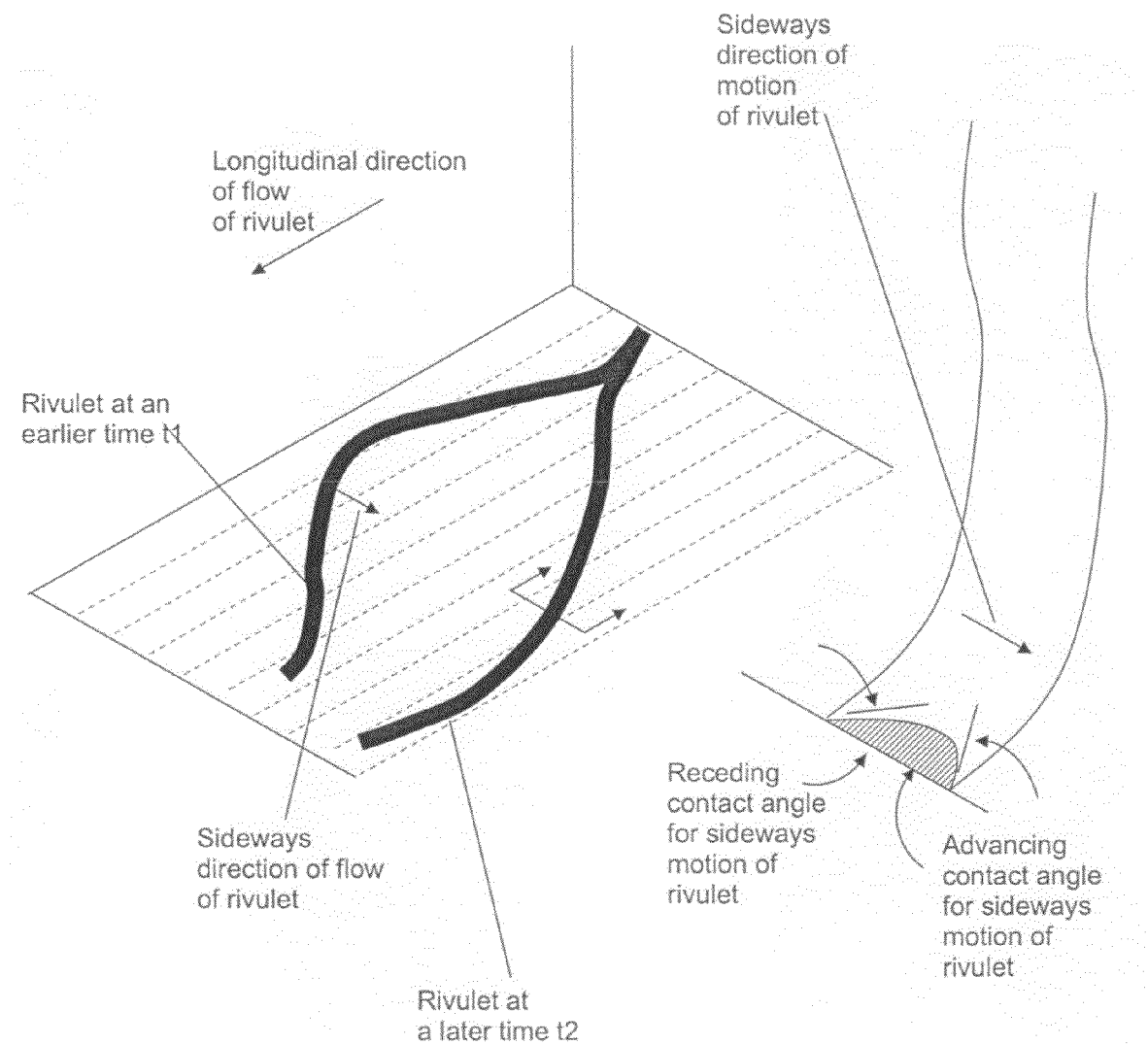
FIG. 3a is an illustration of a meandering rivulet on a flat plate, including an illustration of advancing and receding contact angles due to sideways motion of the rivulet.
Figure 3B:
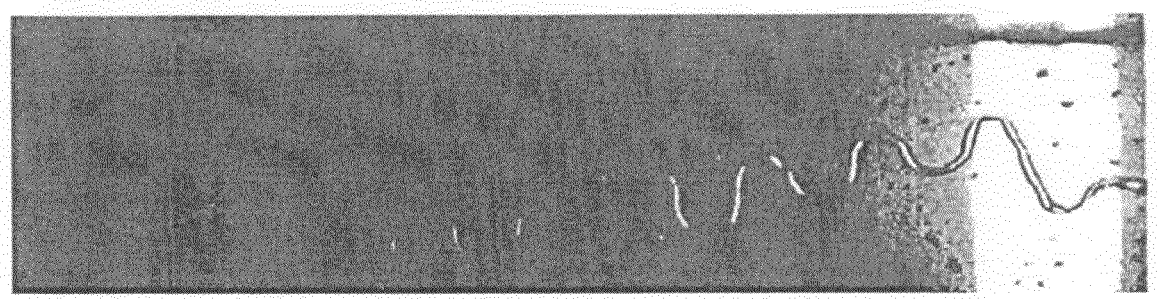
FIG. 3b is a reproduction of a photograph from a journal article illustrating meandering rivulet flow of liquid on an inclined flat plate in stationary gas.

At a somewhat larger liquid flowrate or inclination angle, there begin to be meandering shape of the liquid flow, which may change shape as a function of time. A meandering rivulet is illustrated in FIG. 3b, taken from the Schmuki reference.

The path of such a rivulet is curved in a somewhat irregular shape. Furthermore, it has been observed that a rivulet of liquid flowing down a smooth inclined plane can spontaneously "meander" or move in a zig-zag fashion in a direction perpendicular to the general direction of flow of the liquid, as a function of time. In other words, the shape of the rivulet changes. The situation may be such that the rivulet dynamically changes its position on the surface, possibly in a somewhat random or unstable manner as shown in FIG. 3a. In some situations it is possible that rivulets meander because of an instability which could be thought of as resembling the instability of a water-discharging hose whose end is unsecured, causing the hose to whip around somewhat randomly. This can be thought of as related to Rayleigh or other type of hydrodynamic instability. Such a hydrodynamic instability may depend in a complex fashion on the liquid flow rate, local contact angles (both advancing contact angle and receding contact angle), liquid viscosity, and incline angle of the flat plate among other things. In the paper by Grand-Pitiera, it is described that there is a "second critical flowrate Qc2" above which the shape of the meander is unstable and therefore the shape of the rivulet dynamically changes.

For purposes of cleaning interiors of passageways, it is believed that meandering rivulet flow is useful. In particular, the meandering of rivulets in which the position changes as a function of time is believed to be useful. It is particularly believed to be useful when the surface next to the rivulet is dry, thereby providing a three-phase contact interface which moves as shown in FIG. 3a. In this case the advancing and receding contact angles play a definite role regarding whether a rivulet is formed and the shape of the rivulet on the surface of the passageway.

Yet another feature of this flow situation is noted in several of the above references. As the energy or activity level increases still further beyond what has already been described, there is a regime in which the flow restabilizes and again basically moves in straight paths or approximately straight paths. Thus, in order to achieve dynamically meandering rivulets, it is not just a matter that certain parameters must be above a threshold, but rather the somewhat more complicated criterion that certain parameters must be above one threshold while also being below another threshold.

Differences Between Rivulets on a Flat Plate and Rivulets Inside a Channel

The literature referred to is for the situation of liquid flowing down an inclined flat plate surrounded by stationary gas. Relevant situations for cleaning endoscope channels or other luminal medical devices differ from this situation. The situation of a rivulet flowing in an interior of a horizontal passageway differs from the flat plate example in several ways. A rivulet on the interior surface of a passageway is illustrated in FIG. 4. One difference is that the passageway being cleaned may overall be substantially horizontal, which is a typical orientation of a passageway of an endoscope during cleaning. (This is not the only possible orientation of a passageway of an endoscope during cleaning; other possible orientations are discussed elsewhere herein.) Use of a horizontal orientation would remove the incline which was present in the flat plate situation as a driving force for forward motion of the liquid. As a substitute driving force for forward motion of liquid, there may be provided a gas flow inside the passageway along the length of the passageway. In such a situation, the gas may flow through the passageway at a velocity that is higher than the velocity of the liquid entities attached to the internal wall of the passageway, and may thereby exert a drag force on the liquid entities urging them to flow along the passageway. Rivulets may move generally along the direction of the gas flow, but due to meandering, rivulets may also have some variation of their overall position. For example, rivulets can meander so as to attain some motion along the internal surface of the passageway in a direction transverse to the direction of the gas flow.

Another difference is that, with the interior of the passageway being curved, in order for a rivulet at the bottom of the passageway (i.e., at the lowest elevation) to meander transversely to the longitudinal direction of the passageway, the rivulet would have to gain elevation in order to move transversely, i.e., it would have to climb the walls of the passageway by working against the force of gravity. For liquid to gain elevation requires work. Thus, it may be more difficult for a rivulet to move transversely inside a curved-cross-section passageway than it would be for a rivulet to simply move transversely on a flat plate without gaining elevation due to the transverse movement. Yet another difference is that there may be issues related to whether the passageway can provide sufficient cross-sectional area for gas flow, or whether a liquid entity might tend to occupy the entire cross-sectional area of a particular small-diameter passageway.

It is further believed that, in a passageway that is at least somewhat horizontal, a rivulet which tends to concentrate at the bottom of the passageway provides sort of a reservoir or source of liquid for generating fragmentary rivulets that may climb up the walls of the passageway. It is also believed that when a rivulet overtakes any other liquid entity so that the liquid entity merges with the rivulet, the rivulet may provide bulk transport that brings detached contaminants from the other liquid entity to the main rivulet at the bottom of the passageway. The main rivulet may thus serve to rapidly transport detached contaminants through the remaining portion of the passageway and out of the passageway.

Further Liquid Entities, and Conditions

Various forms of liquid entities and flow regimes are further illustrated in FIGS. 5a, 5b and 5c. These include rivulets as discussed but also other liquid entities as well. Still other liquid entities besides those illustrated schematically in FIG. 5a are also possible.

A simple meandering rivulet is illustrated as entity 8 of FIG. 5a and also as entity B of FIG. 5b. Although some rivulets may remain as a simple meandering rivulet, there is also the possibility that rivulets, because they involve instabilities, can fragment or break into sub-rivulets. This is illustrated as entity 6 of FIG. 5a, and is illustrated in illustration C of FIG. 5b.

Kinking of a rivulet or subdividing of a rivulet into additional rivulets is also believed to be a useful cleaning mechanism. In general, multiple rivulets may sweep more area than a single rivulet. The instability which causes rivulets to meander may also be at least partly responsible for rivulets breaking into sub-rivulets.

The breaking up of rivulets does not have to end with sub-rivulets but can still further lead a rivulet or a sub-rivulet to break up into a rivulet fragment. Rivulets or sub-rivulets can further break into isolated threads or "rivulet fragments." This is illustrated as entity 4 of FIG. 5a, and can also be seen in illustration D of FIG. 5b. These rivulet fragments, although not contiguous with the main bottom rivulet or meandering segments nevertheless may move along the internal surface of the tube under the drag force of the flowing gas.

It is still further possible that a rivulet, sub-rivulet or rivulet fragment can further break up into a succession of drops, which may continue to slide along the surface. This can be referred to as a linear droplet array. This is illustrated as the group of three of entity 2 in FIG. 5a, and can also be seen in illustration D of FIG. 5b. Such-drops may exist on the internal surface of the passageway and may be able to move along the internal surface of the passageway. However, it is believed that in general rivulets may be able to move at a greater velocity than isolated droplets and may be able to sweep at a greater velocity than isolated droplets, and may therefore accomplish cleaning faster than droplets. For example, rivulets may be more able to sweep the surface with a three-phase interface in a direction transverse to the overall flow direction, and sub-rivulets or rivulet fragments may also be able to sweep in the direction of longitudinal motion. Droplets may move just in the general direction of flow and may sweep in that direction, but perhaps at a smaller rate of motion and sweeping compared to rivulets.

All of these liquid entities, and any others that might form, can continue to move along the internal surface of the passageway along the longitudinal direction or transversely or any combination thereof, and can sweep passageway internal surface as they do so.

It is further possible that a meandering rivulet may overtake and swallow up isolated droplets or arrays of droplets, may swallow up a rivulet fragment or branched rivulet. These entities may then re-join a larger rivulet. Such a process may be useful also for providing bulk transport of detached contaminants out of the passageway being cleaned.

Any of these entities may be referred to as a sliding or moving liquid entity.

This process may in effect be repeated many times during the cleaning the surface of the passageway. Another possible advantage of meandering rivulet would be to remove liquid film from the surface and provides necessary conditions for cleaning with the three phase contact interface by other moving liquid entities.

It is believed, although it is not wished to be restricted to this explanation, that when a rivulet or other liquid entity changes position, and a previously dry piece of surface becomes wet as a rivulet reaches it, or when a rivulet leaves a surface which it has wetted, there may be generated a force to dislodge a contaminant from the surface.

At a still greater level of detail, it can be realized that the gas flowing longitudinally in the passageway is compressible. For a constant cross-section passageway and a generally constant temperature, gas at a more upstream location generally has a larger density and smaller velocity and gas at a more downstream location has a smaller density and a larger velocity. Thus, the conditions which might drive motion of the rivulets (either longitudinally or transversely) and which might influence the formation of liquid entities in general are not identical everywhere along the length of a passageway. It has been discovered during the present work that the flow parameters which produced optimal rivulet flow and fragmentation for cleaning depended among other things, upon the internal diameter and length of passageway being cleaned, position along the length of the passageway, and the surfactant composition of the cleaning liquid (FIG. 5c). This is further illustrated elsewhere herein.

Taking various considerations into account, there are described elsewhere herein conditions that are favorable for the formation of rivulet droplet flow such as meandering rivulets, fragmenting rivulets, drops and other forms of sliding liquid entities that are favorable for cleaning. The apparatus may be such as to deliver liquid flowrate and a gas flowrate appropriate to operate in the desired regime at at least some places along a passageway.

It has been experimentally found (photographically) in the present work that at 30 psig gas pressure, for a 1.8 mm inside diameter passageway 2 m long, the longitudinal sliding velocity of a rivulet can be, from 1 cm/sec to 10 cm/sec with a mean of perhaps 2 to 3 cm/sec. For a 2.8 mm inside diameter passageway, the longitudinal sliding velocity of a rivulet can be, from 5 cm/sec to 20 cm/sec with a mean of perhaps 12.5 cm/sec. For a 3.8 mm inside diameter passageway, the longitudinal sliding velocity of a rivulet can be, from 7 cm/sec to 35 cm/sec with a mean of perhaps 22 cm/sec. These velocities were measured for liquid entities having dimensions of the order of 100 microns. Larger entities could have even faster velocities.

Corresponding to these, for a meandering rivulet, the transverse velocity may be as large as 25% to 50% of the longitudinal velocity.

For still other modes of flow or cleaning, other than meandering rivulets, it is possible to achieve still larger velocities of surface flow entities. Also, for a flow mode such as plug flow, larger velocities of moving meniscus or surface flow entities are also possible.

The overall effect of the sliding of these surface flow entities may be the sweeping of the surface of the channel by multiple moving three-phase contact interfaces and menisci. The internal surface of the passageway may be swept with a variety of liquid surface flow entities including meandering rivulets, sub-rivulets, rivulet fragments, linear droplets arrays and individual droplets of various sizes all in contact with the surface of the channel. Each of these entities may have an associated three-phase gas/liquid/solid contact interface and meniscus. It is believed, although it is not desired to be limited to this explanation, that the existence of a three-phase boundary and air/water interface (meniscus) create localized forces that can act to detach a contaminant from a surface. This may especially be true if the three-phase boundary is moving relative to the contaminant. The three phases may be the solid contaminant, and an edge of a liquid, and a gas. At least some of the surface may be dry or nearly dry some of the time during the cleaning process. It can be helpful if the surface of the channel is at least somewhat hydrophobic. The three phases can also be the liquid surface, the gas, and the solid surface which may be dry where it is not wetted by the liquid entity.

It is possible that different flow regimes may exist in different portions of a given passageway, and flow may transition from one flow regime or mode to another. At any given location, more than one flow regime may coexist, e.g., some drops and some rivulets. At different locations along a passageway, different regimes or combinations of regimes may exist.

It is the nature of multi-phase flow to be complex and somewhat statistical in nature and somewhat unpredictable, and more specifically for the geometry and behavior of liquid entities that are attached to the surface of the channel to be somewhat statistical in nature and somewhat unpredictable. Some of the behavior may be driven by fluid instabilities on the surface of the passageway (rather than bulk effects in the core of the passageway) which are inherently somewhat unpredictable. Empirical data is important in the science of multi-phase flow.

As examples of what can be observed, FIG. 5b shows both photographic examples and line drawings of five different types of flow. These are approximately in order of wetness. FIG. 5b Illustration A shows isolated droplets, which would be the case for a flow of liquid and gas which is somewhat dry, with not enough liquid to sustain a stream. FIG. 5b Illustration B shows a meandering rivulet. Occasional isolated droplets are also shown. FIG. 5b Illustration C shows meandering rivulet which also is fragmenting into sub-rivulets. FIG. 5b Illustration D shows rivulets that co-exist with linear droplet arrays. In this illustration, the rivulets have somewhat straightened out. FIG. 5b Illustration E shows a flow with so much liquid that the tube wall which is mostly wet and there are essentially no dry regions to help define rivulets, droplets or any other liquid entities.

At relatively high liquid flow rates or gas flowrates is yet another possible flow regime which is not illustrated, namely foam. In present situations, if foam forms anywhere it tends to form near the exit of the passageway, and may extend for some distance back toward the inlet. If foam forms, the passageway surface where foam is present can become covered with liquid film with no chance to form three-phase contact interface. For present purposes, it has been found that generally foam suppress cleaning employing the present method. This is probably because the presence of foam discourages the formation of discrete wet and dry regions exhibiting a contact interface therebetween. Also, the presence of foam can increase overall flow resistance for gas flow. The formation of foam can be significantly influenced by the nature of the surfactant used, as discussed elsewhere herein.

FIG. 5c shows the same illustrations arranged in lengthwise sequence. Sometimes some of the same sequence is observed spatially as one progresses downstream along a passageway. The liquid first flow as meandering rivulet, then as rivulets that break up, and later as straight rivulets. This sequence of events may be driven at least in part by the tendency for the gas velocity to increase as one progresses downstream along a passageway. Eventually as one progresses downstream the gas velocity increases beyond an upper threshold for meandering and the rivulets or rivulet fragments become generally straight. However, this is only representative, and events do not have to happen exactly as described here.

Rivulet droplet flow (RDF) may be considered to comprise either rivulets or droplets or both in any combination. Rivulet droplet flow may include any one or more of meandering rivulets, sub-rivulets, fragments of rivulets, and arrays of drops, and individual drops. Rivulet droplet flow may be formed, as described elsewhere herein, by supplying liquid and gas to a passageway wherein both the liquid and the gas are supplied at substantially constant flowrates. Alternatively, as also described elsewhere herein, rivulet droplet flow may be formed by supplying liquid and gas to a passageway such that the flowrate of at least one of the supplied liquid and the supplied gas is time-varying. This can include plug rivulet droplet flow.

When it is discussed herein that it is desirable for a surface to de-wet, this can be accomplished through either or both of the following mechanisms. If by its nature a surface is sufficiently hydrophobic with respect to the liquid passing over it, the surface may become substantially dry as soon as a liquid entity finishes passing over it. On the other hand, it is possible that a surface may still be somewhat wet after a liquid entity has finished passing over it, but due to evaporation the surface still becomes substantially dry with the passage of time after a liquid entity has finished passing over the surface. When the term dry is used herein, it is intended to include any of these meanings.

Photographs and Flow Maps

The regimes of gas and liquid flow have been studied empirically by carrying out systematic microscopic observations through straight transparent Teflon® tubes of various diameters under various liquid and gas flow rates at different distances from the inlet of the tube. This has included still photography and high-speed motion photography as well as stroboscopic illumination with multiple-exposure photography. Photographs were taken looking vertically downward through the wall of a clear horizontally oriented tube. By varying the focal plane of the optics, the flow along either the top or bottom hemicylindrical surfaces of the tube could be observed. All photographs presented here were taken of the top surface. Sequential images as a function of time could be analyzed so that the flow and flow entities could be analyzed over time and their movements tracked.

Experimental observations are further illustrated in FIGS. 6a, 6b and 6c, which is only a small subset of a large amount of photographic data. For the illustrated photographs, the gas flow was air. The flow exited the downstream end of the passageway at atmospheric pressure. The gas flow was supplied to the inlet of the passageway at a pressure of 30 psig. For the photographs and the flow regime maps, both liquid and gas were supplied to the passageway at room temperature (approximately 20° C.). The length of the passageway was 2 m. All of these photographs are taken for a particular diameter of passageway, which was 4.5 mm. As discussed elsewhere herein the fluid mechanics can be influenced by details of the surfactant which is added to the water.

For generating the photographs in FIG. 6, the test solution was water containing the following additives:
Sodium Triphosphate, (Fisher Scientific) 30 g/L;
Sodium Silicate, (Fisher Scientific) 1.3 g/L;
Tomah AO-455 made by Air Products—0.24 g/L;
Surfynol 485W made by Tomah-Air Products—0.36 g/L.
The surface tension of this composition at room temperature was approximately 38 to 44 dyne/cm. It is believed that this composition gives good fragmentation and not so many surviving sub-rivulets, but rather rivulet fragments.

FIG. 6 shows photographs of flow conditions in a passageway having an internal diameter of 4.5 mm. Conditions are shown at five different locations along a total flow length of 2 m.

FIG. 6a shows hydrodynamic conditions for a liquid flowrate of 20 milliliters/minute, which is considered to be undesirably small and therefore less effective for cleaning (treatment number is small). In such a situation, there is a fairly large proportion of isolated droplets rather than rivulets, and the isolated droplets slide along the surface at a relatively smaller velocity than the rivulets, producing a slower rate of cleaning which may lengthen process time. Cleaning may occur at places where the three phase contact interface passes by due to the sliding of these liquid entities, but the fact that there are not so many of these liquid entities, and the fact that the entities are mostly drops, which move somewhat slowly, may limit the achievement of cleaning in a reasonable time (2-10 minutes).

FIG. 6b shows hydrodynamic conditions for a liquid flowrate of 45 ml/minute, which was considered to produce good cleaning.

FIG. 6c shows hydrodynamic conditions for a liquid flowrate of 70 ml/minute, which is considered to be undesirably large and therefore less effective for cleaning. In such a situation, the internal surface of the passageway may be wet a large fraction of the time so that there is not a sufficiently frequent occurrence of a dry or substantially dry surface so as to achieve a moving three-phase contact interface. This is believed to limit the achievement of cleaning if the surface is as wet as is shown in FIG. 6c. It is not wished to be limited to these explanations, however.

Conditions which are conducive to achieving cleaning by moving solid-liquid-gas interfaces flow can be further described by parameter diagrams which describe a flow regime for particular input flow and dimensional conditions. The photographic information such as illustrated in FIG. 6a, 6b, 6c were all taken for a particular passageway inside diameter (4.5 mm) but even that information provides only a few of the many data points needed to construct such a diagram.

For reference, the conditions illustrated in FIG. 6a (a low flowrate of 20 milliliters/minute) are characterized as being more in the nature of isolated droplets (sparse) rather than rivulets. The isolated droplets have slower sliding velocity than rivulets and there are fewer of them, and for these reasons there is somewhat limited opportunity to accomplish cleaning by moving three-phase contact interfaces. The conditions illustrated in FIG. 6b (a medium flowrate of 45 milliliters/minute) are characterized as being rivulet droplet flow with some rivulet fragments and some drops, which provides good cleaning. The rivulets sweep area with three-phase contact interfaces at a desirable rate and therefore accomplish cleaning. The conditions illustrated in FIG. 6c (a high flowrate of 70 milliliters/minute) are characterized as being overly wet flow, such that there are not so many places on the passageway internal surface that are actually dry at any given time, and for that reason there is somewhat limited opportunity to accomplish cleaning by moving three-phase contact interfaces.

As can be understood, a multitude of such observations are used to construct a flow diagram such as is given in FIG. 7. Such a diagram may be unique to a particular passageway inside diameter or range of inside diameters. Flow regime maps for five different passageway inside diameters are given in FIGS. 7a through 7e.

As mentioned, the photographs were taken for an inlet air pressure of 30 psi, which for many channels of many endoscopes is approximately a maximum allowable input pressure. In order to have flow conductive to cleaning, it may be aimed that conditions be chosen which provide rivulets and rivulet fragments in much of the passageway and droplets in places where rivulet flow is not achieved. This may be termed rivulet droplet flow. As can be seen from the maps, choosing a particular liquid flowrate does not guarantee the same flow regime will exist all the way from the beginning (inlet) to the end (exit) of the passageway. Also, the five maps are presented for five different passageway inside diameters, and it can be seen that the maps differ from each other both qualitatively and quantitatively as a function of the inside diameter of the passageway.

In order to help summarize and collect the information presented in FIGS. 7a through 7e, some representative useful ranges of liquid flowrates from FIGS. 7a through 7e are selected and are plotted in FIG. 8. These are flowrates which provide rivulet droplet flow for a significant portion of the length of the particular passageway, although not necessarily the entire length of the passageway. These flowrates are somewhat optimum for achieving rivulet droplet flow for the respective passageway inside diameter, although it is not to be implied that these are the only liquid flowrates that could be useful for cleaning. It also may be kept in mind that these data may be somewhat specific to still other operating parameters including but not limited to surfactant composition, flowpath length, inlet gas pressure, and other parameters.

Although FIG. 8 presents specific numerical values of liquid flowrate associated with specific numerical values of passageway inside diameter, it is also possible to describe desirable liquid flowrates in terms of volumetric liquid flowrate per unit of perimeter of the passageway. This is in recognition of the fact that the liquid flow primarily attaches to the perimeter of the passageway.

For example, for a relatively large passageway of inside diameter 6 mm, a representative useful range of liquid flowrate is 30 to 65 ml/minute. For such a passageway, the inside perimeter is 18.84 mm. The corresponding liquid flowrate per unit of internal perimeter is from 30/18084 or 1.59, to 65/18.84 or 3.45 ml/minute per mm of perimeter.

For a passageway of inside diameter 4.5 mm, as depicted in FIG. 6, a representative useful range of liquid flowrate is 15 to 40 ml/minute. For such a passageway, the inside perimeter is 14.13 mm. The corresponding liquid flowrate per unit of internal perimeter is from 15/14.13 or 1.06, to 40/14.13 or 2.83 ml/minute per mm of perimeter.

Similarly, for a 2.8 mm inside diameter passageway, a representative useful range of liquid flowrate is 15 to 25 ml/minute. This passageway has an inside perimeter of 8.79 mm. The liquid flowrate per unit of internal perimeter is 15/8.79 or 1.71, to 25/8.79 or 2.84 ml/minute per mm of perimeter.

Similarly, for a 1.8 mm inside diameter passageway, a representative useful range of liquid flowrate is 6 to 10 ml/minute. This passageway has an inside perimeter of 5.65 mm. The liquid flowrate per unit of internal perimeter is from 6/5.65 or 1.06, to 10/5.65 or 1.77 ml/minute per mm of perimeter.

Similarly, for a 0.6 mm inside diameter passageway, a representative useful range of liquid flowrate is 5 to 10 ml/minute. This passageway has an inside perimeter of 1.88 mm. The liquid flowrate per unit of internal perimeter is from 5/1.88 or 2.66, to 10/1.88 or 5.32 ml/minute per mm of perimeter.

Combining these observations, it can be seen that this perimeter-normalized liquid flowrate clusters in a range of from about 1.5 to 4 milliliters/minute per mm of perimeter, or, defined slightly more broadly, in the range of from approximately 1 to approximately 5 milliliters/minute per mm of perimeter.

It can also be noted that for achieving meandering rivulets, a desirable gas velocity may be in the range of approximately 5 m/s to approximately 15 m/s at least somewhere along the length of the passageway. Meandering rivulets are useful but are not absolutely required for achieving good cleaning in a reasonable time. Another gas velocity range that may be useful for cleaning is a broader range that is appropriate for achieving fragmentation and sliding liquid entities or surface flow entities on the wall of the passageway may be from approximately 2 m/s to 80 m/s depending on the diameter of the passageway.

It can be noted that the flow regime can depend on at least the liquid flowrate, the gas flowrate, the position along the length of the passageway, and the inside diameter of the passageway. The flow regime can depend on the overall length of the passageway at least because the overall length can affect the gas flowrate given a typical maximum supply pressure of the gas. Surfactant composition and concentration can also affect the flow regime. The data presented in FIGS. 6, 7 and 8 were obtained for input liquid flow and gas flow which were both steady with respect to time.

Still further data about flow regimes is presented in FIG. 9. It may be recalled that FIGS. 6, 7 and 8 all are for data taken at an inlet air pressure of 30 psig. That was a maximum allowable air pressure for typical channels of typical endoscopes. However, it is also possible to operate at inlet air supply pressures less than the maximum allowable pressure. This may be considered in view of the suggestion from the literature that meandering may occur within a specific operating range, rather than there being a simple threshold above which meandering always occurs. This is discussed elsewhere herein. For the data presented in FIG. 9, both inlet air pressure and liquid flowrate were varied. Again, several different passageway diameters were used as indicated. The passageway length was 2 meters. The composition of the liquid was the same as was used for FIGS. 6, 7 and 8.

It can be appreciated from FIGS. 9a and 9b that it may not be possible to achieve meandering rivulet flow everywhere along the length of the passageway, especially with a single liquid flowrate. Also, meandering occurs for some gas supply pressures such as moderate pressures but not for other pressures such as more extremely high or low gas supply pressures. Meandering rivulet flow is useful for cleaning, but is not the only useful flow regime. Rivulet droplet flow is also useful. Straight rivulet flow is believed to be not so useful for cleaning, because not much sweeping occurs nor does fragmentation of rivulets occur. Foam/film also is not believed to be useful for cleaning because it basically impedes flow and perhaps also keeps the surface wet. However, it is not wished to be limited to this explanation. In FIG. 9, the following notation is used. Y means achieving meandering rivulet flow suitable for cleaning. R means RDF (rivulet droplet flow) which is believed to be useful for cleaning; S means a straight rivulet with no meandering, which is believed to be not so useful for cleaning; F means film/foam, which is believed to be not so useful for cleaning.

It can be appreciated that FIG. 9a and 9b illustrate an observation that is consistent with the observations of the fluid mechanics literature for inclined flat plates in stationary gas. Achieving meandering rivulets is not just a matter of operating above a certain lower threshold so as to enter a region of instability. In addition to the existence of a lower threshold, there can also be an upper threshold, such that it is also necessary to remain below the upper threshold in order to have meandering rivulets.

One parameter that the upper threshold can pertain to is gas velocity. It has been discussed elsewhere herein that as compressible gas flows along a long passageway, the gas velocity increases. Thus, it is possible that even if meandering rivulets exist in a middle portion along a length of a passageway, as one approaches the exit of a long passageway, the gas velocity may become so large that it re-stabilizes the rivulets. It is furthermore possible that even if meandering rivulets exist in a middle portion along a length of a passageway, the gas velocity very near the inlet may be too small to create meandering rivulets. This helps explain why in some regions along the length of passageways in FIGS. 9a and 9b, meandering rivulet flow exists only at certain places along the passageway.

Gas velocity is somewhat related to supplied inlet gas pressure. Therefore, it is possible that a supplied inlet gas pressure could be too small to create meandering rivulets anywhere in the passageway, or could be too large to create meandering rivulets anywhere in the passageway. Similarly, it is possible that a supplied liquid flowrate could be too small to create meandering rivulets anywhere in the passageway, or could be too large to create meandering rivulets anywhere in the passageway. These conditions also are a function at least of the inside diameter of the passageway being cleaned. These criteria also are a function of the surfactant and composition of the cleaning liquid used.

For typical operating conditions, a range of gas velocity that is conducive to meandering rivulets is from approximately 5 m/sec to approximately 15 m/s. In an embodiment of the invention, the operating conditions may be such as to operate in this range for at least a portion of the length of the passageway.

It can also be observed from FIG. 9 that there are optimum values of liquid flowrate. If the liquid flowrate is too small or too large, meandering rivulets may not be achieved or may only be achieved for a limited portion of the length of the passageway.

It is believed, although it is not wished to be limited to this observation, that for larger inside diameters in the range of interest, the range of liquid flowrates acceptable for achieving cleaning is relatively wide, and for smaller inside diameters in the range of interest, the range of liquid flowrate acceptable for achieving cleaning is relatively narrow.

In view of the observations such as presented in FIGS. 6, 7, 8 and 9, in embodiments of the invention, the apparatus may be configured so as to provide a gas flowrate and a liquid flowrate that are in a proper relationship to each other so as to provide a desired rivulet-droplet flow regime of liquid and gas. In view of the observations such as presented in FIG. 9, in embodiments of the invention, the apparatus may be configured so as to provide a gas flowrate and a liquid flowrate that are in a proper relationship to each other so as to provide a meandering rivulet flow regime of liquid and gas, at least in some portions of the length of the passageway. However, meandering is not essential to achieving good cleaning.

The flow regime may be such as to provide rivulets which slide along the internal surfaces of the passageway being cleaned, or at least on a portion of the internal surfaces of the passageway being cleaned. It is further possible that rivulets may subdivide into sub-rivulets. Such division into sub-rivulets may occur at kinks or points of curvature of a rivulet. It is possible that sub-rivulets may further break into rivulet fragments, being still smaller than sub-rivulets. It is possible that rivulet fragments may in turn break into an array of drops. All of these entities may be able to move along the internal surface of the passageway being cleaned. The flow regime may be such as to provide meandering rivulets which are unsteady in time on the internal surfaces of the passageway being cleaned, or at least on a portion of the internal surfaces of the passageway being cleaned, although meandering is not essential.

As still further guidance for achieving appropriate flow regimes, it is possible that flow of liquid cleaning medium suspended as droplets in the gas prior to entering the passageway may be less than 10% of the total flow of liquid cleaning medium, and may be less than 1% of the flow of liquid cleaning medium. That is to say the volume of liquid flowing through the internal channel may be predominantly in the form of rivulets and surface flow entities fragmented from these rivulets.

It is possible that at the exit of the passageway, flow of liquid cleaning medium suspended as droplets in the gas may be less than 50% of the total flow of liquid cleaning medium, or less than 10% of the flow of liquid cleaning medium, or less than 5% or less than 1%.

It is possible that at the exit of the passageway, the amount of liquid which is in the form of foam may be less than 10% of the total flow of liquid, or less than 1% of the total flow of liquid.

Multi-Stage Cleaning

As described, an aim can be to achieve a desired flow regime such as rivulet flow and moving liquid flow entities with three-phase contact interface essentially everywhere along the length of the passageway. If a desired flow regime is achieved at only a portion of the length of the passageway, that can still be useful, but achieving the desired flow regime everywhere along the length of the passageway would be more convenient. This can be adjusted, among other ways, by adjusting the liquid flow rate.

However, it may not be possible to provide desired cleaning conditions for the entire length of the passageway using a single set of operating conditions. If this is the case, then another possible strategy may be to perform cleaning of a first portion of a length of a passageway using a first set of parameters that are appropriate for cleaning a first portion of the length of the passageway, followed by performing cleaning of a second portion of the length of the passageway using a second set of parameters that are appropriate for cleaning the second length of the same passageway. Cleaning conditions for different passageways could differ in inlet air pressure, or in liquid flowrate, or both, or in other parameters.

If such a multi-stage cleaning process is used, it is possible that the portion of the passageway which is cleaned first may be upstream of the portion of the passageway which is cleaned later. That way, contaminants and debris which are dislodged from the later-cleaned portion of the passageway may be expected to wash downstream and out of the passageway without possibly contaminating the earlier-cleaned portion of the passageway.

It can be appreciated that all of the data presented in FIGS. 6, 7, 8 and 9 are for constant operating conditions, i.e., constant inputted flowrate of liquid and constant inputted flowrate of gas.

Additional Strategies for Specific Portions of Internal Surface, and Unsteady Flow Inputs It may be appreciated from the preceding discussion that for a horizontally oriented passageway (which is a possible orientation of a channel of an endoscope being cleaned), it may be more difficult for rivulets to reach the upper surface (ceiling) of a substantially horizontal passageway than it is to reach lower-elevation portions. This may be especially true for a relatively large-diameter passageway. Thus, it is possible that the ceiling could be undesirably dry. In addition, there is another basic possible problem, which is that it is likely that the lowest-elevation portion of the passageway (floor) is wet an undesirably large percentage of the time during a cleaning process, and therefore the floor may be less likely to receive sweeping by three-phase contact interfaces involving alternation of wetness and dryness.

Still another consideration, apart from comparison between floor and ceiling, is that a passageway may experience an inlet or developing-flow region where desired flow regimes might not be immediately established at the inlet of the passageway, at least for certain operating conditions. This phenomenon is illustrated in FIGS. 9a and 9b, and it can also be somewhat seen in FIG. 6 that flow regimes can change as a function of position along the length of the passageway.

Accordingly, another basic strategy is that the apparatus may be such as to provide time-varying wetness and dryness conditions for certain portions of the passageway internal surface by providing time-varying input flow conditions. In general it is desired that the apparatus provide liquid entities that have three phase contact interface that will sweep the entire internal surface of the passageway at least once at some time or another during a reasonable cleaning time. It is also possible to design that the internal surface be swept multiple times during a treatment. Without such manipulation some sections of the passageway may not receive sufficient treatment number as others.

FIG. 10a illustrates, with respect to one of the flow maps of FIG. 7, that desirable rivulet droplet flow may be achieved for more downstream regions along the length of the passageway, but are not achieved for some of the more upstream regions of the length of the passageway. This may provide impetus for use of a cleaning mechanism involving non-steady-state input of either liquid flow or gas flow or both.

Some fluid mechanic considerations relating to surface tension are illustrated in FIG. 10b, 10c, 10d, 10e. The passageways shown in FIG. 10b, 10c, 10d, 10e are substantially horizontal, although the same discussion is also at least somewhat applicable to passageways of other orientation.

For passageways of a small inside diameter that contain both liquid and gas under static conditions, a possible situation is the situation in which a meniscus bridges across the entire cross-section of the passageway. This is illustrated in FIG. 10b. FIG. 10b shows a dynamic situation in which the liquid is moving in the direction indicated, displaying advancing and receding contact angles. (If the situation were static, the menisci on each sides would be essentially symmetric with each other.)

There is also a larger range of internal dimension of passageway which do not support the type of meniscus illustrated in FIG. 10b. For such larger passageways that contain both liquid and gas under static conditions, the passageway cannot support a meniscus across the entire passageway, but rather there will naturally be a configuration in which liquid collects at the bottom of the passageway and the rest of the passageway cross-section is substantially occupied by gas. This is illustrated in FIG. 10c. The distinction between the situation of FIG. 10b and the situation of FIG. 10c can be understood with reference to a critical inside diameter, which is the borderline between the two situations. The critical inside diameter is a function of the surface tension and other properties of the liquid. For pure water, the critical inside diameter is approximately 1.8 mm.

For passageways having an inside diameter greater than this critical inside diameter, it may be still possible to attain a cross-section fully or mostly filled with liquid, in a dynamic situation, by causing liquid to flow for a period of time, such that for at least a portion of the liquid flow there is liquid substantially completely filling the cross-section of the passageway. This may produce essentially a moving plug of liquid, whose meniscus sweeps internal surfaces of the passageway. The periods of liquid flow may be separated by a periods of gas flow that are of long enough duration to effectively separate the liquid entities from each other, and possibly also to create dryout of passageway internal surfaces between passage of successive liquid plugs. This is illustrated in FIG. 10d. This pattern may be repeated as many times as desired. This fluid flow regime is termed discontinuous plug flow (DPF). The velocity of the moving meniscus in this case may be several meters per second depending on the gas pressure, tube diameter and the length of the liquid plug among other factors. The high sliding velocities generated in this case were found to produce effective cleaning of passageways according to the mechanisms described herein.

Referring now to FIG. 10e, it is illustrated that as a plug progresses to a further downstream portion of a passageway, the leading face of the plug may become irregular even if the plug started out fairly regularly shaped as shown in FIG. 10d. This increasing irregularity of the leading face of the plug can be due to surface instabilities due to gravity, Rayleigh instabilities etc. In FIG. 10e it is also shown that the plug may spread preferentially toward the bottom of the passageway due to gravity. It is believed that irregularity at the leading edge of the plug can be helpful for creating liquid entities that are useful for cleaning the internal surfaces of the passageway. If at least some portion of the plug breaks up into smaller liquid entities, that is believed to be useful for cleaning the internal surfaces of the passageway. This regime may be termed discontinuous plug droplet flow (DPDF).

It is still further possible that still other flow regimes can be used which accomplish a moving three-phase interface using alternating periods of liquid flow and gas flow of liquid and gas, or other flow variants, as described elsewhere herein. It is still further possible that combinations or sequences of these described fluid flow regimes may be used, possibly also involving periods or sequences of rivulet droplet flow, in any desired sequence or combination.

Time-varying input flow characteristics are illustrated in FIG. 11.

First, in FIG. 11 there is illustrated, for reference, steady-state flow inputs such as were used for generating FIG. 6 through FIG. 9.

Next, there are illustrated various forms of non-steady-state supply of either liquid or gas of both, which may produce useful forms of rivulet droplet flow under conditions other than steady-state or quasi-steady-state conditions.

One of the timelines in FIG. 11 illustrates alternating switching on and off of gas flow and liquid flow. For example, there may be provided a liquid pulse having a duration of approximately 1 second to 3 seconds. Following a liquid pulse, in order to achieve dryout of passageway internal surfaces prior to re-exposure to liquid, there may be provided a duration of dry or warm or dehumidified air having a duration of approximately 5 seconds to 15 seconds, appropriate to achieve dryout or de-wetting of the passageway internal surface. In this timeline, at any given instant, either liquid is supplied or gas is supplied but never both. This can be described as plug flow or plug rivulet droplet flow.

It is also illustrated that it is possible to pulse either one of the supplies while the other supply remains on. For example, liquid supply could be pulsed while gas is remains on, or gas could be pulsed while liquid remains on.

It is possible to perform pulsed liquid flow followed by continuous liquid flow, or in general to perform any sequence of unsteady liquid flow and steady liquid in any sequence.

Of course, even though these illustrations show one flowrate going exactly to zero during certain time periods, for phenomena that do not involve dryout, it is possible for variations to be more general and not necessarily involve decreasing exactly to zero.

As yet another possibility, it is possible to use a first gas supply pressure at a time to promote formation of liquid entities, and then to change to another gas supply pressure for a period of time to cause the motion of these entities along the passageway. The second pressure could be smaller than the first, although the opposite is also possible. It is further possible that during whatever time a lower gas supply pressure is used in cleaning one channel, there could be performed in another channel a flow that requires a relatively high gas source pressure. This could be performed in such a way that the total demand for gas at any instant throughout the entire reprocessing cycle is less than it would be if peak demands for gas flow occurred simultaneously with each other.

Various possible sequences are also described in the following Table 1A.

TABLE 1

|  | Cycle 1 | Cycle 2 | Cycle 3 |
| --- | --- | --- | --- |
| Pulsing Mode 1: | | | |
| Air OFF/Liquid ON | 10 sec | 8 sec | 6 sec |
| Air ON/Liquid OFF | 10 sec | 12 sec | 3 sec |
| Pulsing Mode 2: | | | |
| Air OFF/Liquid ON | 10 sec | 8 sec | 6 sec |
| Air ON/Liquid ON | 10 sec | 12 sec | 3 sec |
| Pulsing Mode 3: | | | |
| Air ON/Liquid ON | 0.3-3 sec | | |
| Air ON/Liquid OFF | 0.3-3 sec | | |

The waveforms or sequences of liquid flowrate which are repeated do not have to be as simple as a substantially constant "on" value of flowrate followed by a zero flowrate for the "off" situation. More generally, the waveform of liquid flowrate could be triangular waveforms, trapezoidal waveforms, sinusoidal waveforms, or other waveforms. The waveforms describing the liquid flow could have a monotonically increasing portion, optionally followed by a constant portion, and followed by a monotonically decreasing portion. There could be a dry interval between waveforms of liquid flow, but more generally there does not have to be such a dry interval. Waveforms of liquid flowrate could be repeated identically, or alternatively they do not have to be identical. The gas flowrate has been illustrated as being steady (constant flowrate), but it does not have to be. In this illustration, the "on" liquid flowrate is considered to be appropriate to achieve meandering rivulet flow in at least a portion of the length of the passageway being cleaned. These alteration in admitting the gas and liquid in the passageway may be considered to permit more meandering and more fragmentation during the cleaning or rinsing cycles.

Endoscopes are frequently cleaned such that the endoscope or at least a large portion of the endoscope is in the horizontal orientation. For any passageway but especially for a horizontal passageway, such random positioning of the meandering rivulet may be advantageous for achieving cleaning of the entire internal surface of the passageway. However, it is also possible that, especially in some of the larger diameter passageways, due to gravity there may be a tendency for rivulets to spend more time than average at or near the bottom of the cross-section of the passageway. This may deprive upwardly-located surfaces of cleaning because rivulets might not reach those surfaces sufficiently often, and those surfaces might not experience alternations of wetness and dryness sufficiently often because of being dry a high percentage of the time. Furthermore, the presence of a bottom rivulet may deprive bottom-located surfaces of cleaning because those surfaces may be wet a rather large portion of the time and those surfaces might not experience alternations of wetness and dryness sufficiently often because of being wet a high percentage of the time.

Accordingly, it is also possible to operate endoscope reprocessing apparatus such that passageway internal surfaces experience alternations of exposure to moving three phase contact line conditions by pushing alternate periods of liquid flow and gas flow through the passageway. The period of gas flow may be sufficiently long, and the gas as introduced may be sufficiently dry so that the internal surfaces of the channel substantially dry out (remaining liquid film thickness is more or less lower than the contaminant particle dimension) before the next introduction of liquid.

It is also possible that the period of liquid flow in this described strategy helps to flush out debris that has already been detached but has not yet been moved to the exit of the passageway.

Still a further possibility is that for a certain period there could be rivulet droplet flow using supplied flowrates of liquid and gas that are substantially steady-state, and for another period there could be a flow regime that includes any of the described regimes that involve non-steady-state fluid supply such as pulsed fluid supply (either gas or liquid). These periods of time could be combined in any sequence or combination.

Enhancement of Hydrodynamic Detachment by Decrease of Liquid Plug Length in DPF Mode When the liquid plug is shorter than passageway length, after it is separated from the liquid pump, it is driven by air pressure $P_a$. The resistance to flow will consist of two terms: i) resistance along the liquid plug and ii) resistance along the air portion in the passageway. Since the viscosity and density of air are significantly smaller than those of liquid, it may be possible to disregard the small pressure drop along air portion of tube. This simplification becomes crude when the length of water plug, $L_{pl}$, is extremely smaller than compared to the length of the passageway. This simplification can be illustrated by introduction the nominations for pressures on plug front $P_f$, plug rear $P_{re}$ and passageway inlet $P_a$, while the pressure at tube outlet is zero. Hence, $$P_a = P_f + (P_{re} - P_f) + P_a - P_{re} \quad (16)$$

$P_f \approx 0$ and $P_a - P_{re}$ are pressure drops within air and they may be disregarded as being proportional to small air viscosity (or inertia). Hence, we have on r.h.s. $P_{re} - P_f$, i.e. the pressure drop over plug $$P_f \approx 0 << P_a; \; P_a - P_{re} << P_a \quad (17)$$

Hence $$P_{re} - P_f = P_a \quad (18)$$

There is a balance between pressure drop applied to the liquid plug and shear stress, $\tau$, between plug and adjacent channel wall, area $2\pi R_t L_{pl}$ where $L_{pl}$ is the plug length. The total shear stress applied to the plug is $2\pi R_t L_{pl} \tau_{pl}$ is overcome due to applied pressure $P_{re} - P_{fr} = P_a$, i.e.

$$2\pi R_t L_{pl} \tau_{pl} = P_a (\pi R_t^2) \quad (19a)$$

or $$\tau_{pl} = P_a (R_t/2)(1/L_{pl}) \quad (19b)$$

This equation is valid, in particular, when the plug fills the entire tube, i.e. when $L_{pl} = L_t$ $$\tau_t = P_a (R_t/2)(1/L_t) \quad (20a)$$

However, at this initial moment the plug is yet not disconnected from the liquid pump, i.e. in this moment the plug is driven by pump pressure $P_{pu}$ $$\tau_t = P_{pu} (R_t/2)(1/L_t) \quad (20b)$$

For the sake of simplicity we assume that $$P_a = P_{pu} \quad (21)$$

which reduces two equations (19a) and (19b) to one. The joint consideration of Eqs (18) and (19a) shows that they have identical multiplier in the bracket. The ratio of l.h.s. of these equations equals to ratio of r.h.s., while the mentioned multiplier cancels $$\tau_{pl}/\tau_t = L_t/L_{pl} \quad (22a)$$

or $$\tau_{pl} = \tau_t (L_t/L_{pl}) \quad (22b)$$

Since the cleaning is caused by shear stress, the specification $\tau$ for either laminar or for turbulent regime is excessive. The Eq(22b) is valid for both regimes as well as for the laminar-turbulent transition mode. The equation shows that as the plug length decrease approximately 50 times, $\tau_{pl}$ increases 50 times. The further decrease $L_{pl}$ will lead to slower increase in $\tau_{pl}$ because the requirements expressed by Eq(17) fail. However, this requirement may be omitted and more general equation can be derived. It is noteworthy to note that $\tau_{pl}$ in Eq(22b) is shear stress of liquid flow for the condition of plug flow.

In order to clarify the effect of plug length influence on cleaning by hydrodynamic detachment near the three phase contact line, we need to consider the dependence of front meniscus velocity on plug length for turbulent or transition flow, especially for the case of suction channel because at 30 psi Reynolds number Re is rather high even for continuous liquid flow. For Pentax endoscope Model FG-36UX suction channel, using liquid velocity $U_o$=146 cm/sec yields $Re_o$= $(0.38 \times 146)/0.01$=5548, at 35 psi. For the water channel $Re_o$= $(0.18 \times 108)/0.01$=1950. With decreasing plug length, its velocity increases that causes Re increase and transition to turbulent flow even for water channel. Accordingly, we need to apply the main equation for turbulent flow in tubes, namely the equation for resistance coefficient for tube (L. D. Landau, E. M. Lifshits, "Mechanics of Continuous Media-Hydrodynamics", Adison-Wesley Publishing Company, 1958):

$$\lambda = P_a (2R_t/L_{pl})/(\tfrac{1}{2}) \rho U_{pl}^2 \tag{23}$$

Where $\rho$ is the density of liquid. The pressure, velocity and length are specified for the case of a short plug. $\lambda$ is a sophisticated function of Re. As we are interested in plug velocity dependence on its length, the Eq(23) is rewritten $$U_{pl} = (4P_a R_t / \rho \lambda_{pl})^{0.5} (1/L_{pl})^{0.5} \tag{24}$$

This equation is valid for extreme case when the plug length equals to tube length $$U_o = (4P_a R_t / \rho \lambda_t)^{0.5} 1/(1/L_t)^{0.5} \tag{25}$$

The ratio of r.h.s. equals to the ratio of l.h.s. that yields $$U_{pl}/U_o = (L_t/L_{pl})^{0.5} (\lambda_t / \lambda pl)^{0.5} \sim (L_t/L_{pl})^{0.5} \tag{26a}$$

FIG. 22 in (1. L. D. Landau, E. M. Lifshits, "Mechanics of Continuous Media-Hydrodynamics", Adison-Wesley Publishing Company, 1958) shows that the friction coefficient $\lambda$(Re) decreases less than twice in the Reynolds range 5000 to 30000. The Eq(11b) shows that the plug velocity increases as its length decrease $$U_{pl} = U_o (L_t/L_{pl})^{0.5} \tag{26b}$$

Table 1B shows the relationship between liquid plug length in the suction tube of a typical endoscope and plug sliding velocity that can be achieved during the DPF mode at two air pressures, 15 and 25 psig. The results of this analysis supports the inherent advantages of using the discontinuous modes to enhance the cleaning according to the instant invention. This is further supported by the results on Example 19.

TABLE 1B

Plug velocity as a function of plug length/total channel length at two pressures

| | Plug Velocity ($U_{pl}$), m/s | |
|---|---|---|
| ($L_{pl}/L_t \times 100$) | @15 psig | @25 psig |
| 1% | 11.0 | 17.0 |
| 5% | 4.9 | 7.6 |
| 10% | 3.5 | 5.4 |
| 20% | 2.5 | 3.8 |
| 30% | 2.0 | 3.1 |
| 40% | 1.7 | 2.7 |
| 50% | 1.6 | 2.4 |
| 100% | 1.1 ($U_0$) | 1.7 ($U_0$) |

Achieving Dryout and Dewetting

It is discussed herein that it is useful for surface adjacent to the rivulets or liquid entities to be substantially dry, and if alternating flow of liquid and gas is used, it is useful for the gas flow to be sufficiently long so that the internal surface substantially dries out before liquid flow is introduced again. Drying or de-wetting can occur by either or both of two mechanisms. One mechanism is that if the internal surface of the passageway is sufficiently hydrophobic, when the rivulet or liquid entity moves away from a particular portion of the surface, the surface will naturally de-wet due to the absence of the rivulet or liquid entity. Another mechanism is that if any of the surface remains wet or covered by a film of liquid, the liquid can evaporate. For this purpose it may be useful for the air to be supplied to the passageway in a condition which is dehumidified or warmer than room temperature or both. In such a situation, approximate times for the duration of the period of gas flow are as given here. These are for a passageway that is approximately 2 meters long, with air being supplied at an inlet pressure of approximately 28 psig at a temperature of about 40 C. For a passageway having an inside diameter of approximately 2.8 mm to 4 mm, a time period of 5 seconds to 7 seconds should be sufficient. For a passageway having an inside diameter of approximately 1 mm to 1.8 mm, a time period of approximately 15 seconds should be sufficient. Shorter time periods are possible if it is not necessary that the surface be absolutely dry, or if the surface is extremely hydrophobic such as Teflon® (polytetrafluoroethylene). It is also possible that de-wetting can be aided by the flowing gas simply pushing rivulets or liquid entities to the downstream end of the passageway, without replenishing them. The purpose of dewetting and drying is to prepare the surface such that optimal detachment force may be achieved by the mechanisms described in this invention. It is believed that the thickness of the residual liquid film remaining after passage of three phase contact line may be made less than the dimension of the contaminant particles. The dryout and dewetting may be represented by a statistical distribution and it may not be possible to achieve during every time after passage of three phase contact line. However, it is required to achieve high level cleaning according to this invention.

It is further possible that the endoscope could be cleaned while the endoscope is in a position other than horizontal. For example, the position could be vertical, such as vertical with flow in the downward direction. Still other orientations are also possible.

Composition of Cleaning Liquid Including Surfactant

So far we have discussed the physical parameters (gas and liquid flow rates, gas pressure, hydrophobicity of channel surface, etc.) that affect the performance of the present cleaning method and how these can be optimized for any channel width and length. However, the actual composition of the liquid cleaning medium also has an important role on the effectiveness of the instant cleaning process.

Surfactants

It may be desirable to include one or more surfactants in the cleaning medium. Surfactant mixtures have been found particularly useful. However, only limited classes of surfactants are useful. Based on numerous experimentation surfactants could be divided into three classes when tested in endoscope channels by the flow mapping as in FIGS. 7a to 7e.

Class I surfactants were observed to produce a wetting liquid film without foaming which prevented the rivulet droplet flow (RDF), discontinuous plug flow (DPF) or discontinuous plud droplet flow (DPDF) flow regime from fully developing even at a surfactant concentration of 0.05% by weight. These surfactants generally have both a low HLB (hydrophilic-lipophilic balance) and are water insoluble. Some nonionic alkyl ethoxylates where the alkyl group is linear or branched, some members of the PLURONIC®, REVERSE PLURONIC®, TETRONIC® and the REVERSE TETRONIC® series belong to this class. However, surprisingly the HLB quoted by the manufacturer alone was not sufficient to predict the formation of a wetting film on the hydrophobic channel, e.g., TEFLON®. However, when water solubility was also very low, a wetting film usually developed. Both HLB and water solubility appear to determine a surfactant potential to form wetting films in two-phase flow. HLB<9.2 and water insolubility normally lead to formation of a wetting film that covers the entire surface of the hydrophobic channel of endoscope at a surfactant concentration greater than about 0.05% by weight of liquid composition at 30 psi air pressure and low liquid flow rates. These surfactants are not desirable by themselves for cleaning by the instant invention since they do not produce surface flow entities having three phase contact line on the channel wall during flow.

Class II surfactants produce foam throughout the channel which also inhibits RDF (and DPDF) even at a low surfactant concentration of 0.05% by weight. These surfactants have a foaming potential as measured by an initial Ross-Miles foam height of greater than 50 mm at 0.1% concentration and were found to produce foam that fills the entire tube (cross-section and length). The Ross Miles foam test is a well known measure of the foaming potential of surfactants and is described in J. Ross and G. D. Miles, Am Soc for Testing Materials, Method D1173-53, Philadelphia Pa. 1953. Most anionic surfactants tend to fall in this class, except for hydrotropes which do not normally foam but also do not lower surface tension much below 50 to 55 dynes/cm. Most cationic and quaternary ammonium surfactants were also found to be fall into class II when introduced into narrow channels in the presence of gas flow. Alkyl (alcohol) ethoxylates, castor-oil ethoxylates, sodium dodecyl sulfate (SDS/SLS), alkyl phenyl sulfonates, octyl and nonyl phenol ethoxylates that have high Ross-Miles foam index, HLB>9 and lower surface tension to 25 to 35 dynes/cm are examples of this class.

Class III surfactants are those that when used individually produce the RDF and DPDF flow regimes and are desirable surfactants for cleaning and detachment by the instant method. These surfactants normally give liquid fragments at concentrations at or above 0.05% by weight. Class III surfactants normally have very low Ross-Miles Index foam height of less than 50 mm, preferably less 20 mm and more preferable below 5 mm or close to zero. Many surfactants even optimal ones tend to lose their ability to produce RDF flow above 0.1% concentration either because of the formation of some foam or wetting films.

Several general conclusions can be drawn from our experimental observations with respect to surfactants and RDF/DPDF flow regimes.

Suitable surfactants for DRF/DPF tend to be mostly nonionic and various alkoxylated surfactants although some low foaming anionic surfactants are also suitable.

Surfactants that produce a surface tension greater than 50 dynes/cm tends to produce poor liquid fragmentation on channel wall. Although the level of fragmentation is better than that with water, such surfactants only achieve low treatment number. They normally lack detergency to solubilize and desorb the organic soils encountered in dirty endoscopes. These types of weakly surface active surfactants include hydrotropes such as xylene sulfonate, hexyl sulfate, octyl sulfate and ethyl hexyl sulfates, or short alkyl ethoxylates and other similar nonionic or cationic agents. The liquid fragments are usually oval-shaped and do not produce linear droplet array at their trailing ends. The advancing and receding contact angles are high (e.g., 90 degrees or greater).

Surfactants that have surface tension less than 30 dyne/cm, especially surfactants that have low HLB and are water insoluble tend to produce a wetting film covering the entire surface of hydrophobic channels, as measured by a receding contact angle of zero degrees at a surfactant concentration in the range from about 0.05% to about 0.1% concentration at 30 psig and typical liquid flow rate required for RDF/DPDF flow (see examples). Forced wetting prevails and the flow map generated can be described as entirely in the "film mode" at most liquid flow rates. The wetting film normally covers the entire surface of channel. These may or not be associated with foam depending on other properties of the surfactant.

Surfactants that have a low Ross-Miles foam height less than about 50 mm, preferable 0 to about 5 mm and have equilibrium surface tension between 33 to 50 dynes/cm can achieve RDF flow modes as shown in the flow regime maps of Examples 2-7. However, some surfactants in this class tend to produce some foam in the channels, especially when used at high concentration and when used at high gas or liquid flow rates. Surfactants with surface tension of 33 to 47 dynes/cm, especially 35 to 45 dynes/cm give suitable RDF regimes and provide better cleaning performance. Mono-disperse surfactants with HLB 10-17 tend to encompass this group of surfactants. Foam can form near the outlet of the channel when surface tension is about 30-34 dynes/cm.

Based on the above discussion of our experimental result, the liquid cleaning medium providing optimal flow regimes for the cleaning method of the invention preferably should includes one or more surfactants at a concentration that provides an equilibrium surface tension between about 33 and 50 dynes/cm, preferably about 35 to about 45 dynes/cm. The surfactant(s) should have a low potential to generate foam as measured by having a Ross Miles foam height measured at a surfactant concentration of 0.1% that is less than 50 mm, preferably less than 20 mm, more preferable below 5 mm, and most preferable close to zero, e.g., less than 1 mm. The cleaning medium should not form a wetting film on the channel surface (the interior wall of the channel) as measured by a receding contact angle greater than zero degrees. Preferably the surfactants are water soluble and have an HLB greater than about 9.2, preferably about 10 to about 14.

Suitable surfactants for use in the cleaning mediums according to the invention include polyethylene oxide-polypropylene oxide copolymers such as PLURONIC® L43 and PLURONIC® L62LF, and reverse PLURONIC® 17R2, 17R4, 25R2, 25R4, 31R1 sold by BASF; glycidyl ether-capped acetylenic diol ethoxylates (designated "acetylinic surfactants" such as SURFYNOL® 465 and 485 as described in U.S. Pat. No. 6,717,019 sold by Air Products; alcohol ethoxylates such as TERGITOL® MINFOAM 1X® AND MINFOAM 2X® sold by Dow Chemical Company and tallow alcohol ethoxylates such as Surfonic T-15; alkoxylated ether alkoxylated ether amine oxides such as AO-455 and AO-405 described in U.S. Pat. No. 5,972,875 available from Air Products and alkyldiphenyloxide disulfonates such as DOWFAX® 8390 from Dow Chemicals. Still other potentially suitable nonionic surfactants include ethoxylated amides, and ethoxylated carboxylic acids, alkyl or fatty alcohol PEO-PPO surfactants and the like provided they meet the surface tension, low foaming and non-wetting requirements.

Surfactant mixtures are also suitable in the cleaning medium and have been found in some cases to perform better than individual surfactants in providing RDF and DPDF regimes. Although surfactants belonging to Class III are preferred, Class I and II surfactants may be suitable as one of the components in a surfactant mixture especially when used in minor proportions. For example, the mixture may be chosen so that the mixture is soluble and has an average HLB in the preferred range. However, the mixture must satisfy the non-wetting film criteria properties, non-foaming criteria and provide a surface tension in the required range.

A particularly suitable surfactant mixture is a mixture of the acetylinic surfactant SURFYNOL® 485 and the alkoxylated ether amine oxide AO-455 at about 0.06% total surfactant concentration. The mixture unexpectedly provides highly effective RDF regimes in endoscope channels compared with the individual members of the mixture when used at the same concentration.

It is important to note that the concentration of the surfactants and other optional ingredients will generally affect the surface activity, wetting and foaming properties of the liquid cleaning medium. Thus, for example, a surfactant which is suitable at one concentration may not be suitable at either a lower concentration where its surface tension lowering is insufficient or at a higher concentration where foaming or wetting (annular film formation) properties may be unsuitable. The optimization of the surfactant concentration to achieve optimal flow regime for cleaning is considered well within the scope of a person of ordinary skill in the art with the understanding of the basic principles disclosed herein.

Optional Cleaning Ingredients

Various optional ingredients can be incorporated in the liquid cleaning medium of the invention. Preferred optional ingredients include:

pH adjusting agents: The pH of the cleaning medium should generally be above 8.0, preferably between about 9.5 and 11.5 and more preferable 10.0 to 11.0. Suitable pH adjusting agents include alkali hydroxides such as NaOH, KOH and sodium metasilicate, sodium carbonate and the like.

Builders or sequestering agents: These materials complex Calcium and other di- and polyvalent metal ions in the water or soil. Examples of suitable builders/sequestering agents include complex phosphates such as sodium tripolyphosphate (STP) or tetrasodium pyrophosphate (TTPP) or their mixtures; EDTA or other organic chelating agents; polycarboxylates including citrates, and low molecular weight polyacrylates and acrylate-maleate copolymers. It has been found that some organic chelating agents may interfere with achieving the RDF mode and each candidate should therefore be evaluated by the methods disclosed in Example 1.

Cloud point antifoams: The cleaning solution may include additional surfactants that can reduce the foaming of the primary surfactants used in the composition. For example low cloud point surfactants such as PLURONIC® L61 or L81 can be added in small concentration (e.g., 0.01 to 0.025%) to decrease foaming. The concentration of the latter should be selected such that the RFD mode is maintained and that no liquid film formation occurs in the spaces between the surface flow entities.

Dispersants: These materials promote electrostatic repulsion and prevent deposition or re-attachment of detached contaminants or bacteria to channel surface. Suitable dispersants include polycarboxylic acid such as for example ACCU-SOL® 455N, 460N and 505N from Rohm and Haas Company, SOKALAN CP5 or CP7 from BASF and related copolymers of methacrylic acid or maleic anhydride/acid and polysulfates or sulfonates.

Solvents and hydrotropes: These materials can be used to compatibilized the surfactant system or help soften or solubilze soil components as long as they do not interfere with the efficient production of optimal flow regimes for the instant cleaning method as evaluated by the method of Example 1. Suitable hydrotropes include for example xylene sulfonates and lower alkyl sulfate. Suitable solvents include for example glycol ethers.

Oxidizing agents: As discussed above oxidizing agent suitable oxidizing agents include peroxy acids such as peracetic acid, sodium hypochlorite or sources of the same, and hydrogen peroxide or sources thereof such as percarbonate or perborate.

It has been found that the addition of about 300 to 1000 ppm sodium hypochlorite to the cleaning liquid is effective in the removal of fibrinogen form hydrophobic endoscope channels, e.g., TEFLON®. Sodium hypochlorite may be optionally added in the cleaning composition to avoid complications arising from blood contamination of endoscopes.

Preservatives: Preservatives known in the art can be employed to prevent growth of organisms during storage of the cleaning composition.

In practical applications of the method, it is convenient to formulate the liquid cleaning medium as a concentrate (2× to 20×) which is diluted with water before use. In order to compatibilize the various ingredients in the concentrate, a solvent or hydrotrope may be required.

Treatment Number

It is useful to create some description of how much "sweeping" occurs of the internal surface of the passageway by three phase contact interface with sliding liquid entities or rivulets. There is limited theoretical information about, for example, the transverse velocity of a meandering rivulet. In the absence of theoretical information on this subject, high-speed photography has been utilized.

For example, from multiple photographic images taken closely together in time, it may be possible to identify the same sliding flow entity such as a rivulet in more than one photograph, and to correlate its position in successive photographic frames separated in time by a known time interval. This information in combination can provide information about the velocity of meandering, such as a transverse velocity, of a rivulet, or similar information for other types of sliding flow entities. This knowledge can in turn be used to calculate a rate at which surface area is swept by the wet-dry interface at a three-phase contact. For sliding liquid entities other than meandering rivulets, such as for fragmenting rivulets and liquid droplet arrays, it is also possible to calculate similar information.

The net effect is the sweeping of the internal surface of the channel by a variety of sliding liquid entities including meandering rivulets, sub-rivulets, rivulet fragments, linear droplets arrays and individual droplets of various sizes all in contact with the surface of the channel. Each of these entities has an associated three-phase gas/liquid/solid contact interface and meniscus. The overall effect of the sliding of these surface flow entities is the sweeping of the surface of the channel by multiple moving three-phase contact interfaces and menisci.

A criterion of some significance would be the situation in which the amount of area swept by the motion of sliding liquid entities is equal to the internal surface of the passageway. In this situation, if there were no duplication of sweeping any particular points, each point on the internal surface of the passageway would be swept once and therefore would experience at least one cleaning action. Of course, given the random and statistical nature of the processes described herein, it is possible that some points could be swept more than once by the motion of a sliding liquid entity while some other points might not be not swept at all. Therefore, it may be desirable for cleaning to be performed such that the Treatment Number is greater than 1. First of all, having a Treatment Number somewhat larger than 1 would make it likely that every individual point is swept at least once, even if some points are swept more than once. Furthermore, having a Treatment Number sufficiently larger than 1 could make it likely that most points or all points are swept several times. This would further improve the quality of the cleaning. Of course, it is possible that there might be contaminants for which one sweep by a sliding liquid entity is not sufficient to remove the contaminant, but several such sweeps might accomplish the removal.

Therefore, for example, cleaning might be performed such that cleaning accomplishes a Treatment Number of at least 5, or at least 10, or at least 25.

It is possible that cleaning by the described methods can be performed for a sufficient length of time so as to achieve a log-reduction of about 5 to 6 in the number of organisms and organic soils, including proteins, from long and narrow internal passageways.

The treatment number may be different at different places along the length of the endoscope channel. The treatment number also may be different locally at a given cross-section of an endoscope channel, such as at different places around the perimeter of a particular cross-section of the endoscope channel. For example, cleaning conditions may be chosen such that a minimum value of treatment number is achieved at all locations, and larger values are achieved at some locations.

A quantitative measure of the extent to which the surface of the channel is swept by surface flow entities is provided by a parameter designated as a Treatment Number, NT, defined as the total area that is swept by all the surface flow entities divided by the total internal surface area of the channel. Treatment number equals one means that the entire channel is swept one time by surface flow entity. The Treatment Number can be computed from high speed photography of sample areas of specific dimensions (e.g., 400 μm by 300 μm) taken at various positions on the internal surface of the channel at different locations along its length by the following procedure. The determination of Treatment Number can be combined with the hydrodynamic flow mapping outlined above and described in detail below.

The total area swept in a fixed time $t_{cl}$ (e.g., 300 sec) by a particular surface flow entity (SFE), e.g., a drop or cylindrical body, of diameter $d_{SFE,i}$ is:

$$A_{SFE,i} = d_{SFE,i} U_{SFE,i} t_{cl} \quad (12)$$

where $U_{SFE,i}$ is the sliding velocity of the $i_{th}$ SFE, i.e., the rate at which the three-phase contact line at the leading edge of the rivulet fragment moves over the surface.

The total area swept during $t_{cl}$ for all the types of SFE that appear within a sample volume element (e.g., the field of view), including those SFE that enter and leave during the total observation time is:

$$\text{Total Area Swept by Rivulet Fragments} = \Sigma_i d_{SFE,i} U_{SFE,i} t_{cl} \quad (13)$$

where the sum is taken over all rivulet fragments.

Eq. 2 can be generalized for all types of surface flow entities (meandering rivulets, cylindrical bodies, linear droplet arrays, large drops, small drops, etc.) as $$\text{Total Area Swept by All Surface Flow Entities} = A_{cl,To,i} = t_{cl} \Sigma_k \Sigma_i d_{k,i} U_{k,i} \quad (14)$$

where $d_{k,i}$ is the diameter of the $i_{th}$ SFE of the "$k_{th}$" type, e.g., discrete droplet, having an average sliding velocity $U_{k,i}$.

The average sliding velocity of each surface flow entity can be measured by observing the movement of the flow entity in the axial direction or for meandering rivulets both axial and radial direction over time. Because of their rapid movement under the influence of gas flow, we have utilized multi-exposure time-lapse photography in which the camera shutter is allowed to remain open and exposure is controlled by a strobe light. By measuring the change in position of the moving three-phase contact line over time, the velocity of each SFE, can be determined and a distribution function of sliding velocity computed for each type of flow entity.

The Treatment number, $N^j_T$, is defined as the total area swept by all SFE divided by the total area of the channel, $A_C$ at the particular position being viewed, i.e., the "$j_{th}$" section or volume element of the channel along its length. For channels that are circular cylinders, $A^j_C$ is equal to $\pi D l$ where $\pi D$ is the channel perimeter, and l is the length of the visual area being viewed in axial direction. The treatment number at the "$j_{th}$" section (volume lement) is then given by:

$$N^j_T = A^j_{cl,To} / A^j_C = (t_{cl} / \pi D^2 l^j) \Sigma_k \Sigma_i d^j_{k,i} U^j_{k,l} \quad (15)$$

where the superscript "J" refers to the "$j_{th}$" viewing area.

The terms in Eq. 4 can be separated into different flow entities and further subdivided into discrete size ranges. The average sliding velocity of each type of flow entity falling into each size range can then be computed from the measured average velocities or a velocity distribution function.

The inspection of a large number images revealed that the distribution of SFE (Surface Flow Entities) within any image is non uniform and only a relatively small strip of available area is cleaned at any instant of time. However, the time of residence of a particular SFE within the visual area is much less than a second and the number and type of SFE observed within the viewing area will change more than 300 times, if the cleaning time is for example 300 sec. Since the location of specific entities are different for different moments of time, a rather uniform treatment is achieved provided a sufficient time is allowed for cleaning and the treatment number is sufficiently large. On the other hand, the shorter the cleaning time, the larger will be the manifestation of large non-uniformities in the momentary distribution of SFE.

When the Treatment Number is ~1, the treatment uniformity is low. Although the area of the channel swept by SFE is equal to the geometric area of the channel, large regions of the channel remain untreated. However, when $N^j_T$ exceeds 30, and preferably exceeds 50, the treatment of the particular section being viewed is sufficiently uniform such that all areas of the section are cleaned. When the treatment number reaches about 100 or more, a very high degree of uniformity in terms of fraction of total area swept by three-phase contact lines is observed.

Based on the above analysis, the Treatment number $N^j_T$ at substantially all positions along the length of the tube (from inlet to outlet) should be greater than 10, preferably at least about 30, more preferably between and most preferably greater than about 50. Be the term substantially all positions along the length of the tube is meant at least about 75% of length of the tube, preferably greater than 80% of the tube length and most preferably greater than 95% of the tube length.

The instant method is in fact capable of routinely achieving very high treatment numbers of 100 or more and under some conditions 300 to 1000. These high treatment numbers achieve very high log reduction, e.g. pLog 6 in contaminant microorganisms.

Inspection of Eq. 4, indicates that treatment number depends upon the total number of surface flow entities formed over the course of the cleaning operation and their sliding velocities. Operationally, these variables are controlled by the liquid and gas flow rates and by interfacial properties and other properties such as viscosity of the liquid cleaning medium.

As the liquid flow rate increases the amount and type of SFE increases. This leads to an increase in Treatment Number with increasing liquid flow rate which is well documented experimentally by the analysis of photomicrographic images taken under various conditions.

Similarly, an increase in gas flow rate increases the number of surface flow entities and their sliding velocity since it is the drag force provided by the flowing gas which induces fragmentation and rapid sliding in the first place.

In a further embodiment of the instant cleaning method utilizing the RDF flow regime either or both the rivulet flows of liquid cleaning medium or the flow of gas are pulsed during the cleaning cycle which has been found to aid detachment of contaminants in some cases.

Endoscope Structure

There are a variety of endoscope designs for particular surgical or diagnostic procedures, and even endoscopes for the same surgical procedure can have design differences among different models produced by different manufacturers. Typical features of an endoscope are illustrated in FIG. 12. As a general feature, an endoscope may have a distal end 100 which goes inside the patient. Some distance back from the distal end 100 there may be a control handle 90 at which certain controls can be operated and access may be obtained to the channels inside the endoscope. Between the distal end 100 and the control handle 90, the endoscope is flexible. Continuing further back from the control handle 90, there may be another flexible length, umbilical cable 80, which ends at an umbilical end 70.

For any of the channels, the lengths of the various channels may typically be the same for all of the channels, because the lengths of all of the channels are related to the length of the endoscope itself. The portion of the endoscope from the control handle to the distal end 100 may have a maximum length of approximately 2 to 2.6 m. The umbilical portion of the endoscope (between the control handle 90 and the umbilical end 70) may have a length of approximately 1.4 m.

An endoscope may comprise an air channel 132 and a water channel 131. These channels 131, 132 may be similar to each other or even identical to each other. These may be some of the smaller-diameter channels within the endoscope. For example, the inside diameter of the air channel 132 and the water channel 131 may be relatively small, approximately 1 mm. Air channel 132 and water channel 131 may extend the entire length of the endoscope, from the umbilical end 70 to the distal end 100, with access points at the control handle 90. Air channel 132 and water channel 131 may come together at the distal end 100 of the endoscope and may discharge at the distal end 100 through a common orifice (or air-water nozzle) 133. The common orifice 133 may have an inside diameter that is smaller than the inside diameter of the air channel 132 or the water channel 131.

An endoscope may comprise a suction channel 109A which may also serve as a biopsy channel. The internal diameter of such channel 109A can vary over a significant range, such as from 1.2 mm to 6.0 mm depending on the purpose and design of that channel and that endoscope.

Some endoscopes may further comprise a forward water jet or irrigation channel. This channel may have an inside diameter which is also in the range of 1 mm. It is possible that the forward water jet or irrigation channel may extend from the control handle 90 to the distal end 100 without having another channel segment between the control handle 90 and the umbilical end 70. Alternatively, it is possible that the water jet or irrigation channel may extend from the umbilical end 70 all the way to the distal end 100 without having an access point at the control handle 90.

For any of the channels that extend from the control handle 90 to the distal end 100 and also from the control handle 90 to the umbilical end 70, it is possible that the inside diameter of the segment from the control handle 90 to the distal end 100 may be different from the inside diameter of the segment from the control handle 90 to the umbilical end 70. Typically, if there is a difference, the inside diameter of the segment from the control handle 90 to the distal end 100 may be smaller than the inside diameter of the segment from the control handle 90 to the umbilical end 70.

FIG. 12 shows details at the control handle of a typical endoscope. In FIG. 12 there is shown a suction cylinder well 103 having connections to the suction channel. At this cylinder well 103 there is one connection 105 heading toward the distal end 100, and the other connection 104 heading toward the umbilical end 70.

In FIG. 12 there are shown an air/water cylinder well 126 that contains connections to the air channel and connections to the water channel, both meeting at a common air/water cylinder well 126. Thus, this cylinder well 126 has four ports. Port 128 is for the water channel heading toward the distal end 100 of the endoscope, and port 127 is for the water channel heading toward the umbilical end 70 of the endoscope. Port 130 is for the air channel heading toward the distal end 100 of the endoscope, and port 129 is for the air channel heading toward the umbilical end 70 of the endoscope.

A suction/biopsy channel 102, may extend from the suction nipple 101 located at the umbilical end 70, to the suction control cylinder well 103 located at the control handle 90, and may further extend through channel 107 from the suction control cylinder well 103, to meet with channel 109 which is connected with the biopsy insert port 108. The suction/biopsy channel is then continued with a plastic tubing 109A to meet with the discharge port 108, located at the distal end. A suction/biopsy control cylinder well 103, is a metal housing used to accommodate a suction control valve during application where an inlet port 104, and an outlet port 105, are included to connect with the plastic tubing 107 and the plastic tubing 102.

The air channel 124 may extend from the air/water port 121, located at the umbilical plug 70, to the air/water cylinder well 126, located at the control handle 90, and may further comprise channel 132 extending from the air/water cylinder well 126, to the air/water nozzle 133, located at the distal end of the endoscope. The water channel 123 may extend from the air/water port 121, located at the umbilical end 70, to the air/water cylinder well 126, located at the control handle 90, and may further comprise channel 131 extending from the air/water cylinder well 126 to the air/water nozzle 133, located at the distal end 100 of the endoscope. The various channels may be tubing made of polymer such as polytetrafluoroethylene.

In many types of endoscopes, the air/water nozzle 133, located at the distal end 100 is the point where the air channel 124 and water channel 123 meet. The inside diameter of nozzle 133 may be smaller than the inside diameter of the air channel 124 or the water channel 123 itself.

An endoscope may comprise a forward water jet (or irrigation) channel 142. This channel 142 may extend from the forward water jet port 141 located at the control handle 90 or at the umbilical plug 70, to the discharge port 143 located at the distal end 100.

Some endoscopes may contain an elevator channel 111, which is a tube having a wire inside it which is used to steer the tip of the endoscope. The elevator channel 111 may extend from the elevator wire channel cleaning port 110 located at the control handle 90, to the distal end 100. Thus, the elevator wire channel may be shorter than some other channels that may extend the entire length of the endoscope. A wire 112 may be installed inside the elevator wire channel 111. One end of the wire 112 is attached to an elevator raiser 113 which is hinged near the suction discharge port 108 at the distal end. The other end of the wire 112 may be attached to a control knob mechanism at the control handle 90 which starts from the elevator wire channel cleaning port 110. The dimensional space between the elevator wire and the tubing which surrounds the elevator wire may be approximately 0.18 mm. Typically the elevator channel is pressure-tested to a higher pressure than any other passageway of the endoscope.

Among various endoscopes, typical lengths and inside diameters of certain channels can be tabulated, or at least ranges of these dimensions can be tabulated. These are summarized in Table 2.

TABLE 2

| Channels—Umbilical to Control Handle: | | | | | |
|---|---|---|---|---|---|
| Air & Water Channels | | Suction Channel | | Water Channel** | |
| Internal Diameter | Length | Internal Diameter | Length | Internal Diameter | Length |
| 1.4 to 1.6 mm | 1.4 m | 1.2 to 5.0 mm | 1.4 m | 1.2 to 1.4 mm | 1.4 m |
| Channels—Control Handle to Distal End: | | | | | |
| Air & Water Channels | | Suction Channel | | Forward Water Jet/ Elevator Wire/Irrigation Channels | |
| Internal Diameter | Length | Internal Diameter | Length | Internal Diameter | Length |
| 1.0 mm (smallest) | 2.0 to 2.6 m | 1.2 to 5.0 mm | 2.0 to 2.6 m | ≧1.0 mm (FWJ) <0.8 mm (EW) ≧1.0 mm (Irrigation) | 2.5 m |

Endoscopes may further comprise still other components such as fiber optics and electronics, which are omitted here for clarity of illustration.

Endoscope Cleaning Apparatus Circuits

An endoscope cleaning apparatus 50 may comprise a variety of fluid flow circuits and other apparatus. These are illustrated in FIGS. 13*a*-13*d*. FIG. 13*a* is an overall system schematic. FIGS. 13*b*, 13*c* and 13*d* illustrate portions of FIG. 13*a* in more detail. For example, FIGS. 13*b*, 13*c* and 13*d* include valves that are omitted from FIG. 13*a* for sake of clarity.

i) Air Circuit: The air-flow circuit design 1 may include an air inlet 1G from an outside source or compressor, air distribution branches 1E and 1F to perform pressure leak test of Scopes A and B, to inject air into distribution manifold A (8), distribution manifold B (9) and elevator manifold (10) via lines 1A, 1D and 1C for rivulet-droplet flow cleaning and rinsing and also for drying the internal channels. The air may be dehumidified or less-than-fully-humid. As illustrated, the air passes through a dehumidifier 1I before entering the rest of the apparatus 50. It is also possible, that air may pass through a heater 1J before being used for various purposes. Heating of air can be expected to further reduce its humidity. Air from this air circuit may also be used for purging water lines 1H and disinfectant lines 1B of the apparatus 50.

ii) Water Circuit: The water circuit design 2 may include a heated water inlet 2I from outside, supplies water to rinse all the endoscope internal channels through the distribution manifold A (8), distribution manifold B (9) and elevator manifold (10) via lines 2A, 2C and 2D, as well as to rinse the external surfaces of endoscopes through the basin via line 1E. This circuit also provides water to perform channel patency measurements for Scopes A and B via lines 6 and 12, to rinse the disinfectant circuit via line 2B, and the cleaner circuit via line 2G and to mix it with the concentrated cleaning solution for final dilution via line 2H.

iii) Cleaner Circuit: This circuit design 3 may include a concentrated cleaning solution inlet 3F from the bottle, a water source for mixing with concentrated cleaning solution (2H) and a water source for rinsing the cleaner circuit (2G). The cleaner circuit provides cleaning solution to the distribution manifold A (8), distribution manifold B (9) and elevator manifold (10) via lines 3A, 3B and 3D to perform rivulet-droplet flow cleaning of the internal channels and provides cleaning solution to the basin via line 3C to perform external cleaning of endoscope surfaces. This circuit is also used to supply peracetic acid (PAA) to the basin via line 3E during the self-disinfection cycle.

iv) Disinfectant Circuit: The high-level disinfection circuit design 7 includes: a storage tank and a recirculation loop (7A and 4E) with an in-line heater 4F to maintain the disinfectant at 35° C. This circuit supplies disinfectant to the basin to achieve complete immersion for 5 minutes at 35° C. The internal channels are flooded with the disinfectant during the disinfection cycle from the basin through distribution manifold A (8), distribution manifold B (9) and elevator manifold (10) via lines 4A, 4B and 4D. During disinfection, the spray arm and eductors direct the disinfectant to endoscope surfaces and cover the surfaces of the basin, including the lid of the apparatus. The disinfectant circuit design simultaneously supplies disinfectant to the basin and then recirculates it through the distribution manifolds and the eductors for high-level disinfection of internal channels and external surfaces, respectively. This circuit also maintains the temperature of disinfectant in the reservoir by recirculating it through a heater 4F.

v) Alcohol Circuit: The alcohol circuit 5 supplies alcohol to distribution manifold A (8), distribution manifold B (9) and elevator manifold (10) via lines 5A, 5B and 5C before the final drying step with air to facilitate drying.

vi) Distribution Manifold Circuits: Distribution manifold A (8) and distribution manifold B (9) are used to generate rivulet-droplet flow and to supply different fluids to the internal channels of two endoscopes, A & B. Each distribution manifold has five inlet ports (air (1A, 1D), water (2A, 2C), cleaning solution (3A, 3B), alcohol (5A, 5B) and basin (4A, 4B)) and five outlet ports (air (8A, 9A), water (8B, 9B), suction (8C, 9C), biopsy (8D, 9D) and irrigation (8E, 9E) channels). Elevator manifold 10 is also used to generate rivulet-droplet flow and has the same five inlet ports (1C, 2D, 3D, 5C and 4D) but only two outlet ports, one for the elevator wire channel of Scope A (10A) and the other for the elevator wire channels of Scope B (10B). FIG. 13*b* shows a schematic of Manifold A (8) in detail. The air (1A), water (2A), cleaner (3A), basin (4A) and alcohol (5A) inlets to manifold A (8) are controlled by valves 8F, 8G, 8H, 8I and 8J, respectively. The outlet from the manifold to air port (8A), water port (8B), suction port (8C), biopsy port (8D) and water irrigation port (8E) are controlled by valves 8K, 8L, 8M, 8N and 8O, respectively.

vii) Basin Circuit: This circuit design shown in FIG. 13*d* provides cleaning solution 3C, water 2E and disinfectant 7A through eductors 4G using circulation pump 4H and valve 4I and spray arm 4J using circulation pump 4H and valve 4K to clean, rinse and disinfect the external surfaces of two endoscopes. For simplicity, in FIG. 13*d* only one eductor (4G) is illustrated. The basin 4 circuit circulates disinfectant through the endoscope internal channels using distribution manifold A (8), distribution manifold B (9) and elevator manifold (10) via lines 4A, 4B and 4D, and discharges the contents of the basin to an outside drain 4C. The temperature of disinfectant 7 in the basin 4 is maintained by circulating it through the disinfectant bottle via a heater 4F and lines 4E and 7A. The vent 4L is also provided in the basin 4 to prevent any pressure build up inside the basin 4. This circuit also supplies sterilant such as peracetic acid (PAA) (11) sterilant from the PAA bottle through the cleaner lines 3E and 3C to the basin 4 to execute the self-disinfection cycle.

Patency testing. FIG. 13c shows a schematic of the patency testing circuit for Scope A in detail. Water (6) from the water circuit (2) is passed at a fixed pressure (pressure monitored by pressure sensor 6G) through a water regulator 6F and one of the following five channels: air (6A), water (6B), suction (6C), water irrigation (6D), and biopsy (6E), by their respective valves. Likewise, for Scope B, water (12) from the water circuit (2) is passed through one of the following five channels: air (12A), water (12B), suction (12C), water irrigation (12D) and biopsy (12E), by their respective valves. The water flowrate through a channel is measured by water flowmeter (6H). The water injection to the air (6A), water (6B), suction (6C), water irrigation (6D) and biopsy (6E) channels is controlled by valves 6I, 6J, 6K, 6L and 6M, respectively.

Reprocessing Cycle for a Single Channel

During reprocessing, the apparatus 50 (FIG. 13a) may supply all or any subset of the following fluids to an endoscope at appropriate times, or may perform all or any subset of the following actions. The reprocessing cycle for any given channel may include the following steps: i) pre-cleaning, ii) leak and patency testing, iii) rivulet-droplet flow cleaning, iv) rinsing, v) disinfection, vi) rinsing, vii) alcohol flushing, and viii) air drying. This sequence of events is further illustrated in FIG. 14.

In preparation for reprocessing of an endoscope, it is possible that upon completion of an endoscopic procedure, channels of the endoscope can be filled with liquid or wetted in some manner so that debris that may have been deposited during the endoscopic procedure remains wet during the time between the endoscopic procedure and the reprocessing. This can help to maintain the debris in a condition such that it can be removed more easily.

i) Pre-Cleaning

The pre-cleaning step may include a pulsed rivulet-droplet flow with the cleaning solution through the endoscope channel to remove gross patient material from the channel. A mixture of water from water circuit 2 and cleaning solution from cleaner circuit 3 may be passed through the channel for a period of time, followed by an air pulse from air circuit 1 for a period of time, and this process may be repeated several times throughout this step. It is also possible that toward the end of this pre-cleaning step, there can be a flushing of the channel with a flow entirely of liquid such as water using water circuit 2.

ii) Leak and Patency Testing

In a leak test, air from air circuit 1 at a modest pressure such as approximately 3 psig may be applied to the endoscope sheath, and the decay of pressure as a function of time may be monitored by a pressure sensor. If the pressure decay is outside the acceptable range, then the endoscope fails the leak test. In a patency/obstruction testing of an endoscope internal channel, a flow of water from water circuit 2 at known constant temperature and pressure may be applied to the channel and then the flow rate in the channel may be monitored with a precision flow meter/sensor. This patency-testing system may determine the channel obstruction or blockage in either or both of two ways: (1) by comparing the flow rates obtained against baseline values of that particular channel of that particular endoscope (new condition) which may be stored in the database of the apparatus, and (2) by comparing the measured flow rate measured against a default value for a channel having the same diameter and length whose values are also stored in the database of the apparatus.

iii) Rivulet-Droplet Flow Cleaning

In this step, a channel may be cleaned for a period of time using, at least some of the time, the rivulet-droplet flow regime. In the rivulet-droplet flow cleaning, warm air from air circuit 1 at known pressure and warm cleaning solution from cleaner circuit 3 at known flow rate may be caused to flow through the channel. The flowrates may be chosen based on the internal diameter and length of the channel so as to form rivulet droplet flow so as to detach contaminants from the surface of the channel. At the end of this rivulet-droplet flow cleaning, the channel may be purged with air from air circuit 1 for a short period of time to remove cleaning solution from the channel.

iv) Rinsing

A special rinsing step may be performed to remove detached contaminants from the endoscope internal channel or to remove cleaning solution from the channel. This rinsing step may be performed using substantially pure water. This rinsing step may include two sub-steps: pulsed rivulet-droplet flow rinsing and continuous water rinsing. In the pulsed rivulet-droplet flow rinsing, water from water circuit 2 may be passed through the channel for a period of time followed by an air pulse from air circuit 1 for a period of time, and this process may be repeated several times. In the continuous water rinsing, water from water circuit 2 may be passed through the channel. At the end of rinsing, the channel may be purged with air from air circuit 1 for a short period of time to remove water from the channel.

v) Disinfection

High-level disinfection may be performed using an FDA approved disinfectant (for example, glutaraldehyde at 35° C. for 5 minutes or peracetic acid (PAA)). In this step, the disinfectant from disinfectant circuit 7 may be circulated from the basin 4 through the internal channel while the endoscope is completely immersed in the disinfectant inside the basin 4. At the end of disinfection step, the channel may be purged with air from air circuit 1 for a short period of time to remove disinfectant from the channel.

vi) Rinsing

In this step, water from water circuit 2 may be passed through the channel to remove traces of disinfectant. At the end of rinsing, the channel may be purged with air from air circuit 1 for a short period of time to remove water from the channel.

vii) Alcohol Flushing

In this step, alcohol from alcohol circuit 5 may be passed through the channel for a period of time. The alcohol may be or may comprise ethanol. This may serve the purpose of facilitating drying because the alcohol may evaporate more easily than water.

viii) Air Drying

In this step, the channel may be purged with warm air from air circuit 1 to dry the endoscope internal channels.

Separate from the described cycle for cleaning internal channels of an endoscope, the apparatus may also provide a special cycle for performing self-disinfection where a disinfectant is used to disinfect the fluid lines within the endoscope reprocessing apparatus itself, such as to remove possible biofilm. Self-disinfection may, for example, be performed on a periodic basis such as weekly. The substance used for self-disinfection may, for example, be peracetic acid.

The apparatus 50 (FIG. 13a) may also provide a special cycle for water sampling where the basin is filled with water and a water sample is taken through a special port.

Cleaning Two Endoscopes at the Same Time Non-Identically

For sake of efficiency or convenience, it may be desirable for a single apparatus to be able to clean two endoscopes at the same time or approximately at the same time. A sequence of events for accomplishing this is illustrated in FIG. 15.

The two endoscopes may be either identical to each other or different from each other. Even if the endoscopes are identical to each other, at any given instant of time, the cleaning operation being performed on one endoscope (or a particular passageway of that endoscope) may or may not be identical to the cleaning operation being performed on the other endoscope (or a particular passageway of that endoscope).

Certain passageways may have greater needs than other passageways. This need may be expressed in terms of consumption of electrical power, or in terms of consumption of compressed air, or consumption of still other utilities. Any utility such as electricity or compressed air or other utility may be in limited supply, or may be such that it is desirable to keep its maximum demand below a certain limit, or to minimize such magnitude of maximum demand. For example, it is the maximum instantaneous demand that determines electrical supply requirements. Similarly, in regard to compressed air consumption, although storage of compressed air is possible to some degree, still in general the maximum instantaneous consumption of compressed air is likely to significantly influence the necessary capacity of the air compressor (and therefore to some extent the electrical power consumption of the apparatus).

Figure 15A:
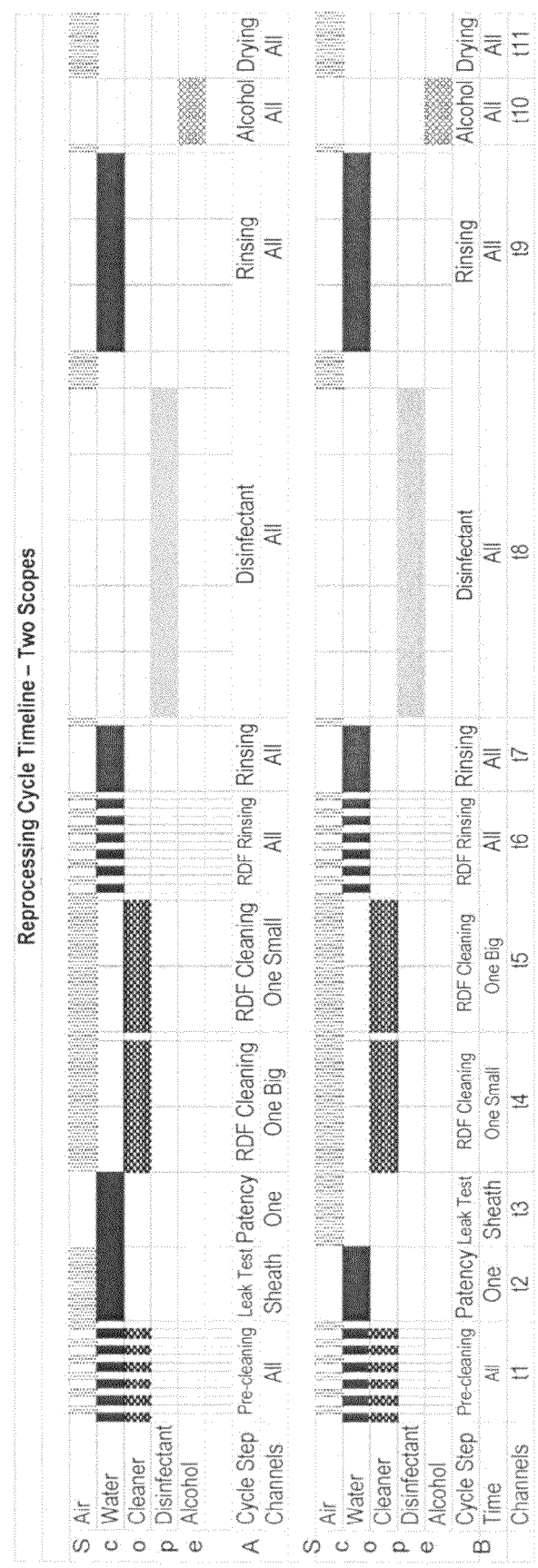

FIG. 15a illustrates a possible sequence of events for cleaning two endoscopes at least approximately simultaneously but not with the identical sequence of events. For sake of illustration, FIG. 15a uses the example of a Scope A and a Scope B. As illustrated in FIG. 15, it is possible to schedule operations during simultaneous processing of two endoscopes, such that cleaning of a relatively low-air-flowrate-consumption passageway is performed in one endoscope at the same time that cleaning of a relatively larger-air-flowrate-consumption passageway is performed on the other endoscope. At a later time, the operations can be reversed. In this way, it is possible to clean two endoscopes simultaneously, and yet the peak demand for consumption of compressed air can be kept at less than twice the air consumption of the largest-air-consumption passageway.

It may be desirable to minimize the peak rate of consumption of compressed air not only for reasons of minimizing the peak rate of consumption of electrical energy, but also for other reasons such as capital cost of an air compressor, peak noise generation, overall size or weight of the equipment, and other reasons.

Of course as described elsewhere herein, the conditions for achieving good cleaning of one geometric passageway may be different from the conditions for achieving good cleaning of one geometric passageway. These conditions may differ in liquid/gas ratio, or may differ in timing and scheduling, or both. Equipment which cleans two endoscopes simultaneously, or even which cleans different passageways within a single endoscope simultaneously, may be operated so as to supply to individual passageways the conditions which are appropriate to that particular passageway.

If the apparatus is capable of cleaning more than one different design or model or brand of endoscope, it may be capable of cleaning more than one different design or model or brand of endoscope simultaneously. In that case, the apparatus may be capable of being programmed to identify which type of endoscope is being cleaned at a particular station within the apparatus, or the apparatus may be capable of recognizing what type of endoscope is present at a particular station. Furthermore, the apparatus may be capable of delivering air appropriately for each endoscope.

Figure 15B:
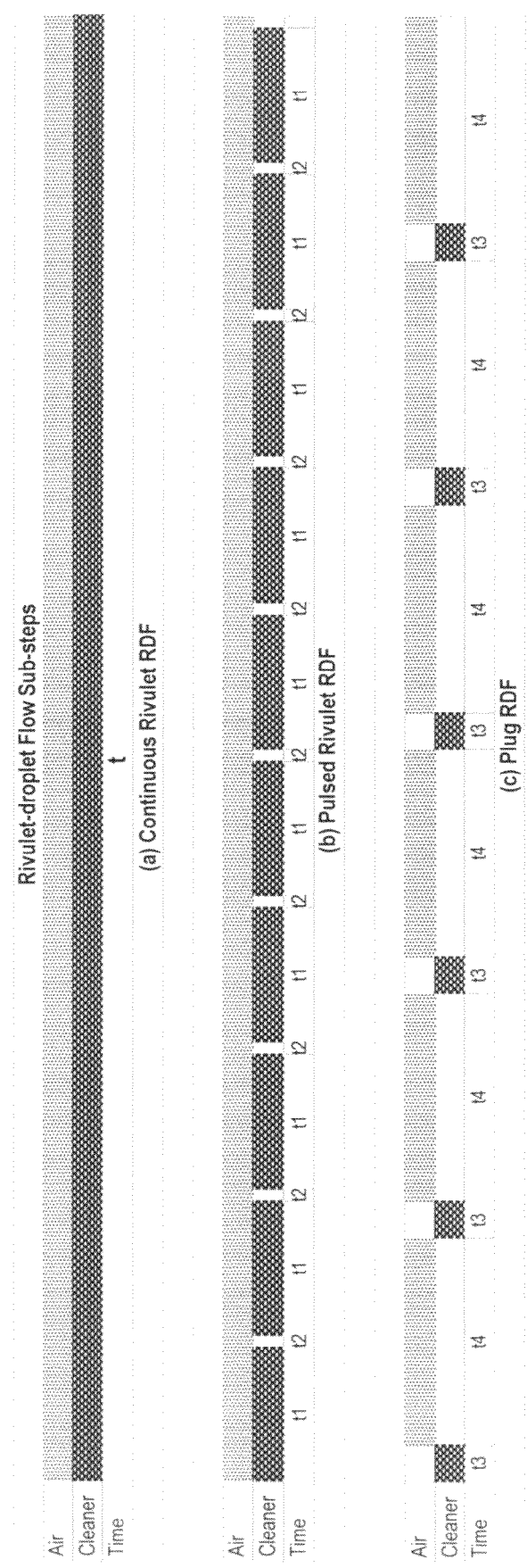

FIG. 15b illustrates various details of types of flow inputs that could be performed during cleaning. Such flow inputs could also be applied during pre-cleaning or during rinsing.

Reprocessing Cycle for Cleaning Two Endoscopes Approximately Simultaneously:

The reprocessing cycle for two endoscopes may include the following steps as described elsewhere herein for a single endoscope: i) pre-cleaning, ii) leak and patency testing, iii) rivulet-droplet flow cleaning, iv) rinsing, v) disinfection, vi) rinsing, vii) alcohol flushing, and viii) air drying. This sequence of events is further illustrated in FIG. 15. During reprocessing, the apparatus 50 (FIG. 13a) may perform all or any subset of the following steps:

i) Pre-Cleaning:

The pre-cleaning step may include a pulsed rivulet-droplet flow with the cleaning solution through the endoscope channel to remove gross patient material from the channel. A mixture of water from water circuit 2 and cleaning solution from cleaner circuit 3 may be passed through the channel for a period of time, followed by an air pulse from air circuit 1 for a period of time, and this process may be repeated several times throughout this step. It is also possible that toward the end of this pre-cleaning step, there can be a flushing of the channel with a flow entirely of liquid such as water using water circuit 2.

ii) Leak and Patency Testing:

The leak test is performed on Scope A while the patency test is performed on Scope B. This is followed by patency test on Scope A and leak test on Scope B. In the leak test, 3 psi air from air circuit 1 is applied to the endoscope sheath and the pressure decay is monitored by a pressure sensor as a function of time. If the pressure decay is more than the acceptable range then the endoscope fails the leak test. In the patency/obstruction testing of endoscope internal channels, a flow of water from water circuit 2 at known constant temperature and pressure is applied to each channel separately and then the flow rate in the channel is monitored with a precise flow meter/sensor. This patency-testing system determines the channel obstruction or blockage in two ways: 1) by comparing the flow rates obtained with baseline values of the same endoscope (new condition) stored in the database of the apparatus, and 2) by comparing the flow rates measured with a default value of channels of the same diameter and length whose values are also stored in the database of the apparatus (for repaired endoscopes). In our apparatus, we include means to separate all endoscope channels from each other so that the patency of each channel can be tested without any interference from the other channels.

iii) Rivulet-Droplet Flow Cleaning:

In our apparatus, one large channel (for example, suction, biopsy) from Scope A and one small channel (for example, air, water) from Scope B may be cleaned simultaneously for a period of time using distribution manifold A (8) and distribution manifold B (9), respectively. This may be followed by cleaning one small channel from Scope A and one large channel from Scope B for a period of time, again using distribution manifold A (8) and distribution manifold B (9), respectively. This sequence may be continued until all the channels are cleaned. The elevator wire channel may be cleaned continuously throughout the whole rivulet-droplet flow cleaning cycle using elevator manifold (10). In the rivulet-droplet flow cleaning, warm air from air circuit 1 at known pressure and warm cleaning solution from cleaner circuit 3 at known flow rate may be applied through each channel based on the internal diameter and length of the channel to detach contaminants from the surface of the channel. At the end of rivulet-droplet flow cleaning, all the channels may be purged with air from air circuit 1 for a short period of time to remove cleaning solution from the endoscope internal channels.

iv) Rinsing:

A special rinsing step may be performed to remove detached contaminants from the endoscope internal channel or to remove cleaning solution from the channel. This rinsing step may be performed using substantially pure water. This rinsing step may include two sub-steps: pulsed rivulet-droplet flow rinsing and continuous water rinsing. In the pulsed rivulet-droplet flow rinsing, water from water circuit 2 may be passed through Scopes A and B via distribution manifold A (8) and distribution manifold B (9), respectively, for a period of time followed by an air pulse from air circuit 1 for a period of time and this process is repeated several times. In the continuous water rinsing, water from water circuit 2 may be passed through all the channels of Scopes A and B at the same time. At the end of rinsing, all the channels may be purged with air from air circuit 1 for a short period of time to remove water from the endoscope internal channels.

v) Disinfection:

High-level disinfection may be performed using an FDA approved disinfectant (glutaraldehyde at 35° C. for 5 minutes or peracetic acid (PAA)). In this step, the disinfectant from disinfectant circuit 7 may be circulated from the basin 4 through the internal channels of Scopes A and B using distribution manifold A (8) and distribution manifold B (9), respectively while the two scopes are completely immersed in the disinfectant inside the basin 4. At the end of disinfection step, all the channels of Scopes A and B may be purged with air from air circuit 1 for a short period of time to remove disinfectant from the endoscope internal channels.

vi) Rinsing:

In this step, water from water circuit 2 may be passed through all the channels of Scopes A and B at the same time to remove traces of disinfectant. At the end of rinsing, all the channels may be purged with air from air circuit 1 for a short period of time to remove water from the endoscope internal channels.

vii) Alcohol Flushing:

In this step, alcohol from alcohol circuit may be passed through all the channels of Scopes A and B using distribution manifold A (8) and distribution manifold B (9), respectively for a period of time. The alcohol may be or may comprise ethanol. This may serve the purpose of facilitating drying because the alcohol may evaporate more easily than water.

viii) Air Dying:

In this step, all the channels of Scopes A and B are purged with warm air from air circuit 1 using distribution manifold A (8) and distribution manifold B (9) to dry the endoscope internal channels.

As described elsewhere herein, the apparatus may also include special cycles for water sampling where the basin is filled with water and a water sample is taken through a special port. The apparatus may also include special cycles for performing self-disinfection where a second disinfectant is used to disinfect all the fluid lines of the endoscope cleaning apparatus.

Apparatus Supplying Heated or Dehumidified Air

It is described elsewhere herein that a liquid entity travelling over a solid surface which is dry or hydrophobic is believed to help cause detachment of contaminants, by virtue of the moving three-phase contact interface. One way of promoting this situation is to have an appropriate relationship of hydrophobicity between the liquid and the solid surface. Another factor promoting this situation is to help cause evaporation of liquid, such as water, which is used for cleaning. Evaporation may be promoted if the gas which is supplied to the flow is less than fully humid. If air is the gas used for the gas flow, this condition may be achieved by dehumidifying the air before it is supplied to the passageway. Appropriate dehumidification means are known in the art. Alternatively, this may be achieved by heating room-temperature air to a slightly elevated temperature. Even if the air were fully humid or nearly fully humid when it was at room temperature, when it became warmer it would be less than fully humid and therefore would be capable of promoting some evaporation of liquid. Of course, it is also possible to both dehumidify and heat the air or other gas which is supplied of the passageway.

Of course, it is also possible that the liquid supplied to the passageway can be warm or hot. In general, heating of either the liquid or the gas or both may also help cleaning by speeding up diffusion processes, by denaturing protein, by helping to soften of debris or contaminants, and by other mechanisms.

An air heater element 1J is illustrated in the air circuit in FIG. 13a. Heating of the liquid can be accomplished internally in the apparatus, by a liquid heater (similar to air heater element 1J but not shown) or, perhaps more likely, warm or hot water from an external source can be taken into the apparatus, possibly with temperature control either external to the apparatus or internal to the apparatus.

For example, flow of heated gas may be provided, in the absence of liquid being supplied, for a duration of approximately 5 seconds to 15 seconds depending on passageway inside diameter, passageway length, humidity, temperature and possibly other factors. With a gas supply pressure of about 30 psig, a duration of 5 to 15 seconds flow of gas (in the absence of liquid being supplied) may be appropriate for drying or de-wetting the air/water channel. A duration of 5 to 7 seconds may be appropriate for drying or de-wetting a suction channel.

Furthermore, it may be appreciated that this process of drying out and re-wetting may be repeated a number of times. This can insure that even if a particular patch of surface does not experience re-wetting during a particular plug flow or a particular experience of rivulet droplet flow, it may experience re-wetting during a subsequent plug flow or a subsequent experience of rivulet droplet flow. Furthermore, any patch of surface may experience drying out and re-wetting a number of times, to insure good cleaning. This is described by the Treatment Number as discussed elsewhere herein. This differs from the situation in which it is possible that a passageway to be cleaned might possibly start the cleaning process in an initially dry condition and therefore, as sort of a trivial example, would by definition experience wetting once when cleaning actually begins. Similarly, this differs from the trivial example in which a passageway is actively dried out at the end of a conventional all-liquid cleaning cycle. In embodiments of the present invention, there may be repeated drying-outs and re-wettings of the surface being cleaned.

Valving and Directions of Flow Through Particular Endoscope Channels

A typical endoscope has three possible regions of entry or exit of fluid for use during a cleaning process: the control handle 90, the umbilical end 70 and the distal end 100. Typically the distal end 100 may have geometric constraints which would make it most likely that the distal end 100 would be used as an exit for flow used during cleaning. However, the connection points at the other two locations, i.e., the control handle 90 and the umbilical end 70, offer possibilities as to which connection points are inlets for flow and which connection points are exits for flow, and how valves are used to direct flow.

In general, for endoscope channels that have access points at or near the control handle 90, one possibility is that flow is introduced at the control handle 90. This is illustrated in FIG. 16*a*. Flow could be introduced into the air/water cylinder well 126 in control handle 90. Entry of this flow can be controlled by valve V2. Flow could be introduced into suction cylinder well 103 in control handle 90, and this flow could be controlled by valve V3. Flow can be discharged to both distal end 100 and umbilical end 70.

Continuing with the configuration illustrated in FIG. 16*a*, there may further be connection points at the umbilical end 70 for the air (124) and water (123) channels. Flow through this connection point (121) may be controlled by valve V4. There may also be connection point at the umbilical end 70 for the suction channel. Flow through this connection point (101) may be controlled by valve V5. As illustrated in FIG. 16*a*, both of these flows at the umbilical end 70 would be exiting flows. Either valve V4, V5 may be in either the open or the closed position. If valve V4 is open while inlet valve V2 is open, there would be flow through the air (124) and water (123) channels in umbilical cable 80. If valve V4 is closed, there would be no flow there even if corresponding inlet valve V2 is open. Similarly, If valve V5 is open while inlet valve V3 is open, there would be flow through the suction channel 102 in umbilical cable 80. If valve V5 is closed, there would be no flow there even if corresponding inlet valve V3 is open.

As illustrated, there are some channels which originate at or near the control handle 90 and extend to the distal end 100, and are not present in the umbilical cable 80. For such channels, flow may be supplied by a connection at or near the control handle 90 and may proceed to the distal end 100, similar to what was illustrated in FIG. 16*a*. For endoscopes that have a biopsy port 108, flow could be introduced to the suction/biopsy channel 109 at biopsy port 108 which may be near or in the control handle 90, and this flow could be controlled by valve V1. For endoscopes that have an elevator/wire channel 111, flow may be introduced at the elevator/wire port 110, and this flow may be controlled by valve V7. For endoscopes that have a forward water jet channel 142, flow could be introduced at the forward water jet port 141 which may be in the control handle 90 as illustrated (or for other models of endoscopes may be at the umbilical end). This flow may be controlled by valve V6.

A source of liquid and gas flow may be applied to those valves which are inlet valves, namely V1, V2, V3, V6 and V7, or to any subset thereof. As illustrated, the distal end 100 is unvalved. Flow can exit at the distal end 100 through any channel to which flow is supplied anywhere upstream.

Referring now to FIG. 16*b*, there is illustrated an arrangement in which flow through those channels which exist in the umbilical cable 80 is in a direction opposite of that illustrated in FIG. 16*a*. Flow could be introduced into the air/water connection 121 in umbilical end 70. Entry of this flow can be controlled by valve Va. Similarly, flow could be introduced into suction connection 101 in umbilical end 70. Entry of this flow could be controlled by valve Vb.

If exit Valve Vd is open, flow in the air (124) and water (123) channels may exit at the control handle 90. If exit valve Vd is closed, flow in the air/water channel may continue all the way to distal end 100. Similarly, if exit Valve Ve is open, flow in the suction channel 102 may exit at the control handle 90. If exit valve Ve is closed, flow in the suction channel 107 may continue all the way to distal end 100.

As illustrated, there are some channels which originate at or near the control handle 90 and extend to the distal end 100, and are not present in the umbilical cable 80. For such channels, flow may be supplied by a connection at or near the control handle 90 and may proceed to the distal end 100, similar to what was illustrated in FIG. 16*a*. For endoscopes that have a biopsy port 108, flow could be introduced to the suction/biopsy channel 109 at biopsy port 108 which may be near or in the control handle 90, and this flow could be controlled by valve Vc. For endoscopes that have an elevator/wire channel 111, flow may be introduced at the elevator/wire port 110, and this flow may be controlled by valve Vg. For endoscopes that have a forward water jet channel 142, flow could be introduced at the forward water jet port 141 which may be in the control handle 90 as illustrated (or for other models of endoscopes may be at the umbilical end). This flow may be controlled by valve Vf.

A source of liquid and gas flow may be applied to those valves which are inlet valves, namely Va, Vb, Vc, Vf and Vg, or to any subset thereof. As illustrated, the distal end 100 is unvalved. Flow can exit at the distal end 100 through any channel to which flow is supplied anywhere upstream.

It is still further possible that in some channels in the umbilical cable 80, flow could be in one direction while in other channels flow could be in the opposite direction.

Feedback Control of Liquid Flowrate

It is possible that, for some purpose such as achieving conditions favorable to cleaning, there is a desired relationship between liquid flowrate and gas flowrate. It is further possible that if gas is supplied from a source such as a constant pressure source, the gas flowrate through a passageway may change as a function of time. For example, as cleaning is accomplished, contaminants may be removed from the passageway, and the removal of contaminants may result in a passageway having less flow resistance. This, in turn, may result in an increase in the flowrate of gas delivered by the gas source. If this happens, or if in general the gas flowrate changes for any reason, having a pre-set or constant liquid flowrate may fail to achieve optimum or desired liquid flowrate for the gas flowrate which is actually occurring at a particular time. A pre-set constant liquid flowrate for a gas flowrate at one portion of the cleaning cycle may not always be the most appropriate liquid flowrate, such as if the flow resistance changes.

Accordingly, the apparatus may include a feedback control loop. Such apparatus is illustrated in FIG. 17. In such apparatus, gas may be supplied by a gas source 1710. Gas supplied by gas source 1710 may pass through flowmeter 1720 which, at any given time, measures actual gas flowrate provided to the passageway being cleaned. Flow of liquid flow may be provided by a liquid supply system which may be controlled responsive to the gas flowrate measured by flowmeter 1720, so as to provide a desired liquid flowrate. In this way, if the gas flowrate changes, the liquid flowrate can also change to maintain a desired relation to the gas flowrate. In FIG. 17, the liquid supply system is illustrated as comprising a concentrated cleaning solution metering pump 1732, that provides liquid at a desired flowrate from a source of concentrated cleaning solution, and also a water metering pump 1734 that provides water. The water and the concentrated cleaning solution may then meet and mix at junction 1750 so as to form a desired cleaning solution. The desired cleaning solution may then come together with the gas flow at junction 1760 and be provided to the passageway 1780 to be cleaned. The apparatus as illustrated allows the use of a relatively small or long-lasting container of concentrated cleaning solution, in combination with water which is generally available in substantial quantities, so that the container of concentrated cleaning solution need only be replaced or refilled infrequently.

As is also discussed elsewhere herein, there may be apparatus which provides liquid and gas flow to two different passageways simultaneously. FIGS. 18a and 18b illustrate use of a feedback loop, so as to perform cleaning of two different passageways simultaneously. In both FIGS. 18a and 18b, there is provided a gas source 1810. FIGS. 18a, 18b simply illustrate a generic liquid supply system 1840. Liquid supply system 1840 could be a simple reservoir of cleaning solution in the desired condition, or it could be a system which combines concentrated cleaning solution with water as described in connection with FIG. 17. There are provided two gas flowmeters 1820a and 1820b to measure gas flowrates delivered to respective flowpaths 1880a 1880b. The measured gas flowrates are reported to a control board 1835.

In FIG. 18a, control board 1835 operates a first metering pump 1830a that delivers liquid to flowpath 1880a, and also operates a second metering pump 1830b that delivers liquid to flowpath 1880b. In FIG. 18b, control board 1835 operates a single metering pump 1830 whose output is the summation of the desired liquid flowrate for flowpaths 1880a and 1880b. This summation flowrate is then provided to proportional valve 1845 which divides the summation flowrate appropriately between flowpaths 1880a and 1880b.

Of course, it would also be possible to provide a feedback system in which the gas flowrate is feedback-controlled responsive to a liquid flowrate.

Geometry to Promote Faithful Splitting or Distribution of Liquid+Gas Flow

It can be seen from FIG. 19a that a connector may connect to a cylinder well 2060 in the control handle of the endoscope such that a particular type of channel exits in two places from the cylinder well. One exit may lead toward the distal end of the endoscope and the other exit may lead toward the umbilical end of the endoscope. It may be desirable that the connector/introduce provide liquid+gas flow in two different directions such that the flow in each direction has approximately the same liquid/gas ratio as the incoming flow; also don't want too much separation of the liquid from the gas. It can be appreciated that, if gas and liquid are flowing simultaneously in a connector, and if the connector involves a change of direction, gas is likely to achieve a change of direction more easily than the liquid, and the liquid has a likelihood of being carried by its own momentum so that it impacts a downstream feature of its flowpath near the change of direction. In particular, this may be a consideration if more than one exit exists with local geometries that are different from each other. The connector may be designed with features such as smooth geometric transitions which minimize the likelihood of maldistribution of liquid and gas flow.

It is possible that the forward direction of a particular endoscope channel and the rearward direction of the same endoscope channel could have substantially similar local geometries where the connector would introduce flow to the channel. Alternatively, it is possible that the forward and rearward directions of a particular endoscope channel could have different local geometries. Regardless of what the local geometries are, it still is possible to use certain design strategies to provide for a faithful division of gas flow and liquid flow among the two directions if both directions are open to flow simultaneously. These strategies can also provide for good entry of gas+liquid flow even if there is a dedicated flowpath for a particular channel in the endoscope.

For example, sharp changes of direction can be avoided, especially in the immediate vicinity of the entrance to the channel. Approaching the entrance to the channel, the flow of gas and the flow of liquid may be made substantially parallel to each other for some distance. Flow of liquid and flow of gas can be brought in using co-extruded lumens, one lumen to carry the liquid flow and another lumen to carry the air flow. It is possible that the co-extruded lumens could be coaxial, such as with the liquid-carrying lumen being central and the gas-carrying lumen surrounding the liquid-carrying lumen. It is possible that the liquid can be brought together with the gas only very close to the place where the combined fluids enter channel being cleaned. It is possible that the design can be such that any needed expansion of the gas flow has already taken place somewhat upstream of the point where the gas and the liquid meet each other.

Fixed-Position Connectors for Collective Channel Connections

In embodiments of the invention, there may be provided connectors that interface with an appropriate cylinder wall and direct flow as desired. Referring now to FIG. 19, there are illustrated fixed-position connectors that are capable of directing flow collectively to both directions of a channel.

FIG. 19a illustrates an endoscope generically including some details of cylinder wells within the control handle 90.

FIG. 19b illustrates a possible design such that the liquid and gas flow which is supplied by the connector 2000A to a first channel in both directions is brought into the connector by a port 2030.

FIG. 19c illustrates a possible design such that the liquid and gas flow which is supplied by the connector 2500A to a first channel in both directions is brought into the connector by a dedicated first port, and the liquid and gas flow which is supplied by the connector to a second channel direction is brought into the connector by a dedicated second port. An internal region associated with the first port is separated by a seal 2035 from an internal region associated with the second port. Seal 2035 may be an O-ring As illustrated, the first port 2050a is located separate from the second port 2050b. Alternatively, it would be possible for one of the ports to be concentric with the other port.

Fixed-Position Connectors for Individual Channel Connections

Referring now to FIG. 20a, there is illustrated a fixed-position (not actuator-driven) connector that is capable of directing flow individually to either of two directions of a channel. This refers to total of two distinct passageways that all connect to a cylinder well in the control handle. For example, the cylinder well 2010 may connect to a suction channel having a first exiting direction to a distal end of the endoscope and a second exiting direction to an umbilical end of the endoscope. As illustrated, there are two inlet ports 2020a, 2020b, and corresponding introduction paths 2021a, 2021b. Each port and introduction path is associated with a particular direction of a particular channel within the endoscope. As illustrated, introduction path 2021a and introduction path 2021b are coaxial with each other, although they do not have to be. Within connector 2000, there may be seal 2030, such as an O-ring, that may define separation between respective introduction paths or between an introduction path and the exterior. Seals may bear against corresponding interior surfaces of cylinder well 2010 when the connector 2000 is in place in the cylinder well 2010. As illustrated, the passageway that connects with the cylinder well 2020a most deeply into the cylinder well 2010 is the suction channel in the direction to the umbilical end of the endoscope. Flow to the suction channel in the direction to the umbilical end is delivered via the first introduction path 2021a by the port 2020a which is on the centerline of the connector 2000. A second passageway, which is the suction channel in the direction to the distal end of the endoscope, is the next deepest connection point in the cylinder well 2010. Flow is delivered to the suction channel in the direction to the distal end by a second introduction path 2021b that is concentric with the first introduction path 2021a but does not extend as far into the cylinder well 2010 as does the first introduction path 2021a. Using this design of connector, it is possible to supply flow to any of the passageways independently of any other passageways, in any timewise combination such as simultaneously or sequentially or any combination thereof.

Referring now to FIG. 20b, there is illustrated a non-actuator-driven connector 2500 that is capable of directing flow individually to either of two directions of two different channels. This refers to a total of four distinct passageways that all connect to a cylinder well in the control handle. For example, the cylinder well 2060 may connect to an air channel in the direction of the distal end; an air channel in the direction of the umbilical end; a water channel in the direction of the distal end; and a water channel in the direction of the umbilical end. As illustrated, there are four inlet ports 2070a, 2070b, 2070c, 2070d, and corresponding introduction paths 2071a, 2071b, 2071c, 2071d. Each port and introduction path is associated with a particular direction of a particular channel within the endoscope. At least some of these introduction paths may be coaxial with another introduction path. Within connector 2500, there may be seals 2080a, 2080b, 2080c, such as O-rings, that may define separation between respective introduction paths or between an introduction path and the exterior. Seals may bear against corresponding interior surfaces of cylinder well 2060 when the connector 2500 is in place in the cylinder well 2060. As illustrated, the passageway that connects with the cylinder well 2060 most deeply into the cylinder well 2060 is the water channel 2178 in the direction to the umbilical end of the endoscope. Flow to the water channel in the direction to the umbilical end is delivered via the first introduction path 2071a by the port 2070a which is on the centerline of the connector 2500. A second passageway, which is the water channel 2176 in the direction to the distal end of the endoscope, is the next deepest connection point in the cylinder well 2060. Flow is delivered to the water channel in the direction to the distal end by the port 2070b via a second introduction path 2071b that is concentric with the first introduction path 2071a but does not extend as far into the cylinder well 2060 as does the first introduction path 2071a. Still less deep into the cylinder well 2060 is a connection point for the air channel 2174 in the direction of the umbilical end. This is supplied by third introduction path 2071c which is supplied by third port 2070c. Third introduction path 2071c may or may not be concentric with other introduction paths. The connection point least recessed in the cylinder well is the air channel 2172 in the direction of the distal end of the endoscope. Fourth port 2070d and fourth introduction path 2071d bring flow to this passageway. Each introduction path may be controlled by its own dedicated valve (not illustrated). Using this design of connector, it is possible to supply flow to any of the passageways independently of any other passageways, in any timewise combination such as simultaneously or sequentially or any combination thereof.

Of course, other geometries and designs of connectors are also possible. In general, it is possible to use any connection geometry that connects four ports to four passageways in a defined manner and which accommodates the geometry of the cylinder well and the passageways that connect to the cylinder well.

Connector Having an Actuator

It is further possible that the connector could comprise an actuator 2130 which definitively opens or closes or establishes a path for flow to a certain channel or channels of the endoscope or similar medical device. This is illustrated in FIG. 21 for an actuated connector that has four possible positions. FIGS. 21a, 21b, 21c and 21d respectively illustrate all four possible positions of the actuator.

Figure 21A:
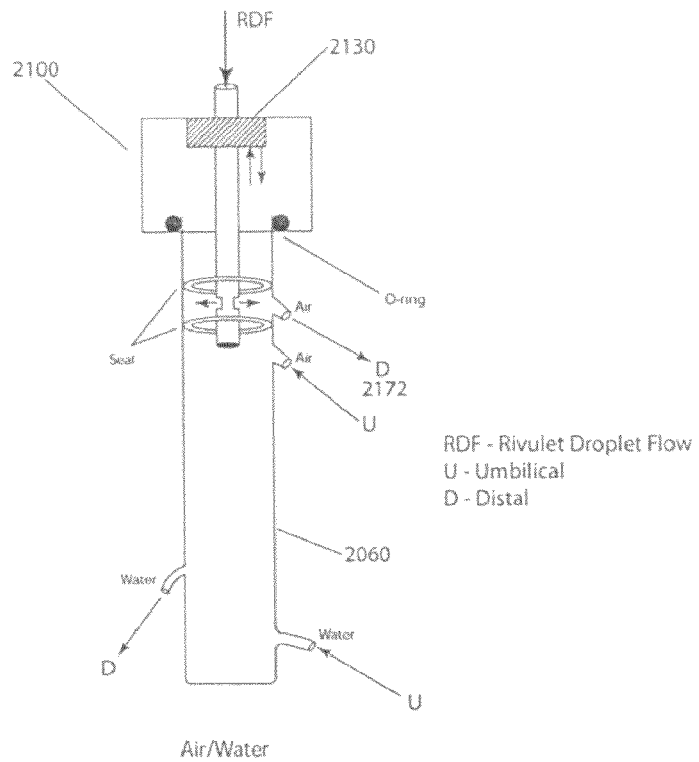
Figure 21B:
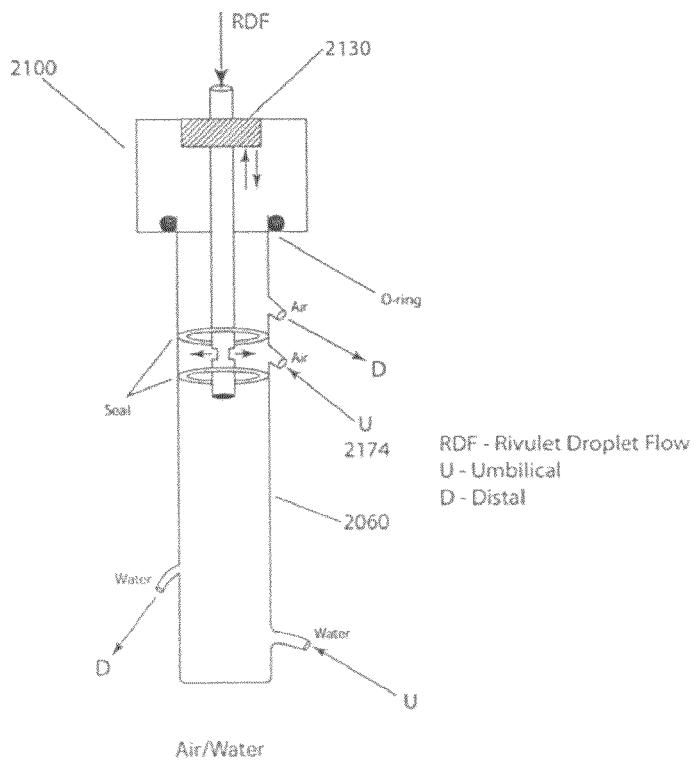
Figure 21C:
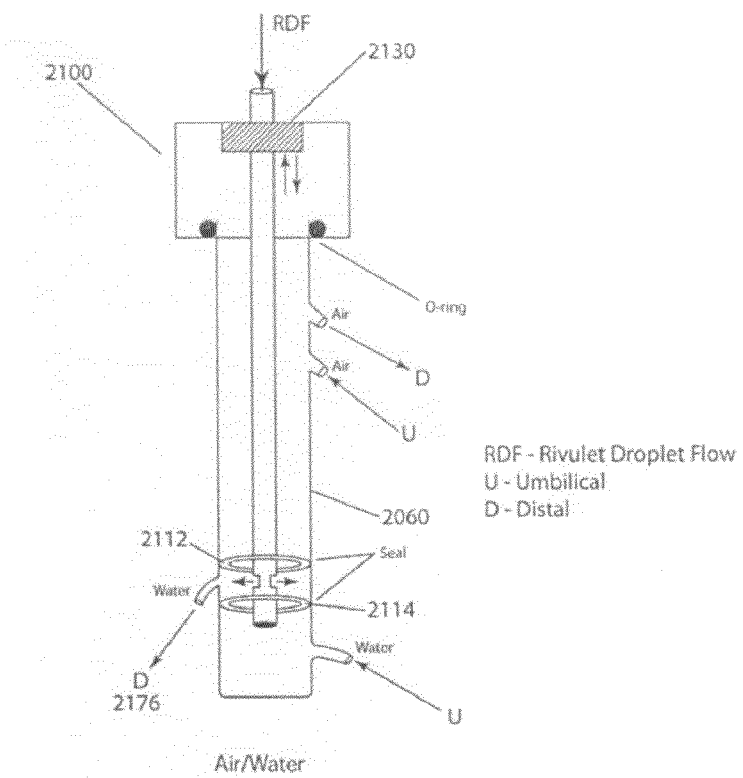
Figure 21D:
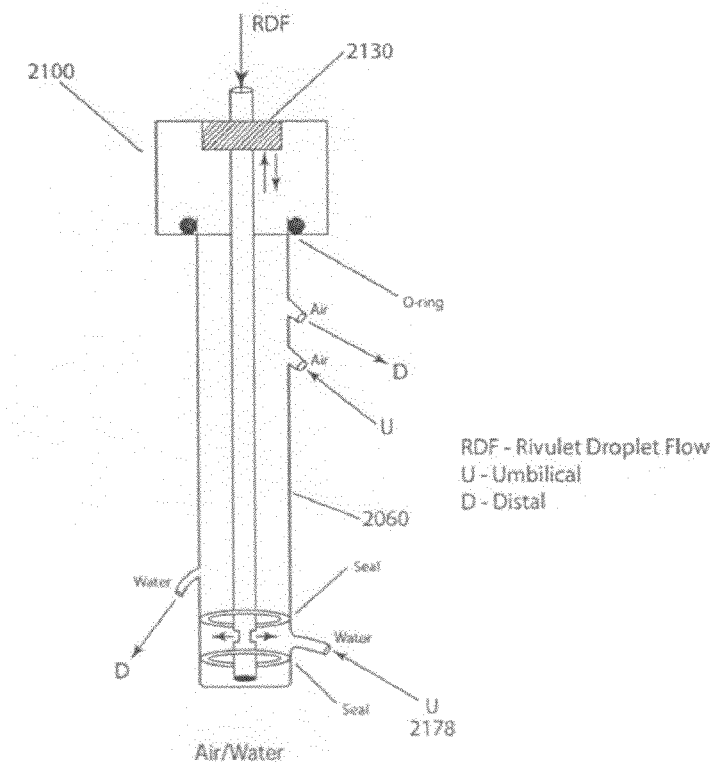

As illustrated, the connector 2100 may comprise two seals 2112 and 2114, with flow being delivered between the two seals 2112 and 2114. In FIG. 21a, the position of the actuator 2130 is such that flow is delivered to the passageway connection 2172 which is closest to the exterior of the cylinder well 2060. As illustrated, this passageway connection is the air channel in the direction of the distal end. FIG. 21b illustrates the actuator in a position such that flow is delivered to the next most outermost position which as illustrated is the passageway connection 2174 to the air channel in the direction of the umbilical end. FIG. 21c illustrates the actuator in a position such that flow is delivered to a still more inner-located position which as illustrated is the passageway connection 2176 water channel in the direction of the distal end. FIG. 21d illustrates the actuator in a position such that flow is delivered to an innermost position which as illustrated is the passageway connection to water channel 2178 in the direction of the umbilical end.

The position of the actuator 2130 may be controlled by a microprocessor or similar control system which may also operate other aspects of an automated endoscope reprocessor or may have knowledge of the status of other components of the reprocessor.

Similarly, it would be possible to design an actuated connector that only has two positions of the actuator. It would also be possible to design an actuator-driven connector able to selectively connect to a desired channel, which involves rotation of a rotatable member, perhaps with a seal. It would still further be possible to design an actuator-driven connector which uses both rotary and translational motion.

With an actuator-driven connector, it may not be possible to simultaneously provide flow to all of the passageways that connect to a particular cylinder well. It may be necessary to provide flow to one passageway or group of passageways to the exclusion of others, and then later to provide flow to another passageway or group of passageways to the exclusion of others.

Latches

It is further possible that the connector could comprise latches which grab onto a feature of the endoscope itself to maintain secure and correct positioning of connector with respect to endoscope. For example, features of the connector could interact with features of the endoscope so that there is only one permitted orientation of the connector with respect to the endoscope. Alternatively, it may be desired that the connector could be permitted to be oriented with respect to the endoscope in more than one permitted orientation, or in any number of permitted orientations. If desired, the connector could be appropriately designed to permit this situation.

Introducer (Providing Extra Flowpath Length Before Cleaning)

It is believed, although again it is not wished to be limited to this explanation, that when gas flow and liquid flow are first introduced into a passageway from a connector or significant change of flow geometry or direction, there is eventually established a flow regime that is somewhat repeated thereafter further downstream and may be described as a fully established flow regime. However, before that happens, there may be an initial region, close to the inlet or change of flow geometry or direction, in which some other flow regime exists. It is possible that even if fully-established conditions further downstream are good for cleaning, conditions in the initial region might not be so desirable for cleaning. It is possible that establishment of appropriate conditions for cleaning, such as fully-established flow, requires a certain length of flowpath to develop or establish themselves. Accordingly, it is possible that a connector to the endoscope or other device to be cleaned may comprise a port or ports for introduction of two phases either separately or at a single port, and may further comprise an appropriate length of passageway which has a cross-sectional shape identical to or similar to that of the passageway to be cleaned, and has a cross-sectional area which is within a factor of two (in either direction) of the cross-sectional area of the passageway to be cleaned. It is further possible that such introduction region can be provided for use in a condition which is at least substantially clean prior to performing the cleaning procedure. The introducer may be clean from being used during a previous cleaning procedure. In such event, even if flow conditions inside the introduction region are themselves not optimum for cleaning, at least the introduction region will not contain contaminants that could be washed downstream into or through the passageways which are intended to be cleaned.

Uniqueness of Supplied Flow

In embodiments of the invention, for any of these described connectors, whether static or actuated, it is possible to supply a predetermined flow (the liquid flowrate and the gas flowrate can both be predetermined) to a particular passageway such as a particular channel in an endoscope or a particular direction of a channel in an endoscope. In particular, if an open connection exists to only one passageway at any given time, then it is assured that the liquid/gas ratio in that passageway is definitely known. Also, the sequencing of supplying flow to particular passageways can be definitively determined.

For example, for a given channel such as the air channel, the flow could be directed for one period of time from the control handle toward the distal end of the endoscope and at another period of time could be directed from the control handle to the umbilical end of the endoscope. If a connector serves two fluid channels of the endoscope, which may be designated first channel and second channel, it is possible that for one period of time the connector could direct flow to one direction of the first channel and for another period of time the connector could direct flow in the opposite direction of the first channel, and for yet another period of time the connector could direct flow in one direction of the second channel and for yet another period of time the connector could direct flow in the opposite direction in the second channel. Of course, the sequence could be arranged in any arbitrary manner, and depending on the design of the connector, it may be possible to perform some of these actions simultaneously with other of these actions.

Of course, for any directing of flow to a particular channel in a particular direction, the liquid flowrate or the gas flowrate or both could be chosen uniquely for that situation. As discussed elsewhere herein, choice of an optimum liquid flowrate can be influenced by the diameter of a particular channel, the length of the channel, and possibly other parameters as well. For example, the liquid flowrate for the forward direction of a particular channel need not be identical to the liquid flowrate for the backward direction of that same channel from the cylinder well at the control handle.

The apparatus as described herein allows separate conditions of liquid and gas flow for each channel of the device so as to produces optimal flow of rivulets and rivulet fragments for contaminant removal in each channel. Liquid flowrate and any other conditions can be unique for particular inside diameter of passageway, for particular length of passageway, for a maximum allowable pressure for a particular passageway, and for any other feature unique to a particular passageway. Although it would be convenient in a practical sense that the same liquid (including composition and concentration of surfactant) be used for all channels within a given endoscope, it is further possible that a different liquid could be used for different channels.

It is possible that an apparatus can have connectors that are unique to a particular brand or model of endoscope, so the apparatus can know a certain amount of information about what is being cleaned simply by virtue of the connectors. Furthermore, it is possible that the apparatus can read information about what is being cleaned by reading a bar code or similar identifying information. It is even possible that the apparatus can store information about a particular endoscope. Any such information can be used for selecting operating conditions for a particular endoscope or for particular passageways of a particular endoscope.

Complex medical devices such as endoscopes may contain various passageways differing in diameter, construction and length. It can be appreciated from the discussion elsewhere herein that desirable flow input conditions may be different for different channels of an endoscope. The apparatus may be able to provide separate conditions of liquid and gas flow for each passageway of the device so as to produces optimal flow of liquid entities such as rivulets and rivulet fragments for contaminant removal in each passageway or channel.

In general, any particular channel of an endoscope could experience a treatment sequence which differs from that of other endoscope channels in any aspect of the chronology of events.

Cleaning a Passageway that has a Wire Inside it

It is also possible to use the described apparatus and methods to clean a passageway that is generally cylindrical with a wire located in the interiors. Such a passageway may be an elevator channel (which may also be referred to as an elevator wire channel) in an endoscope. The elevator wire may be used to steer the tip of the endoscope.

The elevator channel and the wire, taken together, may define an annular space, if the wire is located at least somewhat concentrically with the passageway. The dimensional space between the elevator wire and the channel which surrounds the elevator wire may be approximately 0.18 mm. Of course, it is also possible that the wire could be eccentric with respect to the channel, or could even contact the channel interior. Different ones of such configurations could exit at different places along the length of the elevator channel and the wire therein. It is believed, although it is not wished to be restricted to this explanation, that rivulet droplet flow can contact or slide along both the internal surface of the channel and the external surface of the wire, and can clean both such surfaces.

Typically the elevator channel is pressure-tested to a higher pressure than any other channel of the endoscope, so it may be possible to use a higher gas pressure in the elevator channel, for example, 60 or 80 psig.

Eductors and External Cleaning

In embodiments of the invention, apparatus for the external cleaning of an endoscope may comprise an eductor 800, which is a flow amplification device. This is illustrated in FIG. 22a. An eductor 800 may comprise an entry converging region 822, followed by a body region 824 that may be of at least approximately constant internal cross-section, followed by a diverging or diffuser region 826. All of these regions 822, 824, 826 may be aligned in a common longitudinal direction. These regions 822, 824, 826 may be cylindrical. The eductor 800 may further comprise a nozzle 830 that discharges inside the eductor 800 in approximately the longitudinal direction.

As a pressurized cleaning solution is pumped through the nozzle 830 at a high velocity, the surrounding liquid is entrained/pulled into the main stream. The combination of pumped and pulled flows can be significantly larger than the flow rate of the ejected stream through the nozzle 830 itself. For example, an eductor 800 can pull up to 3 to 5 additional flow volumes from the surrounding liquid for each volume pumped through the nozzle 830. The liquid can be pumped by a recirculating pump 840 which draws liquid from basin 850 within which the endosocope(s) are enclosed. Due to this multiplying effect, a relatively small pump 840 can be used to circulate relatively large flowrates of cleaning solution for cleaning the external surface cleaning of endoscopes. As illustrated, pump 840 draws fluid from basin 850 and returns it through the nozzles 830 of all of the eductors 800.

As illustrated in FIG. 22a, there are eight eductors 800, two in each corner of basin 850. It can be realized that a single eductor 800 can only create a strong flow to cover a single angle of view of a portion of the endoscope which may be coiled in the basin 850. Therefore, it is possible to use a plurality of eductors 800 each facing a particular portion of the endoscope so as to in combination form an effective flow pattern for exterior surface cleaning. As illustrated in FIG. 22a, the basin 850 may be rectangular or approximately square having four corners, and at each corner there may be two eductors 800 pointing from the corner towards the interior of the basin 850, with each of the two eductors 800 pointing in slightly different directions. Of course, other shapes of basin 850 are possible also.

We have found that it is important to integrate both impingement and agitation effects created by the eductor system to achieve the best cleaning results for cleaning external surfaces of endoscopes. Accordingly, the basin may generally be designed with special features, including: proper cavities to accommodate two endoscopes. There can be a combination of eductors located in corners and eductor located on walls. Eductor design and basin design are further described in Examples.

An endoscope reprocessing apparatus may further comprise a spray arm or spray nozzles located above the elevation of the endoscope(s) when endoscope(s) are being cleaned. Such spray may, for example, be used for rinsing the external surfaces of the endoscope(s) after cleaning of the external surfaces of the endoscope(s) has been performed. Of course, it is also possible for such spray nozzles to be used during cleaning of external surfaces of the endoscope(s). These are illustrated in FIG. 22d and FIG. 22e.

It is further possible that eductors can be caused to flow in a sequence or pattern, rather than all of the eductors flowing all of the time. For example, some can be on and some can be off at different times, so as to further create agitation. For example, the patterning and timing of eductor operation could be such as to create swirl in one or another direction or various directions sequentially. There may also be an overhead spray which may be useful for rinsing, for example.

EXAMPLES

The following examples are shown as illustrations of the invention and are not intended in any way to limit its scope.

Examples 1-7 illustrate the method of determining hydrodynamic modes of flow, mapping these modes as a function of flow rates for tubes of different diameters and identifying conditions that produce Rivulet Droplet Flow. The tubes employed are of diameters that cover the channels encountered with typical endoscopes.

Example 1

Method to Construct Flow Regime Maps

This method was developed to identify and define the flow regime (surface flow entities and their distribution) on the channel wall at several positions along channel length from inlet to outlet as a function of the operating parameters. Operating parameters include: channel diameter and length, liquid flow rate, air pressure, air flow rate and velocity, and surfactant type and concentration. The method enables identification and optimization of Rivulet-Droplet-Flow for various endoscope channels ports. In addition, the flow regimes at different positions along channel length has been used to define the operating conditions of the cleaning cycles necessary to achieve high-level cleaning of the entire channel surface area. As will become apparent, the flow regime (collection of fluid flow elements) varies as function of distance from channel inlet to exit and this necessitates different treatment conditions to achieve optimal results for each type of channel. Although the method is illustrated with RDF flow, the method can clearly be used to map DPF and DPDF flow regimes by introducing the liquid plug instead of a rivulet.

Apparatus: The apparatus 200 illustrated schematically in FIG. 23 allows optical examination of transparent endoscope channels, to control the flow conditions used in the test and to measure all operating parameters both under static and dynamic conditions. The apparatus 200 consists of a source of compressed air 202 (Craftsman 6 HP, 150 psi, 8.6 SCFM @ 40 psi, 6.4 SCFM @ 90 psi, 120V/15 amp), various connectors and valves 204, 206, pressure regulators 208, 210 a flow meter 212, pressure gauges 214, 216, 218, a metering pump 220 (Fluid Metering Inc., Model QV-0, 0-144 ml/min), metering pump controller 222 (Fluid Metering Inc., Stroke Rate Controller, Model V200), various stands and clamps (not shown), various tube adapters (not shown), an imaging system 224 which includes a microscope, digital camera, flash, and various illumination sources (not individually shown in FIG. 12 but identified below).

The compressed air source is a 6-HP (30-gallon tank) Craftsman air compressor 202. The compressor 202 has two pressure gauges, one for tank pressure 214 and one for regulated line pressure 216. The maximum tank pressure is 150 psi. The compressor 202 actuates when the tank pressure reaches 110 psi. The line pressure is regulated to 60 psi for the majority of the tests, with the only exceptions being the high pressure test (80 psi) used to define the hydrodynamic mode for the 0.6-mm (ID) "elevator-wire channel". The regulated compressed air is supplied to a second regulator via 15' of ⅜" reinforced PVC tubing. The second regulator is used to regulate the pressure for each test. The air then feeds into a 0-10 SCFM Hedland flowmeter 212 with an attached pressure gauge 218. This gauge 218 is used to set the test pressure via the second regulator 210 that precedes it, as well as to read the dynamic pressure during the experiment. The flow meter 212 feeds into a "mixing" tee 226, where liquid is metered into the air stream via a FMI "Q" metering pump 220. The metering pump 220 is controlled by a FMI pump controller 222. The outlet of the mixing tee 226 is where adapters 228 for varying model endoscope tube diameters 230 are connected.

To acquire an image of the flow mode inside the channel, we used a Bausch and Lomb Stereozoom-7 microscope (1×-7×), a camera to microscope T-mount adapter, a Canon 40D digital SLR camera, and a Canon 580EX speedlite. The camera to microscope adapter's T-mount end is bayoneted to the camera and the opposite end is inserted in place of one of the eyepieces on the binocular microscope. The flash is attached to the camera via a hot shoe off camera flash cable and directed into a mirror/light diffuser mounted below the microscope stage. The mirror/diffuser is a two sided disc with a mirror on one side and a soft white diffuser on the opposing side. This can be rotated to change the angle of the light that is directed towards the stage as well as to switch between the two sides. The microscope also has an open porthole on the rear-bottom that allows for light to be directed onto the mirror/diffuser. A Bausch and Lomb light (Catalog #31-35-30) is inserted into this porthole and used in conjunction with the Canon 40D's live view feature for live viewing as well as for focusing. The live view feature shows a real time image on the 3" LCD screen on the back of the camera. The channel to be photographed is placed on the microscope stage and taped into place. Photographs were taken with an exposure time of $\frac{1}{250}$th of second with the flash on full power using an optional remote to reduce vibration. Certain tests required single shots while other tests required photographs to be taken in "burst mode." In burst mode the camera shoots 5 frames per second at equal intervals. The images are stored on a 2GB compact flash card and transferred to a PC via a multi-slot card reader. Images are processed (for clarity) in Adobe CS3 and analyzed one by one with the naked eye either on a 22" LCD monitor or via color prints from a color laser printer. The latter was used to analyze and compute treatment number under different conditions.

Model Test: Teflon tubing (McMaster-Carr Company) with different internal diameters and lengths was used to create the flow regime maps. The gas pressure for these experiments was set at desired value from 0 to 80 psi at the second regulator. The liquid flow rate was varied from a low flow rate of about 3 mL.min to a high flow of about 120 mL/min, or higher if necessary. Images were taken at generally 5 positions measured from the inlet along the length of the each tube (generally around two meters in length): 1) 35-45 cm; 2) 65-75 cm; 3) 110-120 cm; 4) 143-165 cm; and 5) 190-210 cm near end of the tube. At each position, microphotographs were taken at a range of flow rates, from the low flow rates to the high flow rates with a total of 5 and 9 flow rate steps in each test. 20-30 photographs were taken for each position for analysis.

Image Analysis and Map Construction: The image analysis consisted of examination of all microphotographs from each combination of flow rates and channel positions to determine the prevailing surface flow entities and hydrodynamic mode. The surface flow entities of interest included rivulets (straight and meandering), droplets (random), linear droplet arrays (LDA), sub-rivulets, sub-rivulets "fingering" off of the main rivulet, sub-rivulet fragments, turbulent/foamy rivulets, liquid films, foam, and all transition points between these features. These liquid features were used to describe various modes of flow (flow regimes) and these modes were then put into a "map" which shows the prevailing modes of flow as a function of distance from tube inlet at different liquid flow rates, at the selected air pressure. Qualitative features were used to define the flow regimes observed and quantitative analyses of images were used to compute the Treatment Number.

Descriptions of liquid features and hydrodynamic modes used in mapping flow regimes: The following descriptive definitions are used to classify individual surface flow entities which are observed when a liquid is introduced into channel as a rivulet stream and gas is simultaneously allowed to flow under pressure in the tube. These terms provide a consistent definition of flow elements for the classification of flow regimes defined below.

1. Rivulet: A continuous stream of liquid normally covering the entire length of tube and usually more prevalent near the inlet sections of the tube. Rivulets, depending on their velocity, liquid composition, and tube surface micro-roughness can either be perfectly straight or "kinked." In both cases the rivulet could be "stuck" (no meandering) or could meander ("meandering rivulets") about the tube surface reaching sides or ceiling of the tube due to transversal movement.

2. Droplets: Single beads of liquid that can either be static or moving along the surface of tubing and are not connected to any other feature. These droplets can range from 5 microns to 50 microns. Droplets can be distributed at random, or exist as linear array split from trailing end of rivulet fragments.

3. Sub-rivulets: Cylindrical bodies in the form of long continuous liquid threads that break off of or finger from the main rivulet. They are generally much thinner in comparison to the main rivulet. Dimensions of subrivulets depend on the flow conditions and liquid composition and can range from 100 microns to 300 microns.

4. Sub-rivulet fragments: When sub-rivulets break apart they produce rivulet fragments. A sub-rivulet normally becomes unstable and splits into several equal rivulet fragments that form a linear rivulet fragment array (LRFA). Each fragment becomes tear shaped or pill shaped with an advancing and receding contact angle. The advancing contact angle is normally high (e.g., greater than 60 degrees) while the receding contact angle at the trailing edge of the liquid feature is much lower (e.g., less than 50 degrees). Droplets normally split from the trailing end of a rivulet fragment. These droplets frequently form linear droplet arrays (LDA).

5. Liner droplet arrays (LDA): Long arrays of small (20 microns to 200 microns) droplets deposited on the tube surface, normally formed from the trailing end of a sub-rivulet fragment.

6. Turbulent/foamy rivulet: The main rivulet often reforms near the end of tube in a more chaotic and less structured fashion, and often includes discrete dispersed air bubbles and foam (multiple dispersed air bubbles in close proximity). This rivulet does not tend to meander as much as the main rivulet in the early sections of the tube near the inlet. This foamy mode normally leads to formation of a thick liquid film that covers the entire cross-section of tube depending of the surfactant or surfactant mixture used.

7. Film: A complete annular liquid film covering the entire tube or tube section, normally without traces of air bubbles or foam.

8. Foam: A prevalence of air bubbles dispersed in the liquid phase normally present in the entire tube cross section.

The term "fragments" is used to encompass all surface flow entities that are derived from the initial rivulet and include: droplets, sub-rivulets and sub-rivulet fragments (collectively cylindrical bodies) and linear droplet arrays (LDA).

Generalized Flow Regimes: The following qualitative descriptions are used to qualitatively classify the predominant flow regimes or "modes of flow" that are observed during the experiment. Their typical appearance is given in the photographs and corresponding schematic drawings in FIG. 5b.

Sparse/Dry (FIG. 5b-A): A mode of flow generally observed when the liquid flow rate is very low. The main rivulet is skinny and tends to be broken (not continuous). There are some stray sub-rivulet fragments and random droplets, but these features are few and far between.

Single Rivulet (FIG. 5b-B): When the liquid flow rate reaches a critical level the main rivulet forms and is continuous. The main rivulet can be straight or kinked, can be stationary or meandering depending on the gas velocity. The rivulet thickens with flow rate and does not break apart. Other features are absent in this flow mode because all of the liquid is contained in the rivulet.

Ejection Zone (FIG. 5b-C): When a high enough gas velocity (further distance from the tube inlet or higher pressure) and/or liquid flow rate is achieved, the sub-rivulets begin becomes instable and eject or split from the main rivulet. This mode also contains a few sub-rivulet fragments and random droplets.

Rivulet-Droplet-Flow (FIG. 5b-D): Main rivulet may or may not be present. Sub-rivulets, sub-rivulet fragments and droplets prevails. Sub-rivulet fragments leave linear droplet arrays. Random droplets are also present.

Film/Foam (FIG. 5b-E): Complete coverage of the tube with either a film and/or foam.

Example 2

Flow Regime Map for 2.8 mm Channel

In this example the methods and apparatus of Example 1 were used to construct the flow regime map for a tube with 2.8 mm ID and 2 meter length. The following operating condition were employed: air pressure (30 psi), air flow rate (about 5.0 SCFM), air temperature (21 C—ambient), liquid temperature (21 C—ambient). The cleaning liquid included SUR-FYNOL® 485 and AO-455 (Composition 10A in Table 5). The liquid flow rates ranges from 0 ml/min to 29 ml/min with 7 flow rate steps in between for a total of nine flow rates. In this example the positions for photographs were 45 cm, 73 cm, 112 cm, 146 cm, and 196 cm. Microphotographs were collected at each position and each liquid flow rate, and then analyzed to construct the flow regime map given in FIG. 7c. The following flow modes were observed at each position along the tube (distance from inlet) as a function of liquid flow rate and position along the tube.

At the 45-cm point, the flow mode is sparse/dry up to about 6.5 mL/min at which point it transitions to the single rivulet flow mode which continues with increasing liquid flow rate up to 29 mL/min. At this position, the gas velocity is low near the entrance of the tube and insufficient to produce rivulet instability or fragmentation. The rivulet that forms at this position which appears above 6.5 mL/min liquid flow rate exhibits some meandering due to hydrodynamic instability.

At the 73-cm point, the flow mode is sparse/dry up to 5 mL/in flow rate. As the liquid flow rate increases, the flow mode transitions into the single rivulet mode. The single rivulet flow mode continues up to about 18 mL/min at which point it transitions into an ejection zone mode where sub-rivulets split from the main liquid rivulets. The ejection zone continues up until 29 mL/min. The ejection zone mode appears to arise due to further instability of the liquid on the tube wall which leads to splitting of sub-rivulets from the main rivulet. The main rivulet tends to meander due to transversal movements.

At the 112-cm point, the flow mode is sparse/dry up to about 4.0 mL/min flow rate at which point the flow mode transitions to the single rivulet flow. The single rivulet flow continues up to about 17 mL/min at which point it transitions into an ejection zone. The ejection zone continues up to 23 mL/min at which point it transitions to a film/foam mode. The film/foam mode continues up to 29 mL/min.

At the 146-cm point, the flow mode is sparse/dry up to about 3 mL/min at which point the flow mode transitions to single rivulet flow. The single rivulet flow mode continues up to 12 mL/min at which point it transitions into rivulet-droplet flow (RDF) with various fragments and surface flow entities observed. The RDF mode continues up to 22 mL/min at which point it transitions to the film/foam mode. The film/foam mode continues up to 29 ml/min.

At the 196-cm point, the flow mode is sparse/dry up to 2 mL/min at which point the flow mode transitions to the single rivulet flow mode. The single rivulet flow mode continues up to 12.5 mL/min at which point it transitions into the RDF mode. The RDF mode continues up to 21 mL/min at which point it transitions to the film/foam mode. The film/foam mode continues up to 29 mL/min.

The above data is plotted as a flow regime map as a function of the position along tube length from inlet (0 cm) to outlet (200 cm) and the liquid flow rate at a constant air pressure in FIG. 7c. The map provides a convenient representation of defines the different flow modes observed at each position along the tube length at the different liquid flow rates. The region within the map that provides optimal RDF flow can thus be identified and the controlling parameters selected (e.g., liquid flow rate at a particular gas pressure.

In the case of the 2.8 mm ID tube, liquid flow rates between about 16 to about 22 mL/min appear to provide liquid flow features that would effect high level cleaning over most of tube length. For illustration, the 19 mL/min liquid flow rate the sparse/dry mode is minimized (limited to only short section near entrance) while both the ejection and RDF mode cover most of the tube length without formation of film or foam near the exit of the tube. At very low liquid flow rates (0 to 10 mL/min), flow modes are characterized by spars/dry mode and single rivulet mode; under such conditions the entire surface of the tube cannot be adequately cleaning due to the small amount of surface flow entities and to the low Treatment Number in this case. Treatment time needs to be extended in this case and this becomes impractical in cleaning endoscopes and other medical devices. On the other hand, at very high liquid flow rates, most of the tube length will be dominated by film and foam which result in covering the contaminants with a liquid film, a condition that does not produce high-level cleaning. It should thus be appreciated that cleaning according this method with a single liquid flow rate might not cover the entire length of the tube if cleaning time is short, and that using more than one liquid flow rate or utilizing alternative flow regimes, e.g., DPF or DPDF regimes, to create surface flow entities with moving three phase contact lines may be required. This can be achieved by utilizing alternating liquid plug and gas flow for a part or all of the cleaning cycle. Using other surfactant mixtures may also produce other flow maps under the same conditions depending of the nature of surfactants.

The methods of Example 1 and analysis procedure Example 2 were employed in Examples 3-7 to construct flow regime maps for tubes of different diameters.

Example 3

Flow Regime Map for 1.8-mm Tube

The conditions used were: air pressure (30 psi); air flow rate (about 3.0 SCFM); air temperature (ambient @21 C); liquid temperature (ambient @ 21 C). The test cleaning liquid included Surfynol 485 (0.036%) and AO-455 (0.024%). In this example the liquid flow rates range was from 3.5 mL/min to 12.5 mL/min with 5 flow rate steps in between for a total of seven flow rates. The positions examined with photographs were: 36-cm, 73-cm, 112-cm, 146-cm, and 188-cm, all measured from tube inlet (0-cm). The map for the 1.8-mm tube found for the above conditions is shown in FIG. 7b.

The flow maps for the 1.8-mm (FIG. 7b) and the 2.8-mm channels (FIG. 7c) are clearly different. The RDF and ejection zones are shifted observed in the 1.8 mm tube are shifted to lower liquid flow rates relative to the 2.8 mm tube and cover a greater fraction of the tube length.

The 1.8 mm tube is important since it represents the dimension of the air, water and auxiliary channels in many flexible endoscopes. The flow mode map (FIG. 7b) indicates that liquid flow rates between 6.0 to 9.0 mL/min appears to provide an acceptable range to achieve high-level cleaning at 30 psi air pressure according to the methods of this invention). In this liquid range, rivulets, subrivulets and fragmentation can be created on most of the tube surface. High liquid flow rates with this surfactant mixture (Composition 10A in Table 5) lead to film/foam flow mode which prevents the formation of surface flow entities that produce high detachment force.

Example 4

Flow Regime Map for 4.5 mm Tube

The test conditions were: air pressure (30 psi); air flow rate (about 6.0 SCFM); air temperature (ambient @ 21 C); liquid temperature (ambient @21 C). The cleaning liquid was the same as in Examples 2 and 3. The liquid flow rates ranged from 13 mL/min to 69 mL/min with 7 flow rate steps in between for a total of nine flow rates. The positions along the tube used for microphotographs were: 28-cm, 67-cm, 123-cm, 162-cm, and 196-cm. The map for the 4.5 mm tube found for the above conditions is shown in FIG. 7d and significantly differs from the narrower diameter tubes described in Example 2-3.

At the 28-cm point the 4.5 mm tube is in the ejection mode from the start and transitions into RDF at 33 mL/m. The RDF mode continues until 62 mL/m at which point it transitions into the film/foam mode. At the 67-cm point the 4.5 mm tube is in RDF until 60 mL/m at which point it transitions into the film/foam mode. At the 123-cm point the 4.5 mm tube is in RDF until 39 ml/m at which point it transitions into the film/foam mode. At the 162-cm point the 4.5 mm tube is in the RDF mode until 35 mL/min at which point it transitions into the film/foam flow. At the 196-cm point the 4.5 mm tube is in RDF until 33 ml/m at which point it transitions into the film/foam mode. Due to the larger diameter tube the gas velocities in the 4.5 mm tube are much higher and ejection occurs earlier in the tube (closer to the entrance) and the RDF mode surface flow entities is sustained over a larger portion of the tube and over a larger range of flow rates. In the 4.5 mm tube still lower flow rates are lead to the sparse/dry flow mode.

Example 5

Flow Regime Map for 6.0 mm Tube

The test conditions were: air pressure (30 psi); air flow rate (about 8.0 SCFM); air temperature ambient @ 21° C.; cleaning solution temperature ambient temperature @21° C. The test cleaning liquid in this example was the same as in Example 1. The flow rates ranges from 25 ml/min to 85 ml/min with 7 flow rate steps in between for a total of nine flow rates. The positions for photographs were: 23-cm, 56-cm, 118-cm, 163-cm, and 196-cm. The map for the 6 mm tube found for the above conditions is shown in FIG. 7e and is qualitatively similar to the map for the 4.5 mm ID tube but differs significantly from those of the narrower diameter tubes described in Example 2-3).

At the 23-cm point, the single-rivulet flow mode is observed until about 32 mL/min at which point it transitions to the ejection flow mode. This mode continues up until about 62 mL/min at which point the flow transitions into the RDF mode. At the 56-cm point, the single-rivulet flow is observed up until 32 mL/min at which point it transitions into the RDF flow mode. The RDF mode is observed until about 80 ml/min at which point it shifts to the film/foam mode. At the 118-cm point, the single-rivulet flow is observed up until about 32 mL/min at which point it transitions into the RDF flow. The RDF mode is observed until about 65 ml/min at which point it shifts to the film/foam mode. At the 163-cm, single-rivulet flow mode is observed up until about 32 mL/min at which point it transitions into mixed the RDF mode. The RDF mode is observed until 62 mL/min at which point it shifts to the film/foam mode. At the 196-cm point, the RDF mode is observed until 65 mL/m at which point it shifts to the film/foam mode. This map closely resembles the 4.5-mm tube map (FIG. 7d). However, due to the high air flow rate obtained under these above conditions, the RDF mode can be achieved at most of the tube length, except at a short segment near the entrance of the tube.

Comparison of FIGS. 7b and 7c with FIGS. 7d and 7e indicates that it is easier to achieve optimal zones of RDF flow over most of tube length with larger diameter 4.5 mm and 6 mm tubes.

Example 6

Flow Regime Map for the 0.6 mm Tube @ 30 psi Air Pressure

The test conditions were: air pressure (30 psi); air flow rate (about 0.1 SCFM); air and cleaning solution temperature (ambient @ 21° C.). The cleaning liquid was the same as in Example 1. The liquid flow rates ranged from 3 mL/min to 11.5 mL/min with 4 flow rate steps in between for a total of six flow rates. The positions for photographs were: 28-cm, 73-cm, 118-cm, 157-cm, and 207-cm. The flow map is shown in FIG. 7a.

At the 28-cm point, the single-rivulet mode is observed which continues up to 8.5 mL/min liquid flow rate at which point it transitions to the film/foam mode. At the 73-cm point, the flow mode is single rivulet which continues up to 10.5 mL/min. At higher flow rates it transitions to the film/foam mode. At the 118-cm point, the flow mode is RDF up to 5 mL/min at which point the flow mode transitions to the single rivulet mode. This continues up to 10.5 mL/min at which point it transitions to the film/foam mode. At the 157-cm point, the flow mode is a single-rivulet flow. This continues up to 10.5 mL/min at which point it transitions to the film/foam mode. At the 207-cm point, the flow mode is RDF up to 5 mL/min at which point the flow mode transitions to a single rivulet mode. This continues up to 9.5 mL/min at which point it transitions to the film/foam flow mode.

According to this flow mode map, the RDF mode is only occasionally encountered and is not generally accessible under the above conditions. This is due the high hydrodynamic resistance of this narrow diameter tubing. The air velocity is insufficient to induce instabilities leading to formation of liquid fragments. Cleaning with rivulet flow under these conditions is due solely to the meandering of the single-rivulet flow due to transversal movement. To achieve optimal RDF flow a higher pressures and liquid and gas flow velocities are required as is shown in Example 7 below which was carried out at a gas pressure of 80 psi.

Example 7

Flow Regime Map for the 0.6 mm Tube @ 80 psi Air Pressure

The operating conditions were the same as in Example 6 but the air pressure was controlled at 80 psi which is the maximum rated pressure for this very small diameter endoscope channel (elevator-wire channel). The results are given in FIG. 24.

At the 28-cm to 207 cm (i.e., over the entire length of the tube) the flow mode was RDF which continues up to about 10.5 mL/min at which point it transitions to the single rivulet mode. The results of this example demonstrate that using higher air pressure and air velocity results in the formation of the RDF even in the 0.6 mm channel which is favorable for cleaning. This example is important since these dimensions are similar to the elevator-wire channels of flexible endoscopes.

Example 2-7 demonstrates that the operating conditions in terms of flow rates and gas pressure required to generate optimal RDF flow regimes for cleaning by rivulet flow depend strongly on the diameter of the tubing employed and is different for different diameters. Since there is not a single universal set of parameters for all channel diameters, optimal cleaning of multi-channel devices such as endoscopes requires that the conditions employed for each channel be optimized to produce the optimal flow mode, e.g., RDF in the case of rivulet flow.

Example 8

Examples of Liquid Cleaning Media Containing Single Surfactant

Liquid compositions containing single surfactants were prepared and tested by the flow mapping technique of Example 1 and flow regime maps constructed for endoscope tubes of different diameters (ID 0.6 mm to 6.0 mm) as described in Examples 2-7. The compositions are summarized in Table 3. The air pressure range used in the evaluations was between 10 to 30 psi and in other cases above 30 psi. The liquid flow rates used in the evaluations were in the range defined by flow regime/mode maps similar to those given in Examples 2-7.

The surfactants belong to Class III as described above. The results from all the experiments are summarized by an overall RDF rating and an overall organic soil cleaning rating. All the surfactants provided cleaning media that formed the RDF flow regime in all the different channels and provided soil removal. However, the effectiveness in soil removal varied somewhat. Organic soil removal was evaluated by the procedure described in Example 15.

TABLE 3

| | Composition | | | | | |
|---|---|---|---|---|---|---|
| Ingredient | B | C | E | G | H | M |
| Water | 97.82 | 97.81 | 99.621 | 99.67 | 99.67 | 99.37 |
| SMS | 0.13 | 0.13 | 0.13 | 0.13 | 0.13 | 0.13 |
| STP | 2.000 | 2.000 | | | | |
| EDTA (39%) | | | 0.15 | 0.15 | 0.15 | 0.15 |
| AO-405 | | | 0.024 | | | |

TABLE 3-continued

| | Composition | | | | | |
|---|---|---|---|---|---|---|
| Ingredient | B | C | E | G | H | M |
| TERGITOL ® 1X | 0.050 | | | | | |
| PLURONIC ® L43 | | 0.060 | 0.050 | | | 0.050 |
| 31R1 | | | | 0.050 | | |
| L62D | | | | | 0.050 | 0.000 |
| L81 | | 0.025 | | | | |
| Accusol 505N | | | | | | 0.30 |
| RDF Rating | 3 | 3 | n/a | 3 | 3 | n/a |
| Organic Soil Cleaning | 4 | 2 | n/a | n/a | n/a | n/a |

Notes:
RDF Rating: 1 to 5 scale where 1 = worst, 5 = Best
Organic Soil Cleaning: 1 to 5 scale where 1 = worst, 5 = Best;
Rating was based on SEM acquired at 200X to 5000X magnification as in Example 19

Example 9

Comparative Examples of Liquid Cleaning Media Containing Unsuitable Surfactant

The comparative examples listed in Table 4 were prepared and tested by the identical procedure described in Example 8. However, the individual surfactants belonged to either Class I (formed wetting films) or class II (formed excessive foam).

Comparative C-P employs a hydrotrope (xylene sulfonate) SX-40 which does not provides surface tension less than 55 dynes/cm which appears to be insufficient to produce extensive fragmentation.

Comparatives C-Q and C-R were made with a castor-oil ethoxylate (15 EO), CO-15 and an acetylinic surfactant, SURFYNOL® 420 respectively both produced wetting films on the surface of endoscope channels. No rivulets or liquid fragmentation were observed with Compositions Q and R nor was the RDF regime observed.

Comparative C-S and C-T were made with an alcohol ethoxylated, TERGITOL® TMN-10 and sodium lauryl sulfate (SLS) respectively. These surfactants have a Ross-Miles foam height greater than 50 mm and produced the foam/film regime which covered most of the channel cross-section and length with wither foam (generally) of film at low flow rates. The RDF regime was not observed under the conditions employed. Foaming surfactants such as TMN-10 are not suitable for use in RDF cleaning of endoscope channels or other luminal devices.

TABLE 4

| | Comparative Examples | | | | |
|---|---|---|---|---|---|
| Ingredients | C-P | C-Q | C-R | C-S | C-T |
| Water | 97.77 | 97.82 | 97.82 | 97.82 | 97.77 |
| SMS | 0.13 | 0.13 | 0.13 | 0.13 | 0.13 |
| STP | 2.00 | 2.00 | 2.00 | 2.00 | 2.00 |
| SX-40 | 0.10 | | | | |
| CO-15 | | 0.050 | | | |
| Surfynol 420 | | | 0.050 | | |
| TMN-10 | | | | 0.050 | |
| SDS/SLS | | | | | 0.10 |
| RDF Rating | 2 | 1 | 1 | 2 | 1 |
| Organic Soil Cleaning | 1 | 2 | 2 | 3 | 3 |

Notes:
RDF Rating: 1 to 5 scale where 1 = worst, 5 = Best
Organic Soil Cleaning: 1 to 5 scale where 1 = worst, 5 = Best;
Rating was based on SEM acquired at 200X to 5000X magnification as in Example 19.

Example 10

Examples of Liquid Cleaning Media Containing Surfactant Mixtures

The examples listed in Table 5 were prepared and tested by the identical procedure described in Examples 8 and 9. In contrast to the previous examples, the cleaning compositions contained a mixture of two surfactants: an acetylinic surfactant, SURFYNOL® 485 and an alkoxylated ether amine oxide, AO-455. All the compositions performed well and some provided very effective and robust RDF flow regimes.

TABLE 5

| Ingredients | 10A | 10B | 10C | 10E | 10F | 10G | 10H | 10I | 10J |
|---|---|---|---|---|---|---|---|---|---|
| Water | 97.80 | 97.79 | 99.63 | 97.51 | 97.510 | 97.510 | 97.510 | 99.360 | 97.38 |
| SMS | 0.13 | 0.130 | 0.130 | 0.130 | 0.130 | 0.130 | 0.130 | 0.130 | 0.13 |
| STP | 2.00 | 2.00 | | 1.00 | 1.00 | 1.00 | 1.00 | | 2.00 |
| TSPP | | | | 1.00 | 1.00 | 1.00 | 1.00 | | |
| EDTA (39%) | | | 0.150 | | | | | 0.150 | |
| SURFYNOL ® 485 | 0.036 | 0.036 | 0.036 | 0.036 | 0.036 | 0.036 | 0.036 | 0.036 | 0.036 |
| AO-455 | 0.024 | 0.024 | 0.024 | 0.024 | 0.024 | 0.024 | 0.024 | 0.024 | 0.024 |
| L61 | | | 0.025 | | | | | | 0.025 |
| L81 | | 0.024 | | | | | | | |
| CP5 | | | | 0.30 | | | | | |
| Accusol 455 N | | | | | 0.30 | | | | |
| Accusol 460N | | | | | | 0.30 | | | |
| Accusol 505N | | | | | | | 0.30 | 0.30 | |
| SX-40 | | | | | | | | | 0.40 |
| RDF Rating | 4 | n/a | 3 | n/a | n/a | n/a | n/a | 4 | n/a |
| Organic Soil Cleaning | 3 | n/a | n/a | n/a | n/a | n/a | n/a | n/a | n/a |

Notes:
RDF Rating: 1 to 5 scale where 1 = worst, 5 = Best
Organic Soil Cleaning: 1 to 5 scale where 1 = worst, 5 = Best;
Rating was based on SEM acquired at 200X to 5000X magnification as in Example 19

Example 11

Cleaning Performance Determined by Radionulcide Method (RNM)

This example compare the cleaning of endoscope channels with one phase liquid flow and with RDF mode with the cleaning effectiveness assessed by the Radionulcide Method (RNM). RNM provides direct quantification of contaminants in the channels by counting the Gamma quanta/second/endoscope using a special Gamma camera (Picker, U.S.A.). This method does not require recovery of residual contamination from the endoscope, and thus provides accurate determination of cleaning level. Tc(99) in macroalbumen is mixed with the organic soil which is then used to contaminate endoscope channels by injecting the mixture from one of the endoscope ports. Different channels can be tested separately. Images showing the spatial distribution of contaminants before and after cleaning are also acquired for each test.

A PENTAX® endoscope (Models EG-2901) was tested to determine the effectiveness of liquid flow cleaning. 5 mL of Dry sheep blood was mixed with 5 mL saline solution followed by adding 100 uM protamine sulfate. The desired dose of Tc-99 in macroalbumen was thoroughly mixed with the above solution. 6.5 ml of the mixture was injected into the endoscope via the A/W, port located at the umbilical end of the endoscope following the contamination method of Alfa et al., American Journal of Infection Control, 34 (9), 561-570 (2006). The endoscope was allowed to stand for at least one hour to allow blood clotting and adhesion to channel walls to take place. Gamma-camera images were acquired at the following points during the test: 1) right after contamination, 2) just before cleaning, 3) after each step of pre-cleaning, cleaning, rinsing and drying. At each point, the quanta/second/endoscope was measured to determine the effect of each segment of the cleaning cycle. Normal procedures were used to determine and subtract radioactivity level arising from accidental spillage on the external surface of endoscope or the holding tray.

In this test, summarized in Table 6 under the column labeled "Comparative 11", the initial quanta/sec./endoscope (q/s/e) was 3407 after 5 minutes of liquid flow cleaning of the air/water channel (1.4 mm ID and about 350 cm in length) at a liquid flow rate of 7.5 mL/minute, the radioactivity decreased to 2603 q/s/e. After rinsing and drying, the radioactivity was further decreased to 1855 q/s/e. This example demonstrates that liquid flow cleaning does not effectively clean the A/W channel, as supported by the Gamma camera images given in FIG. 25.

The same PENTAX® endoscope as in the above comparative control was contaminated with dry sheep blood and soiled as described above. The initial count before cleaning was 1044 q/s/e. This was reduced to 321 q/s/e after an initial RDF pre-cleaning step. The residual soil level was further decreased to 59 q/s/e after RDF cleaning and rinsing. The flow was injected from the A/W cylinder at the control handle of endoscope. The experiment and results are described in Table 6 under the column headed "Example 11". The final residual radioactivity in the endoscope after cleaning with the RDF method was 59 q/s/e compared to 1855 q/s/e when cleaning was done by liquid flow (Comparative 11).

TABLE 6

| Steps | Comparative 11 | Example 11 |
|---|---|---|
| Initial | 3407 | 1044 |
| Pre-cleaning | 3440 | 321 |
| Liquid flow | 2603 | |
| Rivulet-droplet flow | | 327 |
| After rinsing and drying | 1855 | 59 |
| Rivulet-droplet flow advantage | | 262 |
| Pentax Endoscope Model | EG-2901 | EG-2901 |
| Soil (see footnote) | PB2 | PB2 |
| Air Pressure (psi) | 0 | 28 |

TABLE 6-continued

| Steps | Comparative 11 | Example 11 |
|---|---|---|
| Liquid flow rate (ml/min) | 75 | 15 |
| Pre-cleaning time (min) | 2.5 | 2.5 |
| Liquid flow time (min) | 2.5 | 0.0 |
| Rivulet-droplet flow cleaning time (min) | 0.0 | 2.5 |
| Two-phase rinsing time (min) | 3.0 | 3.0 |
| Drying time (min) | 2.0 | 2.0 |

Note:
PB2: 5.0 ml dry sheep blood, 5.0 ml saline, 100 μm potamine sulfate and radioactivity material that makes about 11.5 ml of soil.

Further studies have demonstrated that a significant portion of the residual radioactivity in Example 11 is due to one or more hot spots arising from contaminating port.

High-sensitivity images (FIG. 25) comparing endoscopes cleaned by liquid flow (FIG. 25*a*) and with cleaning using Rivulet Droplet Flow (FIG. 25*b*) demonstrate the highly effective cleaning of the surface of the channel by the method of the invention.

Example 12

RDF Cleaning of Air/Water (A/W) Channel Soiled with Clotted Blood

In this series of tests, the soil was based on clotted fresh sheep blood whose formula is given under Table 7 below. Blood contamination of endoscopes is very common and is considered to be a tough soil to clean with liquid flow methods. 6.5 mL of the clotting mixture including Tc-99 isotope was injected into the A/W channel from the umbilical end of the endoscope. Six tests were made where cleaning was performed at 28 or 14 psi air and with liquid flow rate of 15 mL/min or 7.5 ml/min. These operating conditions were selected by the flow mapping method described above to give the RDF flow regime. The test cleaning composition included an alkaline surfactant solution based on 0.0.05% nonionic surface Tergitol (1x) at a pH of about 10.0. The cleaning solution and air were injected from the A/W cylinder located in the control handle of the endoscope (PENTAX® EG-3401).

The results of Test 1 to 6 summarized in Table 7 indicates that the RDF flow regime at air pressures 14-28 psi and liquid flow rates between 7 to 15 ml/min was able to decrease the radioactivity in the endoscope to levels that can be considered "clean" according to published reports (Schrimm et al., Zentr. Steril. 2 (5), 313-324 (1994). For a small hand-held medical device, if the residual radioactivity after cleaning is in the range of 6 quanta/second/device the device is considered "clean" and is presumed to be equivalent to about 10E6 ("6 log") reduction in the number of organisms. In the case of large endoscopes such as PENTAX® (EG-3401), the residual q/s/e were: 0, 6, 36, 41, 75 and 99 (Table 7). These levels indicate that the RDF method is effective in producing "clean" endoscopes since the endoscope is 10 times larger than the hand-held devices used in the published data. The RDF provided cleaning advantage estimated between 176 to 543 q/s/e compared to the level achieved after pre-cleaning step which is assumed to be equivalent to liquid flow only cleaning. The differences between the RDF cleaning advantage in the various tests is due to the different levels of initial contamination and other variable parameters used in the testing.

TABLE 7

| Steps | Test 1 | Test 2 | Test 3 | Test 4 | Test 5 | Test 6 |
|---|---|---|---|---|---|---|
| Initial | 2644 | 3957 | 2982 | 4524 | 5321 | 3115 |
| Pre-cleaning | 237 | 217 | 312 | 493 | 549 | 392 |
| After two-phase rinsing and drying | 0 | 41 | 36 | 99 | 6 | 75 |
| Rivulet-droplet flow advantage | 237 | 176 | 276 | 394 | 543 | 317 |
| Pentax Endoscope Model EG-3401 | | | | | | |
| Soil (see footnote) | PB1 | PB1 | PB1 | PB1 | PB1 | PB1 |
| Air Pressure (psi) | 28 | 28 | 14 | 28 | 14 | 28 |
| Liquid flow rate (ml/min) | 15 | 15 | 7.5 | 15 | 7.5 | 15 |
| Pre-cleaning time (min) | 2.5 | 2.5 | 2.5 | 2.5 | 2.5 | 2.5 |
| Liquid flow time (min) | 0.0 | 0.0 | 0.0 | 0.0 | 0.0 | 0.0 |
| Rivulet-droplet flow cleaning time (min) | 2.5 | 2.5 | 2.5 | 2.5 | 2.5 | 2.5 |
| Two-phase rinsing time (min) | 3.0 | 3.0 | 3.0 | 3.0 | 3.0 | 3.0 |
| Drying time (min) | 2.0 | 2.0 | 2.0 | 2.0 | 2.0 | 2.0 |

Note:
PB1: 2.5 mL pure fresh sheep blood, 2.5 mL saline, 100 μm protamine sulfate and radioactivity material that makes about 6.5 mL of soil.

Example 13

Bioburden Removal as Function of Flow Mode at Three Pressures

This example demonstrates how flow modes in endoscope channels affect the cleaning efficacy as determined by testing Recoverable Bioburden (microorganisms) following an accepted recovery protocol. Another objective was to define the effect of air pressure (velocity) and liquid flow rate on the flow regime and on the effectiveness of removing bioburden form actual endoscopes channels.

The Artificial Testing Soil (ATS) developed by Alfa is now accepted as a simulant for worst-case organic soil found in patient endoscopes after gastrointestinal procedures (U.S. Pat. No. 6,447,990). The detailed protocol for testing the effectiveness of cleaning endoscopes was published by Alfa et al., American Journal of Infection Control, 34 (9), 561-570 (2006), including the citations therein. The basis of the Alfa cleaning evaluation includes contaminating endoscope channels with a sufficient volume of a high-count inoculum (normally >8 log 10 cfu/ml) using a cocktail comprising three organisms covering a representative species from Gram positive, Gram negative and yeast/fungus mixed in the ATS soil. Depending on length and diameter, each channel normally receives 30 to 50 ml/channel of the ATS soil-bioburden mixture and then is allowed to stand for two hours to simulate the recommended practice used in reprocessing endoscopes. This contamination procedure is specific and requires special skill to ensure that each channel receives a complete coverage with ATS soil and organisms. After a waiting time, the endoscope channels is lightly purged with a know volume of air using a syringe to remove excess mixture form the channels. The endoscope is then transferred to the cleaning device for evaluation. At the conclusion of the cleaning and rinsing cycles (including exterior cleaning), residual bioburden in the channel is recovered according to a specific and precise protocol.

The accepted bioburden recovery method from the working channels (suction and biopsy) is to use the Flush/Brush/Flush (F/B/F) protocol for the working channels and the Flush/Flush (F/F) for the narrow A/W channels. The validated F/B/F protocol requires first flushing the entire channel with a sterile reverse osmosis (sRO) water and quantitatively collecting the recovered solution of this step in a sterile vial. The second step requires brushing the entire channel with a specially-designed endoscope brush multiple times using a specific sequence and manipulation to reach the entire surface of the channel and to dislodge the attached organism in a quantitative and reproducible manner. The brush tip is then cut off and placed in the same collecting sterile vial. A third bioburden recovery step involves another flushing of the channel with sRO water to remove the organisms detached by the brushing action as described above. The flushing liquid of this step is added to the same collection vial. The total volume of liquid recovered is maintained at about 40 mL. The contents of the vial are then sonicated to dislodge organisms from the brush or to suspend aggregated bacteria recovered. An aliquot of this recovered fluid is plate cultured as described by Alfa et al., referenced above. Serial dilution practice is used to produce reliable results following strict microbiology laboratory practices and routines. Three replicates are made in each test. The recovered bioburden from the suction/biopsy channel is termed L1. Intimate knowledge of the endoscope and its channel configuration is necessary to perform this protocol.

Recovery of bioburden from the Air/Water (A/W) narrow channels (ID 1.0 to 2.1 mm) is normally performed with the Flush/Flush (F/F) protocol which does not include the brushing step. These narrow endoscope channels cannot be bushed due to their small diameter and to the complex configuration of endsocopes, and there are no available brushes that can be perform this operation. However, the F/F protocol has been validated to produce excellent recovery for the A/W channel. At the conclusion of the cleaning and rinsing cycles, residual bioburden is recovered with a double flushing method using sRO water according to the Alfa protocol. The recovered liquid is collected from both air and water channels and pooled together in one sterile vial. Approximately 30 mLs are collected and subjected to the same preparation and culturing procedures described above. The recovered bioburden from the Air/Water channel is termed L2.

In each test the inoculum is cultured according the accepted protocols and the results expressed in colony forming units per mL, or simply cfu/mL. Generally, the recovered bioburden from the channel after cleaning is expressed as cfu/mL. The product of cfu/mL and volume of the recovered liquid from each channel in mLs yields total cfu/channel. When the latter value is divided by the surface area of the channel in cm2, bioburden surface density can be expressed in cfu/cm2. Since the volume of the liquid recovered from the channel is more or less the same as the volume of inoculum used to contaminate the channel, the log 10 removal (reduction) factor (RF) can be obtained by subtracting the log 10 of cfu/mL of recovered solution form the log 10 cfu/mL of the inoculum used. This calculation may be some what approximate since a positive control of a contaminated endoscope (not cleaned) need to be recovered at the same time to arrive at the actual RF. However, according to our experience with many tests the two methods for estimating RF are close to each other within +/−0.5-1.0 log. Negative controls are used in each test according to the Alfa protocol.

In this example, we assessed the cleaning of endoscope channels using *Enterococcus faecalis* ATCC 29212. *Enterococcus faecalis* is a gram-positive opportunistic pathogen known to form biofilms in vitro. This species is known to possess strong adhesion to endoscope channels and is considered an excellent surrogate worst case organism to reliably assess the cleaning effectiveness.

To demonstrate the effect of flow modes on the effectiveness of removing bioburden according to method of this invention, we selected three air pressures namely: namely 10, 28, and 55 psig. At each air pressure, we tested the cleaning effectiveness at three liquid flow rates. The liquid flow rates used to assess the cleaning of the suction/biopsy channel (ID=3.7 mm; length=400 cm max) are shown in Table 8. The liquid flow rates used to assess the cleaning effectiveness of the A/W (ID=about 1.6 mm; length=400 cm max) channels are shown in Table 8. The range of liquid flow rates was chosen by constructing a flow regime map according to the methods described in Example 1-7 for the particular endoscope channels employed and selecting the controlling parameters set forth above that provided RDF flow regime. The maps used in this case are those described in Example 2—FIG. 26*b* for the 2.8 mm tube and Example 3—FIG. 26*a* for the 1.8 mm tube. The low liquid flow rate was selected where the flow regime is described as dry/sparse over most of the channel length and when the amount of surface flow entities on the channel surface is small. The intermediate liquid flow rate was selected to represent nearly optimal RDF regime with intense rivulet meandering and fragmentation with large amount of moving liquid entities having three-phase contact line. The higher liquid flow rate was chosen such that the flow regime is in the film/foam regime where the surface of the channel is covered by a complete film with some foam and with little opportunity to form liquid entities.

Table 9 summarizes the results of nine tests to assess bioburden removal at three flow modes at three air pressures. At each pressure, the liquid flow rate determines the flow mode that can be obtained at the operating conditions. Examples of large (S/B) and narrow (A/W) channels were tested. The cleaning composition used was Composition 10A in Table 5, where the surfactant mixture was found to give excellent RDF mode when used at appropriate operating conditions. The injection of air and liquid into the endoscope was made according to the sequencing scheme A described in Example 16 where the flow is injected from the control handle following the cycle described here.

At 10 psig air pressure (Table 8), Test No. 2 represents near optimal liquid flow rate where the most of the channel is covered with elements of the RDF mode including rivulets, meandering rivulets and liquid fragments/entities covering the most of the channel length and surface. Test No. 2 results show the best bioburden removal from both S/B (L1) and A/W (L2) channels with RF values of 6.047 and 6.472, respectively. In this test, residual/recoverable organisms after RDF cleaning were only 48 cfu/cm2 and 17 cfu/cm2 form the S/B and A/W, respectively. At lower liquid flow rates where the treatment number is small due to the few number of surface flow entities formed under these conditions (Test No. 1), the results are worse. At higher liquid flow rate where most of the surface is in the film/foam regime and the cleaning with liquid entities is not possible (Test No. 3) the results were also worse compared to those of Test No. 2. Overall, the cleaning effectiveness demonstrates the significance of using the RDF mode (Table 8), especially in the S/B channel (L1). OLYM- PUS® Colonoscopes (model CF Type Q160L) were used to simulate the worst case conditions especially for very long channels.

TABLE 8

| Test No. | Air Pressure (psig) | Liquid Flow Rate (ml/min) | Inoculum (Log10 cfu/ml) | Recoverable Bioburden (cfu/ml) | Recoverable Bioburden (Log10 cfu/ml) | Recoverable Bioburden (cfu/cm2) | Reduction Factor |
|---|---|---|---|---|---|---|---|
| L1—Suction/Biopsy (Flush/Brush/Flush) | | | | | | | |
| 1 | 10 | 5.00 | 8.439 | 7830 | 3.893 | 787 | 4.546 |
| 2 | 10 | 22.5 | 8.710 | 460 | 2.663 | 48 | 6.047 |
| 3 | 10 | 67.50 | 8.393 | 1830 | 3.262 | 171 | 5.131 |
| 4 | 28 | 5.00 | 8.369 | 6400 | 3.806 | 605 | 4.563 |
| 5 | 28 | 22.50 | 8.572 | 173 | 2.238 | 16 | 6.334 |
| 6 | 28 | 67.50 | 8.560 | 1700 | 3.230 | 151 | 5.330 |
| 7 | 55 | 5.00 | 8.423 | 1390 | 3.143 | 135 | 5.280 |
| 8 | 55 | 22.50 | 8.423 | 497 | 2.696 | 56 | 5.727 |
| 9 | 55 | 67.50 | 8.710 | 460 | 2.663 | 40 | 6.047 |
| L2—Air/Water (Flush/Flush) | | | | | | | |
| 1 | 10 | 1.75 | 8.439 | 6830 | 3.834 | 607 | 4.605 |
| 2 | 10 | 5.75 | 8.710 | 173 | 2.238 | 17 | 6.472 |
| 3 | 10 | 16.80 | 8.393 | 190 | 2.279 | 14 | 6.114 |
| 4 | 28 | 1.75 | 8.369 | 293 | 2.467 | 17 | 5.902 |
| 5 | 28 | 5.75 | 8.572 | 150 | 2.176 | 8 | 6.396 |
| 6 | 28 | 16.80 | 8.560 | 1780 | 3.250 | 129 | 5.310 |
| 7 | 55 | 1.75 | 8.423 | 52300 | 4.718 | 3597 | 3.705 |
| 8 | 55 | 5.75 | 8.423 | 70 | 1.845 | 4 | 6.578 |
| 9 | 55 | 16.80 | 8.710 | 57 | 1.754 | 3 | 6.956 |

The same trend is found at 28 psig air pressure (Table 8) where the region corresponding to near optimal RDF mode gives the best result (Test No. 5). Low liquid flow rates (Test No. 4) corresponds to the sparse/dry flow mode with small treatment number and the high flow rate produced the foam/film regime (Test No. 6). Test No. 5 corresponds to the best results for both S/B and A/W channels as supported by the very low recoverable cfu/cm2 and high RF values. Again, cleaning in the RDF mode is demonstrated to give the best results at the 28 psig air pressure; RF values higher than 6.0 could be achieved under these conditions.

At even higher air pressures (55 psig), the main trend remains in that when the RDF and higher treatment number can be achieved within the 300 seconds cleaning yet better cleaning is possible. At this high pressure, the liquid flow rate optimal for the RDF mode appears to shift to higher values because of the high gas velocity obtained at this pressure.

The RF for optimal manual cleaning of endoscope channels has been established by Alfa et al. at 4.32+/−1.03 (Alfa et al., American Journal of Infection Control, 34 (9), 561-570 (2006)). Also, industry estimates RF of manual cleaning of endoscopes in the field about 1-4 or about 3.0 on the average. The manual cleaning results are based on following protocols for manual cleaning recommended which include brushing of the working S/B channels and flushing the A/W (protocol provided in Alfa et al., cited above). The optimal RF value obtained with the RDF cleaning at 10 and 28 psig air pressure is between 6.047 and 6.472 which is significantly better than the best manual cleaning results reported by Alfa et al by about 2 log 10. Based on these results, the RDF cleaning provides significantly better results than manual cleaning with brushing.

Example 14

Bioburden Removal with the RDF Mode Using Multiple Organisms

The three bacterial strains used for this example were *Enterococcus faecalis* ATCC 29212, *pseudomonas aerogi-nosa* ATCC 27853 and *candida albicans* ATCC 14053. This example follows the methods and protocols described in Alfa et al. and the references cited therein. Endoscope channels were contaminated with the ATS including cocktail of the three organisms as described in Example 13. OLYMPUS® Colonoscopes (model CF Type Q160L) were used to simulate the worst case conditions especially for very long channels. Both S/B and A/W channels were tested and the results are summarized in Table 10. The cleaning/rinsing cycles were same as in Example 13. Composition 10A in Table 5 was used as the cleaning liquid. The operating conditions including: air pressure, liquid flow rate and ports of injection were selected to provide optimal or near optimal RDF for the channel sizes present in endoscope used. Flow mode maps similar to those of Example 2-7 were used to define the RDF mode and to select the operating conditions. All tests were made at 28 psig air pressure.

RF values for Ten (10) independent tests regarding the cleaning S/B channel (L1) were as follows: 1) *Enterococcus faecalis* 5.60 (±0.82); 2) *pseudomonas aeroginosa* 7.02 (±1.38); 3) *candida albicans* 5.32 (±0.56). These results are significantly better than the best manual cleaning with brushing as per Alfa et al., and are far superior to published data by Zuhlsdorf (cited in Alfa's paper) where cleaning is performed according other AERs based of liquid flow cleaning methods. The main conclusion of the present example is that cleaning endoscope channels with the RDF mode achieves reliable and robust high-level cleaning better than manual brushing or other methods when the three representative organisms were used in the evaluation.

The RF values obtained in cleaning A/W channels (L2) of the same endoscope were as follows: 1) *Enterococcus faecalis* 5.76 (±1.01); 2) *pseudomonas aeroginosa* 6.92 (±1.02) and 3) *candida albicans* 5.82 (±0.94). These results are significantly better than the best manual cleaning values published by Alfa et al., or published data by zuhlsdorf et al. Comparing the results of this example with published data indicated that the RDF mode provides a clear advantage in cleaning very narrow channels compared to other methods as supported by the RF value obtained in the A/W (L2) case.

TABLE 9

| Test No. | Endoscope Model | E. faecalis Inoculum (Log10 cfu/ml) | E. faecalis R.F. | P. aeruginosa Inoculum (Log10 cfu/ml) | P. aeruginosa R.F. | C. albicans Inoculum (Log10 cfu/ml) | C. albicans R.F. |
|---|---|---|---|---|---|---|---|
| L1—Suction/Biopsy (Flush/Brush/Flush) | | | | | | | |
| 1 | PENTAX ® EG-2910 | 8.49 | 5.04 | 7.44 | 7.36 | 8.06 | 5.01 |
| 2[a] | PENTAX ® EG-2910 | 8.45 | 4.79 | 7.79 | 7.79 | 8.02 | 5.31 |
| 3[b] | PENTAX ® EG-2910 | 8.30 | 6.62 | 8.03 | 8.03 | 7.86 | 5.73 |
| 4c | PENTAX ® EG-2910 | 8.71 | 5.78 | 8.27 | 8.13 | 7.44 | 4.82 |
| 5[d] | PENTAX ® EG-2910 | 8.71 | 6.12 | 8.27 | 8.13 | 7.44 | 5.02 |
| 6[e] | PENTAX ® EG-2910 | 8.51 | 5.28 | 7.70 | 5.62 | 7.94 | 5.30 |
| 7[f] | PENTAX ® EG-2910 | 8.60 | 7.03 | 8.22 | 8.22 | 7.84 | 6.49 |
| 8[g] | OLYMPUS ® CF-Q160L | 8.30 | 4.71 | 8.28 | 4.56 | 7.18 | 4.84 |
| 9[h] | OLYMPUS ® CF-Q160L | 8.38 | 4.75 | 8.48 | 5.15 | 7.28 | 4.78 |
| 10[i] | OLYMPUS ® CF-Q160L | 8.23 | 5.10 | 8.91 | 7.20 | 7.90 | 5.86 |

TABLE 9-continued

| Test No. | Endoscope Model | E. faecalis Inoculum (Log10 cfu/ml) | R.F. | P. aeruginosa Inoculum (Log10 cfu/ml) | R.F. | C. albicans Inoculum (Log10 cfu/ml) | R.F. |
|---|---|---|---|---|---|---|---|
| 11[j] | OLYMPUS® CF-Q160L | 8.57 | 6.33 | | | | |
| | Average: | 8.48 | 5.60 | 8.14 | 7.02 | 7.70 | 5.32 |
| | Standard Deviation: | 0.16 | 0.82 | 0.42 | 1.38 | 0.33 | 0.56 |
| L2—Air/Water (Flush/Flush) | | | | | | | |
| 1 | PENTAX® EG-2910 | 8.49 | 4.64 | 7.44 | 5.43 | 8.06 | 5.33 |
| 2[a] | PENTAX® EG-2910 | 8.45 | 4.66 | 7.79 | 7.46 | 8.02 | 6.06 |
| 3[b] | PENTAX® EG-2910 | 8.30 | 5.89 | 8.03 | 7.41 | 7.86 | 5.73 |
| 4c | PENTAX® EG-2910 | 8.71 | 6.02 | 8.27 | 8.22 | 7.44 | 4.94 |
| 5[d] | PENTAX® EG-2910 | 8.71 | 6.30 | 8.27 | 6.84 | 7.44 | 5.37 |
| 6[e] | PENTAX® EG-2910 | 8.51 | 4.58 | 7.70 | 6.10 | 7.94 | 5.78 |
| 7[f] | PENTAX® EG-2910 | 8.60 | 7.71 | 8.22 | 8.22 | 7.84 | 7.80 |
| 8[g] | OLYMPUS® CF-Q160L | 8.30 | 5.59 | 8.28 | 6.12 | 7.18 | 5.14 |
| 9[h] | OLYMPUS® CF-Q160L | 8.38 | 4.88 | 8.48 | 5.72 | 7.28 | 4.98 |
| 10[i] | OLYMPUS® CF-Q160L | 8.23 | 6.71 | 8.91 | 7.65 | 7.90 | 7.07 |
| 11[j] | OLYMPUS® CF-Q160L | 8.57 | 6.40 | | | | |
| | Average: | 8.48 | 5.76 | 8.14 | 6.92 | 7.70 | 5.82 |
| | Standard Deviation: | 0.16 | 1.01 | 0.42 | 1.02 | 0.33 | 0.94 |

Notes
[a]Two RDF cycles
[b]No water filter/cold water/2 hr. drying time (March 2005)
cWith water filter/cold water
[d]Without water filter/cold water
[e]Flush/Brush/Flush Method of Recovery (July 2005)
[f]Hot tap water (September 2005)
[g]Cold tap water (April 2008)
[h]Cold RO water (April 2008)
[i]Cold RO water with continuous rinse (May 2008)
[j]10 Tap water with continuous rinse (September 2008)

Example 15

Cleaning of Organic Soils from Endoscopes with RDF Flow Regime

One criteria cleaning effectiveness used in the pharmaceutical industry is based on measuring the level of organic soil removal from surfaces of equipment and devices. Transfer of contamination from one drug to another due to the use of the same equipment can lead to serious consequences which requires adhering to cleaning protocols approved by FDA. To apply these principles, two artificial soils, red soil (ISO 15883-5 Annex R) and black soil (ISO 15883-5 Annex P), were chosen to simulate patient soils encountered during various endoscopic procedures. These two soils were used to contaminate the endoscopes by applying the soil and allowing it to dry for at least one hour following application.

The commercial endoscopes tested were OLYMPUS® TJF-160VF duodenoscope and a PENTAX® ED-3470 duodenoscope. These endoscopes were chosen to represent some of the most difficult challenges for the cleaning system, with lumens ranging from 0.8-mm to 4.2-mm ID, and a total length in excess of three meters. Endoscope cleaning was performed using the apparatus described in Example 1 and shown diagrammatically in FIG. 23.

The cleaning efficacy was evaluated by testing water extracts from the cleaned lumens for residual total organic carbon (TOC) and protein. The following protocol was employed. Endoscope lumens were contaminated with black or red soils at a level given within Table 10. Contamination levels were based on recommendations contained within "Worst-case soiling levels for patient-used flexible endoscopes before and after cleaning," published by Michelle Alfa et al., in Amer. J. Infect. Control. 27:392-401, 1999. Total lumen lengths and internal diameters listed in the table were used to calculate total surface area. Cleaning tests included a 5-min cleaning cycle and 5-min rinse cycle with filtered tap water.

TABLE 10

Lumen Test Conditions

| Endoscope | Channel | Length (mm) | ID (mm) | Soil | Dose (ml) | Trials |
|---|---|---|---|---|---|---|
| OLYMPUS® TJF-160VF | Suction/Biopsy | 3048 | 4.2 | Control | 0.0 | 3 |
| | Air/Water | 3048 | 2.7 | Control | 0.0 | 3 |
| | Elevator Wire | 1537 | 0.9 | Control | 0.0 | 3 |
| | Suction/Biopsy | 3048 | 4.2 | Black | 6.5 | 3 |
| | Air/Water | 3048 | 2.7 | Red | 1.0 | 3 |
| | Elevator Wire | 1537 | 0.9 | Red | 0.18 | 3 |
| PENTAX® ED-3470 | Suction/Biopsy | 3105 | 4.2 | Control | 0.0 | 3 |
| | Air/Water | 3105 | 2.5 | Control | 0.0 | 3 |
| | Suction/Biopsy | 3105 | 4.2 | Black | 6.6 | 3 |
| | Air/Water | 3105 | 2.5 | Red | 1.0 | 3 |
| OLYMPUS® TJF-160VF | Suction/Biopsy | 3048 | 4.2 | Control | 0.0 | 1 |
| | Air/Water | 3048 | 2.7 | Control | 0.0 | 1 |
| | Suction/Biopsy | 3048 | 4.2 | Black | 6.5 | 3 |
| | Air/Water | 3048 | 2.7 | Red | 1.0 | 3 |
| PENTAX® ED-3470 | Suction/Biopsy | 3105 | 4.2 | Control | 0.0 | 1 |
| | Air/Water | 3105 | 2.5 | Control | 0.0 | 1 |
| | Suction/Biopsy | 3105 | 4.2 | Black | 6.6 | 3 |
| | Air/Water | 3105 | 2.5 | Red | 1.0 | 3 |

Three method controls (blanks) were performed in every test. These blanks were subjected to the RDF cleaning process (5-min) and rinsing with distilled water (5-min) prior to extraction of residual organic soil. Extraction was performed using deionized water and lumens with larger lumen dimensions (>1.6-mm) were brushed with lumen brushes per a validated method. Extracts were collected in clean glass vials and were analyzed for total organic carbon (TOC) and protein residues. Total organic carbon was determined using a Total Organic Carbon (TOC) analyzer model 1010 from OI Analytical, while protein was determined using a Fluorescence Spectrophotometer model RF 5301 from Shimadzu according to standard methods. The operational parameters included: 1) Air pressure for all lumens 28 psig; 2) Cleaning liquid: Composition 10A in Table 5; 3) Liquid flow rates as per flow mode maps and Example 2-7. Black soil was introduced into the biopsy port near the control handle area of the endoscopes using a syringe. Black soil was introduced into the suction port located at umbilical end of the endoscopes. Red soil was injected into the air/water channel port located at the umbilical end of the endoscopes. All soils were well distributed into their respective channels with multiple injections of air. Table 11 below details extractable residues recovered from endoscope lumens.

TABLE 11

Protein and TOC Residues Following RDF Cleaning of Soiled Lumens

| Endoscope | Channel | Protein (μg/cm²) | TOC (μg/cm²) |
|---|---|---|---|
| OLYMPUS® TJF-160VF | Suction/Biopsy | ND, ND, 0.02 | 0.06, 0.04, 0.05 |
| | Air/Water | 0.02, ND, ND | 0.05, ND, ND |
| | Elevator Wire | 0.97, 0.46, 1.40 | 2.44, 1.17, 3.36 |
| PENTAX® ED-3470 | Suction/Biopsy | ND, 0.19, 0.04 | ND, 0.15, 0.09 |
| | Air/Water | 0.08, 0.04, ND | 0.23, 0.06, ND |
| OLYMPUS® TJF-160VF | Suction/Biopsy | 0.04, 0.12, ND | 0.09, 0.03, ND |
| | Air/Water | ND, ND, ND | 0.01, ND, ND |
| PENTAX® ED-3470 | Suction/Biopsy | ND, ND, 0.10 | ND, ND, ND |
| | Air/Water | 0.08, 0.14, ND | 0.23, 0.25, ND |

ND = Non-Detect/Below the Limit of Detection

The results of this example demonstrate that RDF cleaning provided excellent cleaning capability for suction/biopsy and air/water channels of two commercially available endoscopes representing the range of standard lumen challenges. The RDF method also provided adequate cleaning capability for the elevator-wire channel of the OLYMPUS® TJF-160VF. These experiments demonstrate that the RDF method achieves high level removal organic soils recommended for testing endoscopes. This also confirms that RDF can meet and exceed the 6.2 ug/cm2 cleaning criteria set by Alfa et al for organic soils cleaning. These results are significantly better that liquid cleaning methods reported by Alfa et al. The above tests were repeated using ATS soil with similar results as in Table 11.

Example 16

Devices for Flow Sequencing for Cleaning Endoscopes

This example illustrates devices to produce two flow sequences used for applying rivulet-droplet flow (RDF) and for discharging waste liquids during reprocessing. The two flow sequences are discussed below:

Scheme A. RDF cleaning through handle ports of the endoscope—Custom fabricated adapters are used to connect the endoscope internal channels to the fluid distribution manifold. The rivulet-droplet flow is introduced using two main flow paths: i) the first flow path is dedicated to the suction control port V3 and the biopsy channel inlet V1, and ii) the second flow path directs the RDF into the air-water feeding valve V2. Two separate single flow paths are dedicated to the forward water jet port V6 and elevator wire channel V7, as shown in FIG. 16a. To enhance the cleaning for the air/water channel, V4 is closed during one step of cleaning, thus forcing all the RDF directly towards the distal end.

Scheme B. TPF cleaning connected to the umbilical end—A second flow path is designed to introduce the RDF to the suction port and air/water inlet port at the umbilical end. RDF is introduced using two main flow paths: i) the first flow path is dedicated to the suction port Vb and the biopsy channel inlet Vc, and ii) the second flow path directs the fluid into the air/water inlet Va. Exhaust fluids during reprocessing steps are discharged from the distal end, air/water feeder valve Vd, and suction control valve Ve, as shown in FIG. 16b. Each cleaning step is associated with an ON and OFF cycle to ensure that the dead spaces in the biopsy channel inlet, air/water feeder valve and suction control valve are cleaned and rinsed. In the "ON" cycle, valves Vc, Vd and Ve are open. In the "OFF" cycle, these valves are closed. Cleaning can also be performed with both Vd and Ve closed.

Example 17

Determination of Treatment Number of Water

Analysis of high-speed images reveals that there is usually rivulet meandering and that such meandering mainly provides treatment of the inlet portion of tube. Sub-rivulets and sub-rivulets fragments (various cylindrical bodies, and droplets) are seen on the bottom of tube when this is not covered by the rivulet at certain moment. A set of sliding flow entities provides additional cleaning of the bottom half of tube.

Equation 5 (below) can be used to quantify treatment number of the upper half of tube because variations in the sub-rivulet fragment diameter are usually small for the images obtained at 30 psi air pressure and at a range of liquid flow rates. As a consequence, the variation in sliding velocity is not large as well because the sliding velocity depends on the fragment diameter, while its dependence on fragment length is weaker. Taking altogether into account, 5 takes form for treatment number by subrivulet fragments $$NT_{rf} = 2i_d d_{av}{}^{rf} U_{av}{}^{rf} N_{av}{}^{rf}/S \tag{27}$$

where $N_{av}{}^{rf}$ is the averaged number of subrivulet fragments per image, $U_{av}{}^{rf}$ is the average velocity of the fragment, $t_{cl}$ is the cleaning time (time over which the experiment was carried out) and $d_{av}{}^{rf}$ is the average diameter of the rivulet fragment observed. Since only the upper half of tube is inspected, the multiplier 2 appears because S/2 is used instead of S, where S is the area of tube section of the visual area under microscope at the magnification used.

Treatment number of sure water: This example illustrates a method for calculating the treatment number (NT) based on image analysis for the case of pure water. A tube with diameter 2.8 mm, length 200 cm was examined at 30 psi air pressure and water flow rate 20 mL/min. Images were obtained at 3 positions along tube length corresponding approximately to the beginning, middle and end of the tube. At the beginning of tube (28-cm position) there was no meandering. The bottom rivulet was well visible and occupied the entire bottom of tube. Meandering rivulet was visible at the middle (118-cm position) and at the end (208-cm position). The meandering occurs mainly across the lower half of tube. The rivulet is seen either in the bottom middle, left side, or right side of the tube.

In the case of water, sub-rivulets were present on 2 among 8 images at tube middle. No sub-rivulets were present on 8 images at tube end. Sub-rivulet fragments were present at the middle and the end of the tube. These sub-rivulet fragments were almost of the same diameter, about 100 um, while their length varies within a broad range.

The diameter of droplets was approximately one half of the diameter of sub-rivulet fragments, namely about 50 micron. The averaged values for the number of sub-rivulet fragments and droplets per image at the middle and end viewing areas of the tube are collected in Table 12.

TABLE 12

| Tube section | $N_{av}{}^{rf}$ | $N_{av}{}^{dr}$ |
|---|---|---|
| Middle | 6 | 2 |
| End | 6 | 2 |

For tube with diameter 2.8 mm, S=0.7 cm² per image. The substitution of these values and treatment time $t_{cl}$=300 seconds into Eq 15 yields the following treatment numbers arising for rivulet fragments and droplets:

$$\text{Middle Section: } NT_{av} = 800(6 \cdot 10^{-2} U_{av}{}^{rf} + 10^{-2} U_{av}{}^{dr}) \tag{28}$$

$$\text{End Section: } NT_{av} = 800(6 \cdot 10^{-2} U_{av}{}^{rf} + 10^{-2} U_{av}{}^{dr}) \tag{29}$$

This yields $NT_{av}$ for rivulet fragments of $48 \cdot U_{av}$. The NT term for droplets in this example is very small and can be ignored.

If the sub-rivulet cross section does not change along and its axis, it is straight and moves along tube axis, its role in cleaning is negligible. However, the sub-rivulet cross section was found to change more than about twice per image. Apart from weak meandering, no large kinks in its shape were found in the sub-rivulets. Taking into account about 4 kinks or meandering waves per images and the presence of wider section in the sub-rivulets, the treatment by sub-rivulet may be estimated with $d_{av}^{sub} \sim 3.4 \cdot 10^{-2}$ cm, while $N_{av}^{sub} = 0.25$. This yields:
$$NT_{sub} = 800 \cdot 3 \cdot 10^{-2} U_{av}^{sub} = 24\, U_{av}^{sub} \quad (30)$$

The sum of NT terms for rivulet fragments (rf), droplets (dr) and sub-rivulets (sub) yields total treatment number for water. In order to compute the above terms, the sliding velocity of the corresponding surface flow elements (rf, dr and sub) must be known. The average velocity of was found to 7 cm/sec for rivulet fragments, 4 cm/sec for droplets and 0.7 cm/sec for sub-rivulets. Substitution of these values for the sliding velocity of the appropriate surface flow entity gives an overall Treatment Number for water of 385 in this experiment, i.e., the channel are viewed is swept 385 times during the 300 second cleaning time.

Example 18

Influence of Surfactants on Treatment Number

Many surfactants were tested to assess their influence on sub-rivulet formation and further fragmentation to other surface flow entities and on treatment number. The measurement technique and analysis was similar to that described in Example 16. The conditions employed were: Tubing: 2.8 mm ID, 2 m long; Air Pressure: 30 psig; Liquid Flow Rate: 19.6 ml/min; Treatment Time: 300 sec. All the surfactant solutions (liquid cleaning medium) included: sodium metasilicate (1.3%); sodium triphosphate (SPT) (8.7%) and tetrasodium pyrophosphate (2.0%) and were prepared with deionized water.

The results are summarized in Table 13. The measured sliding velocities for the surface flow elements used to calculate the Treatment Numbers according to Eq 5 are Rivulet Fragments—7 cm/sec; Droplets—4 cm/sec; Sub-Rivulets—0.7 cm/sec

TABLE 13

| Liquid/Surfactant | Conc. (%) | Rivulet Fragments (rf) $NT_{rf}(a)$ | Droplets (dr) $NT_{dr}(a)$ | Sub-rivulets (sub) $NT_{sub}(a)$ | Overall Treatment Number ($\Sigma NT$) |
|---|---|---|---|---|---|
| Pure Water | | 336 | 32 | 17 | 385 |
| Tallow amine 2EO ethoxylate (Surfonic T-2) | 0.05 | 392 | 15 | 10 | 417 |
| EO-PEO copolymer-HLB = 10.5 (Pluronic L43) | 0.05 | 266 | 92 | 175 | 533 |
| Octyl sulfate (NAS-8) | 0.05 | 504 | 32 | 17 | 553 |
| Tallow amine 5 EO ethoxylate (Surfonic T-5) | 0.05 | 490 | 208 | 17 | 715 |
| Butyl-terminated C12 alcohol ethoxylate (Dehypon LT-54) | 0.1 | 560 | 131 | 245 | 936 |
| Tallow amine 15EO ethoxylate (Surfonic T-15) | 0.05 | 700 | 248 | 20 | 968 |
| Acetelynic ethoxylate (HLB 17) (Surfynol 485) + Alkoxylated ether amine oxide (AO-455) | 0.036 + 0.024 | 1260 | 512 | 20 | 1792 |

Inspection of Table 13 indicates that the tallow amine 2EO ethoxylate (Surfonic T-2) which has a low HLB and is insoluble tends to form annular films (receding contact angle close to or equal to water) and provides a Treatment Number again comparable to water. Increasing the degree of ethoxylation to 5EO increases the Treatment Number somewhat while an increase in ethoxylation to 15 EO (Surfonic T-15) provides a much more effective cleaning medium exhibiting a 2.5 fold increase in Treatment Number.

It should be noted that the concentration of surfactant employed is also important parameter governing its ability to generate an optimal flow regime. For example, the Tallow 15 EO ethoxylated (Surfonic T-15) used in this experiment was 0.05%. However, when the concentration is increased to 0.1% the solution generates significant foam and the Treatment Number is found to decrease.

Table 14 also demonstrates mixed surfactant system composed of the Acetelynic ethoxylate (Surfynol 485) and the Alkoxylated ether amine oxide (AO-455) provides provides vastly increased Treatment Number that is 4.6 time more effective than water.

These results indicates that the proper selection of the surfactant and its concentration so as to meet the surface tension, wetting and foaming requirements described above is critical to its performance in the cleaning method of embodiments of the present invention.

Example 19

Channel Cleaning with Discontinuous Plug Droplet Flow (DPDF)

To test the cleaning effectiveness of the Discontinuous Plug Droplet Flow flow regime (DPDF), we performed cleaning experiments using 2.8 mm diameter Teflon channel (2 meter long) contaminated with the black soil as described in Example 15. After contamination the channel was allowed to dry in the channel for 24 hour before cleaning. The cleaning conditions used were: 28 psig air; 19.6 mL/min liquid flow; cleaning liquid included Surynol 485 and AO-455 (designated Composition 10A in Table 5); treatment time 300 seconds; air and liquid used @ room temperature.

The cleaning procedure was based on introducing the cleaning liquid into the channel for 2-3 seconds without air and then introducing the air for 6 seconds. This mode of cleaning first resulted in creating a moving meniscus that swept the entire perimeter of the channel from the inlet to outlet. Almost concurrently, introducing the air transformed the cleaning liquid into surface flow entities including rivulets, sub-rivulets, rivulet fragments and droplets which covered the entire surface of channel during a portion of the time. The latter part of the air pulse resulted in complete dewetting and drying of the surface of the channel. The channel becomes ready to receive effective cleaning with the moving contact line during the next step. The above cleaning step was repeated for the 300 seconds or about 43 times. At the conclusion of cleaning with this mode, the channel was rinsed with water.

Sections were then cut at the beginning, middle and end of the channel for examination by electron microscopy. Representative scanning electron micrographs (SEMs) were acquired at 1000× and 5000× magnifications. Analysis of SEMs revealed that the DPDF flow regime is effective in achieving a high-level cleaning of similar quality as when air and cleaning liquid used in the RDF mode. This mode of cleaning allows better distribution of surface flow entities with three phase contact on the ceiling and bottom of the channel. It can be used alone or can be combined with other RDF mode to ensure achieving high treatment number for all parts of channel surface. High-speed images also indicated that the surface of the channel specially at both inlet and outlet portions of the channel receive more effective treatment and more uniform coverage with surface flow entities during cleaning with the DPDF. The results of this example support that periodic dewetting and drying of channel surface prevents adverse effects of liquid film formation on the surface of the channel which has been found to impede the cleaning with surface flow entities according the instant invention. The selection of the period of time for introducing the liquid, liquid flow rate, air pressure, air duration and surfactant type need to be selected to achieve effect effective cleaning. This cleaning mode is also effective during rinsing and pre-cleaning of endoscopes since it provides more uniform coverage of surface and minimizes incidents of low treatment number in some parts of the channels specially the bottom section and both inlet and outlet sections.

Example 20

Controlling Parameter for Endoscope Cleaning According to the Current Invention

Tables 14-16 provide the suggested liquid and gas flow rates at different pressures for generating optimal RDF flow regimes for cleaning the channels of most endoscopes currently available. The liquid cleaning used included 0.036% Surfynol-485W and 0.024% AO-455.

TABLE 14

Rivulet-droplet Flow Conditions: Endoscope—PENTAX ® EG-2901

| | Channel Inside Diameter (cm) | Flow Rate of Liquid Cleaning Solution (ml/min) | 18 psig | | | | 24 psig | | | | 30 psig | | | |
|---|---|---|---|---|---|---|---|---|---|---|---|---|---|---|
| | | | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) |
| Flow from Umbilical End to Distal End | | | | | | | | | | | | | | |
| Air/Water | 0.18 | 15 | 0.04 | 12.5 | 3.3 | 1.8 | 0.07 | 22.4 | 6.6 | 2.6 | 0.14 | 27.5 | 12.8 | 4.5 |
| Suction | 0.38 | 45 | 0.21 | 12.8 | 8.8 | 4.7 | 1.36 | 15.4 | 56.7 | 27.7 | 1.01 | 26.8 | 41.9 | 14.9 |
| Flow from Control Handle to Distal End | | | | | | | | | | | | | | |
| Air/Water | 0.15 | 15 | 0.07 | 12.6 | 9.8 | 5.3 | 0.11 | 18.3 | 14.3 | 6.4 | 0.21 | 28.0 | 28.4 | 9.8 |
| Suction | 0.38 | 45 | 0.87 | 12.3 | 36.3 | 19.8 | 1.16 | 18.3 | 48.4 | 21.6 | 1.74 | 26.8 | 72.5 | 25.7 |
| Biopsy | 0.38 | 45 | 0.73 | 12.4 | 30.3 | 16.4 | 0.85 | 18.1 | 35.4 | 15.9 | 1.72 | 28.0 | 71.5 | 24.6 |
| Flow from Control Handle to Umbilical End | | | | | | | | | | | | | | |
| Air/Water | 0.18 | 15 | 1.37 | 12.6 | 127.5 | 68.7 | 1.61 | 18.4 | 149.6 | 66.5 | 1.91 | 24.0 | 177.0 | 67.2 |
| Suction | 0.38 | 45 | 1.97 | 12.0 | 81.9 | 45.1 | 2.67 | 18.0 | 111.0 | 49.9 | 3.42 | 24.6 | 142.2 | 53.2 |
| Biopsy | 0.38 | 45 | 1.95 | 12.3 | 81.2 | 44.3 | 2.47 | 18.1 | 103.0 | 46.1 | 3.19 | 25.0 | 132.8 | 49.2 |

TABLE 15

Rivulet-droplet Flow Conditions: Endoscope—PENTAX ® EC-3830TL)

| | | Flow Rate of | Set Pressure | | | | | | | | | | | |
|---|---|---|---|---|---|---|---|---|---|---|---|---|---|---|
| | | | 18 psig | | | | 24 psig | | | | 30 psig | | | |
| | Channel Inside Diameter (cm) | Liquid Cleaning Solution (ml/min) | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) |
| | | | Flow from Umbilical End to Distal End | | | | | | | | | | | |
| Air/Water | 0.18 | 15 | 0.11 | 16.5 | 10.3 | 4.9 | 0.21 | 22.3 | 19.7 | 7.8 | 0.22 | 28.1 | 20.1 | 6.9 |
| Suction | 0.38 | 45 | 1.83 | 16.0 | 76.1 | 36.4 | 2.19 | 22.0 | 91.1 | 36.5 | 2.56 | 27.6 | 106.5 | 37.0 |
| | | | Flow from Control Handle to Distal End | | | | | | | | | | | |
| Air/Water | 0.15 | 15 | 0.15 | 16.4 | 19.7 | 9.3 | 0.29 | 22.3 | 38.9 | 15.5 | 0.44 | 28.0 | 58.2 | 20.0 |
| Suction | 0.38 | 45 | 2.60 | 15.3 | 54.1 | 26.5 | 3.04 | 22.0 | 63.2 | 25.3 | 3.76 | 27.4 | 78.3 | 27.3 |
| Biopsy | 0.38 | 45 | 2.81 | 15.2 | 58.5 | 28.8 | 3.76 | 21.6 | 78.3 | 31.7 | 5.47 | 26.6 | 113.9 | 40.5 |
| | | | Flow from Control Handle to Umbilical End | | | | | | | | | | | |
| Air/Water | 0.18 | 15 | 1.65 | 16.0 | 152.6 | 73.1 | 2.05 | 23.6 | 190.4 | 73.1 | 2.44 | 25.8 | 226.1 | 82.1 |
| Suction | 0.38 | 45 | 2.62 | 15.2 | 109.2 | 53.7 | 3.26 | 21.9 | 135.7 | 54.2 | 3.94 | 27.5 | 163.8 | 57.1 |
| Biopsy | 0.38 | 45 | 2.29 | 15.2 | 95.3 | 46.8 | 2.84 | 23.0 | 118.1 | 46.0 | 4.08 | 27.5 | 169.7 | 59.1 |

TABLE 16

Rivulet-droplet Flow Conditions: Endoscope—OLYMPUS ® TJF-160VF

| | | Flow Rate of | Set Pressure | | | | | | | | | | | |
|---|---|---|---|---|---|---|---|---|---|---|---|---|---|---|
| | | | 30 psig | | | | 40 psig | | | | 60 psig | | | |
| | Channel Inside Diameter (cm) | Liquid Cleaning Solution (ml/min) | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) | Air Flow Rate (scfm) | Pressure Drop (psid) | Channel Outlet Velocity (m/s) | Channel Inlet Velocity (m/s) |
| | | | Flow from Control Handle to Distal End | | | | | | | | | | | |
| Elevator | 0.085 | 3.8 | 0.050 | 26.0 | 82.8 | 29.9 | | | | | | | | |
| Elevator | 0.085 | 7.6 | 0.010 | 26.0 | 16.6 | 6.0 | 0.035 | 36.0 | 58.0 | 16.8 | 0.078 | 56.0 | 129.2 | 26.7 |
| Elevator | 0.085 | 11.5 | 0.001 | 26.0 | 1.7 | 0.6 | 0.014 | 36.0 | 22.4 | 6.5 | 0.050 | 56.0 | 82.8 | 17.2 |

Example 21

Eductor System and Basin Design with Eductor on Two Sides of Basin

To investigate the effectiveness of the eductor system design, an experiment was performed using a simple plastic container of dimensions 24 inch length by 24 inch width by 12 inch depth to test the efficiency of eductors having different nozzle sizes (0.125 inch to 0.375 inch). The eductors were mounted on two sides of the basin as illustrated in FIG. 22b. The preliminary eductor system was driven by a ⅓ Horsepower pump 840 and was controlled with two manual ball valves in a circulation system. These initial test results indicated that eductors with a 0.25" nozzle diameter are the most effective size for cleaning the exterior surfaces of endoscopes. Each eductor delivered up to 3.5 gallons per minute (gpm) of cleaning solution from the driven pump 840 and pulled up to 12.7 gpm additional flow from the surrounding liquid to create a total flow rate of approximately 16.2 gpm that impinged onto the endoscope surface.

Example 22

Eductor System and Basin Design with Eductors in Corners of Basin

An experimental basin was designed and constructed to test the flow pattern and fluid dynamics generated by multiple eductors placed in corners of the basin, with an objective to closely simulate the case for cleaning two endoscopes. This is illustrated in FIG. 22c. The basin was constructed from acrylic plates glued together and measured was 30 inch wide× 28 inch deep×6 inch high. Internal slopes were added to the bottom plates to reduce the total volume needed for both cleaning and disinfection while still achieving full immersion of the endoscopes. Two eductors were installed at each corner of the basin and each eductor was connected with a manual ball valve for testing the effect of different combinations on the flow pattern created in the basin. The eductor system was connected with a ⅓ Horsepower pump to circulate the cleaning liquid at a source pressure of approximately 15~20 psig. In this design, when the eductors were placed about 0.5 inch beneath the cleaning solution level, we observed very strong flow patterns that covered most exterior surfaces of endoscopes, especially when three or four eductors were operated simultaneously, one at each corner. The cleaning liquid level in this experiment was about 3 inch to 4 inch from the bottom of the basin. With this setting, a strong scrubbing and agitation was found to be generated in the spaces near the bottom of the basin, whereas the earlier top spray design could not reach endoscope surfaces facing the basin. A favorable arrangement for cleaning endoscopes was found when two eductors were installed at each front corner (total of 4 in the front of the basin) and one at each back corner of the basin (total of 2 at the bottom of the basin. It is also possible to have two eductors at each corner of the basin.

Example 23

Eductor System and Basin Design for Entrainment of Air in Fluid Moved by Eductors We have also discovered that if part of the entrained liquid pulled into the eductor 800 comprises air such as in the form of air bubbles, then the impingement and agitation forces impacting the exterior surfaces of endoscopes can further enhance the cleaning process. This can be achieved, for example, by placing the eductor 800 close to the level of the surface of the liquid in the basin 850, so that some air can be pulled into the eductor 800 in addition to liquid. This is illustrated in FIG. 22*d*.

Another way of accomplishing this is with a design as shown in FIG. 22*e*. This design, which resembles what was shown in FIG. 13*d*, further includes an air intake tube 862 suitable to provide air from the head space of the basin apparatus to the suction region 822 or mixing region 824 of the eductor 800. The fluid leaving the eductor 800 may thereby include air bubbles as well as liquid.

Example 24

RDF Cleaning Using an Alcohol-Water Solution

It was attempted to perform cleaning using rivulet droplet flow using a liquid which was a solution of alcohol and water. In general, it is easy to adjust the composition of an alcohol-water solution to achieve a desired surface tension, and of course, alcohols are simple readily-available compounds. Experiments were conducted using ethanol and also using methanol, n-butanol and t-butanol. The surface tension of these solutions was adjusted to a value of about 40 dynes/cm, which with other surfactant compositions was found to be a desirable value. None of these alcohol-water solutions produced good cleaning, apparently because of liquid film remaining and the surface not becoming completely dry.

Example 25

RDF Cleaning Using a Higher-Viscosity Liquid

An experiment was performed to investigate cleaning using a liquid having a viscosity larger than the viscosity of water. The liquid was a solution of water containing 0.05% by weight of polyvinyl pyrrolidone (a thickener). It was found that such a liquid resulted in formation of films which prevented achieving a dry surface and led to a significant decrease in the formation of desired surface flow entities. So, this was undesirable for cleaning, even if the surface tension of the liquid was within the desirable range. It may be considered that it is desirable for the liquid to have approximately the viscosity of pure water.

In many applications the passageways have a uniform circular cross section (circular), in which case the "average" diameter is the actual physical internal diameter of the channel. However, the described method can also be used for passageways that are neither circular in cross section nor of uniform diameter, i.e., the passageways may have kinks, restrictions, bends, etc.

It has mostly been described herein that the passageway being cleaned is in a horizontal orientation. However, in general any orientation is possible, including combinations of orientations. For example, the passageway could be vertical, or diagonal (with flow either upward or downward), or any combination of these or any other orientations. For example, bronchoscopes could be cleaned in a vertical orientation.

It is further possible to use the described rivulet droplet flow in processes that are not the actual step which is described herein as the cleaning step. For example, rinsing may be performed at a certain stage of an overall cleaning cycle, and rinsing could be performed using rivulet droplet flow either partly or completely. Similarly, there is a step labeled pre-cleaning which is oriented toward removing macroscopic contaminants from channels. This step also could be performed using rivulet droplet flow either partly or completely. It is possible that some cleaning could be accomplished during these steps even if that is not the primary purpose of these steps. In general, it is possible that cleaning could be accomplished during steps other than the main cleaning step. A pre-cleaning step could involve use of a surfactant composition, which may or may not be the same surfactant composition used in any other step of the process. Use of rivulet droplet flow in any of these steps could be either rivulet droplet flow with steady-state supplied fluid flows, or rivulet flow with unsteady (time-varying) supplied flow of either liquid or gas or both. For example, it is possible that if rivulet droplet flow is used during a step that involves flowing alcohol or alcohol-water through the passageway (a rinsing or drying step), it may be possible to use less alcohol and still accomplish the desired objective.

It is furthermore possible to clean passageways whose cross-sectional shape is other than circular or even annular as described. For example, passageway cross-sectional shapes capable of being cleaned by the described method and apparatus include elliptical and rectangular, and also include other combinations of co-existing shapes beyond the described circular wire in a circular channel. It may be possible to clean something that does not have the geometry of a passageway, using the described method or apparatus, by enclosing it in a passageway or by placing something adjacent to the article so that together the article and the extra thing form a passageway.

Although the cleaning methods have been disclosed for passageways having an inside diameter of the order of 6 mm or less, the usefulness of the method is not limited to such relatively small passageways. It is believed that the method could similarly be applied to passageways having inside diameters at least of the order of centimeters or inches. It is believed that for such extrapolation, a useful scaling parameter may be the perimeter-normalized liquid flowrate as discussed elsewhere herein. It is also possible that the described method or apparatus could be used for passageways smaller in diameter than those investigated, such as for cleaning microfluidic articles.

It is still further possible that the described method or apparatus could be used for still other industrial or household cleaning. Liquid entities could be moved by moving gas even in the absence of a defined passageway, and operations could be sequenced so as to achieve repeated dryout and re-wetting as described elsewhere herein.

It can again be mentioned that the presence of a dry surface encountering a moving liquid entity is believed to contribute to cleaning, and that apparatus and methods of embodiments of the present invention can be arranged so as to create or ensure that dry surface between encounters with moving liquid entities. The dryness can be achieved by evaporation of liquid into the flowing gas, or by hydrophobicity of the surface, or by any combination thereof. In the plug mode of operation, gas flow can be continued between liquid plugs for a time duration sufficient to achieve de-wetting such as by evaporation. It can be appreciated that, in contrast, much of classical two-phase liquid-gas flow never achieves dryness of the wall in between encounters with liquid entities.

Although much of the discussion herein has been about cleaning passageways that have a horizontal orientation, the applicability of this method and apparatus is not limited thereto. It is possible that the method and apparatus described herein could be used to clean passageways that have a horizontal orientation, a vertical orientation, a diagonal orientation, or any combination of any of these orientations. Different portions of the passageway could have different orientations. As described, the driving force for the motion of rivulets and other liquid entities has been motion of gas. However, it is possible that the driving force could be gravity, or a combination of gravity and gas flow.

It is believed that performing the cleaning process a generally somewhat elevated temperature enhances the effectiveness of the cleaning. It is to this end that pre-heating of the liquid and pre-heating of the gas are provided for, as described elsewhere herein.

Most of the experimental data reported herein has been taken using passageways made of polytetrafluoroethylene (Teflon®), which is a relatively hydrophobic material. However, the apparatus and methods could also be used for cleaning passageways made of other materials, possibly with adjustment of the composition of the liquid.

It is possible to record of parameters experienced during the cleaning cycle. Such information may be stored in any form of computer memory or written onto a storage device. The apparatus may comprise User Interface features designed with the device which may include a display, a keyboard, a barcode reader and data transition connectors that will allow the operator to select and set process parameters and document cleaning results for reprocessing different types of endoscopes.

As described, embodiments of the invention can be used in any orientation of passageway, such as horizontal or vertical or sloping orientations or combinations thereof. The achievement of a dry or substantially dry passageway interior surface, prior to being swept by a liquid entity, can be achieved by evaporation or by the inherent hydrophobicity of the surface, or through the use of a surfactant additive in the liquid which increases the hydrophobocity of the surface, or by any combination thereof. It can be appreciated that a flow of liquid which enters a passageway as a plug of liquid might not maintain exactly that geometry during an entire passage through the passageway; however, that can be acceptable because a plug which is developing some irregularities during its passage through the passageway can still sweep the internal surface of the passageway so as to remove contaminants, and if the plug breaks up into other liquid entities, there may be even more sweeping than with an intact plug. Plug flow can refer to Discontinuous Plug Flow (DPF) and Discontinuous Plug Droplet Flow (DPDF), as described elsewhere herein. In plug flow, which may be achieved by supplying liquid for a period of time followed by supplying gas for a period of time, it is possible that the plug may be accelerated to a fairly large velocity. i.e., larger than the velocity of a sliding liquid entity, while still remaining within an overall maximum pressure of gas supplied to the passageway inlet. For example, if the plug only occupies a small fraction such as 10% of the overall length of the passageway, the plug can reach a velocity significantly larger than the velocity of a liquid filling the entire length of the passageway, for the same driving pressure difference, as described elsewhere herein. This can produce correspondingly larger viscous shear at the walls of the passageway. The same is true if there are a number of such plugs having a combined total length that is a small fraction such as 10% of the overall length of the passageway. A flow regime can be rivulet droplet flow, plug flow, or meandering rivulet flow, or still other flow regime. It is believed that use of rivulet droplet flow or plug flow or other flow regimes involving liquid and gas during rinsing can produce rinsing just as can be provided by a flow of water only, and it is further believed that some additional cleaning occurs thereby during the rinsing step. It may be viewed that the entire treatment number during the cleaning/reprocessing cycle is the sum of treatment number components arising from the application of the above flow regimes (RDF, DPF, DPDF) during pre-cleaning, cleaning, rinsing after cleaning and rinsing after disinfection. It is also believed that rinsing with water only according to the above flow regimes may be considered as a portion of the entire cleaning cycle.

Unsteady flow can be provided in a manner which either could be periodic (repeating in a defined pattern) or could be non-periodic, i.e., time-varying in a more irregular manner. A periodic pattern could, for example, comprise at least 10 repeated periods. In general, for various purposes, any timewise pattern of liquid supply (on/off or pulsatile or a more gradual variation) could be combined with any timewise pattern of gas supply (on/off or pulsatile or a more gradual variation). If two passageways or two endoscopes are being cleaned simultaneously, steps in one passageway or endoscope can in general be done in any timewise relationship with steps in the other passageway or endoscope. Mass flux is mass flow per unit cross-sectional flow area per unit time. In the use of eductors for cleaning external surfaces of an endoscope, it is possible to have any time sequence of operating specific eductors. This can provide different flow patterns of liquid in the basin at different times.

An embodiment of the present invention is related to special ability of the rivulet droplet flow and associated three phase contact line and menisci to interact with the organic soils inside the endoscope resulting in their effective removal from the channels. These special abilities may be due to interaction of the organic soil with the three phase contact line and menisci generated during RDF, PDF and DPDF. The higher plug velocities generated in the case of a short plug (compared to channel length) by the gas flow and its associated three phase contact line and menisci were found to be specially effective in dislodging and removing bulky pieces of soil (for example, feces from endoscope channels) compared to liquid flow cleaning.

The apparatus may comprise a tray or similar apparatus for holding an endoscope or other luminal medical device in a desired orientation.

It is found that cleaning with the methods and apparatus described herein may actually provide better results than manual cleaning of endoscopes such as with a brush, and likely more consistent results.

All cited references are incorporated by reference herein in their entirety.

Although embodiments and examples have been given, modifications are possible, and it is desired that the scope be limited only by the scope of the attached claims.

We claim:

1. A method of cleaning an endoscope, comprising:
causing a flow of a gas lengthwise along an interior surface of a passageway of the endoscope; and
causing a flow of a liquid lengthwise along the interior surface of said passageway forming sliding liquid entities along the interior surface of said passageway,
wherein said gas has a velocity at least somewhere along the interior surface of said passageway of approximately 2 m/s to approximately 80 m/s;
wherein said flow of said liquid has a perimeter-normalized liquid flow rate of approximately 1 to approximately 5 milliliters per minute per millimeter of perimeter of said passageway;
wherein said sliding liquid entities provide a moving three-phase interface on the interior surface of said passageway having an advancing contact angle on at least a portion of the interior surface of said passageway greater than approximately 50 degrees and has a receding contact angle greater than 0 degree so that a portion of the interior surface of said passageway is wetted by said liquid and an adjacent portion of the interior surface of said passageway is dry or nearly dry; and wherein said liquid comprises a surfactant that has a Ross Miles foam height measured at a surfactant concentration of 0.1% that is less than 50 mm.

2. The method of claim 1, wherein said liquid flow and said gas flow are such as to achieve rivulet droplet flow on at least some portion of an internal surface of said passageway.

3. The method of claim 1, wherein said gas is supplied to an inlet of said passageway at a pressure of not more than approximately 60 psig.

4. The method of claim 1, wherein said flow of said gas has a velocity at least somewhere in said passageway of approximately 5 m/s to approximately 15 m/s.

5. The method of claim 1, wherein dryout occurs at least some internal surfaces of said passageway when said internal surfaces of said passageway are not contacted by said liquid.

6. The method of claim 1, wherein said flow of said liquid is in a substantially steady-state manner.

7. The method of claim 1, wherein said flow of said gas is in a substantially steady-state manner.

8. A method of cleaning an endoscope, comprising:
causing a flow of a gas lengthwise along a hydrophobic interior surface of a passageway of the endoscope; and
causing a flow of a liquid lengthwise along the hydrophobic interior surface of the passageway forming sliding liquid entities along the hydrophobic interior surface of the passageway,
wherein said gas has a velocity at least somewhere along the hydrophobic interior surface of the passageway of approximately 2 m/s to approximately 80 m/s;
wherein said flow of said liquid has a perimeter-normalized liquid flow rate of approximately 1 to approximately 5 milliliters per minute per millimeter of perimeter of the passageway; and
wherein said sliding liquid entities provide a moving three-phase interface on the hydrophobic interior surface of the passageway so that a portion of the hydrophobic interior surface of the passageway is wetted by said liquid and an adjacent portion of the hydrophobic interior surface of the passageway is dry or nearly dry.

9. The method of claim 8, wherein said liquid comprises a surfactant and has a Ross Miles foam height measured at a surfactant concentration of 0.1% that is less than 50 mm.

10. The method of claim 9, wherein said sliding liquid entities have an advancing contact angle on at least a portion of the hydrophobic interior surface of the passageway greater than approximately 50 degrees and has a receding contact angle greater than 0 degree.

11. The method of claim 8, wherein said liquid flow and said gas flow are such as to achieve rivulet droplet flow on at least some portion of the hydrophobic interior surface of the passageway.

12. The method of claim 8, wherein said gas is supplied to an inlet of the passageway at a pressure of not more than approximately 60 psig.

13. The method of claim 8, wherein said flow of said gas has a velocity at least somewhere in the passageway of approximately 5 m/s to approximately 15 m/s.

14. The method of claim 8, wherein dryout occurs at least some the hydrophobic interior surface of the passageway.

15. The method of claim 8, wherein said flow of said liquid is in a substantially steady-state manner.

16. The method of claim 8, wherein said flow of said gas is in a substantially steady-state manner.

* * * * *

UNITED STATES PATENT AND TRADEMARK OFFICE
CERTIFICATE OF CORRECTION

PATENT NO. : 8,226,774 B2  
APPLICATION NO. : 12/286747  
DATED : July 24, 2012  
INVENTOR(S) : Labib et al.

It is certified that error appears in the above-identified patent and that said Letters Patent is hereby corrected as shown below:

Title page (54), Title and Col. 1, line 2: "SUCH AN ENDOSCOPE CHANNELS" should read --SUCH AS ENDOSCOPE CHANNELS--

Col. 74, line 30: "number of sure water:" should read --number of pure water:--

Col. 86, line 27, claim 14: "dryout occurs at least" should read --dryout occurs at at least--

Signed and Sealed this  
Twenty-fifth Day of December, 2012

David J. Kappos  
*Director of the United States Patent and Trademark Office*